United States Patent
Fu et al.

(10) Patent No.: US 9,868,777 B2
(45) Date of Patent: Jan. 16, 2018

(54) CMV NEUTRALIZING ANTIGEN BINDING PROTEINS

(71) Applicants: Merck Sharp & Dohme Corp., Rahway, NJ (US); Board of Regents of the University of Texas System, Austin, TX (US)

(72) Inventors: Tong-Ming Fu, Ambler, PA (US); Dai Wang, Blue Bell, PA (US); Zhiqiang An, Pearland, TX (US)

(73) Assignees: Merck Sharp & Dohme Corp., Rahway, NJ (US); Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/897,374

(22) PCT Filed: Jun. 9, 2014

(86) PCT No.: PCT/US2014/041504
§ 371 (c)(1),
(2) Date: Dec. 10, 2015

(87) PCT Pub. No.: WO2014/200898
PCT Pub. Date: Dec. 18, 2014

(65) Prior Publication Data
US 2016/0130327 A1    May 12, 2016

Related U.S. Application Data

(60) Provisional application No. 61/833,184, filed on Jun. 10, 2013.

(51) Int. Cl.
*A61K 39/12* (2006.01)
*C07K 16/08* (2006.01)
*C12Q 1/70* (2006.01)

(52) U.S. Cl.
CPC ........ *C07K 16/088* (2013.01); *C07K 2317/24* (2013.01); *C07K 2317/565* (2013.01);
(Continued)

(58) Field of Classification Search
None
See application file for complete search history.

(56) References Cited

U.S. PATENT DOCUMENTS

| 2003/0088086 A1 | 5/2003 | Loosmore et al. |
| 2009/0004198 A1 | 1/2009 | Nakajima et al. |

(Continued)

FOREIGN PATENT DOCUMENTS

WO    WO2013036465    3/2013

OTHER PUBLICATIONS

UniProtKB, Accession No. A8X7X3, Apr. 3, 2013.
UniProtKB, Accession No. C2MC23, Apr. 3, 2013.
UniProtKB, Accession No. D8U209, Mar. 6, 2013.
UniProtKB, Accession No. E3LYQ9, Oct. 3, 2012.

(Continued)

*Primary Examiner* — Janet L Andres
*Assistant Examiner* — Stuart W Snyder
(74) *Attorney, Agent, or Firm* — Henry P. Wu; Gloria M. Fuentes

(57) ABSTRACT

The present invention is directed to antigen binding proteins including, but not limited to, monoclonal antibodies and antigen binding fragments thereof, that specifically bind to and preferably neutralize human cytomegalovirus (CMV). Also encompassed by the invention are antigen binding proteins that have been humanized. The antigen binding proteins of the invention are useful as a therapeutic agent for treating and/or preventing CMV infections in a patient in need thereof.

10 Claims, 12 Drawing Sheets

(52) U.S. Cl.
CPC .... *C07K 2317/734* (2013.01); *C07K 2317/76* (2013.01); *C07K 2317/92* (2013.01); *C12Q 1/70* (2013.01)

(56) References Cited

U.S. PATENT DOCUMENTS

| | | |
|---|---|---|
| 2010/0034822 A1 | 2/2010 | Masignani et al. |
| 2011/0159015 A1 | 6/2011 | Sleeman et al. |
| 2012/0082666 A1 | 4/2012 | Chen et al. |
| 2012/0294865 A1 | 11/2012 | Weiss et al. |
| 2013/0039974 A1 | 2/2013 | Kufe et al. |
| 2013/0089559 A1* | 4/2013 | Grawunder .......... C07K 16/088 424/139.1 |
| 2013/0121915 A1 | 5/2013 | Paas et al. |

OTHER PUBLICATIONS

UniProtKB, Accession No. E4TXK9, Nov. 28, 2012.
UniProtKB, Accession No. H3AK35, Nov. 28, 2012.
UniProtKB, Accession No. I8W0J6, Apr. 3, 2013.
UniProtKB, Accession No. T1PNN1, Nov. 13, 2013.
Cui, Xiaohong et al.; Cytomegalovirus vaccines fail to induce epithelial entry neutralizing antibodies comparable to natural infection; Vaccine; 2008; 5760-5766; 26.
Gerna, Giuseppe et al.; Human cytomegalovirus serum neutralizing antibodies block virus infection of endothelial/epithelial cells, but not fibroblasts, early during primary infection; Journal of General Virology; 2008; 853-865; 89.
Macagno, Annalisa et al.; Isolation of Human Monoclonal antibodies that potently neutralize human cytomegalovirus infection by targeting different epitopes on the gH/gL/UL128-131A complex; Journal of Virology; 2010; 1005-1013; 84(2).

* cited by examiner

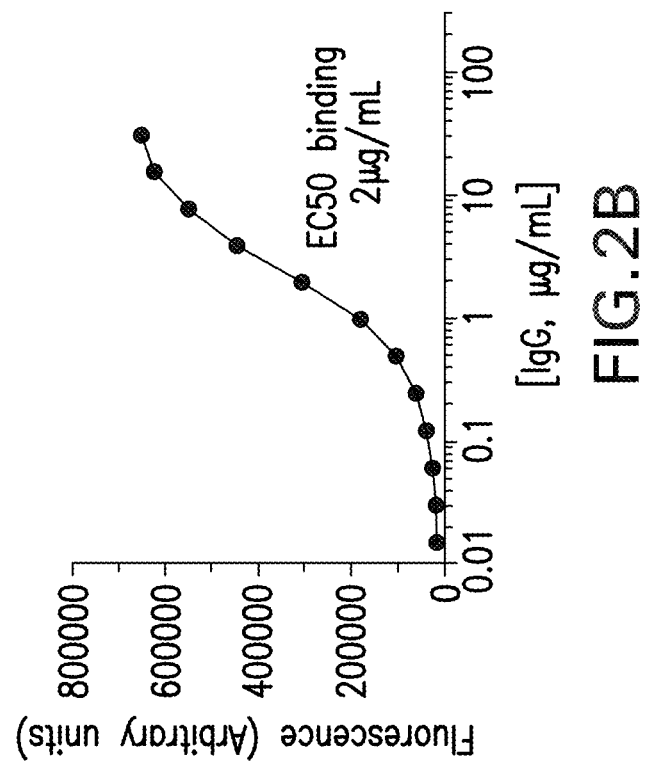
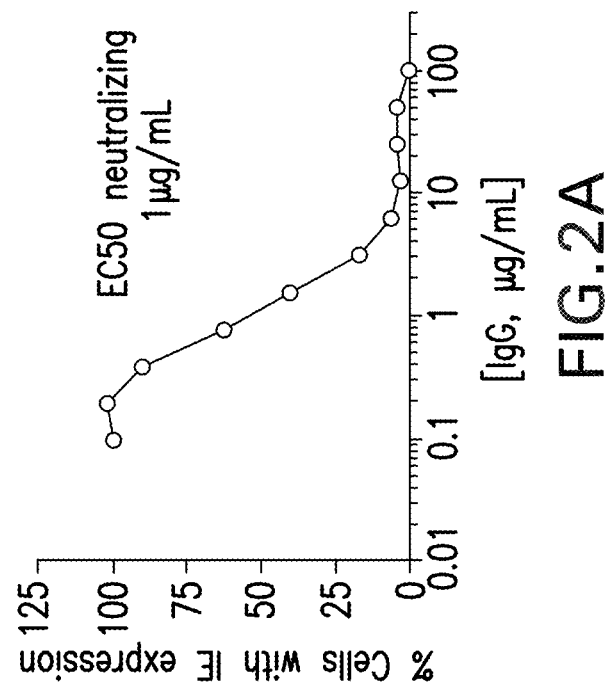
FIG. 2A
FIG. 2B

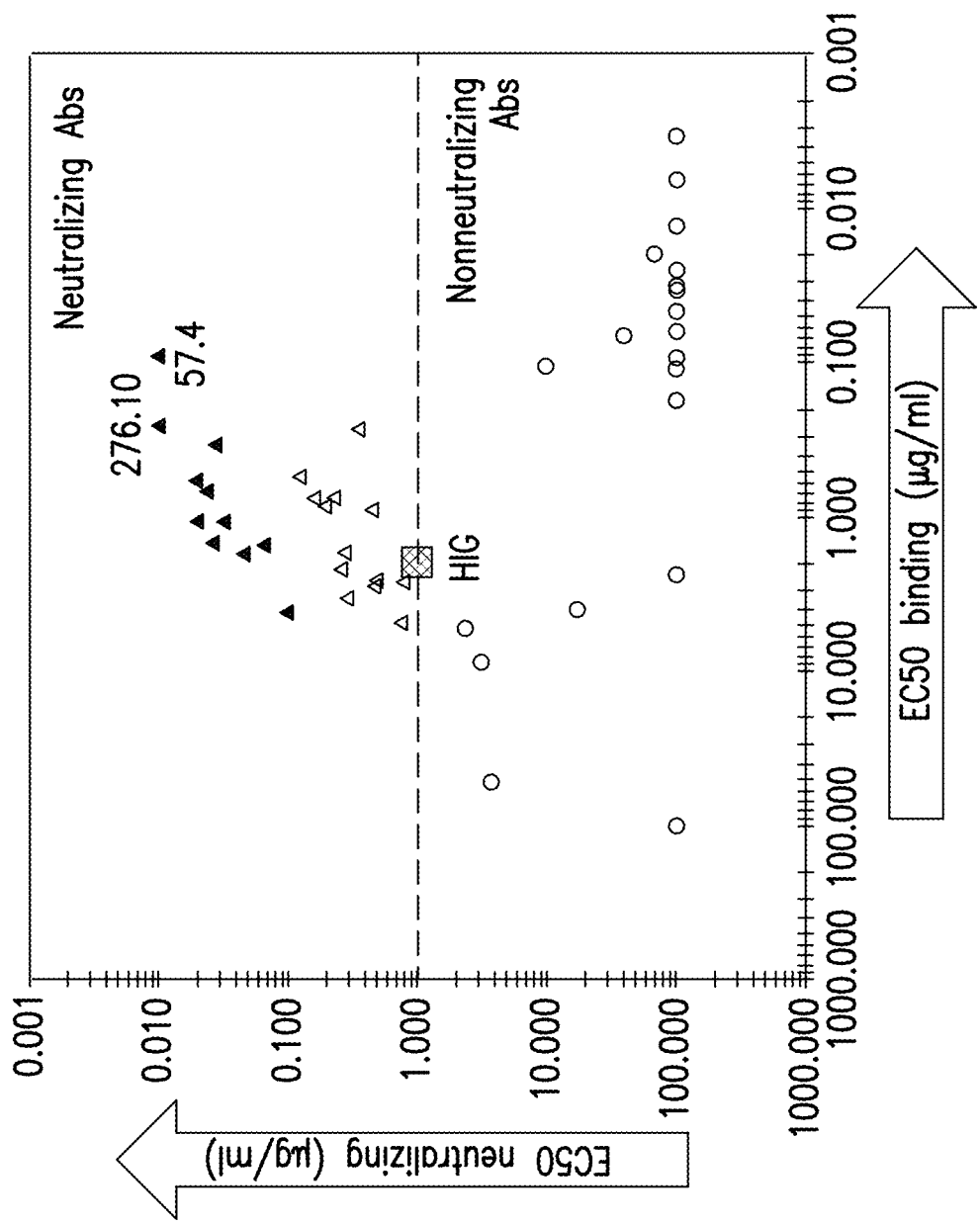

FIG.3

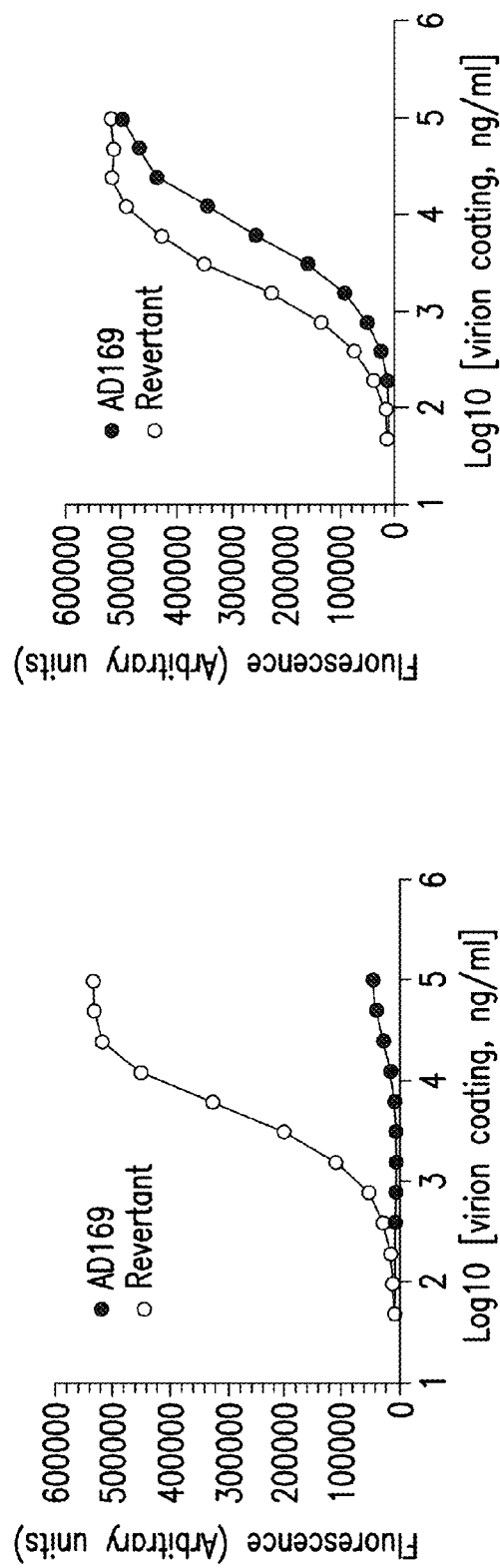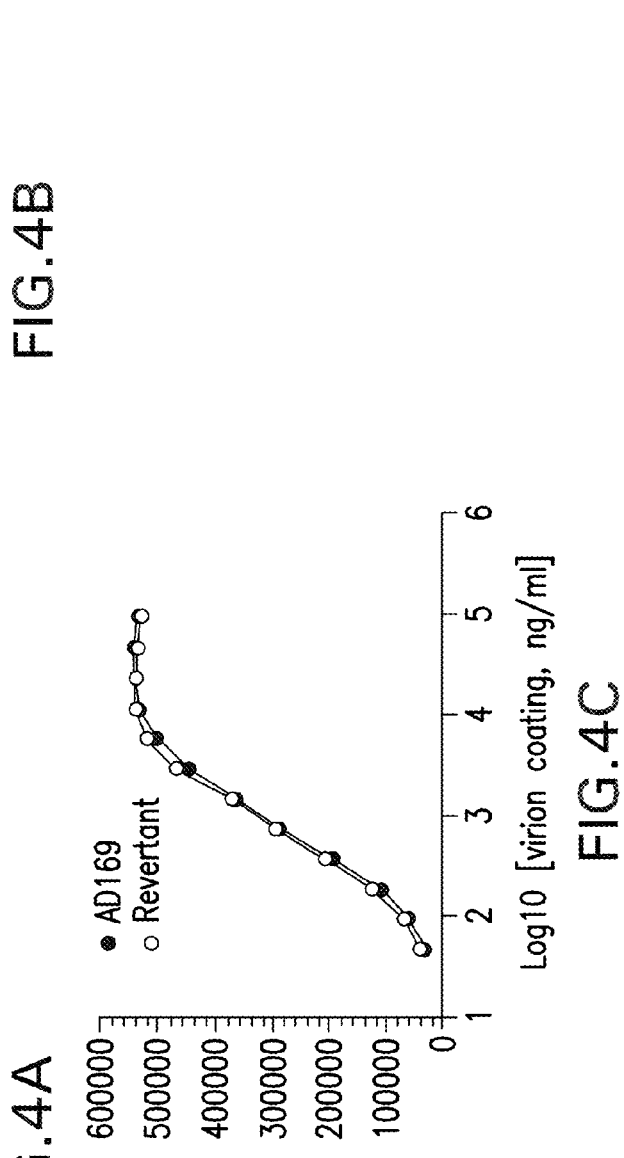

CMV NEUTRALIZING ANTIGEN BINDING PROTEINS

FIELD OF INVENTION

The present invention relates to anti-CMV antigen binding proteins including, but not limited to, monoclonal antibodies. The invention also relates to use of the antigen binding proteins of the present invention in the diagnosis, treatment and/or prevention of CMV infection. Compositions comprising the antigen binding proteins of the invention are also encompassed by the present invention.

CROSS-REFERENCE TO RELATED APPLICATIONS

This application is a §317 National Stage Application of PCT/US2014/041504, having an international filing date of Jun. 9, 2014, which claims the benefit of U.S. Provisional Application No. 61/833,184, filed Jun. 10, 2013, now expired, the contents of which are herein incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "23530USPCT-SEQLIST-10DEC2015.TXT", creation date of Dec. 10, 2015, and a size of 154 KB. This sequence listing submitted via EFS-Web is part of the specification and is herein incorporated by reference in its entirety.

BACKGROUND OF THE INVENTION

Cytomegalovirus (CMV), also known as human herpesvirus 5 (HHV-5), is a herpes virus classified as being a member of the beta subfamily of herpesviridae. According to the Centers for Disease Control and Prevention, CMV infection is found fairly ubiquitously in the human population, with an estimated 40-80% of the United States adult population having been infected. The virus is spread primarily through bodily fluids and is frequently passed from pregnant mothers to the fetus or newborn. In most individuals, CMV infection is latent, although virus activation can result in high fever, chills, fatigue, headaches, nausea, and splenomegaly.

Although most human CMV infections are asymptomatic, CMV infections in immunocompromised individuals, (such as HIV-positive patients, allogeneic transplant patients and cancer patients) or persons whose immune system has yet fully developed (such as newborns) can be particularly problematic (Mocarski et al., Cytomegalovirus, in Field Virology, 2701-2772, Editor: Knipes and Howley, 2007). CMV infection in such individuals can cause severe morbidity, including pneumonia, hepatitis, encephalitis, colitis, uveitis, retinitis, blindness, and neuropathy, among other deleterious conditions. In addition, CMV infection during pregnancy is a leading cause of birth defects (Adler, 2008 J. Clin Virol, 41:231; Arvin et al, 2004 Clin Infect Dis, 39:233; Revello et al, 2008 J Med Virol, 80:1415).

SUMMARY OF THE INVENTION

The present invention relates to anti-CMV antigen binding proteins having one or more desirable properties, including specific binding to and, preferably, neutralization of CMV. The invention also relates to use of the antigen binding proteins of the present invention in the treatment and/or prevention of CMV infection.

In particular embodiments, the antigen binding proteins as disclosed herein specifically bind to and, preferably, neutralize CMV. In more particular embodiments, the antigen binding proteins as disclosed herein block/decrease CMV virions from binding to a cell, fusing with the cellular membrane and/or releasing viral genetic material into the cell.

In particular embodiments, the antigen binding protein is a recombinant antigen binding protein.

In particular embodiments, the antigen binding protein is a monoclonal antibody.

In particular embodiments, the antigen binding protein is a humanized antigen binding protein.

In particular embodiments, the antigen binding protein is a fully-human antigen binding protein.

In particular embodiments, the antigen binding protein is a chimeric antigen binding protein.

In particular embodiments, the antigen binding protein is a bivalent antigen binding protein.

In particular embodiments, the antigen binding protein heavy chain and light chain are connected to form a single-chain antigen binding protein.

In particular embodiments, the antigen binding protein is a Fab fragment, a Fab'fragment, a $(Fab')_2$ fragment, Fv domain fragment and a scFv fragment.

In particular embodiments, the antigen binding protein is a diabody.

In particular embodiments, the antigen binding protein is a domain antibody.

In particular embodiments, the antigen binding protein is a camelized single domain antibody.

In yet additional embodiments, a recombinant nucleic acid encoding any of the antigen binding proteins as disclosed herein is provided.

In yet additional embodiments, the use of an antigen binding protein as disclosed herein is provided for the preparation of a medicament to treat and/or prevent CMV infection in a subject.

In yet a further embodiment, an antigen binding protein as disclosed herein is provided for use in a method for treating and/or preventing CMV infection in a subject.

In yet additional embodiments, the use of any of the antigen binding proteins as disclosed herein is provided for diagnostic use.

The present invention also provides an anti-CMV antigen binding protein that includes one or mutations including, but not limited to, in the Fc region that increases antibody-dependent cellular cytotoxicity (ADCC) activity, complement-dependent cytotoxicity (CDC) activity and/or antibody half-life in vivo.

In yet additional embodiments, an expression vector is provided comprising an isolated nucleic acid encoding any of the antigen binding proteins of the invention. In one embodiment, the isolated nucleic acid encodes any of the $V_H$ or $V_L$ chains described herein. The invention also relates to a host cell comprising any of the expression vectors described herein.

In particular embodiments, these nucleic acids, expression vectors or polypeptides of the invention are useful in methods of making an antibody.

BRIEF DESCRIPTION OF THE DRAWINGS

FIGS. 2A-2C: Correlation analysis of neutralizing and binding properties of a panel of forty-five rabbit mAbs to CMV. The neutralizing and binding properties of each antibody were analyzed in viral neutralization assay and binding assay, respectively. Human CMV hyperimmune IgG (HIG, CytoGam®) was used as a positive control for (A) the ability to inhibit viral entry to ARPE-19 cells and (B) the ability to bind to CMV corresponding to IgG concentration. (C) The 45 identified rabbit monoclonal anti-CMV antibodies were analyzed for their $EC_{50}$ neutralizing and $EC_{50}$ binding. Each mAb is plotted according to its $EC_{50}$ neutralizing (y-axis) and $EC_{50}$ binding (x-axis) for the revertant virus. The solid square symbol in the center represents HIG (CytoGam®) and the dashed horizontal line represents the $EC_{50}$ neutralizing of HIG. Monoclonal antibodies that fell above the line (triangles) are neutralizing mAb while monoclonal antibodies that fell below the line are non-neutralizing mAb (circles). The elite neutralizing mAb are identified as solid triangles.

FIG. 3: Neutralizing properties of the antibodies in ARPE-19 cells do not always correlated with their activity in MRC-5 cells. The neutralizing properties of each antibody in ARPE-19 cells versus MRC-5 cells were analyzed and $EC_{50}$ neutralizing values calculated. The vertical line represents the $EC_{50}$ value in ARPE-19 cells for HIG, (CytoGam®). mAb in group A only neutralize virus in ARPE-19 cells, mAb in group B neutralize virus in both cell types and mAb in group C are non-neutralizing in either cell type.

FIGS. 4A-4D: Preferential binding to the revertant virus of antibodies associated with their neutralizing activity. mAbs were tested for their binding to different concentrations of AD169 virus and the revertant virus (x-axis) and plotted versus their $EC_{50}$ neutralizing value (y-axis). The monoclonal antibodies either (A) reacted only with the revertant virus, (B) reacted with both the revertant virus and the AD169 virus but preferred the revertant virus or (C) reacted with both the revertant virus and the AD169 virus but displayed no preference. (D) The binding characteristics for the elite neutralizing (circle) and elite binding (triangle) mAb are shown.

DETAILED DESCRIPTION

Figure 1B:
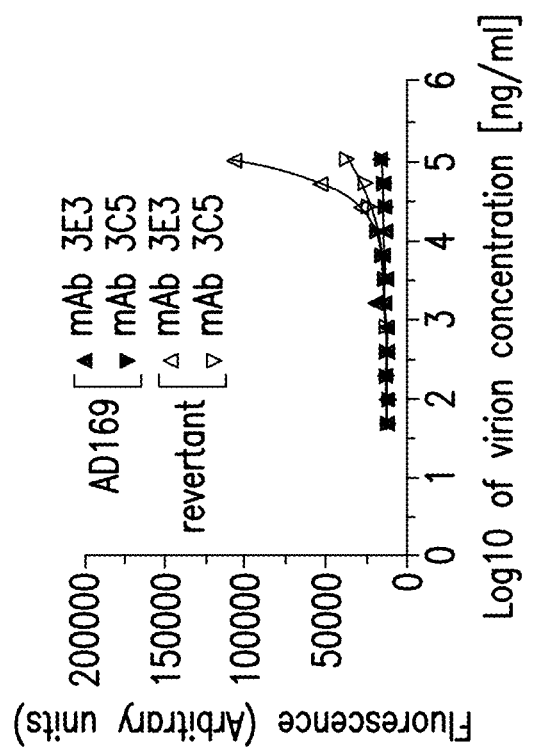
FIGS. 1A-1B: The pentameric gH complex can be detected in revertant virions. AD 169 virus and the revertant virus restored of epithelial tropism were coated on plates and reacted with (A) gB-specific mAbs B8.6 and 35.1 or (B) UL130 protein-specific mAb 3E3 and 3C5 for detection of the pentameric gH complex. Both gB-specific mAbs reacted comparably to AD169 and the revertant virions, while the UL130 protein-specific mAbs react only with the revertant virus.

The present invention provides isolated anti-CMV antigen binding proteins and methods of use of the antigen binding proteins in the treatment and/or prevention of CMV infection. In one embodiment, the invention provides for humanized or fully human anti-CMV antigen binding proteins and methods of use in the treatment and/or prevention of CMV infection.

As used herein, an anti-CMV antigen binding protein refers to an antigen binding protein that specifically binds to CMV. An antigen binding protein that "specifically binds to CMV," is an antigen binding protein that exhibits preferential binding to CMV as compared to other viruses, but this specificity does not require absolute binding specificity. The anti-CMV antigen binding protein has an affinity for CMV that is at least two fold greater, preferably at least ten fold greater, more preferably at least 20 fold greater, and most preferably at least 100 fold greater than the affinity with any other antigen.

Anti-CMV Antigen Binding Proteins

The recombinant antigen binding protein that binds CMV can comprise one, two, three, four, five, or six of the complementarity determining regions (CDRs) of the antigen binding proteins disclosed herein. The one, two, three, four, five, or six CDRs may be independently selected from the CDR sequences of the antigen binding proteins disclosed herein (e.g., Tables 1 and 2). Alternatively, the one, two, three, four, five, or six CDRs may be selected from the CDR sequences of a single described antigen binding protein of the invention.

The recombinant antigen binding protein that binds CMV can comprise at least one light chain variable ($V_L$) domain comprising one or more of CDR1, CDR2 and CDR3 of any antigen binding protein of the invention (see Table 1). In specific embodiments, the antigen binding protein comprises a $V_L$ domain comprising three CDRs of an antigen binding protein of the invention.

In an embodiment, the antigen binding protein comprises a $V_L$ domain comprising the CDR1 of SEQ ID NO: 1, CDR2 of SEQ ID NO: 2 and CDR3 of SEQ ID NO: 3.

In an embodiment, the antigen binding protein comprises a $V_L$ domain comprising the CDR1 of SEQ ID NO: 4, CDR2 of SEQ ID NO: 5 and CDR3 of SEQ ID NO: 6.

In an embodiment, the antigen binding protein comprises a $V_L$ domain comprising the CDR1 of SEQ ID NO: 7, CDR2 of SEQ ID NO: 8 and CDR3 of SEQ ID NO: 9.

In an embodiment, the antigen binding protein comprises a $V_L$ domain comprising the CDR1 of SEQ ID NO: 10, CDR2 of SEQ ID NO: 11 and CDR3 of SEQ ID NO: 12.

In an embodiment, the antigen binding protein comprises a $V_L$ domain comprising the CDR1 of SEQ ID NO: 13, CDR2 of SEQ ID NO: 14 and CDR3 of SEQ ID NO: 15.

In an embodiment, the antigen binding protein comprises a $V_L$ domain comprising the CDR1 of SEQ ID NO: 16, CDR2 of SEQ ID NO: 17 and CDR3 of SEQ ID NO: 18.

In an embodiment, the antigen binding protein comprises a $V_L$ domain comprising the CDR1 of SEQ ID NO: 19, CDR2 of SEQ ID NO: 20 and CDR3 of SEQ ID NO: 21.

In an embodiment, the antigen binding protein comprises a $V_L$ domain comprising the CDR1 of SEQ ID NO: 22, CDR2 of SEQ ID NO: 23 and CDR3 of SEQ ID NO: 24.

In an embodiment, the antigen binding protein comprises a $V_L$ domain comprising the CDR1 of SEQ ID NO: 25, CDR2 of SEQ ID NO: 26 and CDR3 of SEQ ID NO: 27.

In an embodiment, the antigen binding protein comprises a $V_L$ domain comprising the CDR1 of SEQ ID NO: 28, CDR2 of SEQ ID NO: 29 and CDR3 of SEQ ID NO: 30.

In an embodiment, the antigen binding protein comprises a $V_L$ domain comprising the CDR1 of SEQ ID NO: 31, CDR2 of SEQ ID NO: 32 and CDR3 of SEQ ID NO: 33.

In an embodiment, the antigen binding protein comprises a $V_L$ domain comprising the CDR1 of SEQ ID NO: 34, CDR2 of SEQ ID NO: 35 and CDR3 of SEQ ID NO: 36.

In an embodiment, the antigen binding protein comprises a $V_L$ domain comprising the CDR1 of SEQ ID NO: 37, CDR2 of SEQ ID NO: 38 and CDR3 of SEQ ID NO: 39.

In an embodiment, the antigen binding protein comprises a $V_L$ domain comprising the CDR1 of SEQ ID NO: 40, CDR2 of SEQ ID NO: 41 and CDR3 of SEQ ID NO: 42.

In an embodiment, the antigen binding protein comprises a $V_L$ domain comprising the CDR1 of SEQ ID NO: 43, CDR2 of SEQ ID NO: 44 and CDR3 of SEQ ID NO: 45.

In an embodiment, the antigen binding protein comprises a $V_L$ domain comprising the CDR1 of SEQ ID NO: 46, CDR2 of SEQ ID NO: 47 and CDR3 of SEQ ID NO: 48.

In an embodiment, the antigen binding protein comprises a $V_L$ domain comprising the CDR1 of SEQ ID NO: 49, CDR2 of SEQ ID NO: 50 and CDR3 of SEQ ID NO: 51.

In an embodiment, the antigen binding protein comprises a $V_L$ domain comprising the CDR1 of SEQ ID NO: 52, CDR2 of SEQ ID NO: 53 and CDR3 of SEQ ID NO: 54.

In an embodiment, the antigen binding protein comprises a $V_L$ domain comprising the CDR1 of SEQ ID NO: 55, CDR2 of SEQ ID NO: 56 and CDR3 of SEQ ID NO: 57.

In an embodiment, the antigen binding protein comprises a $V_L$ domain comprising the CDR1 of SEQ ID NO: 58, CDR2 of SEQ ID NO: 59 and CDR3 of SEQ ID NO: 60.

In an embodiment, the antigen binding protein comprises a $V_L$ domain comprising the CDR1 of SEQ ID NO: 61, CDR2 of SEQ ID NO: 62 and CDR3 of SEQ ID NO: 63.

In an embodiment, the antigen binding protein comprises a $V_L$ domain comprising the CDR1 of SEQ ID NO: 64, CDR2 of SEQ ID NO: 65 and CDR3 of SEQ ID NO: 66.

In an embodiment, the antigen binding protein comprises a $V_L$ domain comprising the CDR1 of SEQ ID NO: 67, CDR2 of SEQ ID NO: 68 and CDR3 of SEQ ID NO: 69.

In an embodiment, the antigen binding protein comprises a $V_L$ domain comprising the CDR1 of SEQ ID NO: 70, CDR2 of SEQ ID NO: 71 and CDR3 of SEQ ID NO: 72.

In an embodiment, the antigen binding protein comprises a $V_L$ domain comprising the CDR1 of SEQ ID NO: 73, CDR2 of SEQ ID NO: 74 and CDR3 of SEQ ID NO: 75.

In an embodiment, the antigen binding protein comprises a $V_L$ domain comprising the CDR1 of SEQ ID NO: 76, CDR2 of SEQ ID NO: 77 and CDR3 of SEQ ID NO: 78.

In an embodiment, the antigen binding protein comprises a $V_L$ domain comprising the CDR1 of SEQ ID NO: 79, CDR2 of SEQ ID NO: 80 and CDR3 of SEQ ID NO: 81.

In an embodiment, the antigen binding protein comprises a $V_L$ domain comprising the CDR1 of SEQ ID NO: 82, CDR2 of SEQ ID NO: 83 and CDR3 of SEQ ID NO: 84.

In an embodiment, the antigen binding protein comprises a $V_L$ domain comprising the CDR1 of SEQ ID NO: 85, CDR2 of SEQ ID NO: 86 and CDR3 of SEQ ID NO: 87.

In an embodiment, the antigen binding protein comprises a $V_L$ domain comprising the CDR1 of SEQ ID NO: 88, CDR2 of SEQ ID NO: 89 and CDR3 of SEQ ID NO: 90.

In an embodiment, the antigen binding protein comprises a $V_L$ domain comprising the CDR1 of SEQ ID NO: 91, CDR2 of SEQ ID NO: 92 and CDR3 of SEQ ID NO: 93.

In an embodiment, the antigen binding protein comprises a $V_L$ domain comprising the CDR1 of SEQ ID NO: 94, CDR2 of SEQ ID NO: 95 and CDR3 of SEQ ID NO: 96.

In an embodiment, the antigen binding protein comprises a $V_L$ domain comprising the CDR1 of SEQ ID NO: 97, CDR2 of SEQ ID NO: 98 and CDR3 of SEQ ID NO: 99.

In an embodiment, the antigen binding protein comprises a $V_L$ domain comprising the CDR1 of SEQ ID NO: 100, CDR2 of SEQ ID NO: 101 and CDR3 of SEQ ID NO: 102.

In an embodiment, the antigen binding protein comprises a $V_L$ domain comprising the CDR1 of SEQ ID NO: 103, CDR2 of SEQ ID NO: 104 and CDR3 of SEQ ID NO: 105.

In an embodiment, the antigen binding protein comprises a $V_L$ domain comprising the CDR1 of SEQ ID NO: 106, CDR2 of SEQ ID NO: 107 and CDR3 of SEQ ID NO: 108.

In an embodiment, the antigen binding protein comprises a $V_L$ domain comprising the CDR1 of SEQ ID NO: 109, CDR2 of SEQ ID NO: 110 and CDR3 of SEQ ID NO: 111.

In an embodiment, the antigen binding protein comprises a $V_L$ domain comprising the CDR1 of SEQ ID NO: 112, CDR2 of SEQ ID NO: 113 and CDR3 of SEQ ID NO: 114.

In an embodiment, the antigen binding protein comprises a $V_L$ domain comprising the CDR1 of SEQ ID NO: 115, CDR2 of SEQ ID NO: 116 and CDR3 of SEQ ID NO: 117.

In an embodiment, the antigen binding protein comprises a $V_L$ domain comprising the CDR1 of SEQ ID NO: 118, CDR2 of SEQ ID NO: 119 and CDR3 of SEQ ID NO: 120.

In an embodiment, the antigen binding protein comprises a $V_L$ domain comprising the CDR1 of SEQ ID NO: 121, CDR2 of SEQ ID NO: 122 and CDR3 of SEQ ID NO: 123.

In an embodiment, the antigen binding protein comprises a $V_L$ domain comprising the CDR1 of SEQ ID NO: 124, CDR2 of SEQ ID NO: 125 and CDR3 of SEQ ID NO: 126.

In an embodiment, the antigen binding protein comprises a $V_L$ domain comprising the CDR1 of SEQ ID NO: 127, CDR2 of SEQ ID NO: 128 and CDR3 of SEQ ID NO: 129.

In an embodiment, the antigen binding protein comprises a $V_L$ domain comprising the CDR1 of SEQ ID NO: 130, CDR2 of SEQ ID NO: 131 and CDR3 of SEQ ID NO: 132.

In an embodiment, the antigen binding protein comprises a $V_L$ domain comprising the CDR1 of SEQ ID NO: 133, CDR2 of SEQ ID NO: 134 and CDR3 of SEQ ID NO: 135.

In other embodiments, the antigen binding protein comprises a $V_L$ domain with at least 50%, 75%, 80%, 85%, 90%, 95%, 98% or 99% sequence identity with the $V_L$ domains described above.

The isolated antigen binding protein that binds CMV can comprise at least one heavy chain variable ($V_H$) domain comprising one or more of CDR1, CDR2 and CDR3 of any of the antigen binding proteins of the invention (see Table 2). In specific embodiments, the antigen binding protein comprises a $V_H$ domain comprising three CDRs of an antigen binding protein of the invention.

In one embodiment, the antigen binding protein comprises a $V_H$ domain comprising the CDR1 of SEQ ID NO: 136, CDR2 of SEQ ID NO: 137 and CDR3 of SEQ ID NO: 138.

In one embodiment, the antigen binding protein comprises a $V_H$ domain comprising the CDR1 of SEQ ID NO: 139, CDR2 of SEQ ID NO: 140 and CDR3 of SEQ ID NO: 141.

In one embodiment, the antigen binding protein comprises a $V_H$ domain comprising the CDR1 of SEQ ID NO: 142, CDR2 of SEQ ID NO: 143 and CDR3 of SEQ ID NO: 144.

In one embodiment, the antigen binding protein comprises a $V_H$ domain comprising the CDR1 of SEQ ID NO: 145, CDR2 of SEQ ID NO: 146 and CDR3 of SEQ ID NO: 147.

In one embodiment, the antigen binding protein comprises a $V_H$ domain comprising the CDR1 of SEQ ID NO: 148, CDR2 of SEQ ID NO: 149 and CDR3 of SEQ ID NO: 150.

In one embodiment, the antigen binding protein comprises a $V_H$ domain comprising the CDR1 of SEQ ID NO: 151, CDR2 of SEQ ID NO: 152 and CDR3 of SEQ ID NO: 153.

In one embodiment, the antigen binding protein comprises a $V_H$ domain comprising the CDR1 of SEQ ID NO: 154, CDR2 of SEQ ID NO: 155 and CDR3 of SEQ ID NO: 156.

In one embodiment, the antigen binding protein comprises a $V_H$ domain comprising the CDR1 of SEQ ID NO: 157, CDR2 of SEQ ID NO: 158 and CDR3 of SEQ ID NO: 159.

In one embodiment, the antigen binding protein comprises a $V_H$ domain comprising the CDR1 of SEQ ID NO: 160, CDR2 of SEQ ID NO: 161 and CDR3 of SEQ ID NO: 162.

In one embodiment, the antigen binding protein comprises a $V_H$ domain comprising the CDR1 of SEQ ID NO: 163, CDR2 of SEQ ID NO: 164 and CDR3 of SEQ ID NO: 165.

In one embodiment, the antigen binding protein comprises a $V_H$ domain comprising the CDR1 of SEQ ID NO: 166, CDR2 of SEQ ID NO: 167 and CDR3 of SEQ ID NO: 168.

In one embodiment, the antigen binding protein comprises a $V_H$ domain comprising the CDR1 of SEQ ID NO: 169, CDR2 of SEQ ID NO: 170 and CDR3 of SEQ ID NO: 171.

In one embodiment, the antigen binding protein comprises a $V_H$ domain comprising the CDR1 of SEQ ID NO: 172, CDR2 of SEQ ID NO: 173 and CDR3 of SEQ ID NO: 174.

In one embodiment, the antigen binding protein comprises a $V_H$ domain comprising the CDR1 of SEQ ID NO: 175, CDR2 of SEQ ID NO: 176 and CDR3 of SEQ ID NO: 177.

In one embodiment, the antigen binding protein comprises a $V_H$ domain comprising the CDR1 of SEQ ID NO: 178, CDR2 of SEQ ID NO: 179 and CDR3 of SEQ ID NO: 180.

In one embodiment, the antigen binding protein comprises a $V_H$ domain comprising the CDR1 of SEQ ID NO: 181, CDR2 of SEQ ID NO: 182 and CDR3 of SEQ ID NO: 183.

In one embodiment, the antigen binding protein comprises a $V_H$ domain comprising the CDR1 of SEQ ID NO: 184, CDR2 of SEQ ID NO: 185 and CDR3 of SEQ ID NO: 186.

In one embodiment, the antigen binding protein comprises a $V_H$ domain comprising the CDR1 of SEQ ID NO: 187, CDR2 of SEQ ID NO: 188 and CDR3 of SEQ ID NO: 189.

In one embodiment, the antigen binding protein comprises a $V_H$ domain comprising the CDR1 of SEQ ID NO: 190, CDR2 of SEQ ID NO: 191 and CDR3 of SEQ ID NO: 192.

In one embodiment, the antigen binding protein comprises a $V_H$ domain comprising the CDR1 of SEQ ID NO: 193, CDR2 of SEQ ID NO: 194 and CDR3 of SEQ ID NO: 195.

In one embodiment, the antigen binding protein comprises a $V_H$ domain comprising the CDR1 of SEQ ID NO: 196, CDR2 of SEQ ID NO: 197 and CDR3 of SEQ ID NO: 198.

In one embodiment, the antigen binding protein comprises a $V_H$ domain comprising the CDR1 of SEQ ID NO: 199, CDR2 of SEQ ID NO: 200 and CDR3 of SEQ ID NO: 201.

In one embodiment, the antigen binding protein comprises a $V_H$ domain comprising the CDR1 of SEQ ID NO: 202, CDR2 of SEQ ID NO: 203 and CDR3 of SEQ ID NO: 204.

In one embodiment, the antigen binding protein comprises a $V_H$ domain comprising the CDR1 of SEQ ID NO: 205, CDR2 of SEQ ID NO: 206 and CDR3 of SEQ ID NO: 207.

In one embodiment, the antigen binding protein comprises a $V_H$ domain comprising the CDR1 of SEQ ID NO: 208, CDR2 of SEQ ID NO: 209 and CDR3 of SEQ ID NO: 210.

In one embodiment, the antigen binding protein comprises a $V_H$ domain comprising the CDR1 of SEQ ID NO: 211, CDR2 of SEQ ID NO: 212 and CDR3 of SEQ ID NO: 213.

In one embodiment, the antigen binding protein comprises a $V_H$ domain comprising the CDR1 of SEQ ID NO: 214, CDR2 of SEQ ID NO: 215 and CDR3 of SEQ ID NO: 216.

In one embodiment, the antigen binding protein comprises a $V_H$ domain comprising the CDR1 of SEQ ID NO: 217, CDR2 of SEQ ID NO: 218 and CDR3 of SEQ ID NO: 219.

In one embodiment, the antigen binding protein comprises a $V_H$ domain comprising the CDR1 of SEQ ID NO: 220, CDR2 of SEQ ID NO: 221 and CDR3 of SEQ ID NO: 222.

In one embodiment, the antigen binding protein comprises a $V_H$ domain comprising the CDR1 of SEQ ID NO: 223, CDR2 of SEQ ID NO: 224 and CDR3 of SEQ ID NO: 225.

In one embodiment, the antigen binding protein comprises a $V_H$ domain comprising the CDR1 of SEQ ID NO: 226, CDR2 of SEQ ID NO: 227 and CDR3 of SEQ ID NO: 228.

In one embodiment, the antigen binding protein comprises a $V_H$ domain comprising the CDR1 of SEQ ID NO: 229, CDR2 of SEQ ID NO: 230 and CDR3 of SEQ ID NO: 231.

In one embodiment, the antigen binding protein comprises a $V_H$ domain comprising the CDR1 of SEQ ID NO: 232, CDR2 of SEQ ID NO: 233 and CDR3 of SEQ ID NO: 234.

In one embodiment, the antigen binding protein comprises a $V_H$ domain comprising the CDR1 of SEQ ID NO: 235, CDR2 of SEQ ID NO: 236 and CDR3 of SEQ ID NO: 237.

In one embodiment, the antigen binding protein comprises a $V_H$ domain comprising the CDR1 of SEQ ID NO: 238, CDR2 of SEQ ID NO: 239 and CDR3 of SEQ ID NO: 240.

In one embodiment, the antigen binding protein comprises a $V_H$ domain comprising the CDR1 of SEQ ID NO: 241, CDR2 of SEQ ID NO: 242 and CDR3 of SEQ ID NO: 243.

In one embodiment, the antigen binding protein comprises a $V_H$ domain comprising the CDR1 of SEQ ID NO: 244, CDR2 of SEQ ID NO: 245 and CDR3 of SEQ ID NO: 246.

In one embodiment, the antigen binding protein comprises a $V_H$ domain comprising the CDR1 of SEQ ID NO: 247, CDR2 of SEQ ID NO: 248 and CDR3 of SEQ ID NO: 249.

In one embodiment, the antigen binding protein comprises a $V_H$ domain comprising the CDR1 of SEQ ID NO: 250, CDR2 of SEQ ID NO: 251 and CDR3 of SEQ ID NO: 252.

In one embodiment, the antigen binding protein comprises a $V_H$ domain comprising the CDR1 of SEQ ID NO: 253, CDR2 of SEQ ID NO: 254 and CDR3 of SEQ ID NO: 255.

In one embodiment, the antigen binding protein comprises a $V_H$ domain comprising the CDR1 of SEQ ID NO: 256, CDR2 of SEQ ID NO: 257 and CDR3 of SEQ ID NO: 258.

In one embodiment, the antigen binding protein comprises a $V_H$ domain comprising the CDR1 of SEQ ID NO: 259, CDR2 of SEQ ID NO: 260 and CDR3 of SEQ ID NO: 261.

In one embodiment, the antigen binding protein comprises a $V_H$ domain comprising the CDR1 of SEQ ID NO: 262, CDR2 of SEQ ID NO: 263 and CDR3 of SEQ ID NO: 264.

In one embodiment, the antigen binding protein comprises a $V_H$ domain comprising the CDR1 of SEQ ID NO: 265, CDR2 of SEQ ID NO: 266 and CDR3 of SEQ ID NO: 267.

In one embodiment, the antigen binding protein comprises a $V_H$ domain comprising the CDR1 of SEQ ID NO: 268, CDR2 of SEQ ID NO: 269 and CDR3 of SEQ ID NO: 270.

In other embodiments, the antigen binding protein comprises a $V_H$ domain with at least 50%, 75%, 80%, 85%, 90%, 95%, 98% or 99% sequence identity with the $V_H$ domains described above.

In a further embodiment, the antigen binding protein is a humanized anti-CMV antigen binding protein including, but not limited to, a humanized monoclonal antibody. Examples of such humanized anti-CMV antigen binding proteins include, but are not limited to, antigen binding proteins comprising a light chain variable region and/or a heavy chain variable region as disclosed in Example 9.

In one embodiment, the humanized antigen binding protein comprises a $V_L$ domain of SEQ ID NO:631 or 632 and a $V_H$ domain of SEQ ID NO:633 or 634.

In one embodiment, the humanized antigen binding protein comprises a $V_L$ domain of SEQ ID NO: 635 or 636 and a $V_H$ domain of SEQ ID NO: 637 or 638.

In one embodiment, the antigen binding protein comprises a $V_L$ domain of SEQ ID NO: 639 or 640 and a $V_H$ domain of SEQ ID NO:641.

In one embodiment, antigen binding protein comprises a $V_L$ domain of SEQ ID NO: 642 or 643 and a $V_H$ domain of SEQ ID NO: 644 or 645.

In other embodiments, the antigen binding protein comprises a $V_L$ and/or $V_H$ domain with at least 50%, 75%, 80%, 85%, 90%, 95%, 98% or 99% sequence identity with the $V_L$ and $V_H$ domains described above.

As used herein, the term "antigen binding protein" refers to a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies and antigen binding fragments thereof including, but not limited to, recombinant antibodies, monoclonal antibodies, human antibodies, humanized antibodies, chimeric antibodies, bispecific antibodies, single chain antibodies, diabodies, triabodies, tetrabodies, Fv fragments, scFv fragments, Fab fragments, Fab' fragments, F(ab')$_2$ fragments and camelized single domain antibodies. The antigen binding protein can comprise, for example, an antibody-derived protein scaffold or an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, e.g., Korndorfer et al., 2003, Proteins: Structure, Function, and Bioinformatics, 53(1):121-129 (2003); Roque et al., Biotechnol. Prog. 20:639-654 (2004). In addition, peptide antibody mimetics ("PAMs") can be used, as well as scaffolds based on antibody mimetics utilizing fibronectin components as a scaffold.

As used herein, the term "antibody" refers to a protein including at least one or two, heavy (H) chain variable regions (abbreviated herein as $V_H$), and at least one or two light (L) chain variable regions (abbreviated herein as $V_L$). The $V_H$ and $V_L$ regions can be further subdivided into regions of hypervariability, termed "complementarity determining regions"("CDR"), interspersed with regions that are more conserved, termed "framework regions" (FR). The extent of the framework region and CDRs has been precisely defined (see, Kabat, E. A., et al. Sequences of Proteins of Immunological Interest, Fifth Edition, U.S. Department of Health and Human Services, NIH Publication No. 91-3242, 1991, and Chothia, C. et al., J. Mol. Biol. 196:901-917, 1987, which are incorporated herein by reference). Preferably, each $V_H$ and $V_L$ is composed of three CDRs and four FRs, arranged from amino-terminus to carboxy-terminus in the following order: FR1, CDR1, FR2, CDR2, FR3, CDR3 and FR4.

The $V_H$ or $V_L$ chain of the antibody can further include all or part of a heavy or light chain constant region. In one embodiment, the antibody is a tetramer of two heavy immunoglobulin chains and two light immunoglobulin chains, wherein the heavy and light immunoglobulin chains are inter-connected by, e.g., disulfide bonds. The heavy chain constant region includes three domains, CH1, CH2 and CH3. The light chain constant region is comprised of one domain, CL. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system. The term "antibody" includes intact immunoglobulins of types IgA, IgG, IgE, IgD, IgM (as well as subtypes thereof), wherein the light chains of the immunoglobulin may be of types kappa or lambda.

Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

As used herein, the term "hypervariable region" refers to the amino acid residues of an antibody that are responsible for antigen binding. The hypervariable region comprises amino acid residues from the light chain variable region CDRs and the heavy chain variable region CDRs.

As used herein, the term "monoclonal antibody" refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, that are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al. (1991) *Nature* 352: 624-628 and Marks et al. (1991) *J. Mol. Biol.* 222: 581-597, for example. See also Presta (2005) *J. Allergy Clin. Immunol.* 116:731.

As used herein, a "chimeric antibody" is an antibody having the variable domain from a first antibody and the constant domain from a second antibody, where the first and second antibodies are from different species. (U.S. Pat. No. 4,816,567; and Morrison et al., (1984) *Proc. Natl. Acad. Sci. USA* 81: 6851-6855). Typically the variable domains are obtained from an antibody from an experimental animal (the "parental antibody"), such as a rodent, and the constant domain sequences are obtained from human antibodies, so that the resulting chimeric antibody will be less likely to elicit an adverse immune response in a human subject than the parental (e.g. rodent) antibody.

As used herein, the term "humanized antibody" refers to forms of antibodies that contain sequences from both human and non-human (e.g., murine, rat) antibodies. In general, the humanized antibody will comprise substantially all of at least one, and typically two, variable domains, in which all or substantially all of the hypervariable loops correspond to those of a non-human immunoglobulin, and all or substantially all of the framework (FR) regions are those of a human immunoglobulin sequence. The humanized antibody may optionally comprise at least a portion of a human immunoglobulin constant region (Fc).

The term "fully human antibody" refers to an antibody that comprises human immunoglobulin protein sequences only. A fully human antibody may contain murine or rat carbohydrate chains if produced in a mouse or rat, in a mouse or rat cell, or in a hybridoma derived from a mouse or rat cell.

As used herein, the terms "antibody fragment" or "antigen binding fragment" refer to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, Fv fragments, diabodies, linear antibodies, single-chain antibody molecules, e.g., scFv, and multispecific antibodies formed from antibody fragments.

A "Fab fragment" is comprised of one light chain and the $C_H1$ and variable regions of one heavy chain. The heavy chain of a Fab molecule cannot form a disulfide bond with another heavy chain molecule. A "Fab fragment" can be the product of papain cleavage of an antibody.

A "Fab' fragment" contains one light chain and a portion or fragment of one heavy chain that contains the $V_H$ domain and the $C_H1$ domain and also the region between the $C_H1$ and $C_H2$ domains, such that an interchain disulfide bond can be formed between the two heavy chains of two Fab' fragments to form a F(ab')$_2$ molecule.

A "F(ab')$_2$ fragment" contains two light chains and two heavy chains containing a portion of the constant region between the $C_H1$ and $C_H2$ domains, such that an interchain disulfide bond is formed between the two heavy chains. A F(ab')$_2$ fragment thus is composed of two Fab' fragments that are held together by a disulfide bond between the two heavy chains. An "F(ab')$_2$ fragment" can be the product of pepsin cleavage of an antibody.

The "Fv region" comprises the variable regions from both the heavy and light chains, but lacks the constant regions.

As used herein, the term "camelized antibody" refers to single domain antibodies derived from Camelidae heavy chain Ig (see e.g., Muyldermans et al., 2001, Trends Biochem. Sci. 26: 230; Nuttall et al., 2000, Cur. Pharm. Biotech. 1: 253; Reichmann and Muyldermans, 1999, J. Immunol. Meth. 231: 25; International Publication Nos. WO 94/04678 and WO 94/25591; U.S. Pat. No. 6,005,079).

As used herein, the term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv, see Pluckthun (1994) THE PHARMACOLOGY OF MONOCLONAL ANTIBODIES, vol. 113, Rosenburg and Moore eds. Springer-Verlag, New York, pp. 269-315. See also, International Patent Application Publication No. WO 88/01649 and U.S. Pat. Nos. 4,946,778 and 5,260,203.

As used herein, the term "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

As used herein, the term "bivalent antibody" comprises two antigen binding sites. In some instances, the two binding sites have the same antigen specificities. However, bivalent antibodies may be "bispecific" such that each antigen binding site has different antigen specificity. The different antigen specificities may be different antigens on the same molecule or they may be directed to antigens on different molecules.

As used herein, the term "diabody" refers to small antibody fragments with two antigen binding sites, which fragments comprise a heavy chain variable domain ($V_H$) connected to a light chain variable domain ($V_L$) in the same polypeptide chain ($V_H$-$V_L$ or $V_L$-$V_H$). By using a linker that is too short to allow pairing between the two domains on the same chain, the domains are forced to pair with the complementary domains of another chain and create two antigen binding sites. Diabodies are described more fully in, e.g., EP 404,097; WO 93/11161; and Holliger et al. (1993) Proc. Natl. Acad. Sci. USA 90: 6444-6448. For a review of engineered antibody variants generally see Holliger and Hudson (2005) Nat. Biotechnol. 23:1126-1136.

As used herein, the term "recombinant" refers to a polypeptide or nucleic acid that does not exist in nature. The term "recombinant" antibody refers to antibodies that are prepared, expressed, created, or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes or antibodies prepared, expressed, created, or isolated by any other means that involves splicing of human immunoglobulin gene sequences to other DNA sequences. Such recombinant antibodies include humanized, CDR grafted, chimeric, in vitro generated (e.g., by phage display) antibodies, and may optionally include constant regions derived from human germline immunoglobulin sequences. A recombinant polynucleotide includes two or more nucleotide sequences that are present together in a longer polynucleotide sequence, wherein the two sequences are not found together (e.g. attached or fused) in nature, e.g. a promoter and a heterologous nucleotide sequence encoding a polypeptide that are normally not found together in nature or a vector and a heterologous nucleotide sequence.

As used herein, the terms "isolated" or "purified" refer to a molecule (e.g., antibody, nucleic acid, etc.) that is at least partially separated from other molecules normally associated with it in its native state. An "isolated or purified polypeptide" is substantially free of other biological molecules such as nucleic acids, proteins, lipids, carbohydrates, cellular debris and growth media. An "isolated or purified nucleic acid" is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. Generally, the terms "isolated" and "purified" are not intended to refer to a complete absence of such material or to an absence of water, buffers, or salts, unless they are present in amounts that substantially interfere with experimental or therapeutic use of the molecule. Antigen binding proteins of the invention and nucleic acids that encode antigen binding proteins of the invention are isolated/purified.

As used herein, "homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared×100. For example, if 6 of 10 of the positions in two sequences are matched or homologous when the sequences are optimally aligned then the two sequences are 60% homologous. Generally, the comparison is made when two sequences are aligned to give maximum percent homology.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences may be used. Human germline sequences may be obtained, for example, from JOINSOLVER® germline databases on the website for the National Institute of Arthritis and Musculoskeletal and Skin Diseases of the United States National Institutes of Health. Mouse germline sequences may be obtained, for example, as described in Giudicelli et al. (2005) Nucleic Acids Res. 33:D256-D261.

TABLE 1

Light Chain Sequences (SEQ ID NOs)

| Clone ID | FR1 | CDR1 | FR2 | CDR2 | FR3 | CDR3 | FR4 |
|---|---|---|---|---|---|---|---|
| 3.4 | 271 | 1 | 272 | 2 | 361 | 3 | 362 |
| 15.1 | 273 | 4 | 274 | 5 | 363 | 6 | 364 |
| 21.4 | 275 | 7 | 276 | 8 | 365 | 9 | 366 |
| 30.2 | 277 | 10 | 278 | 11 | 367 | 12 | 368 |
| 41.1 | 279 | 13 | 280 | 14 | 369 | 15 | 370 |
| 44.3 | 281 | 16 | 282 | 17 | 371 | 18 | 372 |
| 57.4 | 283 | 19 | 284 | 20 | 373 | 21 | 374 |
| 58.5 | 285 | 22 | 286 | 23 | 375 | 24 | 376 |
| 60.6 | 287 | 25 | 288 | 26 | 377 | 27 | 378 |
| 62.5 | 289 | 28 | 290 | 29 | 379 | 30 | 380 |
| 70.7 | 291 | 31 | 292 | 32 | 381 | 33 | 382 |
| 76.3 | 293 | 34 | 294 | 35 | 383 | 36 | 384 |
| 90.4 | 295 | 37 | 296 | 38 | 385 | 39 | 386 |

TABLE 1-continued

Light Chain Sequences (SEQ ID NOs)

| Clone ID | FR1 | CDR1 | FR2 | CDR2 | FR3 | CDR3 | FR4 |
|---|---|---|---|---|---|---|---|
| 117.8 | 297 | 40 | 298 | 41 | 387 | 42 | 388 |
| 124.4 | 299 | 43 | 300 | 44 | 389 | 45 | 390 |
| 202.3 | 301 | 46 | 302 | 47 | 391 | 48 | 392 |
| 203.5 | 303 | 49 | 304 | 50 | 393 | 51 | 394 |
| 210.4 | 305 | 52 | 306 | 53 | 395 | 54 | 396 |
| 212.6 | 307 | 55 | 308 | 56 | 397 | 57 | 398 |
| 216.5 | 309 | 58 | 310 | 59 | 399 | 60 | 400 |
| 223.4 | 311 | 61 | 312 | 62 | 401 | 63 | 402 |
| 228.8 | 313 | 64 | 314 | 65 | 403 | 66 | 404 |
| 230.7 | 315 | 67 | 316 | 68 | 405 | 69 | 406 |
| 240.8 | 317 | 70 | 318 | 71 | 407 | 72 | 408 |
| 247.8 | 319 | 73 | 320 | 74 | 409 | 75 | 410 |
| 250.5 | 321 | 76 | 322 | 77 | 411 | 78 | 412 |
| 269.6 | 323 | 79 | 324 | 80 | 413 | 81 | 414 |
| 270.7 | 325 | 82 | 326 | 83 | 415 | 84 | 416 |
| 271.1 | 327 | 85 | 328 | 86 | 417 | 87 | 418 |
| 272.7 | 329 | 88 | 330 | 89 | 419 | 90 | 420 |
| 275.2 | 331 | 91 | 332 | 92 | 421 | 93 | 422 |
| 276.10 | 333 | 94 | 334 | 95 | 423 | 96 | 424 |
| 283.7 | 335 | 97 | 336 | 98 | 425 | 99 | 426 |
| 289.3 | 337 | 100 | 338 | 101 | 427 | 102 | 428 |
| 292.1 | 339 | 103 | 340 | 104 | 429 | 105 | 430 |
| 295.5 | 341 | 106 | 342 | 107 | 431 | 108 | 432 |
| 302.1 | 343 | 109 | 344 | 110 | 433 | 111 | 434 |
| 316.2 | 345 | 112 | 346 | 113 | 435 | 114 | 436 |
| 324.4 | 347 | 115 | 348 | 116 | 437 | 117 | 438 |
| 331.4 | 349 | 118 | 350 | 119 | 439 | 120 | 440 |
| 339.4 | 351 | 121 | 352 | 122 | 441 | 123 | 442 |
| 340.6 | 353 | 124 | 354 | 125 | 443 | 126 | 444 |
| 345.1 | 355 | 127 | 356 | 128 | 445 | 129 | 446 |
| 347.3 | 357 | 130 | 358 | 131 | 447 | 132 | 448 |
| 350.1 | 359 | 133 | 360 | 134 | 449 | 135 | 450 |

TABLE 2

Heavy Chain Sequences (SEQ ID NOs)

| Clone ID | FR1 | CDR1 | FR2 | CDR2 | FR3 | CDR3 | FR4 |
|---|---|---|---|---|---|---|---|
| 3.4 | 451 | 136 | 452 | 137 | 541 | 138 | 542 |
| 15.1 | 453 | 139 | 454 | 140 | 543 | 141 | 544 |
| 21.4 | 455 | 142 | 456 | 143 | 545 | 144 | 546 |
| 30.2 | 457 | 145 | 458 | 146 | 547 | 147 | 548 |
| 41.1 | 459 | 148 | 460 | 149 | 549 | 150 | 550 |
| 44.3 | 461 | 151 | 462 | 152 | 551 | 153 | 552 |
| 57.4 | 463 | 154 | 464 | 155 | 553 | 156 | 554 |
| 58.5 | 465 | 157 | 466 | 158 | 555 | 159 | 556 |
| 60.6 | 467 | 160 | 468 | 161 | 557 | 162 | 558 |
| 62.5 | 469 | 163 | 470 | 164 | 559 | 165 | 560 |
| 70.7 | 471 | 166 | 472 | 167 | 561 | 168 | 562 |
| 76.3 | 473 | 169 | 474 | 170 | 563 | 171 | 564 |
| 90.4 | 475 | 172 | 476 | 173 | 565 | 174 | 566 |
| 117.8 | 477 | 175 | 478 | 176 | 567 | 177 | 568 |
| 124.4 | 479 | 178 | 480 | 179 | 569 | 180 | 570 |
| 202.3 | 481 | 181 | 482 | 182 | 571 | 183 | 572 |
| 203.5 | 483 | 184 | 484 | 185 | 573 | 186 | 574 |
| 210.4 | 485 | 187 | 486 | 188 | 575 | 189 | 576 |
| 212.6 | 487 | 190 | 488 | 191 | 577 | 192 | 578 |
| 216.5 | 489 | 193 | 490 | 194 | 579 | 195 | 580 |
| 223.4 | 491 | 196 | 492 | 197 | 581 | 198 | 582 |
| 228.8 | 493 | 199 | 494 | 200 | 583 | 201 | 584 |
| 230.7 | 495 | 202 | 496 | 203 | 585 | 204 | 586 |
| 240.8 | 497 | 205 | 498 | 206 | 587 | 207 | 588 |
| 247.8 | 499 | 208 | 500 | 209 | 589 | 210 | 590 |
| 250.5 | 501 | 211 | 502 | 212 | 591 | 213 | 592 |
| 269.6 | 503 | 214 | 504 | 215 | 593 | 216 | 594 |
| 270.7 | 505 | 217 | 506 | 218 | 595 | 219 | 596 |
| 271.1 | 507 | 220 | 508 | 221 | 597 | 222 | 598 |
| 272.7 | 509 | 223 | 510 | 224 | 599 | 225 | 600 |
| 275.2 | 511 | 226 | 512 | 227 | 601 | 228 | 602 |
| 276.10 | 513 | 229 | 514 | 230 | 603 | 231 | 604 |
| 283.7 | 515 | 232 | 516 | 233 | 605 | 234 | 606 |
| 289.3 | 517 | 235 | 518 | 236 | 607 | 237 | 608 |

TABLE 2-continued

Heavy Chain Sequences (SEQ ID NOs)

| Clone ID | FR1 | CDR1 | FR2 | CDR2 | FR3 | CDR3 | FR4 |
|---|---|---|---|---|---|---|---|
| 292.1 | 519 | 238 | 520 | 239 | 609 | 240 | 610 |
| 295.5 | 521 | 241 | 522 | 242 | 611 | 243 | 612 |
| 302.1 | 523 | 244 | 524 | 245 | 613 | 246 | 614 |
| 316.2 | 525 | 247 | 526 | 248 | 615 | 249 | 616 |
| 324.4 | 527 | 250 | 528 | 251 | 617 | 252 | 618 |
| 331.4 | 529 | 253 | 530 | 254 | 619 | 255 | 620 |
| 339.4 | 531 | 256 | 532 | 257 | 621 | 258 | 622 |
| 340.6 | 533 | 259 | 534 | 260 | 623 | 261 | 624 |
| 345.1 | 535 | 262 | 536 | 263 | 625 | 264 | 626 |
| 347.3 | 537 | 265 | 538 | 266 | 627 | 267 | 628 |
| 350.1 | 539 | 268 | 540 | 269 | 629 | 270 | 630 |

Antigen Binding Protein Derivatives

In other embodiments, the invention provides antigen binding proteins that are derivatives of the antigen binding proteins disclosed herein. Antigen binding protein derivatives of the invention specifically bind CMV and have $V_L$ domains and $V_H$ domains with at least 50%, 75%, 80%, 85%, 90%, 95%, 98% or 99% sequence identity with the $V_L$ domains and $V_H$ domains of the antibodies disclosed herein (e.g., in Tables 1 and 2 and Example 9) while still exhibiting the desired binding and functional properties (e.g., CMV neutralization). In another embodiment the antigen binding protein derivatives of the present invention comprises $V_L$ and $V_H$ domains having up to 0, 1, 2, 3, 4, 5, 6, 7, 8, 9, 10 or more conservative or non conservative amino acid substitutions, while still exhibiting the desired binding and functional properties.

Antigen binding protein derivatives of the invention also encompass those derivatives that specifically bind CMV and have CDRs (i.e., CDR1, CDR2 and CDR3) of a $V_L$ domain and CDRs of a $V_H$ domain with at least 50%, 75%, 80%, 85%, 90%, 95%, 98% or 99% sequence identity with the CDRs disclosed herein for the $V_L$ domains and $V_H$ domains of the antigen binding proteins of the invention (e.g., in Tables 1 and 2 and Example 9) while still exhibiting the desired binding and functional properties (e.g., CMV neutralization). In another embodiment the antigen binding protein derivative of the invention comprises CDRs of disclosed $V_L$ and $V_H$ domains having up to 0, 1, 2, 3 or more conservative or non conservative amino acid substitutions, while still exhibiting the desired binding and functional properties.

Sequence identity refers to the degree to which the amino acids of two polypeptides are the same at equivalent positions when the two sequences are optimally aligned. Sequence identity can be determined using a BLAST algorithm wherein the parameters of the algorithm are selected to give the largest match between the respective sequences over the entire length of the respective reference sequences. The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

Typically, an antigen binding protein derivative of the invention retains at least 10% of its CMV binding and/or neutralization activity (when compared to the parental antigen binding protein) when that activity is expressed on a molar basis. Preferably, an antigen binding protein derivative of the invention retains at least 20%, 50%, 70%, 80%, 90%, 95% or 100% of the CMV binding affinity and/or neutralization activity as the parental antigen binding protein.

As used herein, the term "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering or substantially altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Various embodiments of the antigen binding proteins of the present invention comprise polypeptide chains with the sequences disclosed herein, e.g. in Tables 1 and 2 and Example 9, or polypeptide chains comprising up to 1, 2, 3, 4, 5, 6, 7, 8, 9, 10, 12, 15, 20 or more conservative amino acid substitutions. Exemplary conservative substitutions are set forth in Table 3.

TABLE 3

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |

TABLE 3-continued

Exemplary Conservative Amino Acid Substitutions

| Original residue | Conservative substitution |
| --- | --- |
| Tyr (Y) | Trp; Phe |
| Val (V) | Ile; Leu |

Function-conservative derivatives of the antigen binding proteins of the invention are also contemplated by the present invention. As used herein, the term "function-conservative derivative" refers to antigen binding proteins in which one or more amino acid residues have been changed without altering a desired property, such an antigen affinity and/or specificity and/or neutralizing activity. Such variants include, but are not limited to, replacement of an amino acid with one having similar properties, such as the conservative amino acid substitutions of Table 3.

Also provided are recombinant polypeptides comprising the $V_L$ domains of the anti-CMV antigen binding proteins of the invention and recombinant polypeptides comprising the $V_H$ domains of the anti-CMV antigen binding proteins of the invention having up to 1, 2, 3, 4, or 5 or more amino acid substitutions, while still exhibiting the ability to bind to CMV with high affinity and specificity and/or can neutralize CMV.

In another embodiment, provided is an antigen binding protein that has a $V_L$ domain and/or a $V_H$ domain with at least 95%, 90%, 85%, 80%, 75% or 50% sequence homology to one or more of the $V_L$ domains or $V_H$ domains described herein, and exhibits specific binding to CMV and/or can neutralize CMV. In another embodiment the antigen binding protein of the present invention comprises $V_L$ and $V_H$ domains (with and without signal sequence) having up to 1, 2, 3, 4, or 5 or more amino acid substitutions, and exhibits specific binding to CMV and/or can neutralize CMV.

Nucleic Acids

The present invention further comprises the recombinant nucleic acids encoding the anti-CMV antigen binding proteins disclosed herein.

In one embodiment, the recombinant nucleic acid encodes an antigen binding protein comprising a light chain variable ($V_L$) domain comprising the CDR1, CDR2 and CDR3 of any of the antigen binding proteins disclosed herein (SEQ ID NOs:1-135).

In one embodiment, the recombinant nucleic acid encodes antigen binding protein comprising a heavy chain variable ($V_H$) domain comprising the CDR1, CDR2 and CDR3 of any of the antigen binding proteins disclosed herein (SEQ ID NOs:136-270).

In one embodiment, the recombinant nucleic acid encodes an antigen binding protein comprising at least one light chain variable ($V_L$) domain and at least one heavy chain variable ($V_H$) domain, wherein the $V_L$ domain comprises at least three CDRs having a sequence selected from SEQ ID NOs:1-135, and the $V_H$ domain comprises at least at least three CDRs having a sequence selected from SEQ ID NOs:136-270. In one embodiment, the isolated nucleic acid encodes the light chain variable region (see Table 1) and heavy chain variable region (see Table 2) disclosed herein. In some embodiments the isolated nucleic acid encodes both a light chain and a heavy chain on a single nucleic acid molecule, and in other embodiments the light and heavy chains are encoded on separate nucleic acid molecules. In another embodiment the nucleic acids further encodes a signal sequence.

The present invention further comprises nucleic acids which hybridize to nucleic acids encoding the anti-CMV antigen binding proteins disclosed herein. In general, the nucleic acids hybridize under moderate or high stringency conditions to nucleic acids that encode antigen binding proteins disclosed herein and also encode antigen binding proteins that maintain the ability to specifically bind to CMV. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical moderate stringency hybridization conditions are 40% formamide, with 5× or 6×SSC and 0.1% SDS at 42° C. High stringency hybridization conditions are 50% formamide, 5× or 6×SSC (0.15M NaCl and 0.015M Na-citrate) at 42° C. or, optionally, at a higher temperature (e.g., 57° C., 59° C., 60° C., 62° C., 63° C., 65° C. or 68° C.). Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

Also included in the present invention are nucleic acids encoding the anti-CMV antigen binding proteins derivatives.

This present invention also provides expression vectors comprising the recombinant nucleic acids of the invention, wherein the nucleic acid is operably linked to control sequences that are recognized by a host cell when the host cell is transfected with the vector. Also provided are host cells comprising an expression vector of the present invention and methods for producing the antigen binding proteins disclosed herein comprising culturing a host cell harboring an expression vector encoding the antigen binding protein in culture medium, and isolating the antigen binding protein from the host cell or culture medium.

Biological Properties of Anti-CMV Antigen Binding Proteins

The anti-CMV antigen binding proteins of the present invention are capable of binding to and, preferably, neutralizing CMV.

Binding to CMV can be measured by methods known in the art. For example, binding is measured in antigen-titration ELISA (EIA). The antigen, either recombinant viral proteins or portions thereof or purified recombinant revertant virions, are immobilized on 96-well microtiter plates. Antigen binding protein reactivity to the immobilized antigen is measured in EIA. A strong reactivity signal of a test antigen binding protein as compared to a control antigen binding protein reflects high affinity of the test antigen binding protein to the viral antigen.

Ability of an antigen binding protein to neutralize CMV can be measured by methods known in the art. For example, neutralization is measured in a viral neutralization assay. The antigen binding protein is mixed with a defined number of infectious CMV virions and the mixture is applied to cells vulnerable to CMV infection (i.e., epithelial cells such as ARPE-19 or MRC-5 cells). Cells that become infected with CMV can be detected by assaying for expression of viral antigens such as the viral immediate early (IE) antigen. Reduction of the number of cells with viral antigen expression as compared to cells infected in the absence of the antigen binding protein reflects neutralizing capacity (i.e, the antigen binding protein can reduce viral infectivity to cells). Reduced viral infectivity can be due to any mechanism including, but not limited to, the ability of the antigen binding protein to decrease binding of CMV to cells, the ability of the antigen binding protein to decrease viral fusion with cellular membranes and/or the ability of the antigen binding protein to decrease the release of viral genetic material into the cell.

Competitive Antigen Binding Proteins

The present invention also encompasses antigen binding proteins that bind to the same epitope or an overlapping epitope on CMV as any of the antigen binding proteins disclosed herein. Such competitive antigen binding proteins are able to cross-block binding of any of the disclosed antigen binding proteins disclosed herein. In one embodiment, the competitive antigen binding proteins can cross-block an antigen binding protein comprising a light chain variable region comprising CDRs disclosed in Table 1 and/or comprising a heavy chain variable region comprising CDRs disclosed in Table 2. In another embodiment, the competitive antigen binding proteins can cross-block an antigen binding protein comprising a light chain variable region disclosed in Table 1 and/or comprising a heavy chain variable region disclosed in Table 2.

A first antigen binding protein is considered to cross-block binding of a second antigen binding protein if pre-binding the target with the first antigen binding protein to saturation increases the concentration of second antigen binding protein needed to achieve half-maximal binding of the target by 2-, 3-, 4-, 5-, 10-, 20-, 50-, 100-, 200-fold or more.

Alternatively, a first antigen binding protein is considered to cross-block binding of a second antigen binding protein if the epitopes to which each bind is the same or significantly overlaps. In one embodiment, determination of epitope binding is conducted by crystallography.

Target

CMV infects various cells in vivo, including monocytes, macrophages, dendritic cells, neutrophils, endothelial cells, epithelial cells, fibroblasts, neurons, smooth muscle cells, hepatocytes, and stromal cells (Plachter et al. 1996, Adv. Virus Res. 46:195). Although clinical CMV isolates replicate in a variety of cell types, laboratory strains AD169 (Elek & Stern, 1974, Lancet 1:1) and Towne (Plotkin et al., 1975, Infect. Immun. 12:521) replicate almost exclusively in fibroblasts (Hahn et al., 2004, J. Virol. 78:10023). The restriction in tropism, which results from serial passages and eventual adaptation of the virus in fibroblasts, is stipulated a marker of attenuation (Gerna et al., 2005, J. Gen. Virol. 86:275; Gerna et al, 2002, J. Gen Virol. 83:1993; Gerna et al, 2003, J. Gen Virol. 84:1431; Dargan et al, 2010, J. Gen Virol. 91:1535). Mutations causing the loss of epithelial cell, endothelial cell, leukocyte, and dendritic cell tropism in human CMV laboratory strains have been mapped to three open reading frames (ORFs): UL128, UL130, and UL131 (Hahn et al., 2004, J. Virol. 78:10023; Wang and Shenk, 2005 J. Virol. 79:10330; Wang and Shenk, 2005 Proc Natl Acad Sci USA. 102:18153). Biochemical and reconstitution studies show that UL128, UL130 and UL131 assemble onto a gH/gL scaffold to form a pentameric gH complex (Wang and Shenk, 2005 Proc Natl Acad Sci USA. 102:1815; Ryckman et al, 2008 J. Virol. 82:60). Restoration of this complex in virions restores the viral epithelial tropism in the laboratory strains (Wang and Shenk, 2005 J. Virol. 79:10330).

Loss of endothelial and epithelial tropism has been suspected as a deficiency in the previously evaluated as vaccines such as Towne (Gerna et al, 2002, J. Gen Virol. 83:1993; Gerna et al, 2003, J. Gen Virol. 84:1431). Neutralizing antibodies in sera from human subjects of natural CMV infection have more than 15-fold higher activity against viral epithelial entry than against fibroblast entry (Cui et al, 2008 Vaccine 26:5760). Humans with primary infection rapidly develop neutralizing antibodies to viral endothelial and epithelial entry but only slowly develop neutralizing antibodies to viral fibroblast entry (Gerna et al, 2008 J. Gen. Virol. 89:853). Furthermore, neutralizing activity against viral epithelial and endothelial entry is absent in the immune sera from human subjects who received Towne vaccine (Cui et al, 2008 Vaccine 26:5760). More recently, a panel of human monoclonal antibodies from four donors with CMV infection was described, and the more potent neutralizing clones from the panel recognized the antigens of the pentameric gH complex (Macagno et al, 2010 J. Virol. 84:1005).

As used herein, the terms "pentameric gH complex" or "gH complex" refer to a complex of five viral proteins on the surface of the CMV virion. The complex is made up of proteins encoded by UL128, UL130, and UL131 assembled onto a gH/gL scaffold (Wang and Shenk, 2005 Proc Natl Acad Sci USA. 102:1815; Ryckman et al, 2008 J. Virol. 82:60). The sequences of the complex proteins from CMV strain AD169 are shown at GenBank Accession Nos. NP_783797.1 (UL128), NP_040067 (UL130), CAA35294.1 (UL131), NP_040009 (gH, also known as UL75) and NP_783793 (gL, also known as UL115). Some attenuated CMV strains have one or more mutations in UL131 such that the protein is not expressed and therefore the gH complex is not formed.

As used herein, the terms "revertant virus" or "revertant virion" refer to CMV that has had the gH complex restored and thus expresses the gH complex on its envelope.

Methods of Making Antigen Binding Proteins

Antigen binding proteins that are monoclonal antibodies can be produced by methods commonly known in the art using hybridoma cells that produce parental (e.g. rodent) monoclonal anti-CMV antibodies. These methods include, but are not limited to, the hybridoma technique originally developed by Kohler, et al., (1975) (Nature 256:495-497), as well as the trioma technique (Hering, et al., (1988) Biomed. Biochim. Acta. 47:211-216 and Hagiwara, et al., (1993) Hum. Antibod. Hybridomas 4:15), the human B-cell hybridoma technique (Kozbor, et al., (1983) Immunology Today 4:72 and Cote, et al., (1983) Proc. Natl. Acad. Sci. U.S.A 80:2026-2030), the EBV-hybridoma technique (Cole, et al., in *Monoclonal Antibodies and Cancer Therapy*, Alan R. Liss, Inc., pp. 77-96, 1985), and electric field based electrofusion using a Cyto Pulse large chamber cull fusion electroporator (Cyto Pulse Sciences, Inc., Glen Burnie, Md.). Preferably, mouse splenocytes are isolated and fused with PEG or by electrofusion to a mouse myeloma cell line based upon standard protocols. The resulting hybridomas may then be screened for the production of antigen-specific antibodies. For example, single cell suspensions of splenic lymphocytes from immunized mice may by fused to one-sixth the number of P3×63-Ag8.653 nonsecreting mouse myeloma cells (ATCC, CRL 1580) with 50% PEG. Cells may be plated at approximately $2 \times 10^5$ cells/mL in a flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells may be cultured in medium in which the HAT is replaced with HT. Individual wells may then be screened by ELISA for anti-X monoclonal IgG antibodies. Once extensive hybridoma growth occurs, medium can be observed usually after 10-14 days. The antibody secreting hybridomas may be replated, screened again, and if still positive for human IgG, anti-CMV monoclonal antibodies, can be subcloned at least twice by limiting dilution. The stable subclones may then be cultured in vitro to generate small amounts of antibody in tissue culture medium for characterization.

The anti-CMV antigen binding proteins disclosed herein may also be produced recombinantly (e.g., in an *E. coli*/T7 expression system as discussed above). In this embodiment, nucleic acids encoding the antigen binding proteins of the invention (e.g., $V_H$ or $V_L$) may be inserted into a pET-based plasmid and expressed in the *E. coli*/T7 system. There are several methods by which to produce recombinant antigen binding proteins which are known in the art. One example of a method for recombinant production of antigen binding proteins is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Anti-CMV antigen binding proteins can also be synthesized by any of the methods set forth in U.S. Pat. No. 6,331,415.

Mammalian cell lines available as hosts for expression of the antigen binding proteins disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen binding portion or fragment thereof, the light chain and/or antigen binding fragment thereof are introduced into mammalian host cells, the antigen binding proteins are produced by culturing the host cells for a period of time sufficient to allow for expression of the antigen binding protein in the host cells or, more preferably, secretion of the antigen binding protein into the culture medium in which the host cells are grown.

Antigen binding proteins can be recovered from the culture medium using standard protein purification methods (e.g., Protein A affinity chromoatography). Further, expression of antigen binding proteins of the invention from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

In general, glycoproteins produced in a particular cell line or transgenic animal will have a glycosylation pattern that is characteristic for glycoproteins produced in the cell line or transgenic animal. Therefore, the particular glycosylation pattern of an antigen binding protein will depend on the particular cell line or transgenic animal used to produce the antigen binding protein. In particular embodiments, antigen binding proteins with a glycosylation pattern comprising only non-fucosylated N-glycans may be advantageous, because these antigen binding proteins have been shown to typically exhibit more potent efficacy than their fucosylated counterparts both in vitro and in vivo (See for example, Shinkawa et al., J. Biol. Chem. 278: 3466-3473 (2003); U.S. Pat. Nos. 6,946,292 and 7,214,775). These antigen binding proteins with non-fucosylated N-glycans are not likely to be immunogenic themselves because their carbohydrate structures are a normal component of the population that exists in human serum IgG.

A bispecific or bifunctional antigen binding protein is an artificial hybrid antigen binding protein having two different heavy/light chain pairs and two different binding sites. Bispecific antigen binding proteins can be produced by a variety of methods including fusion of hybridomas or linking of Fab' fragments. See, e.g., Songsivilai, et al., (1990) Clin. Exp. Immunol. 79: 315-321, Kostelny, et al., (1992) J Immunol. 148:1547-1553. In addition, bispecific antigen binding proteins may be formed as "diabodies" (Holliger, et al., (1993) PNAS USA 90:6444-6448) or as "Janusins" (Traunecker, et al., (1991) EMBO J. 10:3655-3659 and Traunecker, et al., (1992) Int. J. Cancer Suppl. 7:51-52).

Antigen binding proteins of the present invention include antibody fragments of the anti-CMV antibodies disclosed herein. The antibody fragments include F(ab)$_2$ fragments, which may be produced by enzymatic cleavage of an IgG by, for example, pepsin. Fab fragments may be produced by, for example, reduction of F(ab)$_2$ with dithiothreitol or mercaptoethylamine. A Fab fragment is a $V_L$-$C_L$ chain appended to a $V_H$-$C_{H1}$ chain by a disulfide bridge. A F(ab)$_2$ fragment is two Fab fragments which, in turn, are appended by two disulfide bridges. The Fab portion of an F(ab)$_2$ molecule includes a portion of the $F_c$ region between which disulfide bridges are located. An $F_v$ fragment is a $V_L$ or $V_H$ region.

In some embodiments, different constant domains may be appended to humanized $V_L$ and $V_H$ regions derived from the CDRs provided herein. For example, if a particular intended use of an antigen binding protein of the present invention were to call for altered effector functions, a heavy chain constant domain other than human IgG1 may be used, or hybrid IgG1/IgG4 may be utilized.

Although human IgG1 antibodies provide for long half-life and for effector functions, such as complement activation and antibody-dependent cellular cytotoxicity, such activities may not be desirable for all uses of the antibody. In such instances a human IgG4 constant domain, for example, may be used. In one embodiment, the IgG4 constant domain can differ from the native human IgG4 constant domain (Swiss-Prot Accession No. P01861.1) at a position corresponding to position 228 in the EU system and position 241 in the KABAT system, where the native Ser108 is replaced with Pro, in order to prevent a potential inter-chain disulfide bond between Cys106 and Cys109 (corresponding to positions Cys 226 and Cys 229 in the EU system and positions Cys 239 and Cys 242 in the KABAT system) that could interfere with proper intra-chain disulfide bond formation. See Angal et al. (1993) Mol. Imunol. 30:105. In other instances, a modified IgG1 constant domain which has been modified to increase half-life or reduce effector function can be used.

Antigen Binding Protein Engineering

Further included are embodiments in which the anti-CMV antigen binding proteins are engineered to include modifications to framework residues within the variable domains of a parental antigen binding proteins, e.g. to improve the properties of the antigen binding proteins. Typically such framework modifications are made to decrease the immunogenicity of the antigen binding protein. This is usually accomplished by replacing non-CDR residues in the variable domains (i.e. framework residues) in a parental antigen binding proteins with analogous residues from the immune repertoire of the species in which the antigen binding protein is to be used, e.g. human residues in the case of human therapeutics. Such an antibody is referred to as a "humanized" antigen binding protein. In some cases it is desirable to increase the affinity, or alter the specificity of an engineered (e.g. humanized) antigen binding protein. One approach is to "backmutate" one or more framework residues to the corresponding germline sequence. More specifically, an antigen binding protein that has undergone somatic mutation can contain framework residues that differ from the germline sequence from which the antigen binding protein is derived. Such residues can be identified by comparing the framework sequences to the germline sequences from which the antigen binding protein is derived. Another approach is to revert to the original parental residue at one or more positions of the engineered (e.g. humanized) antigen binding protein, e.g. to restore binding affinity that may have been lost in the process of replacing the framework residues. (See, e.g., U.S. Pat. Nos. 5,693,762, 5,585,089 and 5,530,101.)

Another type of framework modification involves mutating one or more residues within the framework region, or even within one or more CDR regions, to remove T cell epitopes to thereby reduce the potential immunogenicity of the antigen binding protein. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antigen binding protein as follows. The deamidation of asparagine may occur on N-G or D-G sequences and result in the creation of an isoaspartic acid residue that introduces a kink into the polypeptide chain and decreases its stability (isoaspartic acid effect). In certain embodiments, the antigen binding proteins of the present disclosure do not contain asparagine isomerism sites.

For example, an asparagine (Asn) residue may be changed to Gln or Ala to reduce the potential for formation of isoaspartate at any Asn-Gly sequences, particularly within a CDR. A similar problem may occur at an Asp-Gly sequence. Reissner and Aswad (2003) Cell. Mol. Life Sci. 60:1281.

Isoaspartate formation may debilitate or completely abrogate binding of an antibody to its target antigen. See, Presta (2005) *J. Allergy Clin. Immunol.* 116:731 at 734. In one embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs may be changed to Lys, Leu, Ala, or Phe in order to reduce the possibility that the methionine sulfur would oxidize, which could reduce antigen binding affinity and also contribute to molecular heterogeneity in the final antibody preparation. Id. In one embodiment, the methionine is changed to alanine (Ala). Additionally, in order to prevent or minimize potential scissile Asn-Pro peptide bonds, it may be desirable to alter any Asn-Pro combinations found in a CDR to Gln-Pro, Ala-Pro, or Asn-Ala. Antigen binding proteins with such substitutions are subsequently screened to ensure that the substitutions do not decrease the affinity or specificity of the antibody for CMV, or other desired biological activity to unacceptable levels.

TABLE 4

Exemplary stabilizing CDR variants

| CDR Residue | Stabilizing Variant Sequence |
|---|---|
| Asn-Gly (N-G) | Gln-Gly, Ala-Gly, or Asn-Ala (Q-G), (A-G), or (N-A) |
| Asp-Gly (D-G) | Glu-Gly, Ala-Gly or Asp-Ala (E-G), (A-G), or (D-A) |
| Met (typically solvent exposed) (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

The variations for the $V_H$ and/or $V_L$ CDRs can be independently selected in any combination. Additionally, any variation described herein can be independently selected in any combination, as long as the desired activity or binding ability is maintained.

Engineering of the Fc Region

The antigen binding proteins disclosed herein can also be engineered to include modifications within the Fc region, typically to alter one or more functional properties of the antigen binding protein, such as serum half-life, complement fixation, Fc receptor binding, and/or effector function (e.g., antigen-dependent cellular cytotoxicity). Furthermore, the antigen binding proteins disclosed herein can be chemically modified (e.g., one or more chemical moieties can be attached to the antigen binding protein) or be modified to alter its glycosylation, again to alter one or more functional properties of the antigen binding protein. Each of these embodiments is described in further detail below. The numbering of residues in the Fc region is that of the EU index of Kabat.

The antigen binding proteins disclosed herein also include antigen binding proteins with modified (or blocked) Fc regions to provide altered effector functions. See, e.g., U.S. Pat. No. 5,624,821; WO2003/086310; WO2005/120571; WO2006/0057702. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antigen binding proteins, enabling less frequent dosing and thus increased convenience and decreased use of material. See Presta (2005) *J. Allergy Clin. Immunol.* 116: 731 at 734-35.

In one embodiment, the antigen binding protein is an antibody or fragment thereof of an IgG4 isotype antibody comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the antigen binding protein is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antigen binding protein can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antigen binding proteins. For example, one or more amino acids selected from amino acid residues 234, 235, 236, 237, 297, 318, 320 and 322 can be replaced with a different amino acid residue such that the antigen binding protein has an altered affinity for an effector ligand but retains the antigen binding ability of the parent antigen binding protein. The effector ligand to which affinity is altered can be, for example, an Fc receptor or the C1 component of complement. This approach is described in further detail in U.S. Pat. Nos. 5,624,821 and 5,648,260.

In another example, one or more amino acid residues within amino acid positions 231 and 239 are altered to thereby alter the ability of the antigen binding protein to fix complement. This approach is described further in PCT Publication WO 94/29351.

In yet another example, the Fc region is modified to increase or decrease the ability of the antigen binding proteins to mediate antibody dependent cellular cytotoxicity (ADCC) and/or to increase or decrease the affinity of the antigen binding proteins for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In one embodiment, the Fc region is modified to decrease the ability of the antigen binding proteins to mediate effector function and/or to increase anti-inflammatory properties by modifying residues 243 and 264. In one embodiment, the Fc region of the antigen binding protein is modified by changing the residues at positions 243 and 264 to alanine. In one embodiment, the Fc region is modified to decrease the ability of the antibody to mediate effector function and/or to increase anti-inflammatory properties by modifying residues 243, 264, 267 and 328.

In still another embodiment, the antigen binding protein comprises a particular glycosylation pattern. For example, an aglycosylated antigen binding protein can be made (i.e., the antigen binding protein lacks glycosylation). The glycosylation pattern of an antigen binding protein may be altered to, for example, increase the affinity or avidity of the antigen binding protein for an antigen. Such modifications can be accomplished by, for example, altering one or more of the glycosylation sites within the antigen binding protein sequence. For example, one or more amino acid substitutions can be made that result removal of one or more of the variable region framework glycosylation sites to thereby eliminate glycosylation at that site. Such aglycosylation may increase the affinity or avidity of the antibody for antigen. See, e.g., U.S. Pat. Nos. 5,714,350 and 6,350,861.

An antigen binding protein may also be made in which the glycosylation pattern includes hypofucosylated or afucosylated glycans, such as a hypofucosylated antigen binding proteins or afucosylated antigen binding proteins have reduced amounts of fucosyl residues on the glycan. The antigen binding proteins may also include glycans having an increased amount of bisecting GlcNac structures. Such altered glycosylation patterns have been demonstrated to increase the ADCC ability of antigen binding proteins. Such modifications can be accomplished by, for example, expressing the antigen binding proteins in a host cell in which the glycosylation pathway was been genetically engineered to produce glycoproteins with particular glycosylation patterns. These cells have been described in the art and can be used as host cells in which to express recombinant antigen binding proteins of the invention to thereby produce an antigen binding protein with altered glycosylation. For example, the cell lines Ms704, Ms705, and Ms709 lack the fucosyltransferase gene, FUT8 (α(1,6)-fucosyltransferase), such that antigen binding proteins expressed in the Ms704, Ms705, and Ms709 cell lines lack fucose on their carbohydrates. The Ms704, Ms705, and Ms709 FUT8$^{-/-}$ cell lines were created by the targeted disruption of the FUT8 gene in CHO/DG44 cells using two replacement vectors (see U.S. Patent Publication No. 20040110704 and Yamane-Ohnuki et al. (2004) *Biotechnol Bioeng* 87:614-22). As another example, EP 1 176 195 describes a cell line with a functionally disrupted FUT8 gene, which encodes a fucosyl transferase, such that antigen binding proteins expressed in such a cell line exhibit hypofucosylation by reducing or eliminating the α-1,6 bond-related enzyme. EP 1 176 195 also describes cell lines which have a low enzyme activity for adding fucose to the N-acetylglucosamine that binds to the Fc region of the antigen binding protein or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antigen binding proteins expressed in that host cell (see also Shields et al. (2002) *J. Biol. Chem.* 277:26733-26740). Antigen binding proteins with a modified glycosylation profile can also be produced in chicken eggs, as described in PCT Publication WO 06/089231. Alternatively, antigen binding proteins with a modified glycosylation profile can be produced in plant cells, such as *Lemna* (U.S. Pat. No. 7,632,983). Methods for production of antigen binding proteins in a plant system are disclosed in the U.S. Pat. Nos. 6,998,267 and 7,388,081. PCT Publication WO 99/54342 describes cell lines engineered to express glycoprotein-modifying glycosyl transferases (e.g., β(1,4)-N-acetylglucosaminyltransferase III (GnTIII)) such that antigen binding proteins expressed in the engineered cell lines exhibit increased bisecting GlcNac structures which results in increased ADCC activity of the antibodies (see also Umana et al. (1999) *Nat. Biotech.* 17:176-180).

Alternatively, the fucose residues of the antigen binding proteins can be cleaved off using a fucosidase enzyme; e.g., the fucosidase α-L-fucosidase removes fucosyl residues from antibodies (Tarentino et al. (1975) *Biochem.* 14:5516-23).

Antigen binding proteins disclosed herein further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antigen binding proteins that have predominantly particular N-glycan structures (See for example, Li et al., (2006) *Nat. Biotechnol.* 24: 210-215).

In addition, since fungi such as yeast or filamentous fungi lack the ability to produce fucosylated glycoproteins, antigen binding proteins produced in such cells will lack fucose unless the cells are further modified to include the enzymatic pathway for producing fucosylated glycoproteins (See for example, PCT Publication WO2008112092).

In particular embodiments, the antigen binding proteins disclosed herein further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antigen binding protein compositions provided herein may comprise antigen binding proteins having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the antigen binding protein compositions provided herein comprise antigen binding proteins having at least one complex N-glycan selected from the group consisting of GlcNAcMan$_3$GlcNAc$_2$; GalGlcNAcMan$_3$GlcNAc$_2$; NANAGalGlcNAcMan$_3$GlcNAc$_2$; GlcNAc$_2$Man$_3$GlcNAc$_2$; GalGlcNAc$_2$Man$_3$GlcNAc$_2$; GalGlcNAc$_2$Man$_3$GlcNAc$_2$; NANAGalGlcNAc$_2$Man$_3$GlcNAc$_2$; and NANA$_2$Gal$_2$GlcNAc$_2$Man$_3$GlcNAc$_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man$_5$GlcNAc$_2$(Fuc), GlcNAcMan$_5$GlcNAc$_2$(Fuc), Man$_3$GlcNAc$_2$(Fuc), GlcNAcMan$_3$GlcNAc$_2$(Fuc), GlcNAc$_2$Man$_3$GlcNAc$_2$(Fuc), GalGlcNAc$_2$Man$_3$GlcNAc$_2$(Fuc), GalGlcNAc$_2$Man$_3$GlcNAc$_2$(Fuc), NANAGalGlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$)Man$_3$GlcNAc$_2$, GalGlcNAc$_2$(Fuc$_{1-2}$)Man$_3$GlcNAc$_2$, GalGlcNAc$_2$(Fuc1-2)Man3GlcNAc2, NANAGal2GlcNAc2(Fuc$_{1-2}$)Man$_3$GlcNAc$_2$, and NANA$_2$Gal$_2$GlcNAc$_2$(Fuc$_{1-2}$)Man$_3$GlcNAc$_2$; or in an α1,2-linkage fucose to produce a glycoform selected from the group consisting of Gal(Fuc)GlcNAc$_2$Man$_3$GlcNAc$_2$, Gal$_2$(Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects, the antigen binding proteins comprise high mannose N-glycans, including but not limited to, Man$_8$GlcNAc$_2$, Man$_7$GlcNAc$_2$, Man$_6$GlcNAc$_2$, Man$_5$GlcNAc$_2$, Man$_4$GlcNAc$_2$, or N-glycans that consist of the Man$_3$GlcNAc$_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetylneuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as GalGlcNAc$_2$Man$_3$GlcNAc$_2$; the term "A1" refers to an N-glycan structure that can be characterized as NANAGalGlcNAc$_2$Man$_3$GlcNAc$_2$; and, the term "A2" refers to an N-glycan structure that can be characterized as NANA$_2$GalGlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glcyan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas $GlcNAc_{(2-4)}Man_3GlcNAc_2$, $Gal_{(1-4)}GlcNAc_{(2-4)}Man_3GlcNAc_2$, or $NANA_{(1-4)}Gal_{(1-4)}GlcNAc_{(2-4)}Man_3GlcNAc_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula $GlcNAc_3Man_3GlcNAc_2$ wherein each mannose residue is linked at its non-reducing end to a GlcNAc residue. In contrast, when a multiantennary N-glycan is characterized as $GlcNAc_3Man_3GlcNAc_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antigen Binding Protein Conjugates

The anti-CMV antigen binding proteins of the invention may also be conjugated to a chemical moiety. The chemical moiety may be, inter alia, a polymer, a radionuclide or a cytotoxic factor. In particular embodiments, the chemical moiety is a polymer which increases the half-life of the antigen binding protein in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antigen binding proteins disclosed herein may also be conjugated with labels such as $^{99}Tc$, $^{90}Y$, $^{111}In$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.

The antigen binding proteins disclosed herein may also be pegylated, for example to increase its biological (e.g., serum) half-life. To pegylate an antigen binding protein, the antigen binding protein typically is reacted with a reactive form of polyethylene glycol (PEG), such as a reactive ester or aldehyde derivative of PEG, under conditions in which one or more PEG groups become attached to the antigen binding proteins. In particular embodiments, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antigen binding proteins. Methods for pegylating proteins are known in the art and can be applied to the antigen binding proteins of the invention. See, e.g., EP 0 154 316 and EP 0 401 384.

The antigen binding proteins disclosed herein may also be conjugated with fluorescent or chemiluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antigen binding proteins to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407. Methods for conjugating antibodies are conventional and very well known in the art.

Therapeutic Uses of Anti-CMV Antigen Binding Proteins

Further provided are methods for treating subjects, including human subjects, in need of treatment with the isolated antigen binding proteins disclosed herein. Methods of treatment include administering one or more antigen binding proteins of the invention to a subject to provide passive immunity.

A "subject" refers to a mammal capable of being infected with CMV. In a preferred embodiment, the subject is a human. A subject can be treated prophylactically or therapeutically. Prophylactic treatment provides sufficient protective immunity to reduce the likelihood or severity of a CMV infection, including primary infections, recurrent infections (i.e., those resulting from reactivation of latent CMV) and super-infections (i.e., those resulting from an infection with a different stain of CMV than previously experienced by the patient). Therapeutic treatment can be performed to reduce the severity of a CMV infection or decrease the likelihood/severity of a recurrent or super-infection.

As used herein, the phase "passive immunity" refers to the transfer of active humoral immunity in the form of antigen binding proteins. Passive immunity provides immediate protective effect to the patient from the pathogen recognized by the administered antigen binding proteins and/or ameliorates at least one pathology associated with pathogen infection. However, the patient does not develop an immunological memory to the pathogen and therefore must continue to receive the administered antigen binding proteins for protection from the pathogen to persist. In preferred embodiments, monoclonal antibodies, more preferably human or humanized monoclonal antibodies, are administered to a patient to confer passive immunity.

Treatment can be performed using a pharmaceutical composition comprising one or more antigen binding proteins of the invention or fragments thereof. Pharmaceutical compositions can be administered to the general population, especially to those persons at an increased risk of CMV infection (either primary, recurrent or super) or for whom CMV infection would be particularly problematic (such as immunocompromised individuals, transplant patients or pregnant women). In one embodiment, females of childbearing age, especially pregnant women, are administered one or more antigen binding proteins of the invention to decrease the likelihood of CMV infection (either primary, recurrent or super) CMV during pregnancy.

Those in need of treatment include those already with an infection, as well as those prone to have an infection or in which a reduction in the likelihood of infection is desired. Treatment can ameliorate the symptoms of disease associated with CMV infection and/or shorten the length and/or severity of CMV infection, including infection due to reactivation of latent CMV.

Persons with an increased risk of CMV infection (either primary, recurrent or super) include patients with weakened immunity or patients facing therapy leading to a weakened immunity (e.g., undergoing chemotherapy or radiation therapy for cancer or taking immunosuppressive drugs). As used herein, "weakened immunity" refers to an immune system that is less capable of battling infections because of an immune response that is not properly functioning or is not functioning at the level of a normal healthy adult. Examples of patients with weakened immunity are patients that are infants, young children, elderly, pregnant or a patient with a disease that affects the function of the immune system such as HIV infection or AIDS.

In particular embodiments, the antigen binding proteins disclosed herein may be used alone, in combination with each other, or in combination with other agents for treating or preventing CMV infection. In particular embodiments, one or more monoclonal antibodies selected from the group consisting of 15.1, 57.4, 58.5, 70.7, 124.4, 223.4, 270.7, 276.10, 316.2, 324.4, 347.3 and 272.7 or antigen binding fragments thereof are administered to a subject to treat or prevent CMV infection. In a more particular embodiment, one or more monoclonal antibodies selected from the group consisting of 57.4, 58.5, 276.10 and 272.7 or antigen binding fragments thereof are administered to a subject to treat or prevent CMV infection.

The one or more anti-CMV antigen binding proteins of the invention may be co-administered with one or other more therapeutic agents including, but not limited to, ganciclovir (GCV), valganciclovir (VGCV), foscarnet (FOS), cidofovir (CDV), and CytoGam® (CSL, Inc. Melbourne, Australia). The antigen binding protein may be linked to the agent (as an immunocomplex) or can be administered separately from the agent. In the latter case (separate administration), the antigen binding protein can be administered before, after or concurrently with the agent or can be co-administered with other known therapies.

"Treat" or "treating" means to administer a therapeutic agent, such as a composition containing any of the antigen binding proteins of the present invention, internally or externally to a subject having a CMV infection, or being suspected of having a CMV infection. Typically, the agent is administered in an amount effective to alleviate one or more symptoms of CMV infection in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the infection state, age, and weight of the patient, and the ability of the therapeutic agent to elicit a desired response in the subject. Whether an infection symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target infection symptom(s) in every subject, it should alleviate the target infection symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

Experimental and Diagnostic Uses

The antigen binding proteins disclosed herein may be used as affinity purification agents. In this process, the antigen binding proteins are immobilized on a solid phase such a Sephadex resin or filter paper, using methods well known in the art. The immobilized antigen binding protein is contacted with a sample containing the CMV to be purified, and thereafter the support is washed with a suitable solvent that will remove substantially all the material in the sample except the CMV, which is bound to the immobilized antigen binding protein. Finally, the support is washed with a solvent which elutes the bound CMV from the column. Such immobilized antibodies form part of the present invention.

Anti-CMV antigen binding proteins disclosed herein may also be useful in diagnostic assays for CMV, e.g., detecting its presence in tissues or serum. Diagnostic assays can use various methods for detection of CMV using the antigen binding proteins of the invention including, but not limited to, ELISA, immunohistochemistry, western blots. The antigen binding protein itself can be labeled and therefore detected directly. Alternatively, the antigen binding protein can be bound by a labeled secondary antibody which is then detected.

Purification, diagnostic and detection uses preferably use monoclonal antibodies selected form the group consisting of 57.4, 210.4, 216.5, 269.6, 271.1, 272.7, 275.2, 283.7, 292.1, 295.5, 340.6 and 350.1 or antigen binding fragments thereof.

Pharmaceutical Compositions and Administration

The invention also relates to pharmaceutical compositions comprising a therapeutically effective amount of an antigen binding protein as described herein, formulated together with a pharmaceutically acceptable carrier or diluent.

To prepare pharmaceutical or sterile compositions of the anti-CMV antigen binding protein is admixed with a pharmaceutically acceptable carrier or excipient. See, e.g., *Remington's Pharmaceutical Sciences* and *U.S. Pharmacopeia: National Formulary*, Mack Publishing Company, Easton, Pa. (1984). Pharmaceutically acceptable carriers include any and all solvents, dispersion media, isotonic and absorption delaying agents, and the like that are physiologically compatible, i.e. suitable for administration to humans. The carriers can be suitable for intravenous, intramuscular, subcutaneous, parenteral, rectal, spinal, or epidermal administration (e.g., by injection or infusion).

As used herein, the term "pharmaceutically acceptable carrier" refers to a substance, as described above, which is admixed with the antigen binding proteins of the invention that is suitable for administration to humans. In embodiments of the invention, the pharmaceutically acceptable carrier does not occur in nature in the same form, e.g. the substance is man-made, either because it does not exist in nature or the purity and/or sterility of the substance is not the same as the corresponding natural substance. For example, sterile water for injection, which is a sterile, bacteria-free, solute-free preparation of distilled water for injection, does not occur in nature in the same form and is considered a pharmaceutically acceptable carrier. In some embodiments, the pharmaceutical compositions of the invention comprise one or more antigen binding proteins disclosed herein and sterile water for injection. In further embodiments, the pharmaceutically acceptable carrier may be another form of water that is appropriate for pharmaceutical or biological preparations and is not the same as water that occurs in nature, including purified water, water for injection, sterile purified water, and bacteriostatic water for injection.

In additional embodiments, the compositions of the invention include a buffer as a pharmaceutically acceptable carrier. When a buffer is employed, the pH of the buffer is preferably in the range of about 5.5 to about 8.0. In additional embodiments, the pH is about 5.5 to about 7.5, about 5.5 to about 7.0, about 5.5 to about 6.5, about 6.0 to about 8.0, about 6.0 to about 7.5, about 6.0 to about 7.0, about 6.5 to about 7.0, about 6.0 to 6.5, about 6.0 to about 6.9, about 6.2 to about 6.75, or about 6.0 to about 6.75.

Pharmaceutical compositions typically should be sterile and stable under the conditions of manufacture and storage. Formulations of therapeutic and diagnostic agents may be prepared by mixing with acceptable carriers, excipients, or stabilizers in the form of, e.g., lyophilized powders, slurries, aqueous solutions, suspensions, microemulsions, dispersions, liposomes, or other ordered structure suitable to high antibody concentration (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Sterile injectable solutions can be prepared by incorporating the active compound (i.e., antibody or antigen binding protein) in the required therapeutically effective amount in an appropriate solvent with one or a combination of ingredients, as required, followed by filtered sterilization. Generally, dispersions are prepared by incorporating the active compound into a sterile vehicle that contains a basic dispersion medium and the required other ingredients. In the case of sterile powders for the preparation of sterile injectable solutions, the useful methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

In one embodiment, anti-CMV antibodies of the present invention or fragments thereof are diluted to an appropriate concentration in a sodium acetate solution pH 5-6, and NaCl or sucrose is added for tonicity. Additional agents, such as polysorbate 20 or polysorbate 80, may be added to enhance stability.

Toxicity and therapeutic efficacy of the antigen binding protein compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, antigen binding proteins exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In a further embodiment, a composition comprising an antigen binding protein disclosed herein is administered to a subject in accordance with the Physicians' Desk Reference 2003 (Thomson Healthcare; 57th edition (Nov. 1, 2002)).

The mode of administration can vary. Suitable routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the anti-CMV antigen binding protein can be administered by an invasive route such as by injection. In further embodiments of the invention, an anti-CMV antigen binding protein, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions disclosed herein may also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556.

The pharmaceutical compositions disclosed herein may also be administered by infusion. Examples of well-known implants and modules form administering pharmaceutical compositions include: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art.

The administration regimen depends on several factors, including the serum or tissue turnover rate of the therapeutic antigen binding protein, the level of symptoms, the immunogenicity of the therapeutic antigen binding protein, and the accessibility of the target cells in the biological matrix. Preferably, the administration regimen delivers sufficient therapeutic antigen binding protein to effect improvement in the target disease state, while simultaneously minimizing undesired side effects. Accordingly, the amount of biologic delivered depends in part on the particular therapeutic antigen binding protein and the severity of the condition being treated. Guidance in selecting appropriate doses of therapeutic antigen binding proteins is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.*

342:613-619; Ghosh et al. (2003) *New Engl. J. Med.* 348: 24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, chimeric, humanized and fully human antigen binding proteins are may be desirable.

Antigen binding proteins disclosed herein may be provided by continuous infusion, or by doses administered, e.g., daily, 1-7 times per week, weekly, bi-weekly, monthly, bimonthly, quarterly, semiannually, annually etc. Doses may be provided, e.g., intravenously, subcutaneously, topically, orally, nasally, rectally, intramuscular, intracerebrally, intraspinally, or by inhalation. A total weekly dose is generally at least 0.05 µg/kg body weight, more generally at least 0.2 µg/kg, 0.5 µg/kg, 1 µg/kg, 10 µg/kg, 100 µg/kg, 0.25 mg/kg, 1.0 mg/kg, 2.0 mg/kg, 5.0 mg/ml, 10 mg/kg, 25 mg/kg, 50 mg/kg or more (see, e.g., Yang, et al. (2003) *New Engl. J. Med.* 349:427-434; Herold, et al. (2002) *New Engl. J. Med.* 346:1692-1698; Liu, et al. (1999) *J. Neurol. Neurosurg. Psych.* 67:451-456; Portielji, et al. (20003) *Cancer Immunol. Immunother.* 52:133-144). Doses may also be provided to achieve a pre-determined target concentration of anti-CMV antigen binding proteins in the subject's serum, such as 0.1, 0.3, 1, 3, 10, 30, 100, 300 µg/ml or more. In other embodiments, an anti-CMV antigen binding protein of the present invention is administered subcutaneously or intravenously, on a weekly, biweekly, "every 4 weeks," monthly, bimonthly, or quarterly basis at 10, 20, 50, 80, 100, 200, 500, 1000 or 2500 mg/subject.

As used herein, "inhibit" or "treat" or "treatment" includes a postponement of development of the symptoms associated with CMV infection and/or a reduction in the severity of the symptoms of CMV infection. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a CMV infection or with the potential to develop such an infection.

As used herein, the terms "therapeutically effective amount", "therapeutically effective dose" and "effective amount" refer to an amount of an anti-CMV antigen binding protein of the invention that, when administered alone or in combination with an additional therapeutic agent to a cell, tissue, or subject, is effective to cause a measurable improvement in one or more symptoms of a CMV infection or condition or the progression of such an infection. A therapeutically effective dose further refers to that amount of the antigen binding protein sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity. In some embodiments of the invention, an effective amount is an amount sufficient to inhibit CMV replication.

Kits.

Also included in the invention are kits including a container comprising an antigen binding protein, antibody or pharmaceutical composition of the invention. The term "container" as used herein refers to a man-made container for holding, storing, or transporting the antigen binding protein, antibody or pharmaceutical composition of the invention, including vials, syringes, cartridges, ampoules, and bottles. Containers can be formed of any material that is suitable for storing pharmaceutical or biologic preparations, i.e. materials that are sterile and non-reactive with the preparation such as glass. The glass container should meet the compendial requirements, e.g. the criteria as defined by the US and European Pharmacopeias (USP and EP) for glass used in pharmaceutical packaging The kits can include one or more other elements including: instructions for use; other reagents, e.g., a label, a therapeutic agent, or an agent useful for chelating, or otherwise coupling, an antibody to a label or therapeutic agent, or other materials for preparing the antibody for administration; pharmaceutically acceptable carriers; and devices or other materials for administration to a subject.

Instructions for use can include instructions for therapeutic application including suggested dosages and/or modes of administration, e.g., in a patient with a symptom of CMV infection. Other instructions can include instructions on coupling of the antibody to a chelator, a label or a therapeutic agent, or for purification of a conjugated antibody, e.g., from unreacted conjugation components.

EXAMPLES

Examples are provided below to further illustrate different features of the present invention. The examples also illustrate useful methodology for practicing the invention. These examples do not limit the claimed invention.

Example 1

Generating a Panel of Rabbit Monoclonal Antibodies

The expression of the pentameric gH complex in AD169 was restored and the revertant virus was capable of infecting both MRC-5 and ARPE-19 cells. AD169 from ATCC (GenBank Accession No. X17403) was propagated in MRC-5 cells (Fu et al., 2012, Vaccine 30: 7469-7474; Tang et al., 2011, Vaccine 29: 8350-8356). The revertant virus was generated by serial passage adaptation of AD169 in culture as described in Fu et al. (2012, Vaccine 30: 7469-7474) and Tang et al. (2011, Vaccine 29: 8350-8356). AD169 virus and its revertant isolate were expanded in MRC-5 (ATCC Accession No. CRL-171) or ARPE-19 (ATCC Accession No. CRL-2302), respectively.

Figure 1A:
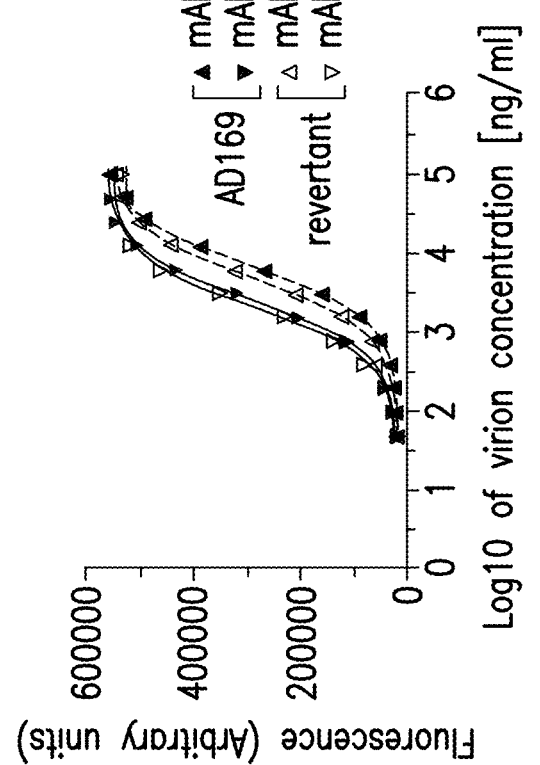

The revertant virus and its parental AD169 virus both contain the same levels of gB as determined using antigen titration enzyme-linked immunoassay (EIA). FIG. 1A shows that gB monoclonal antibodies B8.6 (IgG$_{2a}$κ) and 35.1 (IgG$_{2a}$κ) (both developed internally) reacted comparably to both viruses. In contrast, the UL130 protein-specific monoclonal antibodies (3E3 (IgG$_1$κ) and 3C5 (IgG$_1$κ) (both kindly provided by Thomas Shenk of Princeton University; see Wang et al., 2005, J Virol 79: 2115-2123) showed reactivity only to the revertant virus, not the parental AD169 virus (FIG. 1B).

Monoclonal antibodies were generated in New Zealand White female rabbits of 3-4 months of age (purchased from a specific pathogen-free colony in Covance, Denver, Pa.). Animals were housed individually in a Merck animal facility, in accordance with the *Guide for the Care and Use of Laboratory Animals*. After three intramuscular injections of 100 µg revertant virus at weeks 0, 3 and 8, neutralizing titer in one rabbit rose to 1:3400 at week 11 (Fu et al., 2012, Vaccine 30: 7469-7474; Tang et al., 2011, Vaccine 29: 8350-8356). This rabbit was boosted at week 14 intravenously with 500 µg of the revertant virus, and the spleen was harvested four days later for hybridoma cultures. Rabbit hybridomas were generated at Epitomics, Inc (Burlingame, Calif.) based on the protocol reported previously (Yu et al., 2010, PLoS One 5: e9072). Approximately 500 hybridoma cultures were first screened for production of rabbit IgG, and then screened in a functional assay for neutralizing the revertant virus in ARPE-19 cells or an ELISA for binding to the revertant virus. Seventy-five cultures were selected and cloned through two rounds of limiting dilutions. After confirming their activities, 45 unique lines were established and expanded for antibody production.

Cloning of monoclonal antibody-encoding genes from rabbit hybridoma cells were based the procedures reported previously with minor modifications (Yu et al., 2010, PLoS One 5:e9072). Briefly, mRNA was isolated from rabbit hybridoma cells using Trizal extraction (Invitrogen, Carlsbad, Calif.) and reverse-transcribed to cDNA using Superscript II kits (Invitrogen). Variable (V$_H$ and V$_L$) regions were PCR amplified using L chain and H chain primers. PCR products were gel purified using nucleospin gel extraction kits (Macherey-Nagel, Bethlehem, Pa.), ligated into pCR2.1 TA-clone vectors (Invitrogen) and plated onto S-Gal AmpR plates for the selection of white colonies. The plasmids were extracted from multiple colonies using miniprep kits (Qiagen, Valencia, Calif.) and each clone was sequenced from both directions using M13R and M13F sequencing primers. Final sequences were confirmed by at least three identical sequencing results. The amino acid sequences of the CDRs and Framework Regions of the heavy and light chain variable domains for each monoclonal antibody are shown in Tables 10-15.

Example 2

Binding and Neutralizing Profiles of the Anti-CMV Monoclonal Antibodies

The monoclonal antibodies were assayed for their neutralizing and virus-binding and neutralizing capacities. The neutralization assay evaluated the ability of the monoclonal antibody to prevent viral epithelial cell entry. The virus-binding assay evaluated the ability of the monoclonal antibody to bind virions using ELISA.

Briefly, the neutralization assay used was based on enumeration of cells expressing viral immediate early (IE) antigen 24 hours post-infection and was described previously (Tang et al., 2011, Vaccine 29:8350-6). EC$_{50}$ values, defined as antibody concentration required to block 50% viral entry, were calculated from four-parameter curve fitting using Prism® 5 (GraphPad®Software, San Diego, Calif.).

Briefly, the virus-binding assay used was an antibody-titration enzyme-linked immunoassay (EIA) to determine the relative binding affinity of each monoclonal antibody to the revertant virion as antigen. The antigen was coated at maximal concentration, typically at 2 µg/mL in PBS, on 96-well FluoroNunc MaxiSorp™ microtiter plates (Thermo Fisher Scientific, Waltham, Mass.) at 4° C. overnight. Plates were blocked with 3% nonfat milk in PBS/0.05% Tween 20 and were incubated with the monoclonal antibody in a titration from 0.2 to 30 µg/mL. Plates were washed after antibody incubation and reacted with goat-anti-rabbit-IgG, HRP-conjugated antibody (Southern Biotech, Birmingham, Ala.). After incubation and washing, a fluorogenic HRP substrate, 10-acetyl-3,7-dihroxyphenoxazine (ADHP; Virolabs, Chantilly, Va.) was added at 100 µL per well to generate resorufin at a concentration proportional to the HRP concentration (High et al., 2005, Anal Biochem 347:159-61 and Meng et al., 2005, Anal Biochem 345:227-36). Excitation signals at 531 nm and emission signals at 595 nm were measured with a fluorescent reader (Victor III, Perkin-Elmer, Waltham, Mass.). EC$_{50}$ binding values were calculated from four-parameter curve fitting using Prism® 5.

A human polyclonal CMV hyperimmune IgG (HIG, CytoGam®, commercially manufactured and distributed by CSL, Inc. (Melbourne, Australia)) was used as a positive control in neutralization and binding assays and as a reference to compare the 45 monoclonal antibodies described in Example 1 (see FIG. 2). The ability of the HIG antibody to neutralize a virus (prevent viral infection) was measured as percent cells with viral immediate early (IE) antigen expression (y-axis), inversely correlated with antibody concentration (FIG. 2A). Binding signal in fluorescent units (y-axis) was proportional to antibody concentration (FIG. 2B). The y-axis in FIG. 2A shows the percentage of cells with viral immediate early antigen expression, indicative of viral entry events. The y-axis in FIG. 2B shows the antibody-specific fluorescent signals. EC$_{50}$ neutralizing and EC$_{50}$ binding, defined as the IgG concentration required to block 50% of viral entry (FIG. 2A) or reach 50% maximal binding (FIG. 2B), respectively, were calculated by four-parameter curve fitting. HIG, i.e., CytoGam®, had an EC$_{50}$ neutralizing of 1 µg/mL and an EC$_{50}$ binding of 2 µg/mL.

To quantify the ability of antibody to neutralize virus in ARPE-19 cells or react to virions in ELISA, antiviral activity (EC$_{50}$ neutralizing) and binding affinity (EC$_{50}$ binding) for each of the antibodies described in Example 1 were calculated through four-parameter curve fittings. The lower EC$_{50}$ indicate better neutralizing activity or higher binding affinity, respectively. If a monoclonal antibody had poor binding affinity or antiviral activity, or there was no reliable curve fitting with all datum points not converging to a typical sigmoid distribution, EC$_{50}$ was arbitrarily assigned a value of 100 µg/mL, indicating poor function of neutralizing or binding to virus. Binding and neutralizing properties of all 45 monoclonal antibodies against the revertant virus are listed in Table 5.

TABLE 5

Functional Properties of the anti-CMV Antibodies

| Clone ID | Binding to revertant virion EC$_{50}$ (µg/mL) | Neutralization in ARPE-19 cells EC$_{50}$ (µg/mL) | Neutralization in MRC-5 cells EC$_{50}$ (µg/mL) |
|---|---|---|---|
| 3.4 | 2.13 | 0.25 | 019 |
| 15.1 | 1.07 | 0.03 | 100.00 |
| 21.4 | 2.58 | 0.48 | 0.35 |
| 30.2 | 0.90 | 0.45 | 0.20 |
| 41.1 | 0.18 | 100.00 | 100.00 |
| 44.3 | 8.79 | 3.13 | 100.00 |
| 57.4 | 0.09 | 0.01 | 100.00 |
| 58.5 | 0.59 | 0.02 | 100.00 |
| 60.6 | 0.55 | 0.13 | 0.08 |
| 62.5 | 0.84 | 0.20 | 100.00 |
| 70.7 | 1.46 | 0.03 | 0.09 |
| 76.3 | 0.75 | 0.23 | 0.47 |
| 90.4 | 2.81 | 0.47 | 0.23 |
| 117.8 | 1.66 | 0.27 | 1.47 |
| 124.4 | 1.72 | 0.05 | 0.08 |
| 202.3 | 0.10 | 10.00 | 100.00 |
| 203.5 | 4.03 | 17.03 | 100.00 |
| 210.4 | 0.03 | 100.00 | 100.00 |
| 212.6 | 52.91 | 3.71 | 100.00 |
| 216.5 | 0.06 | 100.00 | 100.00 |
| 223.4 | 1.54 | 0.06 | 100.00 |
| 228.8 | 3.34 | 0.28 | 0.25 |
| 230.7 | 0.27 | 0.34 | 0.34 |
| 240.8 | 2.60 | 0.79 | 100.00 |
| 247.8 | 0.76 | 0.16 | 0.28 |
| 250.5 | 5.27 | 2.31 | 1.26 |
| 269.6 | 0.03 | 100.00 | 100.00 |
| 270.7 | 0.68 | 0.02 | 0.06 |
| 271.1 | 0.07 | 39.66 | 100.00 |
| 272.7 | 0.01 | 100.00 | 100.00 |
| 275.2 | 0.10 | 100.00 | 100.00 |
| 276.10 | 0.25 | 0.01 | 100.00 |
| 283.7 | 0.01 | 100.00 | 100.00 |
| 289.3 | 4.83 | 0.76 | 0.59 |
| 292.1 | 0.02 | 68.67 | 100.00 |
| 295.5 | 0.00 | 100.00 | 100.00 |
| 302.1 | 4.74 | 0.75 | 100.00 |
| 316.2 | 1.06 | 0.02 | 0.08 |
| 324.4 | 4.09 | 0.10 | 0.21 |
| 331.4 | 100.00 | 100.00 | 100.00 |
| 339.4 | 2.36 | 100.00 | 100.00 |
| 340.6 | 0.05 | 100.00 | 100.00 |
| 345.1 | 0.11 | 100.00 | 100.00 |
| 347.3 | 0.34 | 0.03 | 100.00 |
| 350.1 | 0.02 | 100.00 | 100.00 |

The EC$_{50}$ values for neutralizing (y-axis) versus binding (x-axis) for all 45 antibodies were plotted to understand how binding affinity was related to neutralizing activity for each antibody (FIG. 2C). The EC$_{50}$ neutralizing activity for HIG (~1 µg/mL, FIG. 2A) is shown as a horizontal dotted line in FIG. 2C and was used to segregate the monoclonal antibodies based on their antiviral potency. Of the 45 monoclonal antibodies shown in FIG. 2C, the 25 monoclonal antibodies with EC$_{50}$ neutralizing of ≤1 µg/mL were considered neutralizing antibodies (triangles above the line) and the 20 monoclonal antibodies with EC$_{50}$ neutralizing of >1 µg/mL non-neutralizing antibodies (circles below the line).

The EC$_{50}$ binding for all neutralizing monoclonal antibodies ranged from 0.2 to 5 µg/mL, comparable to the HIG (2 µg/mL). In contrast, majority of the non-neutralizing monoclonal antibodies had higher binding affinity to virions than HIG (FIG. 2C, lower left quadrant), indicating that greater binding affinity was not associated with improved antiviral function.

Monoclonal antibodies with EC$_{50}$ neutralizing ≤0.1 µg/mL were classified as elite neutralizing antibodies (see Table 6). Similarly, monoclonal antibodies with EC$_{50}$ binding ≤0.2 µg/mL were designated elite binding antibodies (see Table 6). These monoclonal antibodies were so designated because of their ≥10-fold neutralizing capacity or binding affinity compared to HIG (Table 5). Monoclonal antibody 57.4 is the only antibody that is both an elite neutralizer and an elite binder.

TABLE 6

Elite anti-CMV Antibodies

| Elite Neutralizing mAb | | Elite Binding mAb | |
|---|---|---|---|
| 15.1 | 270.7 | 57.4 | 275.2 |
| 57.4 | 276.10 | 210.4 | 283.7 |
| 70.7 | 316.2 | 216.5 | 292.1 |
| 124.4 | 324.4 | 269.6 | 295.5 |
| 223.4 | 347.3 | 271.1 | 340.6 |
| | | 272.7 | 350.1 |

Example 3

Figure 3:
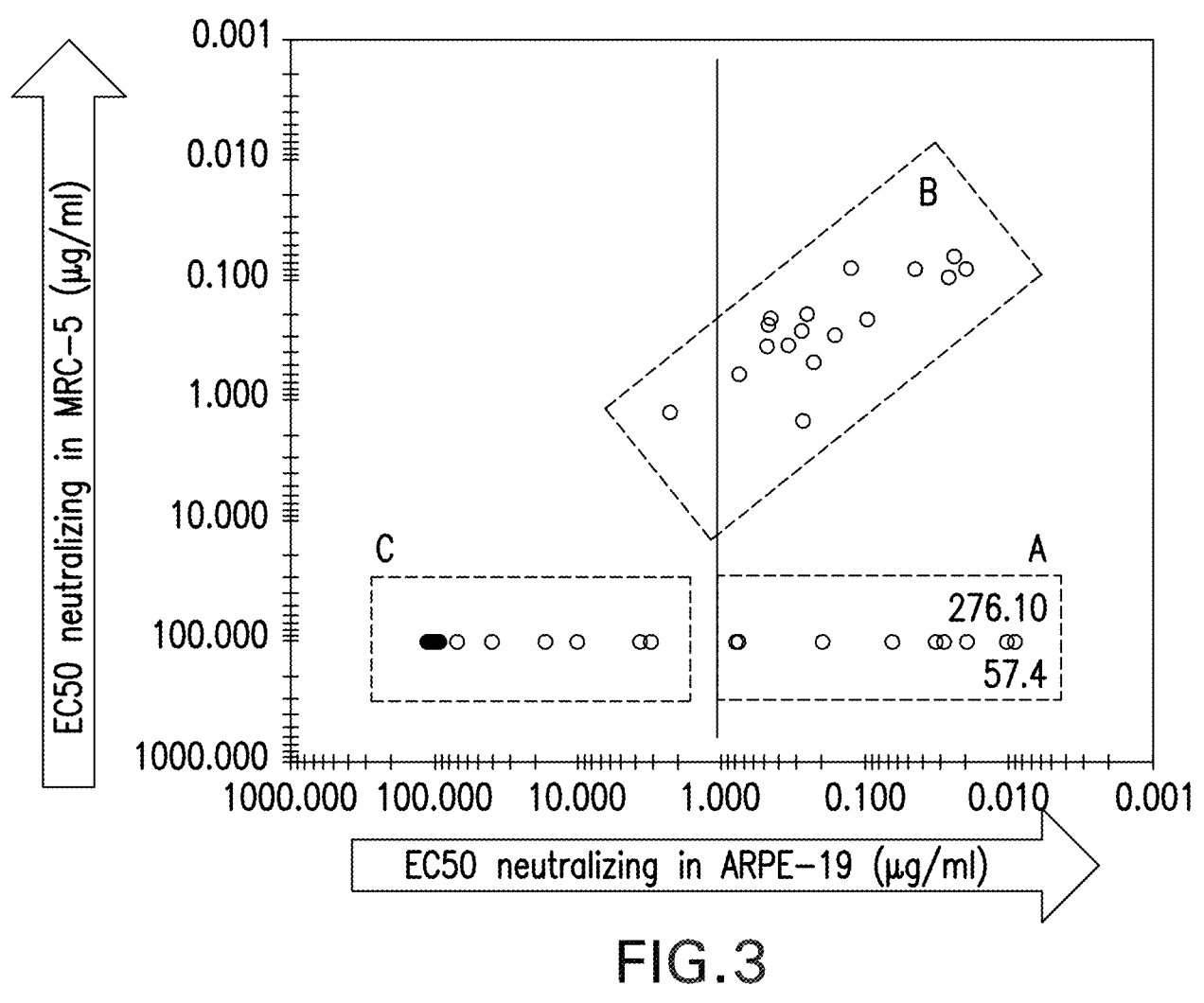

Neutralizing Capacity of an Antibody in Epithelial Cells does not Correlate with its Activity in Fibroblast Cells It is known that HIG can block viral entry to fibroblast cells, such as MRC-5 cells, about 10- to 15-fold less effective at blocking viral entry to epithelial cells, i.e., ARPE-19 cells (Cui et al., 2008, Vaccine 26: 5760-5766). It has been implicated that viruses use different entry mechanism for infection of epithelial versus fibroblast cells (Wang et al., 2007, PNAS 104:20037-42). Thus, the panel of antibodies was evaluated by measuring the EC$_{50}$ neutralizing in MRC-5 cells for each monoclonal antibody (Table 5). The correlation between EC$_{50}$ values of an antibody to block virus entering MRC-5 cells (y-axis) versus ARPE-19 cells (x-axis) is shown in FIG. 3. All 45 antibodies can be categorized into three groups: antibodies in group A only neutralize virus in ARPE-19 cells, antibodies in group B neutralize virus in both cell types, while antibodies in group C are non-neutralizing in either cell lines (see Table 7).

TABLE 7

| Group A | | Group B | | Group C | |
|---|---|---|---|---|---|
| 15.1 | 240.8 | 3.4 | 124.4 | 41.1 | 272.7 |
| 57.4 | 276.10 | 21.4 | 228.8 | 44.3 | 275.2 |
| 58.5 | 302.1 | 30.2 | 230.7 | 202.3 | 283.7 |
| 62.5 | 347.3 | 60.6 | 247.8 | 203.5 | 292.1 |
| 223.4 | | 70.7 | 250.5 | 210.4 | 295.5 |
| | | 76.3 | 270.7 | 212.6 | 331.4 |
| | | 90.4 | 289.3 | 216.5 | 339.4 |
| | | 117.8 | 316.2 | 269.6 | 340.6 |
| | | | 324.4 | 271.1 | 345.1 |
| | | | | | 350.1 |

The monoclonal antibodies with potent activity against viral entry in ARPE-19 cells, such as clones 57.4 and 276.10, failed to block viral entry to fibroblast cells. Only 5 of the 11 elite neutralizing monoclonal antibodies had activity against viral entry to fibroblast cells. Of the remaining 14 neutralizing monoclonal antibodies, 11 antibodies had activity against viral entry to fibroblast cells. Thus, approximately 60% of the monoclonal antibodies can neutralize virus in both epithelial cells and fibroblast cells. The discrepancy between neutralization capacities in ARPE-19 versus MRC-5 cells is consistent with the results of human antibodies (Macagno et al., 2010, J Virol 84:1005-1013) and is consistent with the thought that potent elite neutralizing monoclonal antibodies recognized antigens unique for viral entry to epithelial cells, but not fibroblast cells (Wang et al., 2007, PNAS 104:20037-42).

Example 4

Differential Binding Profiles to Purified Virus

Binding profiles for both elite neutralizing and elite binding antibodies to AD169 virions and revertant virions were generated using antigen-titration EIA. By design, the revertant virus and AD169 virus had identical antigen composition except for the pentameric gH complex. Thus, any difference in the binding affinity of a monoclonal antibody for AD169 versus revertant virus was likely due to the presence of the pentameric gH complex on the revertant virus. The binding profiles were compared to assess if the elite neutralizing antibodies targeted the pentameric gH complex, which is essential for epithelial entry but not fibroblast cell entry.

Figure 4D:
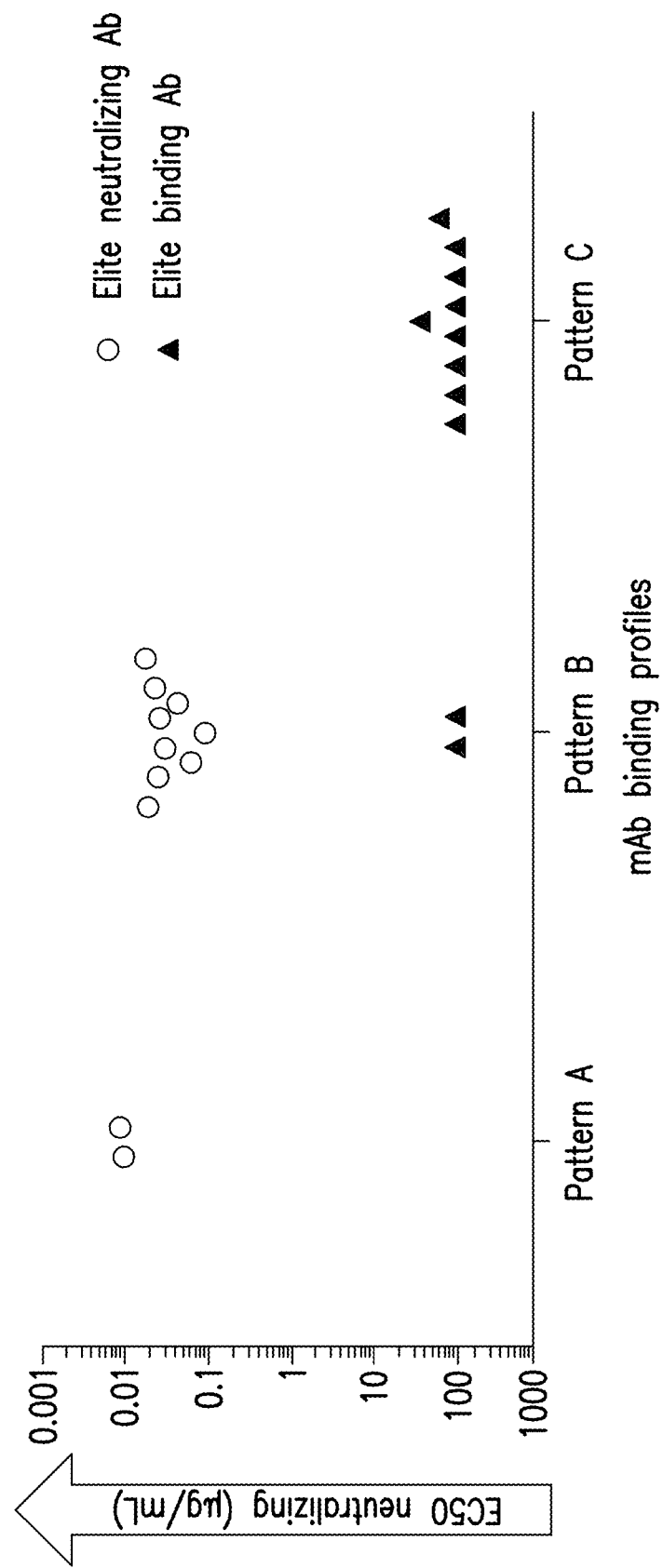

Three binding patterns are illustrated in FIG. 4. The monoclonal antibodies either (a) reacted only with the revertant virus (shown in FIG. 4A for clone 57.4), (b) reacted with both the revertant virus and the AD169 virus but preferred the revertant virus (shown in FIG. 4B for clone 58.5) or (c) reacted with both the revertant virus and the AD169 virus but displayed no preference (shown in FIG. 4C for clone 295.5). When the antibodies were plotted based on their binding patterns in correlation with their $EC_{50}$ neutralizing values in ARPE-19 cells, all elite neutralizers either reacted with only the revertant virus (pattern A) or showed preference for the revertant virus (pattern B). However, 9 out of 11 elite binders displayed no preference between the revertant virus or AD169 (pattern C) (clones 210.4, 269.6, 271.1, 272.7, 275.2, 283.7, 292.1, 295.5 and 350.1). Thus, the antigens for strong neutralizing antibodies are more abundantly displayed on the revertant virus than AD169 virus, and this is consistent with the pentameric gH complex being a dominant target for neutralizing antibodies.

Example 5

Figure 5:
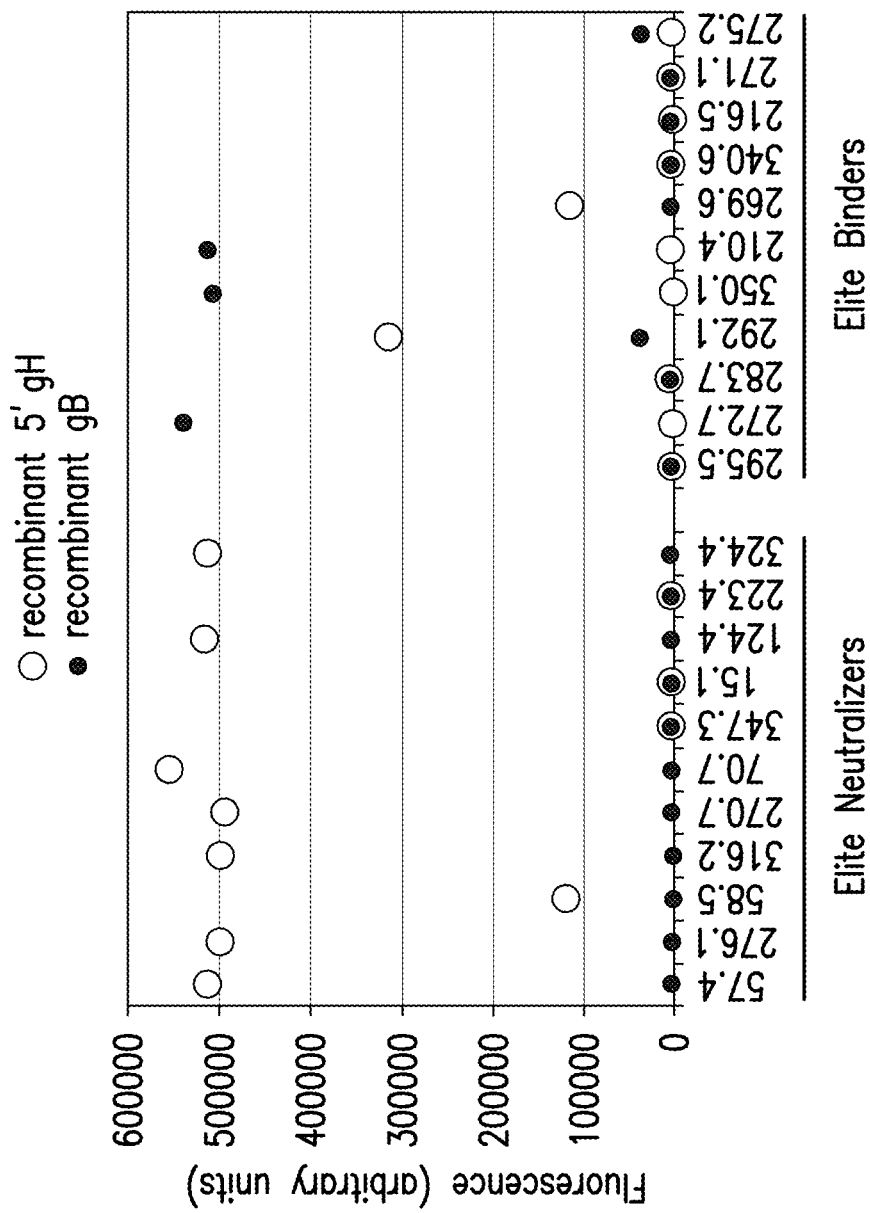
FIG. 5: Eight of the eleven elite neutralizing antibodies recognizing recombinant pentameric gH complex in EIA. The elite neutralizing and elite binding mAbs were assayed for reactivity with 2 μg/mL recombinant gB antigen or pentameric gH complex. The fluorescent signals observed for binding to either recombinant pentameric gH complex (solid bars) or recombinant gB (open bars) are plotted for each antibody at a concentration of ~1 μg/mL. Eight of eleven elite neutralizing antibodies react to pentameric gH complex while only two elite binding antibodies showed specificity for the pentameric gH antigen.

Majority of Neutralizing Antibodies with Reactivity to Recombinant Pentameric gH Complex To further characterize the antigen specificity of elite neutralizing and elite binding antibodies, recombinant gB and the pentameric gH complex were used in an antibody-titration EIA. Antibody reactivity to recombinant pentameric gH versus gB antigens at a single concentration of 1 µg/ml is shown in FIG. 5. None of the elite neutralizing antibodies reacted to gB, consistent with the fact that the elite neutralizers had little neutralizing activity and reduced binding for AD169. Three elite binders (clones 272.7, 350.1 and 210.4) reacted strongly to gB, and none of these monoclonal antibodies neutralized either AD169 or the revertant virus. This result is consistent with previous observations that gB is not effective in eliciting neutralizing antibodies in epithelial cells Cui et al., 2008, Vaccine 26:5760-6; Wang et al., 2011, Vaccine 29:9075-80; Tang et al., 2011, Vaccine 29:8350-6). In contrast, of the 11 elite neutralizers, 8 reacted to the pentameric gH complex (clones 57.4, 70.7, 124.4, 270.7, 276.10, 316.2 and 324.4). Only 2 of 7 elite binders (clones 292.1 and 269.6) reacted to the pentameric gH complex, and they had relatively weak binding to pentameric gH compared to the elite neutralizers. Thus, the pentameric gH complex is the antigen complex recognized by majority of the neutralizing antibodies, and antibody's reactivity to the pentameric gH complex is associated with its neutralization in epithelial cells.

Example 6

Phylogenetic Analysis of the Anti-CMV Monoclonal Antibodies

Figure 6:
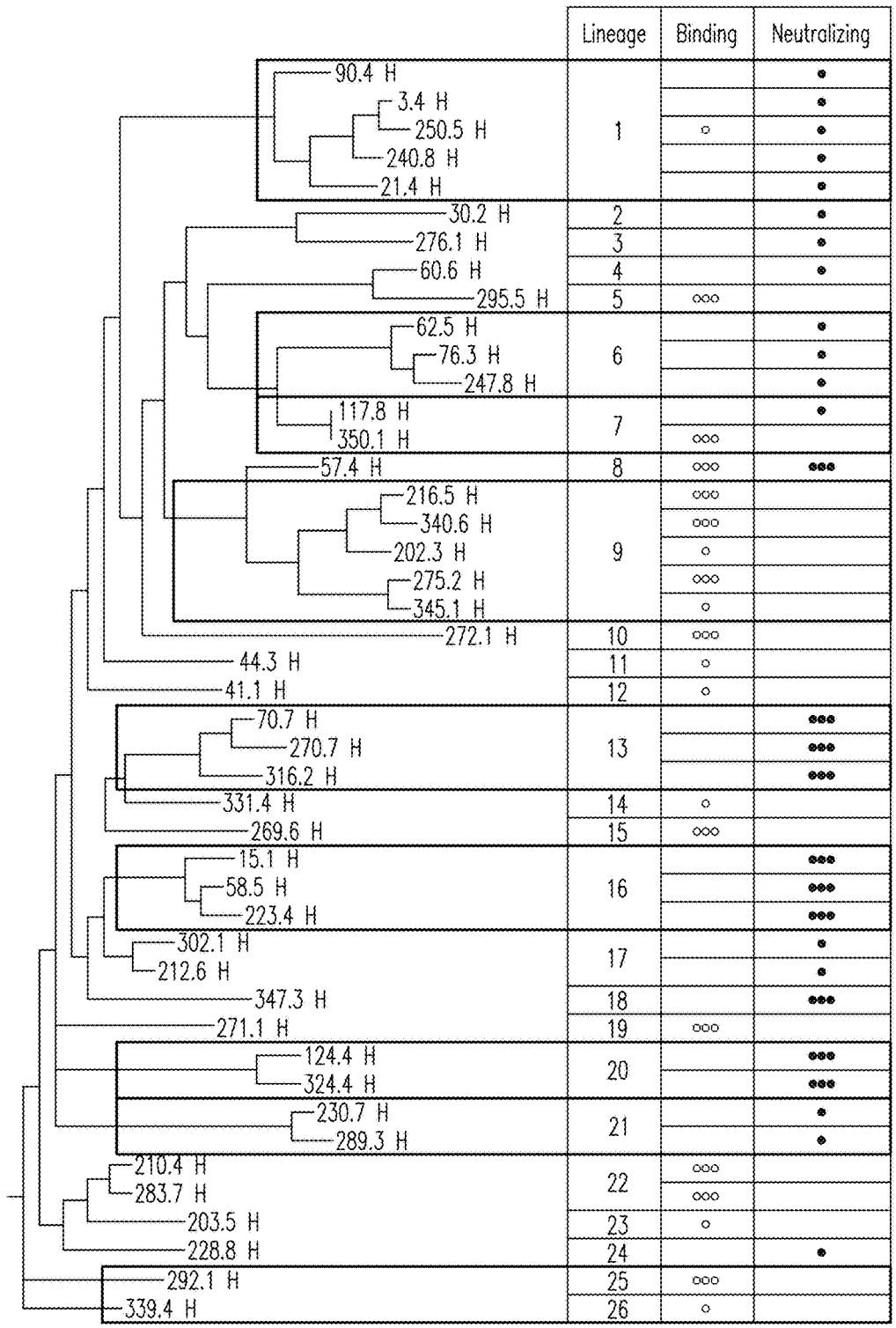
FIG. 6: Phylogenetic analysis of the amino acid sequences of the 45 isolated mAbs in relation to their antigen binding and neutralizing properties. A phylogenetic tree was constructed based on the entire heavy chain variable region amino acid sequence. Lineage groups were classified based on similarities among the antibodies in the heavy chain CDR3. Lineage groups containing two or more antibodies are grouped in boxes. Solid dots indicate neutralizing antibodies while open dots indicate non-neutralizing antibodies. Three dots indicate elite neutralizing or elite binding antibodies.

A phylogenetic tree was constructed based on the amino acid sequences of entire $V_H$ regions (FIG. 6). Since the heavy chain variable domain CDR3 (HCDR3) best represents junction-diversity and clonal specificity, the 45 monoclonal antibodies were grouped into 26 lineage groups based on their HCDR3 sequence homologies. Based on the similarities of HCDR3 sequence between the clustered antibodies, each of the 26 groups may have originated from a single unique B-cell lineage to a distinct epitope. If so, monoclonal antibodies within the same lineage group should have similar neutralizing or binding properties. Indeed, the neutralizing and binding monoclonal antibodies were largely segregated into distinct lineage groups. Eight of the 11 elite neutralizing monoclonal antibodies were clustered in three lineage groups (groups 13, 16, and 20). The elite neutralizing monoclonal antibody 347.3, the only member of lineage group 18, was closely related to the elite neutralizing lineage group 16. The elite neutralizing monoclonal antibody 276.10 was grouped with the weak neutralizing monoclonal antibody 30.2. Like the elite neutralizers, the weak neutralizing monoclonal antibody also tended to cluster in common lineage groups (5 mAbs in group 1; 3 mAbs in group 6; 2 mAbs in group 17 and 2 mAbs in group 21 were all weak neutralizers). Overall, the 7 lineage groups accounted for 20 of the 25 neutralizing monoclonal antibodies. In contrast to the neutralizing monoclonal antibodies, nonneutralizing monoclonal antibodies were more dispersed throughout the lineage groups, with the exception of lineage groups 9 and 22. All 5 monoclonal antibodies in lineage group 9 were elite or intermediate binders, and 2 monoclonal antibodies in lineage group 22 were elite binders. Ten nonneutralizing monoclonal antibodies fell in lineage groups of a single antibody. The large number of independent lineages for nonneutralizing monoclonal antibodies suggests that these monoclonal antibodies were specific for diverse viral antigens and/or epitopes. In addition, the lack of relatedness among these nonneutralizing monoclonal antibodies as compared to the neutralizing monoclonal antibodies suggests that the antigen targets recognized by these monoclonal antibodies are more diverse than those by neutralizing monoclonal antibodies.

However, there are some exceptions to this. Both mAb 250.5 and mAb 57.4 had both binding and neutralizing capabilities, although the former was a weak mAb for both properties and the latter an elite mAb for both properties. Interestingly, mAb 57.4 was closely related to the neutralizing lineage group 6 and the binding lineage group 9. Finally, mAb 350.1, an elite binder, and mAb 117.8, a weak neutralizer, shared identical HCDR3 sequences and were both in lineage group 7.

Figure 7:
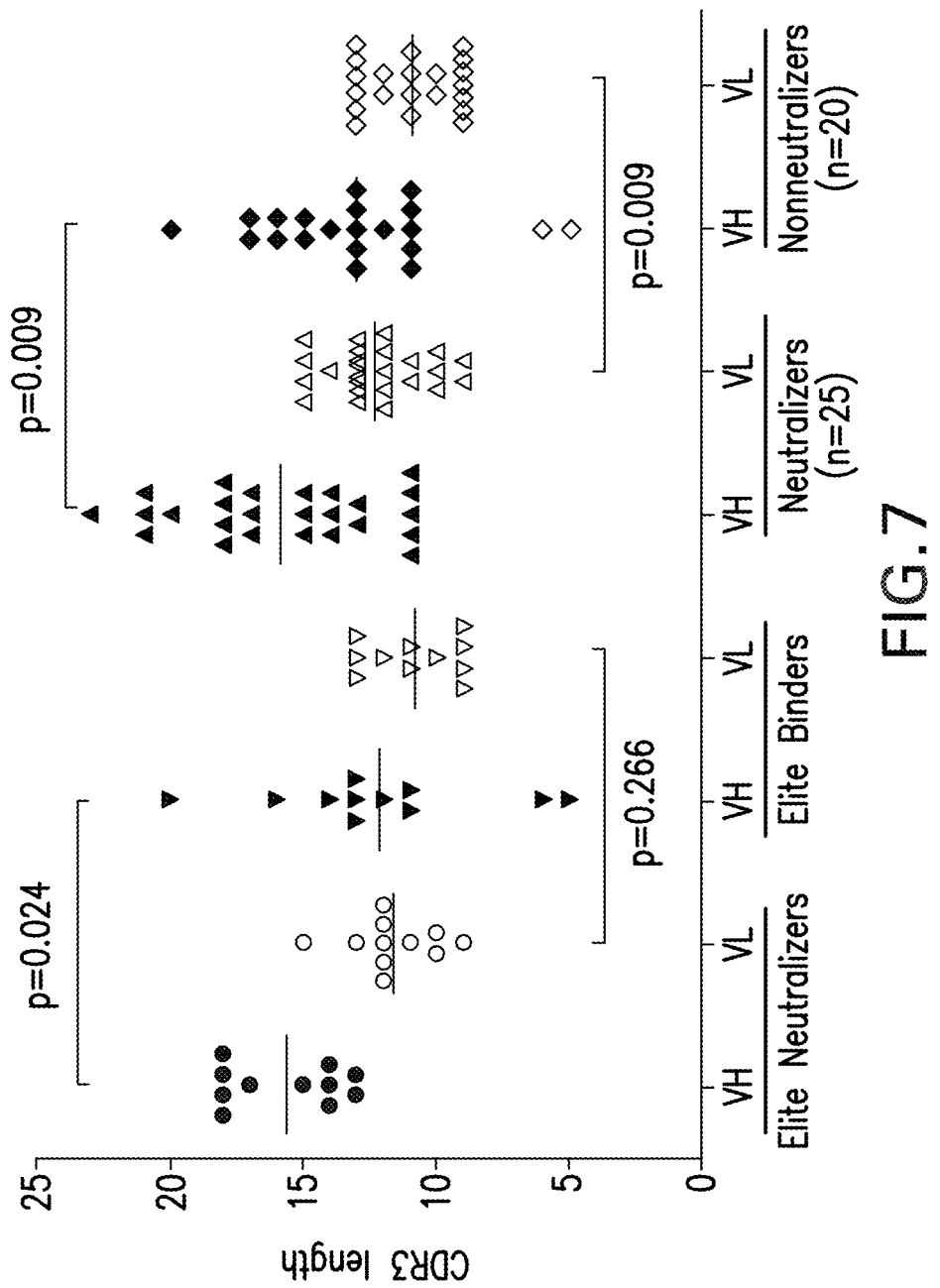
FIG. 7: The average heavy chain CDR3 size of the elite neutralizing antibodies is significantly larger than that of the elite binding antibodies. Heavy (closed symbols) and light chain (open symbols) CDR3 lengths for the isolated monoclonal antibodies were plotted. Average CDR3 length was indicated by the horizontal line. Unpaired two-tailed t-tests were performed for statistical comparisons of the indicated groups. Circles indicate elite neutralizing antibodies, inverted triangles indicate elite binding antibodies, triangles indicate neutralizing antibodies and diamonds indicate non-neutralizing antibodies.

For a given monoclonal antibody, the size of the HCDR3 was sometimes correlated with increased antiviral function (such as neutralization) or physical interaction (such as binding). Thus, the relationship between the HCDR3 and light chain variable domain CDR3 (LCDR3) for an antibody with the functional properties of the antibody were analyzed (FIG. 7). The 11 elite neutralizing mAbs had a longer average HCDR3 than that of the 11 elite binders (15.6 amino acids versus 12.2; p=0.024) while the average lengths of their LCDR3 were about the same with 11.6 amino acids for elite neutralizers versus 10.8 for the elite binders (p=0.266). The comparison was also conducted for all neutralizing mAbs (n=25) versus those with no neutralizing activity (n=20). In this comparison, the average sizes of HCDR3 and LCDR3 for the antibodies with neutralizing function, 15.9 and 12.3 amino acids, respectively, were significantly longer than those of HCDR3 and LCDR3 for the antibodies with no neutralizing activity, 13.0 and 10.9 amino acids, respectively (p=0.009 in both comparisons). This result indicated that targets important for viral neutralization were preferentially recognized by progenitor B cell receptors with long HCDR3 or LCDR3.

Interestingly, the average number of somatic mutations found in the neutralizing antibodies was not significantly different from that in the nonneutralizing antibodies for either $V_H$ or $V_L$ (Tables 8-9). To calculate the rates of somatic mutations, nucleotide sequences of rabbit antibodies were submitted to IMGT (ImMuno GeneTics Informations System®; Lefranc et al., 2003, Dev Comp Immunol 27: 55-77). The determined V-region for each antibody was aligned with the closest germline V-region sequence to calculate the number of amino acid mutations (insertions, deletions or substitutions). The rate was determined based on the number of mutations within the entire V-region.

These observations indicated that targets important for viral neutralization were complex and the interaction with these targets for neutralization favored those antibodies with longer HCDR3 and/or LCDR3. Antibody affinity maturation by somatic mutations played a secondary role for developing such neutralizing antibodies.

TABLE 8

Somatic Mutations for Neutralizing mAb

| Clone ID | $V_H$ amino acids | # changes | % mutation | $V_L$ amino acids | # changes | % mutation |
|---|---|---|---|---|---|---|
| 57.4 | 106 | 33 | 31 | 113 | 21 | 19 |
| 276.1 | 106 | 13 | 12 | 109 | 21 | 19 |
| 58.5 | 106 | 10 | 9 | 111 | 17 | 15 |
| 316.2 | 106 | 16 | 15 | 113 | 21 | 19 |
| 270.7 | 106 | 16 | 15 | 113 | 16 | 14 |
| 70.7 | 106 | 15 | 14 | 113 | 17 | 15 |
| 347.3 | 105 | 10 | 10 | 115 | 8 | 7 |
| 15.1 | 106 | 9 | 8 | 113 | 21 | 19 |
| 124.4 | 106 | 14 | 13 | 112 | 11 | 10 |
| 223.4 | 106 | 10 | 9 | 111 | 20 | 18 |
| 324.4 | 106 | 11 | 10 | 112 | 8 | 7 |
| 60.6 | 106 | 11 | 10 | 114 | 26 | 23 |
| 247.8 | 103 | 30 | 29 | 114 | 17 | 15 |
| 62.5 | 103 | 28 | 27 | 114 | 16 | 14 |
| 76.3 | 103 | 28 | 27 | 114 | 18 | 16 |
| 3.4 | 104 | 23 | 22 | 111 | 25 | 23 |
| 117.8 | 106 | 5 | 5 | 114 | 15 | 13 |
| 228.8 | 106 | 12 | 11 | 112 | 19 | 17 |
| 230.7 | 106 | 10 | 9 | 115 | 11 | 10 |
| 30.2 | 106 | 26 | 25 | 113 | 24 | 21 |
| 90.4 | 104 | 18 | 17 | 112 | 15 | 13 |
| 21.4 | 104 | 21 | 20 | 113 | 20 | 18 |
| 302.1 | 106 | 5 | 5 | 113 | 22 | 19 |
| 289.3 | 106 | 11 | 10 | 111 | 18 | 16 |
| 240.8 | 104 | 24 | 23 | 112 | 24 | 21 |
| | Average = 16% | | | Average = 16% | | |

TABLE 9

Somatic Mutations for Non-Neutralizing mAb

| Clone ID | $V_H$ amino acids | # changes | % mutation | $V_L$ amino acids | # changes | % mutation |
|---|---|---|---|---|---|---|
| 295.5 | 105 | 16 | 15 | 111 | 16 | 14 |
| 272.7 | 104 | 21 | 20 | 110 | 16 | 15 |
| 283.7 | 105 | 6 | 6 | 115 | 12 | 10 |
| 292.1 | 105 | 14 | 13 | 115 | 14 | 12 |
| 350.1 | 106 | 5 | 5 | 111 | 20 | 18 |
| 210.4 | 106 | 6 | 6 | 115 | 11 | 10 |
| 269.6 | 105 | 16 | 15 | 113 | 24 | 21 |
| 340.6 | 106 | 22 | 21 | 113 | 23 | 20 |
| 216.5 | 106 | 21 | 20 | 113 | 23 | 20 |
| 271.1 | 106 | 12 | 11 | 111 | 18 | 16 |
| 275.2 | 106 | 18 | 17 | 113 | 22 | 19 |
| 202.3 | 106 | 20 | 19 | 113 | 23 | 20 |
| 345.1 | 106 | 17 | 16 | 113 | 21 | 19 |
| 41.1 | 106 | 14 | 13 | 111 | 19 | 17 |
| 339.4 | 106 | 7 | 7 | 113 | 22 | 19 |
| 203.5 | 105 | 11 | 10 | 111 | 16 | 14 |
| 250.5 | 104 | 24 | 23 | 114 | 14 | 12 |
| 44.3 | 106 | 17 | 16 | 114 | 23 | 20 |
| 218.6 | 106 | 3 | 3 | 115 | 4 | 3 |
| 331.4 | 106 | 11 | 10 | 111 | 14 | 13 |
| | Average = 13% | | | Average = 16% | | |

Example 7

Complement-Dependent Viral Neutralization by Some Anti-CMV Monoclonal Antibodies Antibodies can exert effector functions by fixation of complement or activation of NK cells through their Fc region (Strohl, 2009, Curr Opin Biotechnol 20:685). By binding to viral antigens displayed on viral particles or virus-infected cells, these antibodies can mediate antigen-specific virolysis or cytotoxicity of virus-infected cells in vivo. All 20 non-neutralizing rabbit monoclonal antibodies were tested for their viral neutralizing ability in the presence of standard rabbit complement.

Briefly, the monoclonal antibody in titration was mixed with virus with or without rabbit complement (1:32 volume dilution, from Cedarlane, #CL3111). After 1 hour incubation at room temperature, the mixture was added to ARPE-19 cells plated in 96-well plates. The cells were fixed the next day and stained for expression of viral IE antigen as previously described.

Figure 8A:
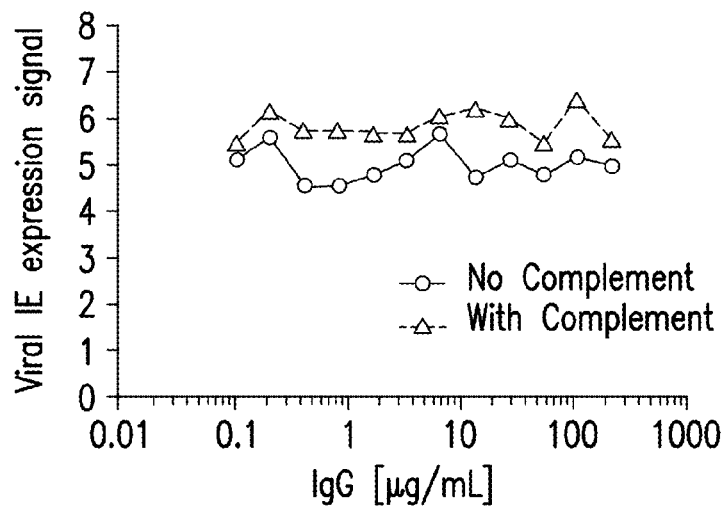
FIGS. 8A-8C: Complement-Dependent Viral Neutralization by Some Anti-CMV Monoclonal Antibodies. Monoclonal antibodies (A) 295.5 (B) 272.7 and (C) 350.1 were mixed with virus either in the presence or absence of rabbit complement and their ability to neutralize CMV infection of ARPE-19 cells was tested. CMV infection was assessed by the expression of viral IE antigen in the ARPE-19 cells.
Figure 8B:
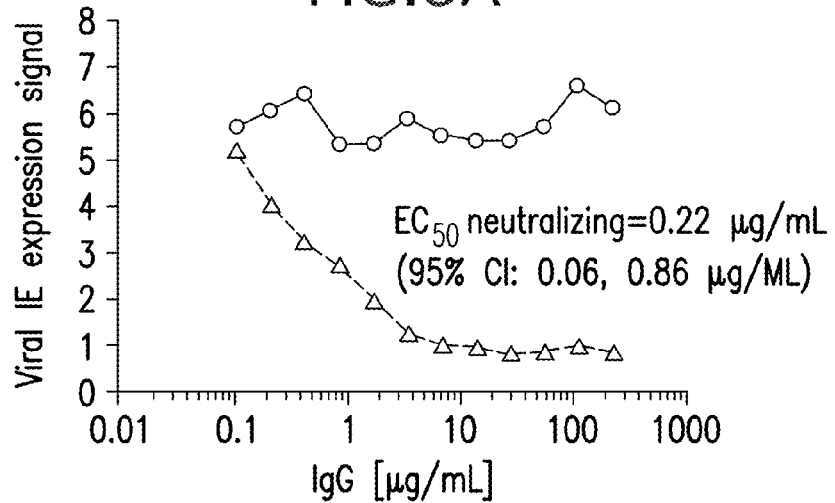
Figure 8C:
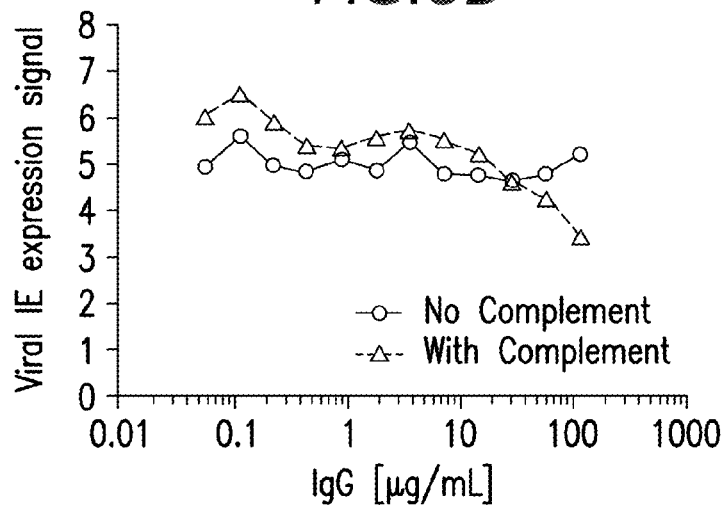

While majority of the monoclonal antibodies showed no neutralizing activity in the presence or absence of rabbit complement, five non-neutralizing monoclonal antibodies (clones 202.3, 216.5, 272.7, 275.2, and 345.1) exhibited antiviral function when complement was present. The complement-dependent viral neutralization was not related with antibody affinity to virions and was not epitope-specific. As shown in FIG. 8, the clone with the highest affinity, clone 295.5, has no antiviral activity with or without complement (FIG. 8A). Both clones 272.7 and 350.1 recognize the gB protein, but only clone 272.7 can neutralize virus when complement was added in the viral neutralization assay (FIGS. 8B and 8C). The antiviral activity by clone 272.7 in the presence of complement was calculated based on four-parameter curve fitting, and the EC50 neutralizing with complement was estimated as 0.22 µg/mL.

Example 8

Identification of Anti-CMV mAb Targets by Western Blot Analysis and ELISA

Figure 9A:
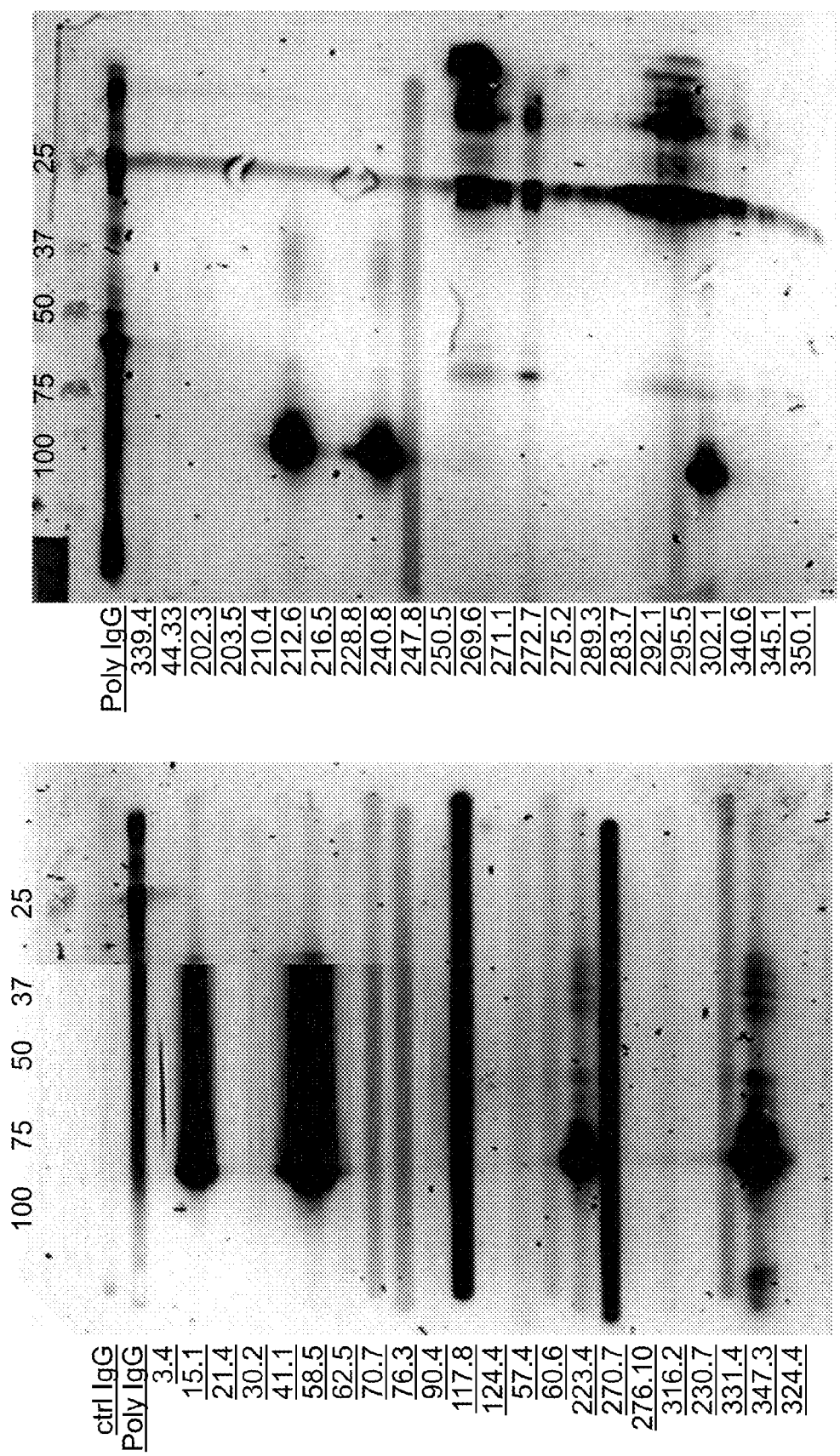
FIGS. 9A-B: Western Blot Analysis of Anti-CMV Monoclonal Antibodies. Purified CMV virus was denatured and the viral proteins were separated on SDS-PAGE. The viral proteins were transferred to nitrocellulose membrane and blotted with (A) the 45 isolated anti-CMV monoclonal antibodies if the invention or (B) clone 58.5. Control IgG (negative control) were isolated from pre-vaccinated rabbit sera and poly IgG (positive control) were isolated from post-vaccinated immune rabbit sera.
Figure 9B:
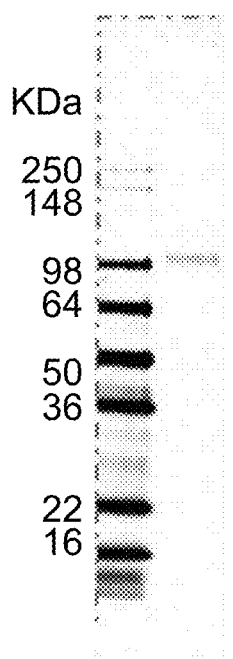

Purified CMV virions were denatured in the Sample Buffer (item #NP0007, Invitrogen, Carlsbad, Calif.) and the viral proteins were separated on SDS-PAGE. A majority of the 45 antibodies failed to recognize specific viral protein band (FIG. 9A) suggesting that the targets recognized by these antibodies were conformational in nature and their epitopes were poorly presented when viral antigens were denatured. However, one specific viral protein close to 100 KDa, the reported molecular weight for gH (UL75), was prominently blotted by clones 15.1, 58.5, 223.4, 347.3, 212.6, 240.8 and 203.1. This result was further confirmed with clone 58.5 in FIG. 9B.

Based on the results from ELISA (FIG. 4 and FIG. 5) and Western blot analysis (FIG. 9A), the viral antigens recognized by clones 57.4, 58.5, 272.7 and 276.10 were assigned. Clone 57.4 and 276.10 bound only to the revertant virus, not AD169 virus (FIG. 4A), and they reacted strongly to the recombinant pentatmeric gH complex, thus their epitopes were uniquely composed of UL128, UL130 and/or UL131 protein. Clone 58.5 recognized the recombinant pentameric gH complex and detected a protein with the same molecular weight of gH in Western blot, thus, its targeted viral antigen was gH. The viral protein recognized by clone 272.7 was gB based on its reactivity to the recombinant form of gB in ELISA (FIG. 5).

Example 9

Humanization of Rabbit Anti-CMV Antibodies

Four rabbit anti-CMV antibodies (clones 57.4, 58.5, 272.7, and 276.10) were humanized based on the concept of CDR grafting according to methods in the art (U.S. Pat. Nos. 5,530,101; 5,225,539; 6,693,762). CDR domains of the rabbit heavy and light chains were identified based on the rules of IMGT (Lefranc et al., 2003, Dev Comp Immunol 27: 55-77) with reference to Kabat/Chothia (Kabat et al., 1980, J Exp Med 152: 72-84; Yu et al., 2010, PLoS ONE 5: e9072; Haidar et al., 2012, Proteins 80: 896-912). Briefly, the best match of a given rabbit monoclonal antibody heavy or light chain to the human germline is identified via IMGT®, the international ImMunoGeneTics information system®. The sequences of the deduced CDRs are shown in Tables 10 (SEQ ID NOs.:1-135) and 13 (SEQ ID NOs.:136-270). Humanization was achieved by the rules of the CDR grafting protocol of U.S. Pat. Nos. 5,530,101 and 6,693,762 with reference to Yu et al., 2010, PLoS ONE 5: e9072 and Haidar et al., 2012, Proteins 80: 896-912. For expression of the humanized antibodies, the heavy chain variable region was fused in-frame with the IgG1 constant region whereas the light chain variable regions were fused in frame with a kappa constant region. In most cases, there are two versions of the heavy and light variable region designed for each antibody differing by one or two amino acid residues relative to each other. The humanized heavy and light chain variable regions are:

Humanized 57.4
$V_L$
(SEQ ID NO: 631)
DIQMTQTPSSVSASVGDRVTIKCQASQSIRRHLSWYQQKPGKRPKLL

IYGASNLASGVPSRFSGSGSGTDFTLTISSLQPEDFATYYCQCTYGV

GFSSTYGDAFGGGTKVEIK (SEQ ID NO: 632)
ELQMTQTPSSVSASVGDRVTIKCQASQSIRRHLSWYQQKPGKRPKLL

IYGASNLASGVPSRFSGSGSGTDFTLTISSLQPEDFATYYCQCTYGV

GFSSTYGDAFGGGTKVEIK $V_H$
(SEQ ID NO: 633)
EVQLLESGGGLVQPGGSLRLSCAASGFSFSSVYDMSWVRQAPGKGLE

WIASIVTGSRTTWYASWAKGRFTVSRDNSKNTLYLQMNSLRAEDTAV

YFCARGEYGHDGYVDGTMGLGLWGPGTTVTVSS (SEQ ID NO: 634)
EVQLLESGGGLVQPGGSLRLSCAASGFSFSSVYDMSWVRQAPGKGLE

WIASIVTGSRTTWYASWAKGRFTVSRDTSKNTLYLQMNSLRAEDTAV

YFCARGEYGHDGYVDGTMGLGLWGPGTTVTVSS

Humanized 58.5
$V_L$
(SEQ ID NO: 635)
DIQLTQTPSFLSASVGDRVTINCQASQNIYSNLAWYQQKPGKPPKWY

GASTLASGVPSRFSGSGSGTEFTLTISSLQPEDFATYYCQSYVYSSS

TADTFGGGTKVEIK (SEQ ID NO: 636)
ELQLTQTPSFLSASVGDRVTINCQASQNIYSNLAWYQQKPGKPPKWY

GASTLASGVPSRFSGSGSGTEFTLTISSLQPEDFATYYCQSYVYSSS

TADTFGGGTKVEIK $V_H$
(SEQ ID NO: 637)
EVQLLESGGGLVQPGGSLRLSCAASGFSLSAYSVSWVRQAPGKGLEW

IGIIGHSGNTYYASWAKGRFTISRDNSKNTVYLQMNSLRAEDTAVYF

CAREDYRYGDYGYYWDFNFWGPGTLVTVSS (SEQ ID NO: 638)
EVQLLESGGGLVQPGGSLRLSCAASGFSLSAYSVSWVRQAPGKGLEW

IGIIGHSGNTYYASWAKGRFTISRDTSKNTVYLQMNSLRAEDTAVYF

CAREDYRYGDYGYYWDFNFWGPGTLVTVSS

Humanized 272.7
$V_L$
(SEQ ID NO: 639)
DIQMTQTPSSVSASVGDRVTIKCQASQSIGSNLAWYQQKPGKPPKLL

IYAASNLASGVPSRFSGSGSGTDFTLTISSLQPEDFATYYCQCNYYL

NNAFGGGTKVEIK (SEQ ID NO: 640)
ELQMTQTPSSVSASVGDRVTIKCQASQSIGSNLAWYQQKPGKPPKLL

IYAASNLASGVPSRFSGSGSGTDFTLTISSLQPEDFATYYCQCNYYL

NNAFGGGTKVEIK $V_H$
(SEQ ID NO: 641)
EVQLVESGGGLVQPGGSLRLSCAASGFDVSSYWMSWVRQAPGKGLEW

IGYIDPVFGTTYYASWVNGRFTISSHNSKNTLYLQMNSLRAEDTAVY

FCATNTHGTGGYYLWGPGTLVTVSS

Humanized 276.10

V$_L$ (SEQ ID NO: 642)
DIQMTQTPSSLSASVGDRVTIKCQASHNINTYLSWYQQKPGKPPKWY

RASDLASGVPSRFSGSGSGTDFTFTISSLQPEDIATYYCQQGFNSLN

VENVFGGGTKVEIK (SEQ ID NO: 643)
ELQMTQTPSSLSASVGDRVTIKCQASHNINTYLSWYQQKPGKPPKWY

RASDLASGVPSRFSGSGSGTDFTFTISSLQPEDIATYYCQQGFNSLN

VENVFGGGTKVEIK

V$_H$ (SEQ ID NO: 644)
EVQLLESGGGLVQPGGSLRLSCAASGFSFSGSYYMCWVRQAPGKGLE

WIACIDGDLSGSAYYANWAKGRFTISRDNSKNTVYLQMNSLRAEDTA

VYYCAREGPVGVGSIYLGFDLWGPGTLVTVSS (SEQ ID NO: 645)
EVQLLESGGGLVQPGGSLRLSCAASGFSFSGSYYMCWVRQAPGKGLE

WIACIDGDLSGSAYYANWAKGRFTISRDTSKNTVYLQMNSLRAEDTA

VYYCAREGPVGVGSIYLGFDLWGPGTLVTVSS

Other embodiments are within the following claims. While several embodiments have been shown and described, various modifications may be made without departing from the spirit and scope of the present invention.

TABLE 10

| | Light Chain Variable Domain CDR Sequences | | | | | |
|---|---|---|---|---|---|---|
| Clone ID | CDR1 | SEQ ID NO. | CDR2 | SEQ ID NO. | CDR3 | SEQ ID NO. |
| 3.4 | QNVGSY | 1 | FAS | 2 | QSYGTGVGYDAY | 3 |
| 15.1 | QNIGSR | 4 | RTS | 5 | QDHDDISHA | 6 |
| 21.4 | QSIRRH | 7 | GAS | 8 | QCTYGVGFSSTYGDA | 9 |
| 30.2 | DNIYSG | 10 | GVS | 11 | QCTIGPVGSSFGDP | 12 |
| 41.1 | RSVYNENY | 13 | TTS | 14 | AGDYDDNEENA | 15 |
| 44.3 | ESIYSG | 16 | QAS | 17 | QQGFSSSNVDNL | 18 |
| 57.4 | QSIRRH | 19 | GAS | 20 | QCTYGVGFSSTYGDA | 21 |
| 58.5 | QNIYSN | 22 | GAS | 23 | QSYVYSSSTADT | 24 |
| 60.6 | ESINNW | 25 | RAS | 26 | ECPFSGGSGRV | 27 |
| 62.5 | QSISSY | 28 | RAS | 29 | QCTYGSSSSGYA | 30 |
| 70.7 | QSIGNL | 31 | DAS | 32 | QQGYMITNVENA | 33 |
| 76.3 | QSISNY | 34 | RAS | 35 | QSTYGSSSSGYA | 36 |
| 90.4 | QTVNSY | 37 | FAS | 38 | QSYYYSGSSYGNA | 39 |
| 117.8 | QSISSY | 40 | RAS | 41 | QCTYGSSSSAYGRA | 42 |
| 124.4 | QSVYNKNY | 43 | GAS | 44 | QGYYSGYIYA | 45 |
| 202.3 | QNIGSR | 46 | RTS | 47 | QDHDDISHA | 48 |
| 203.5 | QSVYNKNA | 49 | KAS | 50 | LGGYSTTSDNA | 51 |
| 210.4 | QSLYNNNF | 52 | KAS | 53 | QGEFSCSSADCNA | 54 |
| 212.6 | TGYSVGKYP | 55 | YHTEEFK | 56 | ATAHATESSLHYV | 57 |
| 216.5 | QNIGSR | 58 | RTS | 59 | QDHDDISHA | 60 |
| 223.4 | RSVYNENY | 61 | TTS | 62 | AGDYDDNEENA | 63 |
| 228.8 | QNVIDKNW | 64 | SAS | 65 | AGGYSGDIYA | 66 |
| 230.7 | QSLYNNNF | 67 | KAS | 68 | QGEFSCSSADCNA | 69 |

TABLE 10-continued

Light Chain Variable Domain CDR Sequences

| Clone ID | CDR1 | SEQ ID NO. | CDR2 | SEQ ID NO. | CDR3 | SEQ ID NO. |
|---|---|---|---|---|---|---|
| 240.8 | HNIGSR | 70 | RTS | 71 | QDHDDISHA | 72 |
| 247.8 | QSIGNY | 73 | RAS | 74 | QSTYGSSSSSGYA | 75 |
| 250.5 | QSISSY | 76 | RAS | 77 | QCTYGSSSSGYA | 78 |
| 269.6 | ESIYSS | 79 | RAS | 80 | QQGWSNINVDNV | 81 |
| 270.7 | QSIGNL | 82 | DAS | 83 | QQGYMITNVENA | 84 |
| 271.1 | QSIGAN | 85 | GAS | 86 | QCTYYGSGNT | 87 |
| 272.7 | QSIGSN | 88 | AAS | 89 | QCNYYLNNA | 90 |
| 275.2 | QNIGSR | 91 | RTS | 92 | QDHDDISHA | 93 |
| 276.10 | HNINTY | 94 | RAS | 95 | QQGFNSLNVENV | 96 |
| 283.7 | QSVYNNNF | 97 | LAS | 98 | QGEFSCISADCNA | 99 |
| 289.3 | QGIYDY | 100 | GAA | 101 | QSAYYSSTDRNA | 102 |
| 292.1 | QSVYNDNY | 103 | YAS | 104 | LGSYDCSSADCYV | 105 |
| 295.5 | KSVYNNNA | 106 | SAS | 107 | AGGYSIISDNG | 108 |
| 302.1 | QSIRRH | 109 | GAS | 110 | QCTYGVGFSSTYGDA | 111 |
| 316.2 | QTIGNL | 112 | DAS | 113 | QQGYMITNVENA | 114 |
| 324.4 | QSVYNNNY | 115 | GAS | 116 | QGYYSGYIYA | 117 |
| 331.4 | QSVNNNW | 118 | GAS | 119 | QGDLTGWIWA | 120 |
| 339.4 | QNIGSR | 121 | RTS | 122 | QDHDDISHA | 123 |
| 340.6 | QNIGSR | 124 | RTS | 125 | QDHDDISHA | 126 |
| 345.1 | QNIGSR | 127 | RTS | 128 | QDHDDISHA | 129 |
| 347.3 | TGYSVGKYP | 130 | YHTEEFK | 131 | VTAHPTESSLHYV | 132 |
| 350.1 | QNVWTNDY | 133 | RAS | 134 | GGTFLSNGDNG | 135 |

TABLE 11

Light Chain Variable Domain Framework Regions 1 and 2 Sequences

| Clone ID | FR1 | SEQ ID NO. | FR2 | SEQ ID NO. |
|---|---|---|---|---|
| 3.4 | ELDLTQTPASVSEPVGGTVTVKCQAS | 271 | LAWYRQKPGQPPKLLIY | 272 |
| 15.1 | ELVMTQTPASVSAAVGGTVTIKCQAS | 273 | LAWYQQEPGQPPKLLIY | 274 |
| 21.4 | ELVMTQTPASVEAAVGGTVAIKCQAS | 275 | LSWYQQKPGQRLKLLIY | 276 |
| 30.2 | ELVLTQTPASVEAAVGGTVTINCQAS | 277 | LAWYRQKPGQRPELLIY | 278 |
| 41.1 | ELVMTQTPSPVSAPVGGTVTISCQAS | 279 | VAWFQHKPGQPPKLLIY | 280 |
| 44.3 | ELDMTQTPASVSAAVGGTVTINCQAS | 281 | LAWYQQKPGQPPKLLIY | 282 |
| 57.4 | ELDLTQTPASVEAAVGGTVAIKCQAS | 283 | LSWYQQKPGQRPKLLIY | 284 |
| 58.5 | ELDLTQTASPVSAPVGGTVTINCQAS | 285 | LAWYQQKPGQPPKLLIY | 286 |
| 60.6 | ELDMTQTPASVSEPVGGTVTIKCQAS | 287 | LAWYQQRPGQPPKPLIY | 288 |
| 62.5 | ELDLTQTPASVEAAVGGTVTIKCQAS | 289 | LSWYQQKPGQPPKLLIY | 290 |
| 70.7 | ERDMTQTPASVEVAVGGTVTIKCQAS | 291 | LAWYQQKPGQRPKLLIY | 292 |
| 76.3 | ELDLTQTPASVEAAVGGTVTIKCRAS | 293 | FSWYQQKPGQPPKLLIY | 294 |

TABLE 11-continued

Light Chain Variable Domain Framework Regions 1 and 2 Sequences

| Clone ID | FR1 | SEQ ID NO. | FR2 | SEQ ID NO. |
|---|---|---|---|---|
| 90.4 | ELVLTQTPASVEA AVGGTVTIKCQAS | 295 | LAWYQQKSGQPPKLLIY | 296 |
| 117.8 | ELDLTQTPASVEA AVGGTVTIKCQAS | 297 | LSWYQQKPGQPPKLLIY | 298 |
| 124.4 | ELDMTQTASPVSA AVGGTVTINCQSS | 299 | LSWYQQKPGQPPKLLIY | 300 |
| 202.3 | ELDLTQTPASVSA AVGGTVTIKCQAS | 301 | LAWYQQEPGQPPKLLIY | 302 |
| 203.5 | ELDLTQTPSPVSA AVGGTVTINCQAS | 303 | LSWFQQKLGQPPKLLIY | 304 |
| 210.4 | ELVLTQTPSPVSA AVGGTVTINCQTS | 305 | LSWYQQKPGQPPKLLIY | 306 |
| 212.6 | ELVLTQSPSLSAS LGTTARLTCTLS | 307 | LVWLQQVPGRPPRYLLT | 308 |
| 216.5 | ELELTQTPASVSA AVGGTVTIKCQAS | 309 | LAWYQQEPGQPPKLLIY | 310 |
| 223.4 | ELVMTQTPSPVSA PVGGTVTISCQAS | 311 | VAWFQHRPGQPPKLLIY | 312 |
| 228.8 | ELVMTQTASSVSA AVGGTVTISCQSS | 313 | LSWYQQKPGQPPKLLIY | 314 |
| 230.7 | ELVLTQTPSPVSA AVGGTVTINCQTS | 315 | LSWYQQKPGQPPKLLIY | 316 |
| 240.8 | ELVMTHPPASVSA PVGGTVTIKCQAS | 317 | LPWYQQEPGQPPKLLIY | 318 |
| 247.8 | ELVLTQTPASVEA AVGGTVTIKCRAS | 319 | FSWYQQKPGQPPKLLIY | 320 |
| 250.5 | ELVLTQTPASVEA AVGGTVTIKCQAS | 321 | LSWYQQKPGQPPKLLIY | 322 |
| 269.6 | ELVLTQTPASVEV GVGGTVTINCQAS | 323 | LAWYQQKPGQPPKLLIY | 324 |
| 270.7 | ELVMTQTPASVEV AVGGTVTIKCQAS | 325 | LAWYQQEPGQRPKLLIY | 326 |
| 271.1 | ELVLTQTPASVSE PVGGTVTIKCQAS | 327 | LAWYHQKPGQPPKLLIY | 328 |
| 272.7 | ELDMTQTPASVSE PVGGTVTIKCQAS | 329 | LAWYQQKPGQPPKLLIY | 330 |
| 275.2 | ELVLTQTPASVSA AVGGTVTIKCQAS | 331 | LAWYQQEPGQPPKLLIY | 332 |
| 276.10 | ELDLTQTPASVEV PVGGTVTIKCQAS | 333 | LSWYQQKPGQPPKLLIY | 334 |
| 283.7 | ELVLTQTPSPVSA AVGGTVTINCKTS | 335 | LSWYQQKPGQPPKLLIY | 336 |
| 289.3 | ELDMTQTPSSVSE PVGGTVTINCQAS | 337 | LAWYQQKPGQRPKLLIY | 338 |
| 292.1 | ELVLTQTPSSVSA AVGGTVTINCQAS | 339 | LAWYQQKPGQPPKRLIY | 340 |
| 295.5 | ELELTQTPSPVSA AVGGTVSISCQAS | 341 | LSWYQQKPGQPPKLLIY | 342 |
| 302.1 | ELDLTQTPASVEA AVGGTVAIKCQAS | 343 | LSWYQQKPGQRLKLLIY | 344 |
| 316.2 | ELVLTQTPASVEV AVGGTVTIKCQAS | 345 | LGWYQQKPGRPPKLLIY | 346 |
| 324.4 | ELDLTQTASPVSA AVGGTVTINCQSS | 347 | LSWYQQKPGQPPKLLIY | 348 |
| 331.4 | ELVLTQTPSPVSA AVGGTVTISCQAS | 349 | LSWYQQKPGQPPKLLIY | 350 |
| 339.4 | ELVLTQTPASVSA AVGGTVTIKCQAS | 351 | LAWYQQEPGQPPKLLIY | 352 |
| 340.6 | VLDLTQTPASVSA AVGGTVTIKCQAS | 353 | LAWYQQEPGQPPKLLIY | 354 |
| 345.1 | ELVMTQTPASVSA AVGGTVTIKCQAS | 355 | LAWYQQEPGQPPKLLIY | 356 |
| 347.3 | ELVLTQSPSLSAS LGTTARLTCTLS | 357 | LVWLQQVPGRPPRYLLT | 358 |
| 350.1 | ELDMTQTPSPVST AVGGTVSISCQSG | 359 | LSWYQQKPGQPPKLLIY | 360 |

TABLE 12

Light Chain Variable Domain Framework Regions 3 and 4 Sequences

| Clone ID | FR3 | SEQ ID | FR4 | SEQ ID |
|---|---|---|---|---|
| 3.4 | TLTSGVPSRFKGSGSGTQ FTLTISDLECADAATYYC | 361 | FGGGTEVVVK | 362 |
| 15.1 | TLASGVPSRFSGSGYGTE FTLTISDLECADAATYYC | 363 | QDHDDISHA | 364 |
| 21.4 | NLASGVSSRFKGSGSGTE FTLTISDLECADAATYYC | 365 | FGGGTNVEIK | 366 |
| 30.2 | TLESGVPSRFKGSRSGTE FTLTISDLECADAATYYC | 367 | FGGGTEVVVK | 368 |
| 41.1 | ILASGVPSRFKGRGSGTQ FTLTISDVQCDDAATYYC | 369 | FGGGTNVEIK | 370 |
| 44.3 | TLASGVPSRFSGSRSGTE YTLTISGVECADAATYYC | 371 | FGGGTNVEIK | 372 |
| 57.4 | NLASGVSSRFKGSGSGTE FTLTISDLECADAATYYC | 373 | FGGGTELEIL | 374 |
| 58.5 | TLASGVSSRFKGSRSGTE FTLTISDLECADAATYYC | 375 | FGGGTEVVVK | 376 |
| 60.6 | TLTSGVSSRFRGSGSGTQ FTLTISDLECADAATYYC | 377 | FGGGTNVEIK | 378 |
| 62.5 | TLESGVPSRFKGSGSGTE FTLTISDLECADAATYHC | 379 | FGGGTEVALK | 380 |
| 70.7 | TLASGVPSRFKGSGSGTE FTLTISGVQCADAATYYC | 381 | FGGGTEVVVK | 382 |
| 76.3 | TLESGVPSRFKGSGSGTE FTLTISDLECADAATYHC | 383 | FGGGTEVVVK | 384 |
| 90.4 | TLASGVPSRFKGSGSGTQ FTLTISDLECADAATYYC | 385 | FGGGTEVVVK | 386 |

TABLE 12-continued

Light Chain Variable Domain Framework Regions 3 and 4 Sequences

| Clone ID | FR3 | SEQ ID | FR4 | SEQ ID |
|---|---|---|---|---|
| 117.8 | TLESGVPSRFKGSGSGTE FTLTISDLECADAATYYC | 387 | FGGGTEVEIK | 388 |
| 124.4 | TLPSGVPSRFKGSGSGTQ FTLTISEVQCDDAATYYC | 389 | FGGGTEVVVK | 390 |
| 202.3 | TLASGVPSRFSGSGYGTE FTLTISDLECADAATYYC | 391 | FGGGTNVEIK | 392 |
| 203.5 | TLASGVPSRFKGSGSGTQ FTLTISDVQCDDAATYYC | 393 | FGGGTEVVVK | 394 |
| 210.4 | TLESGVPSRFKGSGSGTQ FTLTISGVQCDDAATYYC | 395 | FGGGTEVVVK | 396 |
| 212.6 | HQGSGVHSRFSGSKDTSE NAGVLSISGLQPEDEADY YC | 397 | FGGGTQLTVT | 398 |
| 216.5 | TLASGVPSRFSGSGYGTE FTLTISDLECADAATYYC | 399 | FGGGTEVVVK | 400 |
| 223.4 | ILASGVPSRFKGRGSGTQ FTLTISDVQCDDAATYYC | 401 | FGGGTELEIL | 402 |
| 228.8 | TLASGVPSRFKGSGSGTQ FTLTISDLECDDAATYYC | 403 | FGGGTNVEIK | 404 |
| 230.7 | TLESGVPSRFKGSGSGTQ FTLTISGVQCDDAATYYC | 405 | FGGGTEVVVK | 406 |
| 240.8 | TLASGVPSRFTGSGYGTE FTLTISDLECADAATYYC | 407 | FGGGTNVEIK | 408 |
| 247.8 | TLESGVPSRFKGSGSGTE FTLTISDLECADAATYHC | 409 | FGGGTEVVVK | 410 |
| 250.5 | TLESGVPSRFKGSGSGTE FTLTISDLECADAATYYC | 411 | FGGGTEVVVK | 412 |
| 269.6 | TLASGVSSRFEGSGSGTQ FTLTISGVECADAATYYC | 413 | FGGGTEVVVK | 414 |
| 270.7 | TLASGVPSRFKGSGSGTE FTLTISGVQCADAATYYC | 415 | FGGGTNVEIK | 416 |
| 271.1 | NLESGVPSRFKGSGSGTQ FTLTISGVQCDDAATYYC | 417 | FGGGTELEIL | 418 |
| 272.7 | NLASGVPSRFKGSGSGTQ FTLTISGVQCDDAATYYC | 419 | QCNYYLNNA | 420 |
| 275.2 | TLASGVPSRFSGSGYGTE FTLTISDLECADAATYYC | 421 | FGGGTEVVVE | 422 |
| 276.10 | DLASGVSSRFSGSGSGTQ FTLTISGVECADAATYYC | 423 | FGGGTEVVVK | 424 |
| 283.7 | TLESGVPSRFKGSGSGTQ FTLTISGVQCDDAATYYC | 425 | FGGGTKVEIK | 426 |
| 289.3 | ILASGVPSRFKGSRSGTE FTLTISDLECADAATYYC | 427 | FGGGTEVVVK | 428 |
| 292.1 | TLASGVSSRFKGSGSGTQ FTLTISDVQCDDAATYYC | 429 | FGGGTEVVVK | 430 |
| 295.5 | TLASGVPSRFSGSGSGTE FTLTISGVQCDDAATYYC | 431 | FGGGTEVVVK | 432 |
| 302.1 | NLASGVSSRFKGSGSGTE FTLTISDLECADAATYYC | 433 | FGGGTNVEIK | 434 |
| 316.2 | TLASGVPSRFKGSGSATE FTLTIRGVQCDDAATYYC | 435 | FGGGTEVVVK | 436 |
| 324.4 | TLASGVPSRFKGSGSGTQ FTLTISEVQCDDAATYYC | 437 | FGGGTEVVVK | 438 |
| 331.4 | TLASGVPSWFKGSGSGTQ FTLTISEVVCDDAATYYC | 439 | FGGGTNVEIK | 440 |
| 339.4 | TLASGVPSRFSGSGYGTE FTLTISDLECADAATYYC | 441 | FGGGTNEEIK | 442 |
| 340.6 | TLASGVPSRFSGSGYGTE FTLTISDLECADAATYYC | 443 | FGGGTEVVVK | 444 |
| 345.1 | TLASGVPSRFSGSGYGTE FTLTISDLECADAATYYC | 445 | FGGGTNVEIK | 446 |
| 347.3 | HQGSGVHSRFSGSKDTSE NSFVLRIFGLQPEDEADY YC | 447 | FGGGTQLTVT | 448 |
| 350.1 | TLASGVPSRFKGSGSGTQ FTLTISDVQCDDAATYYC | 449 | FGGGTEVVVK | 450 |

TABLE 13

Heavy Chain Variable Domain CDR Sequences

| Clone ID | CDR1 | SEQ ID NO | CDR2 | SEQ ID NO | CDR3 | SEQ ID NO |
|---|---|---|---|---|---|---|
| 3.4 | GIDLSANE | 136 | LSYHNIP | 137 | GRVFTSTSFDP | 138 |
| 15.1 | GFSLSAYS | 139 | IGHSGNT | 140 | AREDYRYGDYGYYWDFNF | 141 |
| 21.4 | GIDLSSHE | 142 | ISYDHTP | 143 | VRVFTGTAFDP | 144 |
| 30.2 | AFSFSSSYY | 145 | IYGGDAT | 146 | ARKYAGTYFSRYFNL | 147 |
| 41.1 | GFSLSDYV | 148 | IYGSGRI | 149 | ARGSNSNGGTMYFNL | 150 |
| 44.3 | GFSLSSYV | 151 | FDRNSGR | 152 | ARGSYGSDISSLYWFDL | 153 |
| 57.4 | GFSFSSVYD | 154 | IVTGSRTT | 155 | RGEYGHDGYVDGTMGLGL | 156 |

TABLE 13-continued

Heavy Chain Variable Domain CDR Sequences

| Clone ID | CDR1 | SEQ ID NO | CDR2 | SEQ ID NO | CDR3 | SEQ ID NO |
|---|---|---|---|---|---|---|
| 58.5 | GFSLSAYS | 157 | IGHSGNT | 158 | AREDYRYGDYGYYWDFNF | 159 |
| 60.6 | GFSFNNAYY | 160 | IYVGSSGGT | 161 | AREFAYYGYIDAGWAYVPYGMDL | 162 |
| 62.5 | GFSFSNSYY | 163 | IYTIIGNT | 164 | RDRYYYSDPYTGYAYATGFNL | 165 |
| 70.7 | GFSLSSYH | 166 | INYNNNP | 167 | ARAAGNYYVGALNL | 168 |
| 76.3 | GFSFSNSYY | 169 | IYTRITNT | 170 | RDRYYYSDPYTGYAYATGFNL | 171 |
| 90.4 | GIDLNSYE | 172 | IGYGGIT | 173 | ARLFTSTAFDP | 174 |
| 117.8 | GFSFSNSYY | 175 | IYAGSSGFT | 176 | ARDRGYYTYGYAGYGYGMDL | 177 |
| 124.4 | GFSLSSCN | 178 | IAASGDA | 179 | ARGSYAAYNAWDL | 180 |
| 202.3 | GFTIGSDYW | 181 | IRDVGGGHT | 182 | ARDNDGDWFYFDL | 183 |
| 203.5 | GFSLSSYA | 184 | IWSSGTS | 185 | ARGIGGDNYGDIWLDL | 186 |
| 210.4 | GFSLSTNA | 187 | IWSGGST | 188 | AKNGDNGQLDL | 189 |
| 212.6 | GFSLSSYA | 190 | IGSSGNT | 191 | ARGGYSDDYTPFDL | 192 |
| 216.5 | GFTISSDYW | 193 | IRDVGGGHT | 194 | ARDNDGDWFYFDL | 195 |
| 223.4 | GFSLSAYS | 196 | IGHSGNT | 197 | AREDYRYGDYGYYWDFNF | 198 |
| 228.8 | GFSLSSHY | 199 | ISGSGSA | 200 | ARGGLGVGLDL | 201 |
| 230.7 | GFSLSNYD | 202 | IGSGNNP | 203 | ARDSLPFTDDSTDYFAL | 204 |
| 240.8 | GIDLSANE | 205 | LSYHNIP | 206 | GRVFTSTSFDP | 207 |
| 247.8 | GFSFSNSYY | 208 | IYTRITNT | 209 | RDRYYYSDPYTGYAYATGFNL | 210 |
| 250.5 | GIDLSANE | 211 | LSYHNIP | 212 | GRVFTSTSFDP | 213 |
| 269.6 | GLSLSNYN | 214 | INAGSTI | 215 | AREDSYGGFFVLDL | 216 |
| 270.7 | RFSLSSNH | 217 | INYNNNP | 218 | ARAAGNYYVGALNL | 219 |
| 271.1 | GFSLSSYD | 220 | IWSGGIT | 221 | ARNFDL | 222 |
| 272.7 | GFDVSSYW | 223 | IDPVFGTT | 224 | ATNTHGTGGYYL | 225 |
| 275.2 | GFTISSDYW | 226 | IRDVGGGDT | 227 | ARDNDGDWFYFDL | 228 |
| 276.10 | GFSFSGSYY | 229 | IDGDLSGSA | 230 | AREGPVGVGSIYLGFDL | 231 |
| 283.7 | GFSLSSNA | 232 | IWSGGST | 233 | AKNGDNGQLDL | 234 |
| 289.3 | GFSLSNYD | 235 | IGSGNNP | 236 | ARDSLPFTDDSTDYFAL | 237 |
| 292.1 | GFSLRSYG | 238 | IWSGGRT | 239 | TTEDL | 240 |
| 295.5 | GFSFSNNYY | 241 | IYPGGSGSL | 242 | AKSIGTGSAYIMGAGL | 243 |
| 302.1 | GFSLSSYA | 244 | IGYSGNS | 245 | ARGGYSDDYTPFDL | 246 |
| 316.2 | GFSLSSYH | 247 | INNNDNP | 248 | ARAAGNYYVGALNL | 249 |
| 324.4 | GFSPSSYN | 250 | ISTSGNT | 251 | ARGSYVAYNAWDL | 252 |
| 331.4 | GFSLSSYH | 253 | INNYGAT | 254 | ARSPGIPGYNL | 255 |
| 339.4 | GFSLSSYY | 256 | IYGGSGRT | 257 | ARGYYDGSIYFSIYLDL | 258 |
| 340.6 | GFTISSDYW | 259 | IRDVGGGHT | 260 | ARDNDGDWFYFDL | 261 |
| 345.1 | GFTISSDYW | 262 | IRDVGGGDT | 263 | ARDNDGDWFYFDL | 264 |

TABLE 13-continued

Heavy Chain Variable Domain CDR Sequences

| Clone ID | CDR1 | SEQ ID NO | CDR2 | SEQ ID NO | CDR3 | SEQ ID NO |
|---|---|---|---|---|---|---|
| 347.3 | GIDLSTYA | 265 | IGSSGGA | 266 | AVSLYTYDDYADYFL | 267 |
| 350.1 | GFSFSNSYY | 268 | IYAGSSGFT | 269 | ARDRGYYTGYAGYGYGMDL | 270 |

TABLE 14

Heavy Chain Variable Domain Framework Regions 1 and 2 Sequences

| Clone ID | FR1 | SEQ ID NO. | FR2 | SEQ ID NO. |
|---|---|---|---|---|
| 3.4 | QSLEESGGGLVTPGGTLTLTCRVS | 451 | MGWVRQAPGEGLEWIGT | 452 |
| 15.1 | QSVKESGGRLVTPGTPLTLTCTVS | 453 | VSWVRQAPGKGLEWIGI | 454 |
| 21.4 | QSVKESEGRLIRPGGSLTLTCTVS | 455 | MGWVRQAPGEGLVWIAT | 456 |
| 30.2 | QEQLVESGGGLVQPEGSLTLTCTAS | 457 | MCWVRQAPGKGLEWIGC | 458 |
| 41.1 | QSVEESGGRLVKPGTPLTLTCTAS | 459 | MSWVRQAPGKGLEWIGV | 460 |
| 44.3 | QSLEESGGRLVTPGTPLTLTCTAS | 461 | MGWVRQAPGKGLEWIGI | 462 |
| 57.4 | QSLEESGGGLVKPGGTLTLTCTAS | 463 | MSWVRQAPGKGLEWIAS | 464 |
| 58.5 | QSLEESGGRLVTPGGSLTLTCTVS | 465 | VSWVRQAPGKGLEWIGI | 466 |
| 60.6 | QSVKESGRDLVKPGASLTLTCTAS | 467 | MCWVRQAPGKGLEWIAC | 468 |
| 62.5 | QSVKESEGDLVKPGASLTPTCTAS | 469 | MCWVRQAPGKGLELIAC | 470 |
| 70.7 | QSVEESRGRLVTPGTPLTLTCTAS | 471 | MIWVRQAPGKGLEWIGY | 472 |
| 76.3 | QSVEESGGDLVKPGASLTPTCTAS | 473 | MCWVRQAPGKGLELIAC | 474 |
| 90.4 | QSLEESGGGLVKPGGTLTLTCTVS | 475 | MGWVRQAPGKGLEWIGT | 476 |
| 117.8 | QSLEESGGDLVKPGASLTLTCTAS | 477 | MCWVRQAPGKGLEWIVC | 478 |
| 124.4 | QSLEESGGRLVTPGTPLTLTCTVS | 479 | MDWVRQAPGEGLEWIGY | 480 |
| 202.3 | QSLEESGGGLVKPGGTLTLTCTAS | 481 | MCWVRQAPGKGLEWIAC | 482 |
| 203.5 | QSVKESEGRLVTPGTPLTLTCTVS | 483 | MDWVRQAPGEGLEWIGY | 484 |
| 210.4 | QSVEESGGRLVTPGTPLTLTCTVS | 485 | MSWVRQAPGKGLEWIGY | 486 |
| 212.6 | QSLEESGGRLVTPGTPLTLTCTVS | 487 | MSWVRQAPGKGLEWIGI | 488 |
| 216.5 | QSVKESGGGLVKPGGTLTLTCTAS | 489 | MCWVRQAPGKGLEWIAC | 490 |
| 223.4 | QSLEESGGRLVTPGTPLTLTCTVS | 491 | VSWVRQAPGKGLEWIGI | 492 |
| 228.8 | QSVKESGGRLVTPGTALTLTCTVS | 493 | MSWVRQAPGKGLEWIGY | 494 |
| 230.7 | QSVEESGGRLVTPGTPLTLTCTGS | 495 | MAWVRQAPGKGLEWIGI | 496 |
| 240.8 | QSVEESGGGLVTPGGTLTLTCGVS | 497 | MGWVRQAPGEGLEWIGT | 498 |
| 247.8 | QSVKESEGDLVKPGASLTPTCTAS | 499 | MCWVRQAPGKGLELIAC | 500 |
| 250.5 | QSLEESGGGLVTPGGTLTLTCRVS | 501 | MGWVRQAPGEGLEWIGT | 502 |
| 269.6 | QSLEESGGRLVTPGTPLTLTCTVS | 503 | MGWVRQGPGKGLEWIGF | 504 |
| 270.7 | QSVEESGGRLVTPGTPLALTCTAS | 505 | MIWVRQAPGKGLEWIGY | 506 |
| 271.1 | EQLVESGGRLVTPGTPLTLTCTVS | 507 | MSWVRQAPGKGLEWIGY | 508 |
| 272.7 | QSLEESGGGLVQPGGSLKLSCKAS | 509 | MSWVRQAPGKGLEWIGY | 510 |
| 275.2 | QSVEESGGGLVKPGGTLTLTCTAS | 511 | MCWVRQAPGKGLEWIAC | 512 |
| 276.10 | QSLEESGGDLVQPEGSLTLTCTAS | 513 | MCWVRQAPGTGLEWIAC | 514 |
| 283.7 | QSVEESRGRLVTPGTPLTLTCTVS | 515 | MSWVRQAPGKGLEWIGY | 516 |
| 289.3 | QSLEESGGRLVTPGTPLTLTCTGS | 517 | MAWVRQAPGKGLEWIGI | 518 |
| 292.1 | QSVKESEGRLVTPGTPLTLTCTVS | 519 | VSWVRQAPGKGLEWIGY | 520 |
| 295.5 | QSLEESGGGLVQPEGSRTFTCTAS | 521 | MCWVRQAPGKGLERIAC | 522 |
| 302.1 | QSVKESGGRLVTPGTPLTLTCTVS | 523 | MSWVRQAPGKGLEWIGI | 524 |
| 316.2 | QSVKESEGRLVTPGTPLTLTCTAS | 525 | MIWVRQAPGKGLEWIGY | 526 |

TABLE 14-continued

Heavy Chain Variable Domain Framework Regions 1 and 2 Sequences

| Clone ID | FR1 | SEQ ID NO. | FR2 | SEQ ID NO. |
|---|---|---|---|---|
| 324.4 | QSVKESEGRLVTPGTPLTLTCTVS | 527 | MGWVRQAPGEGLEWIGY | 528 |
| 331.4 | QSLEESGGRLVTPGTPLTLTCTVS | 529 | MGWVRQAPGKGLEYIGI | 530 |
| 339.4 | QSVEESGGRLVTPGTPLTLTCTVS | 531 | MSWVRQAPGKGLEWIGV | 532 |
| 340.6 | QSVKESEGGLVKPGGTLTLTCTAS | 533 | MCWVRQAPGKGLEWIAC | 534 |
| 345.1 | QSLEESGGGLVKPGGTLTLTCTAS | 535 | MCWVRQAPGKGLEWIAC | 536 |
| 347.3 | QSLEESEGRLVTPGTPLTLTCTVS | 537 | MNWVRQAPGKGLEWIGI | 538 |
| 350.1 | QSLEESGGDLVKPGASLTLTCTAS | 539 | MCWVRQAPGKGLEWIVC | 540 |

TABLE 15

Heavy Chain Variable Domain Framework Regions 3 and 4 Sequences

| Clone ID | FR3 | SEQ ID NO. | FR4 | SEQ ID NO. |
|---|---|---|---|---|
| 3.4 | HYATWAKGRFTISKTSTTVDLKITSPTSADTATYFC | 541 | WGPGTLVTISS | 542 |
| 15.1 | YYANWAKGRFTISKTSTTVDLKITTPTTEDTATYFC | 543 | WGPGTLVTVSS | 544 |
| 21.4 | YYANWAKGRFTISKTSTTVDLKITSLTTEDTATYFC | 545 | WGPGTLVTISS | 546 |
| 30.2 | TYFANWAKGRFTISKASSPTVTLQMTSLTAADTATYFC | 547 | WGPGTLVTVSS | 548 |
| 41.1 | YYAAWAKGRFTLSRTSTTLDLKMTSPTTEDTATYFC | 549 | WGPGTLVTVSS | 550 |
| 44.3 | YHASWVKGRFTISKTSTTSVDLKMTSLTTEDTATYFC | 551 | WGPGTLVTVSS | 552 |
| 57.4 | WYASWAKGRFTVSKTSSTTVTLQMTSLTAADTATYFCA | 553 | WGPGTLVTISS | 554 |
| 58.5 | YYASWAKGRFTISKTSTTVDLKITSLTTEDTATYFC | 555 | WGPGTLVTISS | 556 |
| 60.6 | YYASWAKGRFTISKASSTTVTLQMASLAAADTATYFC | 557 | WGPGTLVTVSS | 558 |
| 62.5 | WYASWAKGRFTISKTSSTTVTLQMTSLTAADTATYFCA | 559 | WGPGTLVTVSS | 560 |
| 70.7 | YYATWAKGRFTISRTSTTVALKITSPTTEDSATYFC | 561 | WGPGTLVTVSS | 562 |
| 76.3 | WYASWAKGRFTISKSSSTTVTLQMTSLTAADTATYFCA | 563 | WGPGTLVTISS | 564 |
| 90.4 | YYATWAKGRFTVSKTSSTTMDLRIARLTTEDTATYFC | 565 | WGPGTLVTVSS | 566 |
| 117.8 | YYANWAKGRFTVSKTSSTTVTLQMTSLTAADTATYFC | 567 | WGPGTLVTISS | 568 |
| 124.4 | FYASWAKGRFTISKTSSTTVDLRITSPTTEDTAAYFC | 569 | WGPGTLVTVSS | 570 |
| 202.3 | FYASWAEGRFTISRTSSTTVTLQMTSLAAADTAIYYC | 571 | WGPGTLVTVSS | 572 |
| 203.5 | YYASWAKGRFTISRTSTTVDLQITGPTTEDTATYFC | 573 | WGQGTLVTVSS | 574 |
| 210.4 | YYASWAKGRFAISKTSTTVDLKITSPTTEDTATYFC | 575 | WGQGTLVTVSS | 576 |
| 212.6 | YYASWAKGRFTISKTSTTVDLKITSPTTEDTATYFC | 577 | WGPGTLVTVSS | 578 |
| 216.5 | FYASWAEGRFTISRTSSTTVTLQMTSLAAADTAIYYC | 579 | WGPGTLVTISS | 580 |
| 223.4 | YYANWAKGRFTISKTSTTVDLKITSLTIEDTATYFC | 581 | WGPGTLVTISS | 582 |
| 228.8 | SYASWVNGPFAISKTSTTVDLKITSPTTEDTATYFC | 583 | WGPGTLVTISS | 584 |
| 230.7 | SYASWAKGRFTISKTSTTVDLKITSPTTEDTATYFC | 585 | WGPGTLVTISS | 586 |
| 240.8 | HYATWAKGRFTISKTSTTVDLKITSPTSADTATYFC | 587 | WGPGTLVTISS | 588 |
| 247.8 | WYASWAKGRFTISKSSSTTVTLQMTSLTAADTATYFCA | 589 | WGPGTLVTISS | 590 |
| 250.5 | HYATWAKGRFTISKASTTVDLKITSPTSADTATYFC | 591 | WGPGTLVTISS | 592 |
| 269.6 | YYANWAKGRFTISKTSTTVDLKITSPIIEDTATYFC | 593 | WGPGTLVTISS | 594 |
| 270.7 | YYATWAKGRFTISRTSTTVALKITSPTTEDTATYFC | 595 | WGPGTLVTISS | 596 |
| 271.1 | DYASWAKGRFIISKTSTTVDLKITSPTTADTATYFC | 597 | WGPGTLVTVSS | 598 |
| 272.7 | YYASWVNGRFTISSHNAQNTLYLQLNSLTAADTATYFC | 599 | WGPGTLVTVSS | 600 |
| 275.2 | FYASWAKGRFTISRTSSTTVTLQMTSLAAADTATYYC | 601 | WGPGTLVTISS | 602 |
| 276.10 | YYANWAKGRFTISGTSSTTVTLQVTSLTAADTATYFC | 603 | WGPGTLVTISS | 604 |
| 283.7 | YYASWAKGRFAISKTSTTVDLKITSPTTEDTATYFC | 605 | WGQGTLVTVSS | 606 |

TABLE 15-continued

Heavy Chain Variable Domain
Framework Regions 3 and 4 Sequences

| Clone ID | FR3 | SEQ ID NO. | FR4 | SEQ ID NO. |
|---|---|---|---|---|
| 289.3 | SYASWAKGRFTISKTSTT VDLKITSPTTEDTATYFC | 607 | WGPGTLVTSSS | 608 |
| 292.1 | DYASWVNGRFTISKTSTT VDLKITSPTTEDTAIYFC | 609 | WGPGTLVTVSS | 610 |
| 295.5 | YYADWASGRFTISKTSST TVTLQMTSLAAADTATHFC | 611 | WGPGTLVTVSS | 612 |
| 302.1 | YYASWAKGRFTISKTSTT VDLKITSPTTEDTATYFC | 613 | WGPGTLVTISS | 614 |
| 316.2 | YYATWAKGRFTISRTSTT VALKITSPTTKDTATYFC | 615 | WGPGTLVTISS | 616 |
| 324.4 | FYASWAKGRFTISKTSTT VDLRITSPTTEDTATYFC | 617 | WGPGTLVTISS | 618 |
| 331.4 | YYASWAKGRFTISRTSTT VDLKMTSLTTEDTATYFC | 619 | WGPGTLVTISS | 620 |
| 339.4 | WYASWAKGRFTISKTSTT VDLKITSPTTEDTATYFC | 621 | WGPGTLVTVSS | 622 |
| 340.6 | FYASWAEGRFTISRTSST TVTLQMTSLAAADTAIYYC | 623 | WGPGTLVTISS | 624 |
| 345.1 | FYASWAKGRFTISRTSST TVTLQMTSLAAADTATYYC | 625 | WGPGTLVTISS | 626 |
| 347.3 | YYASWAKGRCTISKTSTT VDLKITSPTTEDTATYFC | 627 | WGPGTLVTISS | 628 |
| 350.1 | YYANWAKGRFTVSKTSST TVTLQMTSLTAADTATYFC | 629 | WGPGTLVTISS | 630 |

What is claimed is:

1. A recombinant antigen binding protein comprising a heavy chain variable region comprising a CDR1, CDR2 and CDR3 selected from the group consisting of:
(h-a) a CDR1 comprising SEQ ID NO:136, a CDR2 comprising SEQ ID NO:137 and a CDR3 comprising SEQ ID NO:138;
(h-b) a CDR1 comprising SEQ ID NO:139, a CDR2 comprising SEQ ID NO:140 and a CDR3 comprising SEQ ID NO:141;
(h-c) a CDR1 comprising SEQ ID NO:142, a CDR2 comprising SEQ ID NO:143 and a CDR3 comprising SEQ ID NO:144;
(h-d) a CDR1 comprising SEQ ID NO:145, a CDR2 comprising SEQ ID NO:146 and a CDR3 comprising SEQ ID NO:147;
(h-e) a CDR1 comprising SEQ ID NO:148, a CDR2 comprising SEQ ID NO:149 and a CDR3 comprising SEQ ID NO:150;
(h-f) a CDR1 comprising SEQ ID NO:151, a CDR2 comprising SEQ ID NO:152 and a CDR3 comprising SEQ ID NO:153;
(h-g) a CDR1 comprising SEQ ID NO:154, a CDR2 comprising SEQ ID NO:155 and a CDR3 comprising SEQ ID NO:156;
(h-h) a CDR1 comprising SEQ ID NO:157, a CDR2 comprising SEQ ID NO:158 and a CDR3 comprising SEQ ID NO:159;
(h-i) a CDR1 comprising SEQ ID NO:160, a CDR2 comprising SEQ ID NO:161 and a CDR3 comprising SEQ ID NO:162;
(h-j) a CDR1 comprising SEQ ID NO:163, a CDR2 comprising SEQ ID NO:164 and a CDR3 comprising SEQ ID NO:165;
(h-k) a CDR1 comprising SEQ ID NO:166, a CDR2 comprising SEQ ID NO:167 and a CDR3 comprising SEQ ID NO:168;
(h-l) a CDR1 comprising SEQ ID NO:169, a CDR2 comprising SEQ ID NO:170 and a CDR3 comprising SEQ ID NO:171;
(h-m) a CDR1 comprising SEQ ID NO:172, a CDR2 comprising SEQ ID NO:173 and a CDR3 comprising SEQ ID NO:174;
(h-n) a CDR1 comprising SEQ ID NO:175, a CDR2 comprising SEQ ID NO:176 and a CDR3 comprising SEQ ID NO:177;
(h-o) a CDR1 comprising SEQ ID NO:178, a CDR2 comprising SEQ ID NO:179 and a CDR3 comprising SEQ ID NO:180;
(h-p) a CDR1 comprising SEQ ID NO:181, a CDR2 comprising SEQ ID NO:182 and a CDR3 comprising SEQ ID NO:183;
(h-q) a CDR1 comprising SEQ ID NO:184, a CDR2 comprising SEQ ID NO:185 and a CDR3 comprising SEQ ID NO:186;
(h-r) a CDR1 comprising SEQ ID NO:187, a CDR2 comprising SEQ ID NO:188 and a CDR3 comprising SEQ ID NO:189;
(h-s) a CDR1 comprising SEQ ID NO:190, a CDR2 comprising SEQ ID NO:191 and a CDR3 comprising SEQ ID NO:192;
(h-t) a CDR1 comprising SEQ ID NO:193, a CDR2 comprising SEQ ID NO:194 and a CDR3 comprising SEQ ID NO:195;
(h-u) a CDR1 comprising SEQ ID NO:196, a CDR2 comprising SEQ ID NO:197 and a CDR3 comprising SEQ ID NO:198;
(h-v) a CDR1 comprising SEQ ID NO:199, a CDR2 comprising SEQ ID NO:200 and a CDR3 comprising SEQ ID NO:201;
(h-w) a CDR1 comprising SEQ ID NO:202, a CDR2 comprising SEQ ID NO:203 and a CDR3 comprising SEQ ID NO:204;
(h-x) a CDR1 comprising SEQ ID NO:205, a CDR2 comprising SEQ ID NO:206 and a CDR3 comprising SEQ ID NO:207;
(h-y) a CDR1 comprising SEQ ID NO:208, a CDR2 comprising SEQ ID NO:209 and a CDR3 comprising SEQ ID NO:210;
(h-z) a CDR1 comprising SEQ ID NO:211, a CDR2 comprising SEQ ID NO:212 and a CDR3 comprising SEQ ID NO:213;
(h-a') a CDR1 comprising SEQ ID NO:214, a CDR2 comprising SEQ ID NO:215 and a CDR3 comprising SEQ ID NO:216;

(h-b') a CDR1 comprising SEQ ID NO:217, a CDR2 comprising SEQ ID NO:218 and a CDR3 comprising SEQ ID NO:219;
(h-c') a CDR1 comprising SEQ ID NO:220, a CDR2 comprising SEQ ID NO:221 and a CDR3 comprising SEQ ID NO:222;
(h-d') a CDR1 comprising SEQ ID NO:223, a CDR2 comprising SEQ ID NO:224 and a CDR3 comprising SEQ ID NO:225;
(h-e') a CDR1 comprising SEQ ID NO:226, a CDR2 comprising SEQ ID NO:227 and a CDR3 comprising SEQ ID NO:228;
(h-f') a CDR1 comprising SEQ ID NO:229, a CDR2 comprising SEQ ID NO:230 and a CDR3 comprising SEQ ID NO:231;
(h-g') a CDR1 comprising SEQ ID NO:232, a CDR2 comprising SEQ ID NO:233 and a CDR3 comprising SEQ ID NO:234;
(h-h') a CDR1 comprising SEQ ID NO:235, a CDR2 comprising SEQ ID NO:236 and a CDR3 comprising SEQ ID NO:237;
(h-i') a CDR1 comprising SEQ ID NO:238, a CDR2 comprising SEQ ID NO:239 and a CDR3 comprising SEQ ID NO:240;
(h-j') a CDR1 comprising SEQ ID NO:241, a CDR2 comprising SEQ ID NO:242 and a CDR3 comprising SEQ ID NO:243;
(h-k') a CDR1 comprising SEQ ID NO:244, a CDR2 comprising SEQ ID NO:245 and a CDR3 comprising SEQ ID NO:246;
(h-l') a CDR1 comprising SEQ ID NO:247, a CDR2 comprising SEQ ID NO:248 and a CDR3 comprising SEQ ID NO:249;
(h-m') a CDR1 comprising SEQ ID NO:250, a CDR2 comprising SEQ ID NO:251 and a CDR3 comprising SEQ ID NO:252;
(h-n') a CDR1 comprising SEQ ID NO:253, a CDR2 comprising SEQ ID NO:254 and a CDR3 comprising SEQ ID NO:255;
(h-o') a CDR1 comprising SEQ ID NO:256, a CDR2 comprising SEQ ID NO:257 and a CDR3 comprising SEQ ID NO:258;
(h-p') a CDR1 comprising SEQ ID NO:259, a CDR2 comprising SEQ ID NO:260 and a CDR3 comprising SEQ ID NO:261;
(h-q') a CDR1 comprising SEQ ID NO:262, a CDR2 comprising SEQ ID NO:263 and a CDR3 comprising SEQ ID NO:264;
(h-r') a CDR1 comprising SEQ ID NO:265, a CDR2 comprising SEQ ID NO:266 and a CDR3 comprising SEQ ID NO:267; and
(h-s') a CDR1 comprising SEQ ID NO:268, a CDR2 comprising SEQ ID NO:269 and a CDR3 comprising SEQ ID NO:270;
wherein the antigen binding protein specifically binds to CMV.

2. The recombinant antigen binding protein of claim 1 wherein the CDR1, CDR2 and CDR3 are selected from the group consisting of:
(h-b) a CDR1 comprising SEQ ID NO:139, a CDR2 comprising SEQ ID NO:140 and a CDR3 comprising SEQ ID NO:141;
(h-g) a CDR1 comprising SEQ ID NO:154, a CDR2 comprising SEQ ID NO:155 and a CDR3 comprising SEQ ID NO:156;
(h-k) a CDR1 comprising SEQ ID NO:166, a CDR2 comprising SEQ ID NO:167 and a CDR3 comprising SEQ ID NO:168;
(h-o) a CDR1 comprising SEQ ID NO:178, a CDR2 comprising SEQ ID NO:179 and a CDR3 comprising SEQ ID NO:180;
(h-u) a CDR1 comprising SEQ ID NO:196, a CDR2 comprising SEQ ID NO:197 and a CDR3 comprising SEQ ID NO:198;
(h-b') a CDR1 comprising SEQ ID NO:217, a CDR2 comprising SEQ ID NO:218 and a CDR3 comprising SEQ ID NO:219;
(h-d') a CDR1 comprising SEQ ID NO:223, a CDR2 comprising SEQ ID NO:224 and a CDR3 comprising SEQ ID NO:225;
(h-f') a CDR1 comprising SEQ ID NO:229, a CDR2 comprising SEQ ID NO:230 and a CDR3 comprising SEQ ID NO:231;
(h-l') a CDR1 comprising SEQ ID NO:247, a CDR2 comprising SEQ ID NO:248 and a CDR3 comprising SEQ ID NO:249;
(h-m') a CDR1 comprising SEQ ID NO:250, a CDR2 comprising SEQ ID NO:251 and a CDR3 comprising SEQ ID NO:252; and
(h-r') a CDR1 comprising SEQ ID NO:265, a CDR2 comprising SEQ ID NO:266 and a CDR3 comprising SEQ ID NO:267;
wherein the antigen binding protein neutralizes CMV.

3. The recombinant antigen binding protein of claim 1, wherein the antigen binding protein is a humanized antibody.

4. The recombinant antigen binding protein of claim 1 wherein the heavy chain variable region domain is selected from the group consisting of SEQ ID NOs:633, 634, 637, 638, 641, 644 and 645.

5. The recombinant antigen binding protein of claim 1 wherein the heavy chain variable region further comprises a framework region (FR) 1, FR2, FR3 and FR4 selected from the group consisting of:
(a) the CDR1, CDR2 and CDR 3 of (h-a) and a FR1 comprising SEQ ID NO:451, a FR2 comprising SEQ ID NO:452, a FR3 comprising SEQ ID NO:541 and a FR4 comprising SEQ ID NO:542;
(b) the CDR1, CDR2 and CDR 3 of (h-b) and a FR1 comprising SEQ ID NO:453, a FR2 comprising SEQ ID NO:454, a FR3 comprising SEQ ID NO:543 and a FR4 comprising SEQ ID NO:544;
(c) the CDR1, CDR2 and CDR 3 of (h-c) and a FR1 comprising SEQ ID NO:455, a FR2 comprising SEQ ID NO:456, a FR3 comprising SEQ ID NO:545 and a FR4 comprising SEQ ID NO:546;
(d) the CDR1, CDR2 and CDR 3 of (h-d) and a FR1 comprising SEQ ID NO:457, a FR2 comprising SEQ ID NO:458, a FR3 comprising SEQ ID NO:547 and a FR4 comprising SEQ ID NO:548;
(e) the CDR1, CDR2 and CDR 3 of (h-e) and a FR1 comprising SEQ ID NO:459, a FR2 comprising SEQ ID NO:460, a FR3 comprising SEQ ID NO:549 and a FR4 comprising SEQ ID NO:550;
(f) the CDR1, CDR2 and CDR 3 of (h-f) and a FR1 comprising SEQ ID NO:461, a FR2 comprising SEQ ID NO:462, a FR3 comprising SEQ ID NO:551 and a FR4 comprising SEQ ID NO:552;
(g) the CDR1, CDR2 and CDR 3 of (h-g) and a FR1 comprising SEQ ID NO:463, a FR2 comprising SEQ ID NO:464 a FR3 comprising SEQ ID NO:553 and a FR4 comprising SEQ ID NO:554;

(h) the CDR1, CDR2 and CDR 3 of (h-h) and a FR1 comprising SEQ ID NO:465, a FR2 comprising SEQ ID NO:466, a FR3 comprising SEQ ID NO:555 and a FR4 comprising SEQ ID NO:556;
(i) the CDR1, CDR2 and CDR 3 of (h-i) and a FR1 comprising SEQ ID NO:467, a FR2 comprising SEQ ID NO:468, a FR3 comprising SEQ ID NO:557 and a FR4 comprising SEQ ID NO: 558
(j) the CDR1, CDR2 and CDR 3 of (h-j) and a FR1 comprising SEQ ID NO:469, a FR2 comprising SEQ ID NO:470 a FR3 comprising SEQ ID NO:559 and a FR4 comprising SEQ ID NO:560;
(k) the CDR1, CDR2 and CDR 3 of (h-k) and a FR1 comprising SEQ ID NO:471, a FR2 comprising SEQ ID NO:472, a FR3 comprising SEQ ID NO:561 and a FR4 comprising SEQ ID NO:562;
(l) the CDR1, CDR2 and CDR 3 of (h-l) and a FR1 comprising SEQ ID NO:473, a FR2 comprising SEQ ID NO:474, a FR3 comprising SEQ ID NO:563 and a FR4 comprising SEQ ID NO:564;
(m) the CDR1, CDR2 and CDR 3 of (h-m) and a FR1 comprising SEQ ID NO:475, a FR2 comprising SEQ ID NO:476, a FR3 comprising SEQ ID NO:565 and a FR4 comprising SEQ ID NO:566;
(n) the CDR1, CDR2 and CDR 3 of (h-n) and a FR1 comprising SEQ ID NO:477, a FR2 comprising SEQ ID NO:478, a FR3 comprising SEQ ID NO:567 and a FR4 comprising SEQ ID NO:568;
(o) the CDR1, CDR2 and CDR 3 of (h-o) and a FR1 comprising SEQ ID NO:479, a FR2 comprising SEQ ID NO:480, a FR3 comprising SEQ ID NO:569 and a FR4 comprising SEQ ID NO:570;
(p) the CDR1, CDR2 and CDR 3 of (h-p) and a FR1 comprising SEQ ID NO:481, a FR2 comprising SEQ ID NO:482, a FR3 comprising SEQ ID NO:571 and a FR4 comprising SEQ ID NO: 572
(q) the CDR1, CDR2 and CDR 3 of (h-q) and a FR1 comprising SEQ ID NO:483, a FR2 comprising SEQ ID NO:484, a FR3 comprising SEQ ID NO:573 and a FR4 comprising SEQ ID NO:574;
(r) the CDR1, CDR2 and CDR 3 of (h-r) and a FR1 comprising SEQ ID NO:485, a FR2 comprising SEQ ID NO:486, a FR3 comprising SEQ ID NO:575 and a FR4 comprising SEQ ID NO:576;
(s) the CDR1, CDR2 and CDR 3 of (h-s) and a FR1 comprising SEQ ID NO:487, a FR2 comprising SEQ ID NO:488, a FR3 comprising SEQ ID NO:577 and a FR4 comprising SEQ ID NO:578;
(t) the CDR1, CDR2 and CDR 3 of (h-t) and a FR1 comprising SEQ ID NO:489, a FR2 comprising SEQ ID NO:490, a FR3 comprising SEQ ID NO:579 and a FR4 comprising SEQ ID NO:580;
(u) the CDR1, CDR2 and CDR 3 of (h-u) and a FR1 comprising SEQ ID NO:491, a FR2 comprising SEQ ID NO:492, a FR3 comprising SEQ ID NO:581 and a FR4 comprising SEQ ID NO:582;
(v) the CDR1, CDR2 and CDR 3 of (h-v) and a FR1 comprising SEQ ID NO:493, a FR2 comprising SEQ ID NO:494, a FR3 comprising SEQ ID NO:583 and a FR4 comprising SEQ ID NO:584;
(w) the CDR1, CDR2 and CDR 3 of (h-w) and a FR1 comprising SEQ ID NO:495, a FR2 comprising SEQ ID NO:496, a FR3 comprising SEQ ID NO:585 and a FR4 comprising SEQ ID NO: 586
(x) the CDR1, CDR2 and CDR 3 of (h-x) and a FR1 comprising SEQ ID NO:497, a FR2 comprising SEQ ID NO:498, a FR3 comprising SEQ ID NO:587 and a FR4 comprising SEQ ID NO:588;
(y) the CDR1, CDR2 and CDR 3 of (h-y) and a FR1 comprising SEQ ID NO:499, a FR2 comprising SEQ ID NO:500, a FR3 comprising SEQ ID NO:589 and a FR4 comprising SEQ ID NO:590;
(z) the CDR1, CDR2 and CDR 3 of (h-z) and a FR1 comprising SEQ ID NO:501, a FR2 comprising SEQ ID NO:502, a FR3 comprising SEQ ID NO:591 and a FR4 comprising SEQ ID NO:592;
(a') the CDR1, CDR2 and CDR 3 of (h-a') and a FR1 comprising SEQ ID NO:503, a FR2 comprising SEQ ID NO:504, a FR3 comprising SEQ ID NO:593 and a FR4 comprising SEQ ID NO:594;
(b') the CDR1, CDR2 and CDR 3 of (h-b') and a FR1 comprising SEQ ID NO:505, a FR2 comprising SEQ ID NO:506, a FR3 comprising SEQ ID NO:595 and a FR4 comprising SEQ ID NO:596;
(c') the CDR1, CDR2 and CDR 3 of (h-c') and a FR1 comprising SEQ ID NO:507, a FR2 comprising SEQ ID NO:508, a FR3 comprising SEQ ID NO:597 and a FR4 comprising SEQ ID NO:598;
(d') the CDR1, CDR2 and CDR 3 of (h-d') and a FR1 comprising SEQ ID NO:509, a FR2 comprising SEQ ID NO:510, a FR3 comprising SEQ ID NO:599 and a FR4 comprising SEQ ID NO:600;
(e') the CDR1, CDR2 and CDR 3 of (h-e') and a FR1 comprising SEQ ID NO:511, a FR2 comprising SEQ ID NO:512, a FR3 comprising SEQ ID NO:601 and a FR4 comprising SEQ ID NO:602;
(f') the CDR1, CDR2 and CDR 3 of (h-f') and a FR1 comprising SEQ ID NO:513, a FR2 comprising SEQ ID NO:514, a FR3 comprising SEQ ID NO:603 and a FR4 comprising SEQ ID NO:604;
(g') the CDR1, CDR2 and CDR 3 of (h-g') and a FR1 comprising SEQ ID NO:515, a FR2 comprising SEQ ID NO:516, a FR3 comprising SEQ ID NO:605 and a FR4 comprising SEQ ID NO:606;
(h') the CDR1, CDR2 and CDR 3 of (h-h') and a FR1 comprising SEQ ID NO:517, a FR2 comprising SEQ ID NO:518, a FR3 comprising SEQ ID NO:607 and a FR4 comprising SEQ ID NO:608;
(i') the CDR1, CDR2 and CDR 3 of (h-i') and a FR1 comprising SEQ ID NO:519, a FR2 comprising SEQ ID NO:520, a FR3 comprising SEQ ID NO:609 and a FR4 comprising SEQ ID NO:610;
(j') the CDR1, CDR2 and CDR 3 of (h-j') and a FR1 comprising SEQ ID NO:521, a FR2 comprising SEQ ID NO:522 a FR3 comprising SEQ ID NO:611 and a FR4 comprising SEQ ID NO:612;
(k') the CDR1, CDR2 and CDR 3 of (h-k) and a FR1 comprising SEQ ID NO:523, a FR2 comprising SEQ ID NO:524, a FR3 comprising SEQ ID NO:613 and a FR4 comprising SEQ ID NO:614;
(l') the CDR1, CDR2 and CDR 3 of (h-l') and a FR1 comprising SEQ ID NO:525, a FR2 comprising SEQ ID NO:526, a FR3 comprising SEQ ID NO:615 and a FR4 comprising SEQ ID NO:616;
(m') the CDR1, CDR2 and CDR 3 of (h-m') and a FR1 comprising SEQ ID NO:527, a FR2 comprising SEQ ID NO:528, a FR3 comprising SEQ ID NO:617 and a FR4 comprising SEQ ID NO:618;
(n') the CDR1, CDR2 and CDR 3 of (h-n') and a FR1 comprising SEQ ID NO:529, a FR2 comprising SEQ ID NO:530, a FR3 comprising SEQ ID NO:619 and a FR4 comprising SEQ ID NO:620;

(o') the CDR1, CDR2 and CDR 3 of (h-o') and a FR1 comprising SEQ ID NO:531, a FR2 comprising SEQ ID NO:532, a FR3 comprising SEQ ID NO:621 and a FR4 comprising SEQ ID NO:622;

(p') the CDR1, CDR2 and CDR 3 of (h-p') and a FR1 comprising SEQ ID NO:533, a FR2 comprising SEQ ID NO:534, a FR3 comprising SEQ ID NO:623 and a FR4 comprising SEQ ID NO:624;

(q') the CDR1, CDR2 and CDR 3 of (h-q') and a FR1 comprising SEQ ID NO:535, a FR2 comprising SEQ ID NO:536, a FR3 comprising SEQ ID NO:625 and a FR4 comprising SEQ ID NO:626;

(r') the CDR1, CDR2 and CDR 3 of (h-r') and a FR1 comprising SEQ ID NO:537, a FR2 comprising SEQ ID NO:538, a FR3 comprising SEQ ID NO:627 and a FR4 comprising SEQ ID NO:628; and (s') the CDR1, CDR2 and CDR 3 of (h-s') and a FR1 comprising SEQ ID NO:539, a FR2 comprising SEQ ID NO:540, a FR3 comprising SEQ ID NO:629 and a FR4 comprising SEQ ID NO:630.

6. A recombinant antigen binding protein comprising a light chain variable region and a heavy chain variable region selected from the group consisting of:

(a) a light chain variable region comprising a complementarity determining region (CDR) 1 comprising SEQ ID NO:1, a CDR2 comprising SEQ ID NO:2 and a CDR3 comprising SEQ ID NO:3 and a heavy chain variable region comprising a CDR1 comprising SEQ ID NO:136, a CDR2 comprising SEQ ID NO:137 and a CDR3 comprising SEQ ID NO:138;

(b) a light chain variable region comprising a CDR1 comprising SEQ ID NO:4, a CDR2 comprising SEQ ID NO:5 and a CDR3 comprising SEQ ID NO:6 and a heavy chain variable region comprising a CDR1 comprising SEQ ID NO:139, a CDR2 comprising SEQ ID NO:140 and a CDR3 comprising SEQ ID NO:141;

(c) a light chain variable region comprising a CDR1 comprising SEQ ID NO:7, a CDR2 comprising SEQ ID NO:8 and a CDR3 comprising SEQ ID NO:9 and a heavy chain variable region comprising a CDR1 comprising SEQ ID NO:142, a CDR2 comprising SEQ ID NO:143 and a CDR3 comprising SEQ ID NO:144;

(d) a light chain variable region comprising a CDR1 comprising SEQ ID NO:10, a CDR2 comprising SEQ ID NO:11 and a CDR3 comprising SEQ ID NO:12 and a heavy chain variable region comprising a CDR1 comprising SEQ ID NO:145, a CDR2 comprising SEQ ID NO:146 and a CDR3 comprising SEQ ID NO:147;

(e) a light chain variable region comprising a CDR1 comprising SEQ ID NO:13, a CDR2 comprising SEQ ID NO:14 and a CDR3 comprising SEQ ID NO:15 and a heavy chain variable region comprising a CDR1 comprising SEQ ID NO:148, a CDR2 comprising SEQ ID NO:149 and a CDR3 comprising SEQ ID NO:150;

(f) a light chain variable region comprising a CDR1 comprising SEQ ID NO:16, a CDR2 comprising SEQ ID NO:17 and a CDR3 comprising SEQ ID NO:18 and a heavy chain variable region comprising a CDR1 comprising SEQ ID NO:151, a CDR2 comprising SEQ ID NO:152 and a CDR3 comprising SEQ ID NO:153;

(g) a light chain variable region comprising a CDR1 comprising SEQ ID NO:19, a CDR2 comprising SEQ ID NO:20 and a CDR3 comprising SEQ ID NO:21 and a heavy chain variable region comprising a CDR1 comprising SEQ ID NO:154, a CDR2 comprising SEQ ID NO:155 and a CDR3 comprising SEQ ID NO:156;

(h) a light chain variable region comprising a CDR1 comprising SEQ ID NO:22, a CDR2 comprising SEQ ID NO:23 and a CDR3 comprising SEQ ID NO:24 and a heavy chain variable region comprising a CDR1 comprising SEQ ID NO:157, a CDR2 comprising SEQ ID NO:158 and a CDR3 comprising SEQ ID NO:159;

(i) a light chain variable region comprising a CDR1 comprising SEQ ID NO:25, a CDR2 comprising SEQ ID NO:26 and a CDR3 comprising SEQ ID NO:27 and a heavy chain variable region comprising a CDR1 comprising SEQ ID NO:160, a CDR2 comprising SEQ ID NO:161 and a CDR3 comprising SEQ ID NO:162;

(j) a light chain variable region comprising a CDR1 comprising SEQ ID NO:28, a CDR2 comprising SEQ ID NO:29 and a CDR3 comprising SEQ ID NO:30 and a heavy chain variable region comprising a CDR1 comprising SEQ ID NO:163, a CDR2 comprising SEQ ID NO:164 and a CDR3 comprising SEQ ID NO:165;

(k) a light chain variable region comprising a CDR1 comprising SEQ ID NO:31, a CDR2 comprising SEQ ID NO:32 and a CDR3 comprising SEQ ID NO:33 and a heavy chain variable region comprising a CDR1 comprising SEQ ID NO:166, a CDR2 comprising SEQ ID NO:167 and a CDR3 comprising SEQ ID NO:168;

(l) a light chain variable region comprising a CDR1 comprising SEQ ID NO:34, a CDR2 comprising SEQ ID NO:35 and a CDR3 comprising SEQ ID NO:36 and a heavy chain variable region comprising a CDR1 comprising SEQ ID NO:169, a CDR2 comprising SEQ ID NO:170 and a CDR3 comprising SEQ ID NO:171;

(m) a light chain variable region comprising a CDR1 comprising SEQ ID NO:37, a CDR2 comprising SEQ ID NO:38 and a CDR3 comprising SEQ ID NO:39 and a heavy chain variable region comprising a CDR1 comprising SEQ ID NO:172, a CDR2 comprising SEQ ID NO:173 and a CDR3 comprising SEQ ID NO:174;

(n) a light chain variable region comprising a CDR1 comprising SEQ ID NO:40, a CDR2 comprising SEQ ID NO:41 and a CDR3 comprising SEQ ID NO:42 and a heavy chain variable region comprising a CDR1 comprising SEQ ID NO:175, a CDR2 comprising SEQ ID NO:176 and a CDR3 comprising SEQ ID NO:177;

(o) a light chain variable region comprising a CDR1 comprising SEQ ID NO:43, a CDR2 comprising SEQ ID NO:44 and a CDR3 comprising SEQ ID NO:45 and a heavy chain variable region comprising a CDR1 comprising SEQ ID NO:178, a CDR2 comprising SEQ ID NO:179 and a CDR3 comprising SEQ ID NO:180;

(p) a light chain variable region comprising a CDR1 comprising SEQ ID NO:46, a CDR2 comprising SEQ ID NO:47 and a CDR3 comprising SEQ ID NO:48 and a heavy chain variable region comprising a CDR1 comprising SEQ ID NO:181, a CDR2 comprising SEQ ID NO:182 and a CDR3 comprising SEQ ID NO:183;

(q) a light chain variable region comprising a CDR1 comprising SEQ ID NO:49, a CDR2 comprising SEQ ID NO:50 and a CDR3 comprising SEQ ID NO:51 and a heavy chain variable region comprising a CDR1 comprising SEQ ID NO:184, a CDR2 comprising SEQ ID NO:185 and a CDR3 comprising SEQ ID NO:186;

(r) a light chain variable region comprising a CDR1 comprising SEQ ID NO:52, a CDR2 comprising SEQ ID NO:53 and a CDR3 comprising SEQ ID NO:54 and a heavy chain variable region comprising a CDR1 comprising SEQ ID NO:187, a CDR2 comprising SEQ ID NO:188 and a CDR3 comprising SEQ ID NO:189;

(s) a light chain variable region comprising a CDR1 comprising SEQ ID NO:55, a CDR2 comprising SEQ ID NO:56 and a CDR3 comprising SEQ ID NO:57 and a heavy chain variable region comprising a CDR1 comprising SEQ ID NO:190, a CDR2 comprising SEQ ID NO:191 and a CDR3 comprising SEQ ID NO:192;

(t) a light chain variable region comprising a CDR1 comprising SEQ ID NO:58, a CDR2 comprising SEQ ID NO:59 and a CDR3 comprising SEQ ID NO:60 and a heavy chain variable region comprising a CDR1 comprising SEQ ID NO:193, a CDR2 comprising SEQ ID NO:194 and a CDR3 comprising SEQ ID NO:195;

(u) a light chain variable region comprising a CDR1 comprising SEQ ID NO:61, a CDR2 comprising SEQ ID NO:62 and a CDR3 comprising SEQ ID NO:63 and a heavy chain variable region comprising a CDR1 comprising SEQ ID NO:196, a CDR2 comprising SEQ ID NO:197 and a CDR3 comprising SEQ ID NO:198;

(v) a light chain variable region comprising a CDR1 comprising SEQ ID NO:64, a CDR2 comprising SEQ ID NO:65 and a CDR3 comprising SEQ ID NO:66 and a heavy chain variable region comprising a CDR1 comprising SEQ ID NO:199, a CDR2 comprising SEQ ID NO:200 and a CDR3 comprising SEQ ID NO:201;

(w) a light chain variable region comprising a CDR1 comprising SEQ ID NO:67, a CDR2 comprising SEQ ID NO:68 and a CDR3 comprising SEQ ID NO:69 and a heavy chain variable region comprising a CDR1 comprising SEQ ID NO:202, a CDR2 comprising SEQ ID NO:203 and a CDR3 comprising SEQ ID NO:204;

(x) a light chain variable region comprising a CDR1 comprising SEQ ID NO:70, a CDR2 comprising SEQ ID NO:71 and a CDR3 comprising SEQ ID NO:72 and a heavy chain variable region comprising a CDR1 comprising SEQ ID NO:205, a CDR2 comprising SEQ ID NO:206 and a CDR3 comprising SEQ ID NO:207;

(y) a light chain variable region comprising a CDR1 comprising SEQ ID NO:73, a CDR2 comprising SEQ ID NO:74 and a CDR3 comprising SEQ ID NO:75 and a heavy chain variable region comprising a CDR1 comprising SEQ ID NO:208, a CDR2 comprising SEQ ID NO:209 and a CDR3 comprising SEQ ID NO:210;

(z) a light chain variable region comprising a CDR1 comprising SEQ ID NO:76, a CDR2 comprising SEQ ID NO:77 and a CDR3 comprising SEQ ID NO:78 and a heavy chain variable region comprising a CDR1 comprising SEQ ID NO:211, a CDR2 comprising SEQ ID NO:212 and a CDR3 comprising SEQ ID NO:213;

(a') a light chain variable region comprising a CDR1 comprising SEQ ID NO:79, a CDR2 comprising SEQ ID NO:80 and a CDR3 comprising SEQ ID NO:81 and a heavy chain variable region comprising a CDR1 comprising SEQ ID NO:214, a CDR2 comprising SEQ ID NO:215 and a CDR3 comprising SEQ ID NO:216;

(b') a light chain variable region comprising a CDR1 comprising SEQ ID NO:82, a CDR2 comprising SEQ ID NO:83 and a CDR3 comprising SEQ ID NO:84 and a heavy chain variable region comprising a CDR1 comprising SEQ ID NO:217, a CDR2 comprising SEQ ID NO:218 and a CDR3 comprising SEQ ID NO:219;

(c') a light chain variable region comprising a CDR1 comprising SEQ ID NO:85, a CDR2 comprising SEQ ID NO:86 and a CDR3 comprising SEQ ID NO:87 and a heavy chain variable region comprising a CDR1 comprising SEQ ID NO:220, a CDR2 comprising SEQ ID NO:221 and a CDR3 comprising SEQ ID NO:222;

(d') a light chain variable region comprising a CDR1 comprising SEQ ID NO:88, a CDR2 comprising SEQ ID NO:89 and a CDR3 comprising SEQ ID NO:90 and a heavy chain variable region comprising a CDR1 comprising SEQ ID NO:223, a CDR2 comprising SEQ ID NO:224 and a CDR3 comprising SEQ ID NO:225;

(e') a light chain variable region comprising a CDR1 comprising SEQ ID NO:91, a CDR2 comprising SEQ ID NO:92 and a CDR3 comprising SEQ ID NO:93 and a heavy chain variable region comprising a CDR1 comprising SEQ ID NO:226, a CDR2 comprising SEQ ID NO:227 and a CDR3 comprising SEQ ID NO:228;

(f') a light chain variable region comprising a CDR1 comprising SEQ ID NO:94, a CDR2 comprising SEQ ID NO:95 and a CDR3 comprising SEQ ID NO:96 and a heavy chain variable region comprising a CDR1 comprising SEQ ID NO:229, a CDR2 comprising SEQ ID NO:230 and a CDR3 comprising SEQ ID NO:231;

(g') a light chain variable region comprising a CDR1 comprising SEQ ID NO:97, a CDR2 comprising SEQ ID NO:98 and a CDR3 comprising SEQ ID NO:99 and a heavy chain variable region comprising a CDR1 comprising SEQ ID NO:232, a CDR2 comprising SEQ ID NO:233 and a CDR3 comprising SEQ ID NO:234;

(h') a light chain variable region comprising a CDR1 comprising SEQ ID NO:100, a CDR2 comprising SEQ ID NO:101 and a CDR3 comprising SEQ ID NO:102 and a heavy chain variable region comprising a CDR1 comprising SEQ ID NO:235, a CDR2 comprising SEQ ID NO:236 and a CDR3 comprising SEQ ID NO:237;

(i') a light chain variable region comprising a CDR1 comprising SEQ ID NO:103, a CDR2 comprising SEQ ID NO:104 and a CDR3 comprising SEQ ID NO:105 and a heavy chain variable region comprising a CDR1 comprising SEQ ID NO:238, a CDR2 comprising SEQ ID NO:239 and a CDR3 comprising SEQ ID NO:240;

(j') a light chain variable region comprising a CDR1 comprising SEQ ID NO:106, a CDR2 comprising SEQ ID NO:107 and a CDR3 comprising SEQ ID NO:108 and a heavy chain variable region comprising a CDR1 comprising SEQ ID NO:241, a CDR2 comprising SEQ ID NO:242 and a CDR3 comprising SEQ ID NO:243;

(k') a light chain variable region comprising a CDR1 comprising SEQ ID NO:109, a CDR2 comprising SEQ ID NO:110 and a CDR3 comprising SEQ ID NO:111 and a heavy chain variable region comprising a CDR1 comprising SEQ ID NO:244, a CDR2 comprising SEQ ID NO:245 and a CDR3 comprising SEQ ID NO:246;

(l') a light chain variable region comprising a CDR1 comprising SEQ ID NO:112, a CDR2 comprising SEQ ID NO:113 and a CDR3 comprising SEQ ID NO:114 and a heavy chain variable region comprising a CDR1 comprising SEQ ID NO:247, a CDR2 comprising SEQ ID NO:248 and a CDR3 comprising SEQ ID NO:249;

(m') a light chain variable region comprising a CDR1 comprising SEQ ID NO:115, a CDR2 comprising SEQ ID NO:116 and a CDR3 comprising SEQ ID NO:117 and a heavy chain variable region comprising a CDR1 comprising SEQ ID NO:250, a CDR2 comprising SEQ ID NO:251 and a CDR3 comprising SEQ ID NO:252;

(n') a light chain variable region comprising a CDR1 comprising SEQ ID NO:118, a CDR2 comprising SEQ ID NO:119 and a CDR3 comprising SEQ ID NO:120 and a heavy chain variable region comprising a CDR1 comprising SEQ ID NO:253, a CDR2 comprising SEQ ID NO:254 and a CDR3 comprising SEQ ID NO:255;

(o') a light chain variable region comprising a CDR1 comprising SEQ ID NO:121, a CDR2 comprising SEQ ID NO:122 and a CDR3 comprising SEQ ID NO:123 and a heavy chain variable region comprising a CDR1 comprising SEQ ID NO:256, a CDR2 comprising SEQ ID NO:257 and a CDR3 comprising SEQ ID NO:258;

(p') a light chain variable region comprising a CDR1 comprising SEQ ID NO:124, a CDR2 comprising SEQ ID NO:125 and a CDR3 comprising SEQ ID NO:126 and a heavy chain variable region comprising a CDR1 comprising SEQ ID NO:259, a CDR2 comprising SEQ ID NO:260 and a CDR3 comprising SEQ ID NO:261;

(q') a light chain variable region comprising a CDR1 comprising SEQ ID NO:127, a CDR2 comprising SEQ ID NO:128 and a CDR3 comprising SEQ ID NO:129 and a heavy chain variable region comprising a CDR1 comprising SEQ ID NO:262, a CDR2 comprising SEQ ID NO:263 and a CDR3 comprising SEQ ID NO:264;

(r') a light chain variable region comprising a CDR1 comprising SEQ ID NO:130, a CDR2 comprising SEQ ID NO:131 and a CDR3 comprising SEQ ID NO:132 and a heavy chain variable region comprising a CDR1 comprising SEQ ID NO:265, a CDR2 comprising SEQ ID NO:266 and a CDR3 comprising SEQ ID NO:267; and (s') a light chain variable region comprising a CDR1 comprising SEQ ID NO:133, a CDR2 comprising SEQ ID NO:134 and a CDR3 comprising SEQ ID NO:135 and a heavy chain variable region comprising a CDR1 comprising SEQ ID NO:268, a CDR2 comprising SEQ ID NO:269 and a CDR3 comprising SEQ ID NO:270;

wherein the antigen binding protein specifically binds to cytomegalovirus (CMV).

7. The antigen binding protein of claim 6, wherein the antigen binding protein is a humanized antibody.

8. The antigen binding protein of claim 1, wherein the antigen binding protein is selected from the group consisting of a monoclonal antibody, a single chain antibody, a domain antibody, a diabody, a Fab, a Fab', a F(ab')2, a Fv and a scFv.

9. The antigen binding protein of claim 8 that is a monoclonal antibody.

10. The antigen binding protein of claim 9 that is a humanized monoclonal antibody.

* * * * *

SEQUENCE LISTING

<160> NUMBER OF SEQ ID NOS: 645

<210> SEQ ID NO 1
<211> LENGTH: 6
<212> TYPE: PRT
<213> ORGANISM: Oryctolagus cuniculus

<400> SEQUENCE: 1

Gln Asn Val Gly Ser Tyr
1               5

<210> SEQ ID NO 2
<211> LENGTH: 3
<212> TYPE: PRT
<213> ORGANISM: Oryctolagus cuniculus

<400> SEQUENCE: 2

Phe Ala Ser
1

<210> SEQ ID NO 3
<211> LENGTH: 12
<212> TYPE: PRT
<213> ORGANISM: Oryctolagus cuniculus

<400> SEQUENCE: 3

Gln Ser Tyr Gly Thr Gly Val Gly Tyr Asp Ala Tyr
1               5                   10

<210> SEQ ID NO 4
<211> LENGTH: 6
<212> TYPE: PRT
<213> ORGANISM: Oryctolagus cuniculus

<400> SEQUENCE: 4

Gln Asn Ile Gly Ser Arg
1               5

-continued

```
<210> SEQ ID NO 5
<211> LENGTH: 3
<212> TYPE: PRT
<213> ORGANISM: Oryctolagus cuniculus

<400> SEQUENCE: 5

Arg Thr Ser
1

<210> SEQ ID NO 6
<211> LENGTH: 9
<212> TYPE: PRT
<213> ORGANISM: Oryctolagus cuniculus

<400> SEQUENCE: 6

Gln Asp His Asp Asp Ile Ser His Ala
1               5

<210> SEQ ID NO 7
<211> LENGTH: 6
<212> TYPE: PRT
<213> ORGANISM: Oryctolagus cuniculus

<400> SEQUENCE: 7

Gln Ser Ile Arg Arg His
1               5

<210> SEQ ID NO 8
<211> LENGTH: 3
<212> TYPE: PRT
<213> ORGANISM: Oryctolagus cuniculus

<400> SEQUENCE: 8

Gly Ala Ser
1

<210> SEQ ID NO 9
<211> LENGTH: 15
<212> TYPE: PRT
<213> ORGANISM: Oryctolagus cuniculus

<400> SEQUENCE: 9

Gln Cys Thr Tyr Gly Val Gly Phe Ser Ser Thr Tyr Gly Asp Ala
1               5                   10                  15

<210> SEQ ID NO 10
<211> LENGTH: 6
<212> TYPE: PRT
<213> ORGANISM: Oryctolagus cuniculus

<400> SEQUENCE: 10

Asp Asn Ile Tyr Ser Gly
1               5

<210> SEQ ID NO 11
<211> LENGTH: 3
<212> TYPE: PRT
<213> ORGANISM: Oryctolagus cuniculus

<400> SEQUENCE: 11

Gly Val Ser
1

<210> SEQ ID NO 12
<211> LENGTH: 14
```

```
<212> TYPE: PRT
<213> ORGANISM: Oryctolagus cuniculus

<400> SEQUENCE: 12

Gln Cys Thr Ile Gly Pro Val Gly Ser Ser Phe Gly Asp Pro
1               5                   10

<210> SEQ ID NO 13
<211> LENGTH: 8
<212> TYPE: PRT
<213> ORGANISM: Oryctolagus cuniculus

<400> SEQUENCE: 13

Arg Ser Val Tyr Asn Glu Asn Tyr
1               5

<210> SEQ ID NO 14
<211> LENGTH: 3
<212> TYPE: PRT
<213> ORGANISM: Oryctolagus cuniculus

<400> SEQUENCE: 14

Thr Thr Ser
1

<210> SEQ ID NO 15
<211> LENGTH: 11
<212> TYPE: PRT
<213> ORGANISM: Oryctolagus cuniculus

<400> SEQUENCE: 15

Ala Gly Asp Tyr Asp Asp Asn Glu Glu Asn Ala
1               5                   10

<210> SEQ ID NO 16
<211> LENGTH: 6
<212> TYPE: PRT
<213> ORGANISM: Oryctolagus cuniculus

<400> SEQUENCE: 16

Glu Ser Ile Tyr Ser Gly
1               5

<210> SEQ ID NO 17
<211> LENGTH: 3
<212> TYPE: PRT
<213> ORGANISM: Oryctolagus cuniculus

<400> SEQUENCE: 17

Gln Ala Ser
1

<210> SEQ ID NO 18
<211> LENGTH: 12
<212> TYPE: PRT
<213> ORGANISM: Oryctolagus cuniculus

<400> SEQUENCE: 18

Gln Gln Gly Phe Ser Ser Ser Asn Val Asp Asn Leu
1               5                   10

<210> SEQ ID NO 19
<211> LENGTH: 6
<212> TYPE: PRT
<213> ORGANISM: Oryctolagus cuniculus
```

<400> SEQUENCE: 19

Gln Ser Ile Arg Arg His
1               5

<210> SEQ ID NO 20
<211> LENGTH: 3
<212> TYPE: PRT
<213> ORGANISM: Oryctolagus cuniculus

<400> SEQUENCE: 20

Gly Ala Ser
1

<210> SEQ ID NO 21
<211> LENGTH: 15
<212> TYPE: PRT
<213> ORGANISM: Oryctolagus cuniculus

<400> SEQUENCE: 21

Gln Cys Thr Tyr Gly Val Gly Phe Ser Ser Thr Tyr Gly Asp Ala
1               5                   10                  15

<210> SEQ ID NO 22
<211> LENGTH: 6
<212> TYPE: PRT
<213> ORGANISM: Oryctolagus cuniculus

<400> SEQUENCE: 22

Gln Asn Ile Tyr Ser Asn
1               5

<210> SEQ ID NO 23
<211> LENGTH: 3
<212> TYPE: PRT
<213> ORGANISM: Oryctolagus cuniculus

<400> SEQUENCE: 23

Gly Ala Ser
1

<210> SEQ ID NO 24
<211> LENGTH: 12
<212> TYPE: PRT
<213> ORGANISM: Oryctolagus cuniculus

<400> SEQUENCE: 24

Gln Ser Tyr Val Tyr Ser Ser Ser Thr Ala Asp Thr
1               5                   10

<210> SEQ ID NO 25
<211> LENGTH: 6
<212> TYPE: PRT
<213> ORGANISM: Oryctolagus cuniculus

<400> SEQUENCE: 25

Glu Ser Ile Asn Asn Trp
1               5

<210> SEQ ID NO 26
<211> LENGTH: 3
<212> TYPE: PRT
<213> ORGANISM: Oryctolagus cuniculus

<400> SEQUENCE: 26

Arg Ala Ser
1

<210> SEQ ID NO 27
<211> LENGTH: 11
<212> TYPE: PRT
<213> ORGANISM: Oryctolagus cuniculus

<400> SEQUENCE: 27

Glu Cys Pro Phe Ser Gly Gly Ser Gly Arg Val
1               5                   10

<210> SEQ ID NO 28
<211> LENGTH: 6
<212> TYPE: PRT
<213> ORGANISM: Oryctolagus cuniculus

<400> SEQUENCE: 28

Gln Ser Ile Ser Ser Tyr
1               5

<210> SEQ ID NO 29
<211> LENGTH: 3
<212> TYPE: PRT
<213> ORGANISM: Oryctolagus cuniculus

<400> SEQUENCE: 29

Arg Ala Ser
1

<210> SEQ ID NO 30
<211> LENGTH: 13
<212> TYPE: PRT
<213> ORGANISM: Oryctolagus cuniculus

<400> SEQUENCE: 30

Gln Cys Thr Tyr Gly Ser Ser Ser Ser Gly Tyr Ala
1               5                   10

<210> SEQ ID NO 31
<211> LENGTH: 6
<212> TYPE: PRT
<213> ORGANISM: Oryctolagus cuniculus

<400> SEQUENCE: 31

Gln Ser Ile Gly Asn Leu
1               5

<210> SEQ ID NO 32
<211> LENGTH: 3
<212> TYPE: PRT
<213> ORGANISM: Oryctolagus cuniculus

<400> SEQUENCE: 32

Asp Ala Ser
1

<210> SEQ ID NO 33
<211> LENGTH: 12
<212> TYPE: PRT
<213> ORGANISM: Oryctolagus cuniculus

<400> SEQUENCE: 33

Gln Gln Gly Tyr Met Ile Thr Asn Val Glu Asn Ala

<210> SEQ ID NO 34
<211> LENGTH: 6
<212> TYPE: PRT
<213> ORGANISM: Oryctolagus cuniculus

<400> SEQUENCE: 34

Gln Ser Ile Ser Asn Tyr
1               5

<210> SEQ ID NO 35
<211> LENGTH: 3
<212> TYPE: PRT
<213> ORGANISM: Oryctolagus cuniculus

<400> SEQUENCE: 35

Arg Ala Ser
1

<210> SEQ ID NO 36
<211> LENGTH: 13
<212> TYPE: PRT
<213> ORGANISM: Oryctolagus cuniculus

<400> SEQUENCE: 36

Gln Ser Thr Tyr Gly Ser Ser Ser Ser Gly Tyr Ala
1               5                   10

<210> SEQ ID NO 37
<211> LENGTH: 6
<212> TYPE: PRT
<213> ORGANISM: Oryctolagus cuniculus

<400> SEQUENCE: 37

Gln Thr Val Asn Ser Tyr
1               5

<210> SEQ ID NO 38
<211> LENGTH: 3
<212> TYPE: PRT
<213> ORGANISM: Oryctolagus cuniculus

<400> SEQUENCE: 38

Phe Ala Ser
1

<210> SEQ ID NO 39
<211> LENGTH: 13
<212> TYPE: PRT
<213> ORGANISM: Oryctolagus cuniculus

<400> SEQUENCE: 39

Gln Ser Tyr Tyr Tyr Ser Gly Ser Ser Tyr Gly Asn Ala
1               5                   10

<210> SEQ ID NO 40
<211> LENGTH: 6
<212> TYPE: PRT
<213> ORGANISM: Oryctolagus cuniculus

<400> SEQUENCE: 40

Gln Ser Ile Ser Ser Tyr
1               5

```
<210> SEQ ID NO 41
<211> LENGTH: 3
<212> TYPE: PRT
<213> ORGANISM: Oryctolagus cuniculus

<400> SEQUENCE: 41

Arg Ala Ser
1

<210> SEQ ID NO 42
<211> LENGTH: 15
<212> TYPE: PRT
<213> ORGANISM: Oryctolagus cuniculus

<400> SEQUENCE: 42

Gln Cys Thr Tyr Gly Ser Ser Ser Ser Ala Tyr Gly Arg Ala
1               5                   10                  15

<210> SEQ ID NO 43
<211> LENGTH: 8
<212> TYPE: PRT
<213> ORGANISM: Oryctolagus cuniculus

<400> SEQUENCE: 43

Gln Ser Val Tyr Asn Lys Asn Tyr
1               5

<210> SEQ ID NO 44
<211> LENGTH: 3
<212> TYPE: PRT
<213> ORGANISM: Oryctolagus cuniculus

<400> SEQUENCE: 44

Gly Ala Ser
1

<210> SEQ ID NO 45
<211> LENGTH: 10
<212> TYPE: PRT
<213> ORGANISM: Oryctolagus cuniculus

<400> SEQUENCE: 45

Gln Gly Tyr Tyr Ser Gly Tyr Ile Tyr Ala
1               5                   10

<210> SEQ ID NO 46
<211> LENGTH: 6
<212> TYPE: PRT
<213> ORGANISM: Oryctolagus cuniculus

<400> SEQUENCE: 46

Gln Asn Ile Gly Ser Arg
1               5

<210> SEQ ID NO 47
<211> LENGTH: 3
<212> TYPE: PRT
<213> ORGANISM: Oryctolagus cuniculus

<400> SEQUENCE: 47

Arg Thr Ser
1

<210> SEQ ID NO 48
```

```
<211> LENGTH: 9
<212> TYPE: PRT
<213> ORGANISM: Oryctolagus cuniculus

<400> SEQUENCE: 48

Gln Asp His Asp Asp Ile Ser His Ala
1               5

<210> SEQ ID NO 49
<211> LENGTH: 8
<212> TYPE: PRT
<213> ORGANISM: Oryctolagus cuniculus

<400> SEQUENCE: 49

Gln Ser Val Tyr Asn Lys Asn Ala
1               5

<210> SEQ ID NO 50
<211> LENGTH: 3
<212> TYPE: PRT
<213> ORGANISM: Oryctolagus cuniculus

<400> SEQUENCE: 50

Lys Ala Ser
1

<210> SEQ ID NO 51
<211> LENGTH: 11
<212> TYPE: PRT
<213> ORGANISM: Oryctolagus cuniculus

<400> SEQUENCE: 51

Leu Gly Gly Tyr Ser Thr Thr Ser Asp Asn Ala
1               5                   10

<210> SEQ ID NO 52
<211> LENGTH: 8
<212> TYPE: PRT
<213> ORGANISM: Oryctolagus cuniculus

<400> SEQUENCE: 52

Gln Ser Leu Tyr Asn Asn Asn Phe
1               5

<210> SEQ ID NO 53
<211> LENGTH: 3
<212> TYPE: PRT
<213> ORGANISM: Oryctolagus cuniculus

<400> SEQUENCE: 53

Lys Ala Ser
1

<210> SEQ ID NO 54
<211> LENGTH: 13
<212> TYPE: PRT
<213> ORGANISM: Oryctolagus cuniculus

<400> SEQUENCE: 54

Gln Gly Glu Phe Ser Cys Ser Ser Ala Asp Cys Asn Ala
1               5                   10

<210> SEQ ID NO 55
<211> LENGTH: 9
<212> TYPE: PRT
```

<213> ORGANISM: Oryctolagus cuniculus

<400> SEQUENCE: 55

Thr Gly Tyr Ser Val Gly Lys Tyr Pro
1               5

<210> SEQ ID NO 56
<211> LENGTH: 7
<212> TYPE: PRT
<213> ORGANISM: Oryctolagus cuniculus

<400> SEQUENCE: 56

Tyr His Thr Glu Glu Phe Lys
1               5

<210> SEQ ID NO 57
<211> LENGTH: 13
<212> TYPE: PRT
<213> ORGANISM: Oryctolagus cuniculus

<400> SEQUENCE: 57

Ala Thr Ala His Ala Thr Glu Ser Ser Leu His Tyr Val
1               5                   10

<210> SEQ ID NO 58
<211> LENGTH: 6
<212> TYPE: PRT
<213> ORGANISM: Oryctolagus cuniculus

<400> SEQUENCE: 58

Gln Asn Ile Gly Ser Arg
1               5

<210> SEQ ID NO 59
<211> LENGTH: 3
<212> TYPE: PRT
<213> ORGANISM: Oryctolagus cuniculus

<400> SEQUENCE: 59

Arg Thr Ser
1

<210> SEQ ID NO 60
<211> LENGTH: 9
<212> TYPE: PRT
<213> ORGANISM: Oryctolagus cuniculus

<400> SEQUENCE: 60

Gln Asp His Asp Asp Ile Ser His Ala
1               5

<210> SEQ ID NO 61
<211> LENGTH: 8
<212> TYPE: PRT
<213> ORGANISM: Oryctolagus cuniculus

<400> SEQUENCE: 61

Arg Ser Val Tyr Asn Glu Asn Tyr
1               5

<210> SEQ ID NO 62
<211> LENGTH: 3
<212> TYPE: PRT
<213> ORGANISM: Oryctolagus cuniculus

```
<400> SEQUENCE: 62

Thr Thr Ser
1

<210> SEQ ID NO 63
<211> LENGTH: 11
<212> TYPE: PRT
<213> ORGANISM: Oryctolagus cuniculus

<400> SEQUENCE: 63

Ala Gly Asp Tyr Asp Asp Asn Glu Glu Asn Ala
1               5                   10

<210> SEQ ID NO 64
<211> LENGTH: 8
<212> TYPE: PRT
<213> ORGANISM: Oryctolagus cuniculus

<400> SEQUENCE: 64

Gln Asn Val Ile Asp Lys Asn Trp
1               5

<210> SEQ ID NO 65
<211> LENGTH: 3
<212> TYPE: PRT
<213> ORGANISM: Oryctolagus cuniculus

<400> SEQUENCE: 65

Ser Ala Ser
1

<210> SEQ ID NO 66
<211> LENGTH: 10
<212> TYPE: PRT
<213> ORGANISM: Oryctolagus cuniculus

<400> SEQUENCE: 66

Ala Gly Gly Tyr Ser Gly Asp Ile Tyr Ala
1               5                   10

<210> SEQ ID NO 67
<211> LENGTH: 8
<212> TYPE: PRT
<213> ORGANISM: Oryctolagus cuniculus

<400> SEQUENCE: 67

Gln Ser Leu Tyr Asn Asn Asn Phe
1               5

<210> SEQ ID NO 68
<211> LENGTH: 3
<212> TYPE: PRT
<213> ORGANISM: Oryctolagus cuniculus

<400> SEQUENCE: 68

Lys Ala Ser
1

<210> SEQ ID NO 69
<211> LENGTH: 13
<212> TYPE: PRT
<213> ORGANISM: Oryctolagus cuniculus

<400> SEQUENCE: 69
```

```
Gln Gly Glu Phe Ser Cys Ser Ser Ala Asp Cys Asn Ala
1               5                   10
```

<210> SEQ ID NO 70
<211> LENGTH: 6
<212> TYPE: PRT
<213> ORGANISM: Oryctolagus cuniculus

<400> SEQUENCE: 70

```
His Asn Ile Gly Ser Arg
1               5
```

<210> SEQ ID NO 71
<211> LENGTH: 3
<212> TYPE: PRT
<213> ORGANISM: Oryctolagus cuniculus

<400> SEQUENCE: 71

```
Arg Thr Ser
1
```

<210> SEQ ID NO 72
<211> LENGTH: 9
<212> TYPE: PRT
<213> ORGANISM: Oryctolagus cuniculus

<400> SEQUENCE: 72

```
Gln Asp His Asp Asp Ile Ser His Ala
1               5
```

<210> SEQ ID NO 73
<211> LENGTH: 6
<212> TYPE: PRT
<213> ORGANISM: Oryctolagus cuniculus

<400> SEQUENCE: 73

```
Gln Ser Ile Gly Asn Tyr
1               5
```

<210> SEQ ID NO 74
<211> LENGTH: 3
<212> TYPE: PRT
<213> ORGANISM: Oryctolagus cuniculus

<400> SEQUENCE: 74

```
Arg Ala Ser
1
```

<210> SEQ ID NO 75
<211> LENGTH: 13
<212> TYPE: PRT
<213> ORGANISM: Oryctolagus cuniculus

<400> SEQUENCE: 75

```
Gln Ser Thr Tyr Gly Ser Ser Ser Ser Ser Gly Tyr Ala
1               5                   10
```

<210> SEQ ID NO 76
<211> LENGTH: 6
<212> TYPE: PRT
<213> ORGANISM: Oryctolagus cuniculus

<400> SEQUENCE: 76

```
Gln Ser Ile Ser Ser Tyr
1               5
```

<210> SEQ ID NO 77
<211> LENGTH: 3
<212> TYPE: PRT
<213> ORGANISM: Oryctolagus cuniculus

<400> SEQUENCE: 77

Arg Ala Ser
1

<210> SEQ ID NO 78
<211> LENGTH: 13
<212> TYPE: PRT
<213> ORGANISM: Oryctolagus cuniculus

<400> SEQUENCE: 78

Gln Cys Thr Tyr Gly Ser Ser Ser Ser Gly Tyr Ala
1               5                   10

<210> SEQ ID NO 79
<211> LENGTH: 6
<212> TYPE: PRT
<213> ORGANISM: Oryctolagus cuniculus

<400> SEQUENCE: 79

Glu Ser Ile Tyr Ser Ser
1               5

<210> SEQ ID NO 80
<211> LENGTH: 3
<212> TYPE: PRT
<213> ORGANISM: Oryctolagus cuniculus

<400> SEQUENCE: 80

Arg Ala Ser
1

<210> SEQ ID NO 81
<211> LENGTH: 12
<212> TYPE: PRT
<213> ORGANISM: Oryctolagus cuniculus

<400> SEQUENCE: 81

Gln Gln Gly Trp Ser Asn Ile Asn Val Asp Asn Val
1               5                   10

<210> SEQ ID NO 82
<211> LENGTH: 6
<212> TYPE: PRT
<213> ORGANISM: Oryctolagus cuniculus

<400> SEQUENCE: 82

Gln Ser Ile Gly Asn Leu
1               5

<210> SEQ ID NO 83
<211> LENGTH: 3
<212> TYPE: PRT
<213> ORGANISM: Oryctolagus cuniculus

<400> SEQUENCE: 83

Asp Ala Ser
1

```
<210> SEQ ID NO 84
<211> LENGTH: 12
<212> TYPE: PRT
<213> ORGANISM: Oryctolagus cuniculus

<400> SEQUENCE: 84

Gln Gln Gly Tyr Met Ile Thr Asn Val Glu Asn Ala
1               5                   10

<210> SEQ ID NO 85
<211> LENGTH: 6
<212> TYPE: PRT
<213> ORGANISM: Oryctolagus cuniculus

<400> SEQUENCE: 85

Gln Ser Ile Gly Ala Asn
1               5

<210> SEQ ID NO 86
<211> LENGTH: 3
<212> TYPE: PRT
<213> ORGANISM: Oryctolagus cuniculus

<400> SEQUENCE: 86

Gly Ala Ser
1

<210> SEQ ID NO 87
<211> LENGTH: 10
<212> TYPE: PRT
<213> ORGANISM: Oryctolagus cuniculus

<400> SEQUENCE: 87

Gln Cys Thr Tyr Tyr Gly Ser Gly Asn Thr
1               5                   10

<210> SEQ ID NO 88
<211> LENGTH: 6
<212> TYPE: PRT
<213> ORGANISM: Oryctolagus cuniculus

<400> SEQUENCE: 88

Gln Ser Ile Gly Ser Asn
1               5

<210> SEQ ID NO 89
<211> LENGTH: 3
<212> TYPE: PRT
<213> ORGANISM: Oryctolagus cuniculus

<400> SEQUENCE: 89

Ala Ala Ser
1

<210> SEQ ID NO 90
<211> LENGTH: 9
<212> TYPE: PRT
<213> ORGANISM: Oryctolagus cuniculus

<400> SEQUENCE: 90

Gln Cys Asn Tyr Tyr Leu Asn Asn Ala
1               5

<210> SEQ ID NO 91
<211> LENGTH: 6
```

```
<212> TYPE: PRT
<213> ORGANISM: Oryctolagus cuniculus

<400> SEQUENCE: 91

Gln Asn Ile Gly Ser Arg
1               5

<210> SEQ ID NO 92
<211> LENGTH: 3
<212> TYPE: PRT
<213> ORGANISM: Oryctolagus cuniculus

<400> SEQUENCE: 92

Arg Thr Ser
1

<210> SEQ ID NO 93
<211> LENGTH: 9
<212> TYPE: PRT
<213> ORGANISM: Oryctolagus cuniculus

<400> SEQUENCE: 93

Gln Asp His Asp Asp Ile Ser His Ala
1               5

<210> SEQ ID NO 94
<211> LENGTH: 6
<212> TYPE: PRT
<213> ORGANISM: Oryctolagus cuniculus

<400> SEQUENCE: 94

His Asn Ile Asn Thr Tyr
1               5

<210> SEQ ID NO 95
<211> LENGTH: 3
<212> TYPE: PRT
<213> ORGANISM: Oryctolagus cuniculus

<400> SEQUENCE: 95

Arg Ala Ser
1

<210> SEQ ID NO 96
<211> LENGTH: 12
<212> TYPE: PRT
<213> ORGANISM: Oryctolagus cuniculus

<400> SEQUENCE: 96

Gln Gln Gly Phe Asn Ser Leu Asn Val Glu Asn Val
1               5                   10

<210> SEQ ID NO 97
<211> LENGTH: 8
<212> TYPE: PRT
<213> ORGANISM: Oryctolagus cuniculus

<400> SEQUENCE: 97

Gln Ser Val Tyr Asn Asn Asn Phe
1               5

<210> SEQ ID NO 98
<211> LENGTH: 3
<212> TYPE: PRT
<213> ORGANISM: Oryctolagus cuniculus
```

<400> SEQUENCE: 98

Leu Ala Ser
1

<210> SEQ ID NO 99
<211> LENGTH: 13
<212> TYPE: PRT
<213> ORGANISM: Oryctolagus cuniculus

<400> SEQUENCE: 99

Gln Gly Glu Phe Ser Cys Ile Ser Ala Asp Cys Asn Ala
1               5                   10

<210> SEQ ID NO 100
<211> LENGTH: 6
<212> TYPE: PRT
<213> ORGANISM: Oryctolagus cuniculus

<400> SEQUENCE: 100

Gln Gly Ile Tyr Asp Tyr
1               5

<210> SEQ ID NO 101
<211> LENGTH: 3
<212> TYPE: PRT
<213> ORGANISM: Oryctolagus cuniculus

<400> SEQUENCE: 101

Gly Ala Ala
1

<210> SEQ ID NO 102
<211> LENGTH: 13
<212> TYPE: PRT
<213> ORGANISM: Oryctolagus cuniculus

<400> SEQUENCE: 102

Gln Ser Ala Tyr Tyr Ser Ser Thr Asp Arg Asn Ala
1               5                   10

<210> SEQ ID NO 103
<211> LENGTH: 8
<212> TYPE: PRT
<213> ORGANISM: Oryctolagus cuniculus

<400> SEQUENCE: 103

Gln Ser Val Tyr Asn Asp Asn Tyr
1               5

<210> SEQ ID NO 104
<211> LENGTH: 3
<212> TYPE: PRT
<213> ORGANISM: Oryctolagus cuniculus

<400> SEQUENCE: 104

Tyr Ala Ser
1

<210> SEQ ID NO 105
<211> LENGTH: 13
<212> TYPE: PRT
<213> ORGANISM: Oryctolagus cuniculus

<400> SEQUENCE: 105

```
Leu Gly Ser Tyr Asp Cys Ser Ala Asp Cys Tyr Val
1               5                   10

<210> SEQ ID NO 106
<211> LENGTH: 8
<212> TYPE: PRT
<213> ORGANISM: Oryctolagus cuniculus

<400> SEQUENCE: 106

Lys Ser Val Tyr Asn Asn Asn Ala
1               5

<210> SEQ ID NO 107
<211> LENGTH: 3
<212> TYPE: PRT
<213> ORGANISM: Oryctolagus cuniculus

<400> SEQUENCE: 107

Ser Ala Ser
1

<210> SEQ ID NO 108
<211> LENGTH: 11
<212> TYPE: PRT
<213> ORGANISM: Oryctolagus cuniculus

<400> SEQUENCE: 108

Ala Gly Gly Tyr Ser Ile Ile Ser Asp Asn Gly
1               5                   10

<210> SEQ ID NO 109
<211> LENGTH: 6
<212> TYPE: PRT
<213> ORGANISM: Oryctolagus cuniculus

<400> SEQUENCE: 109

Gln Ser Ile Arg Arg His
1               5

<210> SEQ ID NO 110
<211> LENGTH: 3
<212> TYPE: PRT
<213> ORGANISM: Oryctolagus cuniculus

<400> SEQUENCE: 110

Gly Ala Ser
1

<210> SEQ ID NO 111
<211> LENGTH: 15
<212> TYPE: PRT
<213> ORGANISM: Oryctolagus cuniculus

<400> SEQUENCE: 111

Gln Cys Thr Tyr Gly Val Gly Phe Ser Ser Thr Tyr Gly Asp Ala
1               5                   10                  15

<210> SEQ ID NO 112
<211> LENGTH: 6
<212> TYPE: PRT
<213> ORGANISM: Oryctolagus cuniculus

<400> SEQUENCE: 112

Gln Thr Ile Gly Asn Leu
```

```
<210> SEQ ID NO 113
<211> LENGTH: 3
<212> TYPE: PRT
<213> ORGANISM: Oryctolagus cuniculus

<400> SEQUENCE: 113

Asp Ala Ser
1

<210> SEQ ID NO 114
<211> LENGTH: 12
<212> TYPE: PRT
<213> ORGANISM: Oryctolagus cuniculus

<400> SEQUENCE: 114

Gln Gln Gly Tyr Met Ile Thr Asn Val Glu Asn Ala
1               5                   10

<210> SEQ ID NO 115
<211> LENGTH: 8
<212> TYPE: PRT
<213> ORGANISM: Oryctolagus cuniculus

<400> SEQUENCE: 115

Gln Ser Val Tyr Asn Asn Asn Tyr
1               5

<210> SEQ ID NO 116
<211> LENGTH: 3
<212> TYPE: PRT
<213> ORGANISM: Oryctolagus cuniculus

<400> SEQUENCE: 116

Gly Ala Ser
1

<210> SEQ ID NO 117
<211> LENGTH: 10
<212> TYPE: PRT
<213> ORGANISM: Oryctolagus cuniculus

<400> SEQUENCE: 117

Gln Gly Tyr Tyr Ser Gly Tyr Ile Tyr Ala
1               5                   10

<210> SEQ ID NO 118
<211> LENGTH: 7
<212> TYPE: PRT
<213> ORGANISM: Oryctolagus cuniculus

<400> SEQUENCE: 118

Gln Ser Val Asn Asn Asn Trp
1               5

<210> SEQ ID NO 119
<211> LENGTH: 3
<212> TYPE: PRT
<213> ORGANISM: Oryctolagus cuniculus

<400> SEQUENCE: 119

Gly Ala Ser
1
```

```
<210> SEQ ID NO 120
<211> LENGTH: 10
<212> TYPE: PRT
<213> ORGANISM: Oryctolagus cuniculus

<400> SEQUENCE: 120

Gln Gly Asp Leu Thr Gly Trp Ile Trp Ala
1               5                   10

<210> SEQ ID NO 121
<211> LENGTH: 6
<212> TYPE: PRT
<213> ORGANISM: Oryctolagus cuniculus

<400> SEQUENCE: 121

Gln Asn Ile Gly Ser Arg
1               5

<210> SEQ ID NO 122
<211> LENGTH: 3
<212> TYPE: PRT
<213> ORGANISM: Oryctolagus cuniculus

<400> SEQUENCE: 122

Arg Thr Ser
1

<210> SEQ ID NO 123
<211> LENGTH: 9
<212> TYPE: PRT
<213> ORGANISM: Oryctolagus cuniculus

<400> SEQUENCE: 123

Gln Asp His Asp Asp Ile Ser His Ala
1               5

<210> SEQ ID NO 124
<211> LENGTH: 6
<212> TYPE: PRT
<213> ORGANISM: Oryctolagus cuniculus

<400> SEQUENCE: 124

Gln Asn Ile Gly Ser Arg
1               5

<210> SEQ ID NO 125
<211> LENGTH: 3
<212> TYPE: PRT
<213> ORGANISM: Oryctolagus cuniculus

<400> SEQUENCE: 125

Arg Thr Ser
1

<210> SEQ ID NO 126
<211> LENGTH: 9
<212> TYPE: PRT
<213> ORGANISM: Oryctolagus cuniculus

<400> SEQUENCE: 126

Gln Asp His Asp Asp Ile Ser His Ala
1               5

<210> SEQ ID NO 127
```

```
<211> LENGTH: 6
<212> TYPE: PRT
<213> ORGANISM: Oryctolagus cuniculus

<400> SEQUENCE: 127

Gln Asn Ile Gly Ser Arg
1               5

<210> SEQ ID NO 128
<211> LENGTH: 3
<212> TYPE: PRT
<213> ORGANISM: Oryctolagus cuniculus

<400> SEQUENCE: 128

Arg Thr Ser
1

<210> SEQ ID NO 129
<211> LENGTH: 9
<212> TYPE: PRT
<213> ORGANISM: Oryctolagus cuniculus

<400> SEQUENCE: 129

Gln Asp His Asp Asp Ile Ser His Ala
1               5

<210> SEQ ID NO 130
<211> LENGTH: 9
<212> TYPE: PRT
<213> ORGANISM: Oryctolagus cuniculus

<400> SEQUENCE: 130

Thr Gly Tyr Ser Val Gly Lys Tyr Pro
1               5

<210> SEQ ID NO 131
<211> LENGTH: 7
<212> TYPE: PRT
<213> ORGANISM: Oryctolagus cuniculus

<400> SEQUENCE: 131

Tyr His Thr Glu Glu Phe Lys
1               5

<210> SEQ ID NO 132
<211> LENGTH: 13
<212> TYPE: PRT
<213> ORGANISM: Oryctolagus cuniculus

<400> SEQUENCE: 132

Val Thr Ala His Pro Thr Glu Ser Ser Leu His Tyr Val
1               5                   10

<210> SEQ ID NO 133
<211> LENGTH: 8
<212> TYPE: PRT
<213> ORGANISM: Oryctolagus cuniculus

<400> SEQUENCE: 133

Gln Asn Val Trp Thr Asn Asp Tyr
1               5

<210> SEQ ID NO 134
<211> LENGTH: 3
<212> TYPE: PRT
```

<213> ORGANISM: Oryctolagus cuniculus

<400> SEQUENCE: 134

Arg Ala Ser
1

<210> SEQ ID NO 135
<211> LENGTH: 11
<212> TYPE: PRT
<213> ORGANISM: Oryctolagus cuniculus

<400> SEQUENCE: 135

Gly Gly Thr Phe Leu Ser Asn Gly Asp Asn Gly
1               5                   10

<210> SEQ ID NO 136
<211> LENGTH: 8
<212> TYPE: PRT
<213> ORGANISM: Oryctolagus cuniculus

<400> SEQUENCE: 136

Gly Ile Asp Leu Ser Ala Asn Glu
1               5

<210> SEQ ID NO 137
<211> LENGTH: 7
<212> TYPE: PRT
<213> ORGANISM: Oryctolagus cuniculus

<400> SEQUENCE: 137

Leu Ser Tyr His Asn Ile Pro
1               5

<210> SEQ ID NO 138
<211> LENGTH: 11
<212> TYPE: PRT
<213> ORGANISM: Oryctolagus cuniculus

<400> SEQUENCE: 138

Gly Arg Val Phe Thr Ser Thr Ser Phe Asp Pro
1               5                   10

<210> SEQ ID NO 139
<211> LENGTH: 8
<212> TYPE: PRT
<213> ORGANISM: Oryctolagus cuniculus

<400> SEQUENCE: 139

Gly Phe Ser Leu Ser Ala Tyr Ser
1               5

<210> SEQ ID NO 140
<211> LENGTH: 7
<212> TYPE: PRT
<213> ORGANISM: Oryctolagus cuniculus

<400> SEQUENCE: 140

Ile Gly His Ser Gly Asn Thr
1               5

<210> SEQ ID NO 141
<211> LENGTH: 18
<212> TYPE: PRT
<213> ORGANISM: Oryctolagus cuniculus

<400> SEQUENCE: 141

Ala Arg Glu Asp Tyr Arg Tyr Gly Asp Tyr Gly Tyr Tyr Trp Asp Phe
1               5                   10                  15

Asn Phe

<210> SEQ ID NO 142
<211> LENGTH: 8
<212> TYPE: PRT
<213> ORGANISM: Oryctolagus cuniculus

<400> SEQUENCE: 142

Gly Ile Asp Leu Ser Ser His Glu
1               5

<210> SEQ ID NO 143
<211> LENGTH: 7
<212> TYPE: PRT
<213> ORGANISM: Oryctolagus cuniculus

<400> SEQUENCE: 143

Ile Ser Tyr Asp His Thr Pro
1               5

<210> SEQ ID NO 144
<211> LENGTH: 11
<212> TYPE: PRT
<213> ORGANISM: Oryctolagus cuniculus

<400> SEQUENCE: 144

Val Arg Val Phe Thr Gly Thr Ala Phe Asp Pro
1               5                   10

<210> SEQ ID NO 145
<211> LENGTH: 9
<212> TYPE: PRT
<213> ORGANISM: Oryctolagus cuniculus

<400> SEQUENCE: 145

Ala Phe Ser Phe Ser Ser Ser Tyr Tyr
1               5

<210> SEQ ID NO 146
<211> LENGTH: 7
<212> TYPE: PRT
<213> ORGANISM: Oryctolagus cuniculus

<400> SEQUENCE: 146

Ile Tyr Gly Gly Asp Ala Thr
1               5

<210> SEQ ID NO 147
<211> LENGTH: 15
<212> TYPE: PRT
<213> ORGANISM: Oryctolagus cuniculus

<400> SEQUENCE: 147

Ala Arg Lys Tyr Ala Gly Thr Tyr Phe Ser Arg Tyr Phe Asn Leu
1               5                   10                  15

<210> SEQ ID NO 148
<211> LENGTH: 8
<212> TYPE: PRT
<213> ORGANISM: Oryctolagus cuniculus

<400> SEQUENCE: 148

Gly Phe Ser Leu Ser Asp Tyr Val
1               5

<210> SEQ ID NO 149
<211> LENGTH: 7
<212> TYPE: PRT
<213> ORGANISM: Oryctolagus cuniculus

<400> SEQUENCE: 149

Ile Tyr Gly Ser Gly Arg Ile
1               5

<210> SEQ ID NO 150
<211> LENGTH: 15
<212> TYPE: PRT
<213> ORGANISM: Oryctolagus cuniculus

<400> SEQUENCE: 150

Ala Arg Gly Ser Asn Ser Asn Gly Gly Thr Met Tyr Phe Asn Leu
1               5                   10                  15

<210> SEQ ID NO 151
<211> LENGTH: 8
<212> TYPE: PRT
<213> ORGANISM: Oryctolagus cuniculus

<400> SEQUENCE: 151

Gly Phe Ser Leu Ser Ser Tyr Val
1               5

<210> SEQ ID NO 152
<211> LENGTH: 7
<212> TYPE: PRT
<213> ORGANISM: Oryctolagus cuniculus

<400> SEQUENCE: 152

Phe Asp Arg Asn Ser Gly Arg
1               5

<210> SEQ ID NO 153
<211> LENGTH: 17
<212> TYPE: PRT
<213> ORGANISM: Oryctolagus cuniculus

<400> SEQUENCE: 153

Ala Arg Gly Ser Tyr Gly Ser Asp Ile Ser Ser Leu Tyr Trp Phe Asp
1               5                   10                  15

Leu

<210> SEQ ID NO 154
<211> LENGTH: 9
<212> TYPE: PRT
<213> ORGANISM: Oryctolagus cuniculus

<400> SEQUENCE: 154

Gly Phe Ser Phe Ser Ser Val Tyr Asp
1               5

<210> SEQ ID NO 155
<211> LENGTH: 8
<212> TYPE: PRT
<213> ORGANISM: Oryctolagus cuniculus

```
<400> SEQUENCE: 155

Ile Val Thr Gly Ser Arg Thr Thr
1               5

<210> SEQ ID NO 156
<211> LENGTH: 18
<212> TYPE: PRT
<213> ORGANISM: Oryctolagus cuniculus

<400> SEQUENCE: 156

Arg Gly Glu Tyr Gly His Asp Gly Tyr Val Asp Gly Thr Met Gly Leu
1               5                   10                  15

Gly Leu

<210> SEQ ID NO 157
<211> LENGTH: 8
<212> TYPE: PRT
<213> ORGANISM: Oryctolagus cuniculus

<400> SEQUENCE: 157

Gly Phe Ser Leu Ser Ala Tyr Ser
1               5

<210> SEQ ID NO 158
<211> LENGTH: 7
<212> TYPE: PRT
<213> ORGANISM: Oryctolagus cuniculus

<400> SEQUENCE: 158

Ile Gly His Ser Gly Asn Thr
1               5

<210> SEQ ID NO 159
<211> LENGTH: 18
<212> TYPE: PRT
<213> ORGANISM: Oryctolagus cuniculus

<400> SEQUENCE: 159

Ala Arg Glu Asp Tyr Arg Tyr Gly Asp Tyr Gly Tyr Tyr Trp Asp Phe
1               5                   10                  15

Asn Phe

<210> SEQ ID NO 160
<211> LENGTH: 9
<212> TYPE: PRT
<213> ORGANISM: Oryctolagus cuniculus

<400> SEQUENCE: 160

Gly Phe Ser Phe Asn Asn Ala Tyr Tyr
1               5

<210> SEQ ID NO 161
<211> LENGTH: 9
<212> TYPE: PRT
<213> ORGANISM: Oryctolagus cuniculus

<400> SEQUENCE: 161

Ile Tyr Val Gly Ser Ser Gly Gly Thr
1               5

<210> SEQ ID NO 162
<211> LENGTH: 23
<212> TYPE: PRT
```

<210> SEQ ID NO 162
<211> LENGTH: 21
<212> TYPE: PRT
<213> ORGANISM: Oryctolagus cuniculus

<400> SEQUENCE: 162

Ala Arg Glu Phe Ala Tyr Tyr Gly Tyr Ile Asp Ala Gly Trp Ala Tyr
1               5                   10                  15

Val Pro Tyr Gly Met Asp Leu
            20

<210> SEQ ID NO 163
<211> LENGTH: 9
<212> TYPE: PRT
<213> ORGANISM: Oryctolagus cuniculus

<400> SEQUENCE: 163

Gly Phe Ser Phe Ser Asn Ser Tyr Tyr
1               5

<210> SEQ ID NO 164
<211> LENGTH: 8
<212> TYPE: PRT
<213> ORGANISM: Oryctolagus cuniculus

<400> SEQUENCE: 164

Ile Tyr Thr Ile Ile Gly Asn Thr
1               5

<210> SEQ ID NO 165
<211> LENGTH: 21
<212> TYPE: PRT
<213> ORGANISM: Oryctolagus cuniculus

<400> SEQUENCE: 165

Arg Asp Arg Tyr Tyr Tyr Ser Asp Pro Tyr Thr Gly Tyr Ala Tyr Ala
1               5                   10                  15

Thr Gly Phe Asn Leu
            20

<210> SEQ ID NO 166
<211> LENGTH: 8
<212> TYPE: PRT
<213> ORGANISM: Oryctolagus cuniculus

<400> SEQUENCE: 166

Gly Phe Ser Leu Ser Ser Tyr His
1               5

<210> SEQ ID NO 167
<211> LENGTH: 7
<212> TYPE: PRT
<213> ORGANISM: Oryctolagus cuniculus

<400> SEQUENCE: 167

Ile Asn Tyr Asn Asn Pro
1               5

<210> SEQ ID NO 168
<211> LENGTH: 14
<212> TYPE: PRT
<213> ORGANISM: Oryctolagus cuniculus

<400> SEQUENCE: 168

Ala Arg Ala Ala Gly Asn Tyr Tyr Val Gly Ala Leu Asn Leu
1               5                   10

<210> SEQ ID NO 169
<211> LENGTH: 9
<212> TYPE: PRT
<213> ORGANISM: Oryctolagus cuniculus

<400> SEQUENCE: 169

Gly Phe Ser Phe Ser Asn Ser Tyr Tyr
1               5

<210> SEQ ID NO 170
<211> LENGTH: 8
<212> TYPE: PRT
<213> ORGANISM: Oryctolagus cuniculus

<400> SEQUENCE: 170

Ile Tyr Thr Arg Ile Thr Asn Thr
1               5

<210> SEQ ID NO 171
<211> LENGTH: 21
<212> TYPE: PRT
<213> ORGANISM: Oryctolagus cuniculus

<400> SEQUENCE: 171

Arg Asp Arg Tyr Tyr Tyr Ser Asp Pro Tyr Thr Gly Tyr Ala Tyr Ala
1               5                   10                  15

Thr Gly Phe Asn Leu
            20

<210> SEQ ID NO 172
<211> LENGTH: 8
<212> TYPE: PRT
<213> ORGANISM: Oryctolagus cuniculus

<400> SEQUENCE: 172

Gly Ile Asp Leu Asn Ser Tyr Glu
1               5

<210> SEQ ID NO 173
<211> LENGTH: 7
<212> TYPE: PRT
<213> ORGANISM: Oryctolagus cuniculus

<400> SEQUENCE: 173

Ile Gly Tyr Gly Gly Ile Thr
1               5

<210> SEQ ID NO 174
<211> LENGTH: 11
<212> TYPE: PRT
<213> ORGANISM: Oryctolagus cuniculus

<400> SEQUENCE: 174

Ala Arg Leu Phe Thr Ser Thr Ala Phe Asp Pro
1               5                   10

<210> SEQ ID NO 175
<211> LENGTH: 9
<212> TYPE: PRT
<213> ORGANISM: Oryctolagus cuniculus

<400> SEQUENCE: 175

Gly Phe Ser Phe Ser Asn Ser Tyr Tyr
1               5

```
<210> SEQ ID NO 176
<211> LENGTH: 9
<212> TYPE: PRT
<213> ORGANISM: Oryctolagus cuniculus

<400> SEQUENCE: 176

Ile Tyr Ala Gly Ser Ser Gly Phe Thr
1               5

<210> SEQ ID NO 177
<211> LENGTH: 20
<212> TYPE: PRT
<213> ORGANISM: Oryctolagus cuniculus

<400> SEQUENCE: 177

Ala Arg Asp Arg Gly Tyr Tyr Thr Tyr Gly Tyr Ala Gly Tyr Gly Tyr
1               5                   10                  15

Gly Met Asp Leu
            20

<210> SEQ ID NO 178
<211> LENGTH: 8
<212> TYPE: PRT
<213> ORGANISM: Oryctolagus cuniculus

<400> SEQUENCE: 178

Gly Phe Ser Leu Ser Ser Cys Asn
1               5

<210> SEQ ID NO 179
<211> LENGTH: 7
<212> TYPE: PRT
<213> ORGANISM: Oryctolagus cuniculus

<400> SEQUENCE: 179

Ile Ala Ala Ser Gly Asp Ala
1               5

<210> SEQ ID NO 180
<211> LENGTH: 13
<212> TYPE: PRT
<213> ORGANISM: Oryctolagus cuniculus

<400> SEQUENCE: 180

Ala Arg Gly Ser Tyr Ala Ala Tyr Asn Ala Trp Asp Leu
1               5                   10

<210> SEQ ID NO 181
<211> LENGTH: 9
<212> TYPE: PRT
<213> ORGANISM: Oryctolagus cuniculus

<400> SEQUENCE: 181

Gly Phe Thr Ile Gly Ser Asp Tyr Trp
1               5

<210> SEQ ID NO 182
<211> LENGTH: 9
<212> TYPE: PRT
<213> ORGANISM: Oryctolagus cuniculus

<400> SEQUENCE: 182

Ile Arg Asp Val Gly Gly Gly His Thr
```

```
1               5
```

<210> SEQ ID NO 183
<211> LENGTH: 13
<212> TYPE: PRT
<213> ORGANISM: Oryctolagus cuniculus

<400> SEQUENCE: 183

```
Ala Arg Asp Asn Asp Gly Asp Trp Phe Tyr Phe Asp Leu
1               5                  10
```

<210> SEQ ID NO 184
<211> LENGTH: 8
<212> TYPE: PRT
<213> ORGANISM: Oryctolagus cuniculus

<400> SEQUENCE: 184

```
Gly Phe Ser Leu Ser Ser Tyr Ala
1               5
```

<210> SEQ ID NO 185
<211> LENGTH: 7
<212> TYPE: PRT
<213> ORGANISM: Oryctolagus cuniculus

<400> SEQUENCE: 185

```
Ile Trp Ser Ser Gly Thr Ser
1               5
```

<210> SEQ ID NO 186
<211> LENGTH: 16
<212> TYPE: PRT
<213> ORGANISM: Oryctolagus cuniculus

<400> SEQUENCE: 186

```
Ala Arg Gly Ile Gly Gly Asp Asn Tyr Gly Asp Ile Trp Leu Asp Leu
1               5                  10                  15
```

<210> SEQ ID NO 187
<211> LENGTH: 8
<212> TYPE: PRT
<213> ORGANISM: Oryctolagus cuniculus

<400> SEQUENCE: 187

```
Gly Phe Ser Leu Ser Thr Asn Ala
1               5
```

<210> SEQ ID NO 188
<211> LENGTH: 7
<212> TYPE: PRT
<213> ORGANISM: Oryctolagus cuniculus

<400> SEQUENCE: 188

```
Ile Trp Ser Gly Gly Ser Thr
1               5
```

<210> SEQ ID NO 189
<211> LENGTH: 11
<212> TYPE: PRT
<213> ORGANISM: Oryctolagus cuniculus

<400> SEQUENCE: 189

```
Ala Lys Asn Gly Asp Asn Gly Gln Leu Asp Leu
1               5                  10
```

```
<210> SEQ ID NO 190
<211> LENGTH: 8
<212> TYPE: PRT
<213> ORGANISM: Oryctolagus cuniculus

<400> SEQUENCE: 190

Gly Phe Ser Leu Ser Ser Tyr Ala
1               5

<210> SEQ ID NO 191
<211> LENGTH: 7
<212> TYPE: PRT
<213> ORGANISM: Oryctolagus cuniculus

<400> SEQUENCE: 191

Ile Gly Ser Ser Gly Asn Thr
1               5

<210> SEQ ID NO 192
<211> LENGTH: 15
<212> TYPE: PRT
<213> ORGANISM: Oryctolagus cuniculus

<400> SEQUENCE: 192

Ala Arg Gly Gly Tyr Ser Tyr Asp Asp Tyr Thr Pro Phe Asp Leu
1               5                   10                  15

<210> SEQ ID NO 193
<211> LENGTH: 9
<212> TYPE: PRT
<213> ORGANISM: Oryctolagus cuniculus

<400> SEQUENCE: 193

Gly Phe Thr Ile Ser Ser Asp Tyr Trp
1               5

<210> SEQ ID NO 194
<211> LENGTH: 9
<212> TYPE: PRT
<213> ORGANISM: Oryctolagus cuniculus

<400> SEQUENCE: 194

Ile Arg Asp Val Gly Gly Gly His Thr
1               5

<210> SEQ ID NO 195
<211> LENGTH: 13
<212> TYPE: PRT
<213> ORGANISM: Oryctolagus cuniculus

<400> SEQUENCE: 195

Ala Arg Asp Asn Asp Gly Asp Trp Phe Tyr Phe Asp Leu
1               5                   10

<210> SEQ ID NO 196
<211> LENGTH: 8
<212> TYPE: PRT
<213> ORGANISM: Oryctolagus cuniculus

<400> SEQUENCE: 196

Gly Phe Ser Leu Ser Ala Tyr Ser
1               5

<210> SEQ ID NO 197
```

```
<211> LENGTH: 7
<212> TYPE: PRT
<213> ORGANISM: Oryctolagus cuniculus

<400> SEQUENCE: 197

Ile Gly His Ser Gly Asn Thr
1               5

<210> SEQ ID NO 198
<211> LENGTH: 18
<212> TYPE: PRT
<213> ORGANISM: Oryctolagus cuniculus

<400> SEQUENCE: 198

Ala Arg Glu Asp Tyr Arg Tyr Gly Asp Tyr Gly Tyr Tyr Trp Asp Phe
1               5                   10                  15

Asn Phe

<210> SEQ ID NO 199
<211> LENGTH: 8
<212> TYPE: PRT
<213> ORGANISM: Oryctolagus cuniculus

<400> SEQUENCE: 199

Gly Phe Ser Leu Ser Ser His Tyr
1               5

<210> SEQ ID NO 200
<211> LENGTH: 7
<212> TYPE: PRT
<213> ORGANISM: Oryctolagus cuniculus

<400> SEQUENCE: 200

Ile Ser Gly Ser Gly Ser Ala
1               5

<210> SEQ ID NO 201
<211> LENGTH: 11
<212> TYPE: PRT
<213> ORGANISM: Oryctolagus cuniculus

<400> SEQUENCE: 201

Ala Arg Gly Gly Leu Gly Val Gly Leu Asp Leu
1               5                   10

<210> SEQ ID NO 202
<211> LENGTH: 8
<212> TYPE: PRT
<213> ORGANISM: Oryctolagus cuniculus

<400> SEQUENCE: 202

Gly Phe Ser Leu Ser Asn Tyr Asp
1               5

<210> SEQ ID NO 203
<211> LENGTH: 7
<212> TYPE: PRT
<213> ORGANISM: Oryctolagus cuniculus

<400> SEQUENCE: 203

Ile Gly Ser Gly Asn Asn Pro
1               5

<210> SEQ ID NO 204
```

```
<211> LENGTH: 17
<212> TYPE: PRT
<213> ORGANISM: Oryctolagus cuniculus

<400> SEQUENCE: 204

Ala Arg Asp Ser Leu Pro Phe Thr Asp Asp Ser Thr Asp Tyr Phe Ala
1               5                   10                  15

Leu

<210> SEQ ID NO 205
<211> LENGTH: 8
<212> TYPE: PRT
<213> ORGANISM: Oryctolagus cuniculus

<400> SEQUENCE: 205

Gly Ile Asp Leu Ser Ala Asn Glu
1               5

<210> SEQ ID NO 206
<211> LENGTH: 7
<212> TYPE: PRT
<213> ORGANISM: Oryctolagus cuniculus

<400> SEQUENCE: 206

Leu Ser Tyr His Asn Ile Pro
1               5

<210> SEQ ID NO 207
<211> LENGTH: 11
<212> TYPE: PRT
<213> ORGANISM: Oryctolagus cuniculus

<400> SEQUENCE: 207

Gly Arg Val Phe Thr Ser Thr Ser Phe Asp Pro
1               5                   10

<210> SEQ ID NO 208
<211> LENGTH: 9
<212> TYPE: PRT
<213> ORGANISM: Oryctolagus cuniculus

<400> SEQUENCE: 208

Gly Phe Ser Phe Ser Asn Ser Tyr Tyr
1               5

<210> SEQ ID NO 209
<211> LENGTH: 8
<212> TYPE: PRT
<213> ORGANISM: Oryctolagus cuniculus

<400> SEQUENCE: 209

Ile Tyr Thr Arg Ile Thr Asn Thr
1               5

<210> SEQ ID NO 210
<211> LENGTH: 21
<212> TYPE: PRT
<213> ORGANISM: Oryctolagus cuniculus

<400> SEQUENCE: 210

Arg Asp Arg Tyr Tyr Tyr Ser Asp Pro Tyr Thr Gly Tyr Ala Tyr Ala
1               5                   10                  15

Thr Gly Phe Asn Leu
            20
```

```
<210> SEQ ID NO 211
<211> LENGTH: 8
<212> TYPE: PRT
<213> ORGANISM: Oryctolagus cuniculus

<400> SEQUENCE: 211

Gly Ile Asp Leu Ser Ala Asn Glu
1               5

<210> SEQ ID NO 212
<211> LENGTH: 7
<212> TYPE: PRT
<213> ORGANISM: Oryctolagus cuniculus

<400> SEQUENCE: 212

Leu Ser Tyr His Asn Ile Pro
1               5

<210> SEQ ID NO 213
<211> LENGTH: 11
<212> TYPE: PRT
<213> ORGANISM: Oryctolagus cuniculus

<400> SEQUENCE: 213

Gly Arg Val Phe Thr Ser Thr Ser Phe Asp Pro
1               5                   10

<210> SEQ ID NO 214
<211> LENGTH: 8
<212> TYPE: PRT
<213> ORGANISM: Oryctolagus cuniculus

<400> SEQUENCE: 214

Gly Leu Ser Leu Ser Asn Tyr Asn
1               5

<210> SEQ ID NO 215
<211> LENGTH: 7
<212> TYPE: PRT
<213> ORGANISM: Oryctolagus cuniculus

<400> SEQUENCE: 215

Ile Asn Ala Gly Ser Thr Ile
1               5

<210> SEQ ID NO 216
<211> LENGTH: 14
<212> TYPE: PRT
<213> ORGANISM: Oryctolagus cuniculus

<400> SEQUENCE: 216

Ala Arg Glu Asp Ser Tyr Gly Gly Phe Phe Val Leu Asp Leu
1               5                   10

<210> SEQ ID NO 217
<211> LENGTH: 8
<212> TYPE: PRT
<213> ORGANISM: Oryctolagus cuniculus

<400> SEQUENCE: 217

Arg Phe Ser Leu Ser Ser Asn His
1               5
```

```
<210> SEQ ID NO 218
<211> LENGTH: 7
<212> TYPE: PRT
<213> ORGANISM: Oryctolagus cuniculus

<400> SEQUENCE: 218

Ile Asn Tyr Asn Asn Asn Pro
1               5

<210> SEQ ID NO 219
<211> LENGTH: 14
<212> TYPE: PRT
<213> ORGANISM: Oryctolagus cuniculus

<400> SEQUENCE: 219

Ala Arg Ala Ala Gly Asn Tyr Tyr Val Gly Ala Leu Asn Leu
1               5                   10

<210> SEQ ID NO 220
<211> LENGTH: 8
<212> TYPE: PRT
<213> ORGANISM: Oryctolagus cuniculus

<400> SEQUENCE: 220

Gly Phe Ser Leu Ser Ser Tyr Asp
1               5

<210> SEQ ID NO 221
<211> LENGTH: 7
<212> TYPE: PRT
<213> ORGANISM: Oryctolagus cuniculus

<400> SEQUENCE: 221

Ile Trp Ser Gly Gly Ile Thr
1               5

<210> SEQ ID NO 222
<211> LENGTH: 6
<212> TYPE: PRT
<213> ORGANISM: Oryctolagus cuniculus

<400> SEQUENCE: 222

Ala Arg Asn Phe Asp Leu
1               5

<210> SEQ ID NO 223
<211> LENGTH: 8
<212> TYPE: PRT
<213> ORGANISM: Oryctolagus cuniculus

<400> SEQUENCE: 223

Gly Phe Asp Val Ser Ser Tyr Trp
1               5

<210> SEQ ID NO 224
<211> LENGTH: 8
<212> TYPE: PRT
<213> ORGANISM: Oryctolagus cuniculus

<400> SEQUENCE: 224

Ile Asp Pro Val Phe Gly Thr Thr
1               5

<210> SEQ ID NO 225
<211> LENGTH: 12
```

```
<212> TYPE: PRT
<213> ORGANISM: Oryctolagus cuniculus

<400> SEQUENCE: 225

Ala Thr Asn Thr His Gly Thr Gly Gly Tyr Tyr Leu
1               5                   10

<210> SEQ ID NO 226
<211> LENGTH: 9
<212> TYPE: PRT
<213> ORGANISM: Oryctolagus cuniculus

<400> SEQUENCE: 226

Gly Phe Thr Ile Ser Ser Asp Tyr Trp
1               5

<210> SEQ ID NO 227
<211> LENGTH: 9
<212> TYPE: PRT
<213> ORGANISM: Oryctolagus cuniculus

<400> SEQUENCE: 227

Ile Arg Asp Val Gly Gly Gly Asp Thr
1               5

<210> SEQ ID NO 228
<211> LENGTH: 13
<212> TYPE: PRT
<213> ORGANISM: Oryctolagus cuniculus

<400> SEQUENCE: 228

Ala Arg Asp Asn Asp Gly Asp Trp Phe Tyr Phe Asp Leu
1               5                   10

<210> SEQ ID NO 229
<211> LENGTH: 9
<212> TYPE: PRT
<213> ORGANISM: Oryctolagus cuniculus

<400> SEQUENCE: 229

Gly Phe Ser Phe Ser Gly Ser Tyr Tyr
1               5

<210> SEQ ID NO 230
<211> LENGTH: 9
<212> TYPE: PRT
<213> ORGANISM: Oryctolagus cuniculus

<400> SEQUENCE: 230

Ile Asp Gly Asp Leu Ser Gly Ser Ala
1               5

<210> SEQ ID NO 231
<211> LENGTH: 17
<212> TYPE: PRT
<213> ORGANISM: Oryctolagus cuniculus

<400> SEQUENCE: 231

Ala Arg Glu Gly Pro Val Gly Val Gly Ser Ile Tyr Leu Gly Phe Asp
1               5                   10                  15

Leu

<210> SEQ ID NO 232
<211> LENGTH: 8
```

```
<212> TYPE: PRT
<213> ORGANISM: Oryctolagus cuniculus

<400> SEQUENCE: 232

Gly Phe Ser Leu Ser Ser Asn Ala
1               5

<210> SEQ ID NO 233
<211> LENGTH: 7
<212> TYPE: PRT
<213> ORGANISM: Oryctolagus cuniculus

<400> SEQUENCE: 233

Ile Trp Ser Gly Gly Ser Thr
1               5

<210> SEQ ID NO 234
<211> LENGTH: 11
<212> TYPE: PRT
<213> ORGANISM: Oryctolagus cuniculus

<400> SEQUENCE: 234

Ala Lys Asn Gly Asp Asn Gly Gln Leu Asp Leu
1               5                   10

<210> SEQ ID NO 235
<211> LENGTH: 8
<212> TYPE: PRT
<213> ORGANISM: Oryctolagus cuniculus

<400> SEQUENCE: 235

Gly Phe Ser Leu Ser Asn Tyr Asp
1               5

<210> SEQ ID NO 236
<211> LENGTH: 7
<212> TYPE: PRT
<213> ORGANISM: Oryctolagus cuniculus

<400> SEQUENCE: 236

Ile Gly Ser Gly Asn Asn Pro
1               5

<210> SEQ ID NO 237
<211> LENGTH: 17
<212> TYPE: PRT
<213> ORGANISM: Oryctolagus cuniculus

<400> SEQUENCE: 237

Ala Arg Asp Ser Leu Pro Phe Thr Asp Asp Ser Thr Asp Tyr Phe Ala
1               5                   10                  15

Leu

<210> SEQ ID NO 238
<211> LENGTH: 8
<212> TYPE: PRT
<213> ORGANISM: Oryctolagus cuniculus

<400> SEQUENCE: 238

Gly Phe Ser Leu Arg Ser Tyr Gly
1               5

<210> SEQ ID NO 239
<211> LENGTH: 7
```

<212> TYPE: PRT
<213> ORGANISM: Oryctolagus cuniculus

<400> SEQUENCE: 239

Ile Trp Ser Gly Gly Arg Thr
1               5

<210> SEQ ID NO 240
<211> LENGTH: 5
<212> TYPE: PRT
<213> ORGANISM: Oryctolagus cuniculus

<400> SEQUENCE: 240

Thr Thr Glu Asp Leu
1               5

<210> SEQ ID NO 241
<211> LENGTH: 9
<212> TYPE: PRT
<213> ORGANISM: Oryctolagus cuniculus

<400> SEQUENCE: 241

Gly Phe Ser Phe Ser Asn Asn Tyr Tyr
1               5

<210> SEQ ID NO 242
<211> LENGTH: 9
<212> TYPE: PRT
<213> ORGANISM: Oryctolagus cuniculus

<400> SEQUENCE: 242

Ile Tyr Pro Gly Gly Ser Gly Ser Leu
1               5

<210> SEQ ID NO 243
<211> LENGTH: 16
<212> TYPE: PRT
<213> ORGANISM: Oryctolagus cuniculus

<400> SEQUENCE: 243

Ala Lys Ser Ile Gly Thr Gly Ser Ala Tyr Ile Met Gly Ala Gly Leu
1               5                   10                  15

<210> SEQ ID NO 244
<211> LENGTH: 8
<212> TYPE: PRT
<213> ORGANISM: Oryctolagus cuniculus

<400> SEQUENCE: 244

Gly Phe Ser Leu Ser Ser Tyr Ala
1               5

<210> SEQ ID NO 245
<211> LENGTH: 7
<212> TYPE: PRT
<213> ORGANISM: Oryctolagus cuniculus

<400> SEQUENCE: 245

Ile Gly Tyr Ser Gly Asn Ser
1               5

<210> SEQ ID NO 246
<211> LENGTH: 15
<212> TYPE: PRT
<213> ORGANISM: Oryctolagus cuniculus

<400> SEQUENCE: 246

Ala Arg Gly Gly Tyr Ser Tyr Asp Asp Tyr Thr Pro Phe Asp Leu
1               5                   10                  15

<210> SEQ ID NO 247
<211> LENGTH: 8
<212> TYPE: PRT
<213> ORGANISM: Oryctolagus cuniculus

<400> SEQUENCE: 247

Gly Phe Ser Leu Ser Ser Tyr His
1               5

<210> SEQ ID NO 248
<211> LENGTH: 7
<212> TYPE: PRT
<213> ORGANISM: Oryctolagus cuniculus

<400> SEQUENCE: 248

Ile Asn Asn Asn Asp Asn Pro
1               5

<210> SEQ ID NO 249
<211> LENGTH: 14
<212> TYPE: PRT
<213> ORGANISM: Oryctolagus cuniculus

<400> SEQUENCE: 249

Ala Arg Ala Ala Gly Asn Tyr Tyr Val Gly Ala Leu Asn Leu
1               5                   10

<210> SEQ ID NO 250
<211> LENGTH: 8
<212> TYPE: PRT
<213> ORGANISM: Oryctolagus cuniculus

<400> SEQUENCE: 250

Gly Phe Ser Pro Ser Ser Tyr Asn
1               5

<210> SEQ ID NO 251
<211> LENGTH: 7
<212> TYPE: PRT
<213> ORGANISM: Oryctolagus cuniculus

<400> SEQUENCE: 251

Ile Ser Thr Ser Gly Asn Thr
1               5

<210> SEQ ID NO 252
<211> LENGTH: 13
<212> TYPE: PRT
<213> ORGANISM: Oryctolagus cuniculus

<400> SEQUENCE: 252

Ala Arg Gly Ser Tyr Val Ala Tyr Asn Ala Trp Asp Leu
1               5                   10

<210> SEQ ID NO 253
<211> LENGTH: 8
<212> TYPE: PRT
<213> ORGANISM: Oryctolagus cuniculus

<400> SEQUENCE: 253

```
Gly Phe Ser Leu Ser Ser Tyr His
1               5

<210> SEQ ID NO 254
<211> LENGTH: 7
<212> TYPE: PRT
<213> ORGANISM: Oryctolagus cuniculus

<400> SEQUENCE: 254

Ile Asn Asn Tyr Gly Ala Thr
1               5

<210> SEQ ID NO 255
<211> LENGTH: 11
<212> TYPE: PRT
<213> ORGANISM: Oryctolagus cuniculus

<400> SEQUENCE: 255

Ala Arg Ser Pro Gly Ile Pro Gly Tyr Asn Leu
1               5                   10

<210> SEQ ID NO 256
<211> LENGTH: 8
<212> TYPE: PRT
<213> ORGANISM: Oryctolagus cuniculus

<400> SEQUENCE: 256

Gly Phe Ser Leu Ser Ser Tyr Tyr
1               5

<210> SEQ ID NO 257
<211> LENGTH: 8
<212> TYPE: PRT
<213> ORGANISM: Oryctolagus cuniculus

<400> SEQUENCE: 257

Ile Tyr Gly Gly Ser Gly Arg Thr
1               5

<210> SEQ ID NO 258
<211> LENGTH: 17
<212> TYPE: PRT
<213> ORGANISM: Oryctolagus cuniculus

<400> SEQUENCE: 258

Ala Arg Gly Tyr Tyr Asp Gly Ser Ile Tyr Phe Ser Ile Tyr Leu Asp
1               5                   10                  15

Leu

<210> SEQ ID NO 259
<211> LENGTH: 9
<212> TYPE: PRT
<213> ORGANISM: Oryctolagus cuniculus

<400> SEQUENCE: 259

Gly Phe Thr Ile Ser Ser Asp Tyr Trp
1               5

<210> SEQ ID NO 260
<211> LENGTH: 9
<212> TYPE: PRT
<213> ORGANISM: Oryctolagus cuniculus

<400> SEQUENCE: 260
```

-continued

Ile Arg Asp Val Gly Gly Gly His Thr
1               5

<210> SEQ ID NO 261
<211> LENGTH: 13
<212> TYPE: PRT
<213> ORGANISM: Oryctolagus cuniculus

<400> SEQUENCE: 261

Ala Arg Asp Asn Asp Gly Asp Trp Phe Tyr Phe Asp Leu
1               5                   10

<210> SEQ ID NO 262
<211> LENGTH: 9
<212> TYPE: PRT
<213> ORGANISM: Oryctolagus cuniculus

<400> SEQUENCE: 262

Gly Phe Thr Ile Ser Ser Asp Tyr Trp
1               5

<210> SEQ ID NO 263
<211> LENGTH: 9
<212> TYPE: PRT
<213> ORGANISM: Oryctolagus cuniculus

<400> SEQUENCE: 263

Ile Arg Asp Val Gly Gly Gly Asp Thr
1               5

<210> SEQ ID NO 264
<211> LENGTH: 13
<212> TYPE: PRT
<213> ORGANISM: Oryctolagus cuniculus

<400> SEQUENCE: 264

Ala Arg Asp Asn Asp Gly Asp Trp Phe Tyr Phe Asp Leu
1               5                   10

<210> SEQ ID NO 265
<211> LENGTH: 8
<212> TYPE: PRT
<213> ORGANISM: Oryctolagus cuniculus

<400> SEQUENCE: 265

Gly Ile Asp Leu Ser Thr Tyr Ala
1               5

<210> SEQ ID NO 266
<211> LENGTH: 7
<212> TYPE: PRT
<213> ORGANISM: Oryctolagus cuniculus

<400> SEQUENCE: 266

Ile Gly Ser Ser Gly Gly Ala
1               5

<210> SEQ ID NO 267
<211> LENGTH: 15
<212> TYPE: PRT
<213> ORGANISM: Oryctolagus cuniculus

<400> SEQUENCE: 267

Ala Val Ser Leu Tyr Thr Tyr Asp Asp Tyr Ala Asp Tyr Phe Leu

<210> SEQ ID NO 268
<211> LENGTH: 9
<212> TYPE: PRT
<213> ORGANISM: Oryctolagus cuniculus

<400> SEQUENCE: 268

Gly Phe Ser Phe Ser Asn Ser Tyr Tyr
1               5

<210> SEQ ID NO 269
<211> LENGTH: 9
<212> TYPE: PRT
<213> ORGANISM: Oryctolagus cuniculus

<400> SEQUENCE: 269

Ile Tyr Ala Gly Ser Ser Gly Phe Thr
1               5

<210> SEQ ID NO 270
<211> LENGTH: 20
<212> TYPE: PRT
<213> ORGANISM: Oryctolagus cuniculus

<400> SEQUENCE: 270

Ala Arg Asp Arg Gly Tyr Tyr Thr Tyr Gly Tyr Ala Gly Tyr Gly Tyr
1               5                   10                  15

Gly Met Asp Leu
            20

<210> SEQ ID NO 271
<211> LENGTH: 26
<212> TYPE: PRT
<213> ORGANISM: Oryctolagus cuniculus

<400> SEQUENCE: 271

Glu Leu Asp Leu Thr Gln Thr Pro Ala Ser Val Ser Glu Pro Val Gly
1               5                   10                  15

Gly Thr Val Thr Val Lys Cys Gln Ala Ser
            20                  25

<210> SEQ ID NO 272
<211> LENGTH: 17
<212> TYPE: PRT
<213> ORGANISM: Oryctolagus cuniculus

<400> SEQUENCE: 272

Leu Ala Trp Tyr Arg Gln Lys Pro Gly Gln Pro Pro Lys Leu Leu Ile
1               5                   10                  15

Tyr

<210> SEQ ID NO 273
<211> LENGTH: 26
<212> TYPE: PRT
<213> ORGANISM: Oryctolagus cuniculus

<400> SEQUENCE: 273

Glu Leu Val Met Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 274
<211> LENGTH: 17
<212> TYPE: PRT
<213> ORGANISM: Oryctolagus cuniculus

<400> SEQUENCE: 274

Leu Ala Trp Tyr Gln Gln Glu Pro Gly Gln Pro Pro Lys Leu Leu Ile
1               5                   10                  15

Tyr

<210> SEQ ID NO 275
<211> LENGTH: 26
<212> TYPE: PRT
<213> ORGANISM: Oryctolagus cuniculus

<400> SEQUENCE: 275

Glu Leu Val Met Thr Gln Thr Pro Ala Ser Val Glu Ala Ala Val Gly
1               5                   10                  15

Gly Thr Val Ala Ile Lys Cys Gln Ala Ser
            20                  25

<210> SEQ ID NO 276
<211> LENGTH: 17
<212> TYPE: PRT
<213> ORGANISM: Oryctolagus cuniculus

<400> SEQUENCE: 276

Leu Ser Trp Tyr Gln Gln Lys Pro Gly Gln Arg Leu Lys Leu Leu Ile
1               5                   10                  15

Tyr

<210> SEQ ID NO 277
<211> LENGTH: 26
<212> TYPE: PRT
<213> ORGANISM: Oryctolagus cuniculus

<400> SEQUENCE: 277

Glu Leu Val Leu Thr Gln Thr Pro Ala Ser Val Glu Ala Ala Val Gly
1               5                   10                  15

Gly Thr Val Thr Ile Asn Cys Gln Ala Ser
            20                  25

<210> SEQ ID NO 278
<211> LENGTH: 17
<212> TYPE: PRT
<213> ORGANISM: Oryctolagus cuniculus

<400> SEQUENCE: 278

Leu Ala Trp Tyr Arg Gln Lys Pro Gly Gln Arg Pro Glu Leu Leu Ile
1               5                   10                  15

Tyr

<210> SEQ ID NO 279
<211> LENGTH: 26
<212> TYPE: PRT
<213> ORGANISM: Oryctolagus cuniculus

<400> SEQUENCE: 279

Glu Leu Val Met Thr Gln Thr Pro Ser Pro Val Ser Ala Pro Val Gly
1               5                   10                  15

Gly Thr Val Thr Ile Ser Cys Gln Ala Ser

```
                20                  25

<210> SEQ ID NO 280
<211> LENGTH: 17
<212> TYPE: PRT
<213> ORGANISM: Oryctolagus cuniculus

<400> SEQUENCE: 280

Val Ala Trp Phe Gln His Lys Pro Gly Gln Pro Pro Lys Leu Leu Ile
1               5                  10                  15

Tyr

<210> SEQ ID NO 281
<211> LENGTH: 26
<212> TYPE: PRT
<213> ORGANISM: Oryctolagus cuniculus

<400> SEQUENCE: 281

Glu Leu Asp Met Thr Gln Thr Pro Ala Ser Val Ser Ala Ala Val Gly
1               5                  10                  15

Gly Thr Val Thr Ile Asn Cys Gln Ala Ser
            20                  25

<210> SEQ ID NO 282
<211> LENGTH: 17
<212> TYPE: PRT
<213> ORGANISM: Oryctolagus cuniculus

<400> SEQUENCE: 282

Leu Ala Trp Tyr Gln Gln Lys Pro Gly Gln Pro Pro Lys Leu Leu Ile
1               5                  10                  15

Tyr

<210> SEQ ID NO 283
<211> LENGTH: 26
<212> TYPE: PRT
<213> ORGANISM: Oryctolagus cuniculus

<400> SEQUENCE: 283

Glu Leu Asp Leu Thr Gln Thr Pro Ala Ser Val Glu Ala Ala Val Gly
1               5                  10                  15

Gly Thr Val Ala Ile Lys Cys Gln Ala Ser
            20                  25

<210> SEQ ID NO 284
<211> LENGTH: 17
<212> TYPE: PRT
<213> ORGANISM: Oryctolagus cuniculus

<400> SEQUENCE: 284

Leu Ser Trp Tyr Gln Gln Lys Pro Gly Gln Arg Pro Lys Leu Leu Ile
1               5                  10                  15

Tyr

<210> SEQ ID NO 285
<211> LENGTH: 26
<212> TYPE: PRT
<213> ORGANISM: Oryctolagus cuniculus

<400> SEQUENCE: 285

Glu Leu Asp Leu Thr Gln Thr Ala Ser Pro Val Ser Ala Pro Val Gly
1               5                  10                  15
```

-continued

Gly Thr Val Thr Ile Asn Cys Gln Ala Ser
            20                  25

<210> SEQ ID NO 286
<211> LENGTH: 17
<212> TYPE: PRT
<213> ORGANISM: Oryctolagus cuniculus

<400> SEQUENCE: 286

Leu Ala Trp Tyr Gln Gln Lys Pro Gly Gln Pro Pro Lys Leu Leu Ile
1               5                   10                  15

Tyr

<210> SEQ ID NO 287
<211> LENGTH: 26
<212> TYPE: PRT
<213> ORGANISM: Oryctolagus cuniculus

<400> SEQUENCE: 287

Glu Leu Asp Met Thr Gln Thr Pro Ala Ser Val Ser Glu Pro Val Gly
1               5                   10                  15

Gly Thr Val Thr Ile Lys Cys Gln Ala Ser
            20                  25

<210> SEQ ID NO 288
<211> LENGTH: 17
<212> TYPE: PRT
<213> ORGANISM: Oryctolagus cuniculus

<400> SEQUENCE: 288

Leu Ala Trp Tyr Gln Gln Arg Pro Gly Gln Pro Pro Lys Pro Leu Ile
1               5                   10                  15

Tyr

<210> SEQ ID NO 289
<211> LENGTH: 26
<212> TYPE: PRT
<213> ORGANISM: Oryctolagus cuniculus

<400> SEQUENCE: 289

Glu Leu Asp Leu Thr Gln Thr Pro Ala Ser Val Glu Ala Ala Val Gly
1               5                   10                  15

Gly Thr Val Thr Ile Lys Cys Gln Ala Ser
            20                  25

<210> SEQ ID NO 290
<211> LENGTH: 17
<212> TYPE: PRT
<213> ORGANISM: Oryctolagus cuniculus

<400> SEQUENCE: 290

Leu Ser Trp Tyr Gln Gln Lys Pro Gly Gln Pro Pro Lys Leu Leu Ile
1               5                   10                  15

Tyr

<210> SEQ ID NO 291
<211> LENGTH: 26
<212> TYPE: PRT
<213> ORGANISM: Oryctolagus cuniculus

<400> SEQUENCE: 291

Glu Arg Asp Met Thr Gln Thr Pro Ala Ser Val Glu Val Ala Val Gly
1               5                   10                  15

Gly Thr Val Thr Ile Lys Cys Gln Ala Ser
            20                  25

<210> SEQ ID NO 292
<211> LENGTH: 17
<212> TYPE: PRT
<213> ORGANISM: Oryctolagus cuniculus

<400> SEQUENCE: 292

Leu Ala Trp Tyr Gln Gln Lys Pro Gly Gln Arg Pro Lys Leu Leu Ile
1               5                   10                  15

Tyr

<210> SEQ ID NO 293
<211> LENGTH: 26
<212> TYPE: PRT
<213> ORGANISM: Oryctolagus cuniculus

<400> SEQUENCE: 293

Glu Leu Asp Leu Thr Gln Thr Pro Ala Ser Val Glu Ala Ala Val Gly
1               5                   10                  15

Gly Thr Val Thr Ile Lys Cys Arg Ala Ser
            20                  25

<210> SEQ ID NO 294
<211> LENGTH: 17
<212> TYPE: PRT
<213> ORGANISM: Oryctolagus cuniculus

<400> SEQUENCE: 294

Phe Ser Trp Tyr Gln Gln Lys Pro Gly Gln Pro Pro Lys Leu Leu Ile
1               5                   10                  15

Tyr

<210> SEQ ID NO 295
<211> LENGTH: 26
<212> TYPE: PRT
<213> ORGANISM: Oryctolagus cuniculus

<400> SEQUENCE: 295

Glu Leu Val Leu Thr Gln Thr Pro Ala Ser Val Glu Ala Ala Val Gly
1               5                   10                  15

Gly Thr Val Thr Ile Lys Cys Gln Ala Ser
            20                  25

<210> SEQ ID NO 296
<211> LENGTH: 17
<212> TYPE: PRT
<213> ORGANISM: Oryctolagus cuniculus

<400> SEQUENCE: 296

Leu Ala Trp Tyr Gln Gln Lys Ser Gly Gln Pro Pro Lys Leu Leu Ile
1               5                   10                  15

Tyr

<210> SEQ ID NO 297
<211> LENGTH: 26
<212> TYPE: PRT
<213> ORGANISM: Oryctolagus cuniculus

```
<400> SEQUENCE: 297

Glu Leu Asp Leu Thr Gln Thr Pro Ala Ser Val Glu Ala Ala Val Gly
1               5                   10                  15

Gly Thr Val Thr Ile Lys Cys Gln Ala Ser
            20                  25

<210> SEQ ID NO 298
<211> LENGTH: 17
<212> TYPE: PRT
<213> ORGANISM: Oryctolagus cuniculus

<400> SEQUENCE: 298

Leu Ser Trp Tyr Gln Gln Lys Pro Gly Gln Pro Pro Lys Leu Leu Ile
1               5                   10                  15

Tyr

<210> SEQ ID NO 299
<211> LENGTH: 26
<212> TYPE: PRT
<213> ORGANISM: Oryctolagus cuniculus

<400> SEQUENCE: 299

Glu Leu Asp Met Thr Gln Thr Ala Ser Pro Val Ser Ala Ala Val Gly
1               5                   10                  15

Gly Thr Val Thr Ile Asn Cys Gln Ser Ser
            20                  25

<210> SEQ ID NO 300
<211> LENGTH: 17
<212> TYPE: PRT
<213> ORGANISM: Oryctolagus cuniculus

<400> SEQUENCE: 300

Leu Ser Trp Tyr Gln Gln Lys Pro Gly Gln Pro Pro Lys Leu Leu Ile
1               5                   10                  15

Tyr

<210> SEQ ID NO 301
<211> LENGTH: 26
<212> TYPE: PRT
<213> ORGANISM: Oryctolagus cuniculus

<400> SEQUENCE: 301

Glu Leu Asp Leu Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 302
<211> LENGTH: 17
<212> TYPE: PRT
<213> ORGANISM: Oryctolagus cuniculus

<400> SEQUENCE: 302

Leu Ala Trp Tyr Gln Gln Glu Pro Gly Gln Pro Pro Lys Leu Leu Ile
1               5                   10                  15

Tyr

<210> SEQ ID NO 303
<211> LENGTH: 26
<212> TYPE: PRT
```

<213> ORGANISM: Oryctolagus cuniculus

<400> SEQUENCE: 303

Glu Leu Asp Leu Thr Gln Thr Pro Ser Pro Val Ser Ala Ala Val Gly
1               5                   10                  15

Gly Thr Val Thr Ile Asn Cys Gln Ala Ser
            20                  25

<210> SEQ ID NO 304
<211> LENGTH: 17
<212> TYPE: PRT
<213> ORGANISM: Oryctolagus cuniculus

<400> SEQUENCE: 304

Leu Ser Trp Phe Gln Gln Lys Leu Gly Gln Pro Pro Lys Leu Leu Ile
1               5                   10                  15

Tyr

<210> SEQ ID NO 305
<211> LENGTH: 26
<212> TYPE: PRT
<213> ORGANISM: Oryctolagus cuniculus

<400> SEQUENCE: 305

Glu Leu Val Leu Thr Gln Thr Pro Ser Pro Val Ser Ala Ala Val Gly
1               5                   10                  15

Gly Thr Val Thr Ile Asn Cys Gln Thr Ser
            20                  25

<210> SEQ ID NO 306
<211> LENGTH: 17
<212> TYPE: PRT
<213> ORGANISM: Oryctolagus cuniculus

<400> SEQUENCE: 306

Leu Ser Trp Tyr Gln Gln Lys Pro Gly Gln Pro Pro Lys Leu Leu Ile
1               5                   10                  15

Tyr

<210> SEQ ID NO 307
<211> LENGTH: 25
<212> TYPE: PRT
<213> ORGANISM: Oryctolagus cuniculus

<400> SEQUENCE: 307

Glu Leu Val Leu Thr Gln Ser Pro Ser Leu Ser Ala Ser Leu Gly Thr
1               5                   10                  15

Thr Ala Arg Leu Thr Cys Thr Leu Ser
            20                  25

<210> SEQ ID NO 308
<211> LENGTH: 17
<212> TYPE: PRT
<213> ORGANISM: Oryctolagus cuniculus

<400> SEQUENCE: 308

Leu Val Trp Leu Gln Gln Val Pro Gly Arg Pro Pro Arg Tyr Leu Leu
1               5                   10                  15

Thr

<210> SEQ ID NO 309

```
<211> LENGTH: 26
<212> TYPE: PRT
<213> ORGANISM: Oryctolagus cuniculus

<400> SEQUENCE: 309

Glu Leu Glu Leu Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 310
<211> LENGTH: 17
<212> TYPE: PRT
<213> ORGANISM: Oryctolagus cuniculus

<400> SEQUENCE: 310

Leu Ala Trp Tyr Gln Gln Glu Pro Gly Gln Pro Pro Lys Leu Leu Ile
1               5                   10                  15

Tyr

<210> SEQ ID NO 311
<211> LENGTH: 26
<212> TYPE: PRT
<213> ORGANISM: Oryctolagus cuniculus

<400> SEQUENCE: 311

Glu Leu Val Met Thr Gln Thr Pro Ser Pro Val Ser Ala Pro Val Gly
1               5                   10                  15

Gly Thr Val Thr Ile Ser Cys Gln Ala Ser
            20                  25

<210> SEQ ID NO 312
<211> LENGTH: 17
<212> TYPE: PRT
<213> ORGANISM: Oryctolagus cuniculus

<400> SEQUENCE: 312

Val Ala Trp Phe Gln His Arg Pro Gly Gln Pro Pro Lys Leu Leu Ile
1               5                   10                  15

Tyr

<210> SEQ ID NO 313
<211> LENGTH: 26
<212> TYPE: PRT
<213> ORGANISM: Oryctolagus cuniculus

<400> SEQUENCE: 313

Glu Leu Val Met Thr Gln Thr Ala Ser Ser Val Ser Ala Ala Val Gly
1               5                   10                  15

Gly Thr Val Thr Ile Ser Cys Gln Ser Ser
            20                  25

<210> SEQ ID NO 314
<211> LENGTH: 17
<212> TYPE: PRT
<213> ORGANISM: Oryctolagus cuniculus

<400> SEQUENCE: 314

Leu Gly Trp Tyr Gln Gln Lys Pro Gly Gln Pro Pro Lys Leu Leu Ile
1               5                   10                  15

Tyr
```

-continued

<210> SEQ ID NO 315
<211> LENGTH: 26
<212> TYPE: PRT
<213> ORGANISM: Oryctolagus cuniculus

<400> SEQUENCE: 315

Glu Leu Val Leu Thr Gln Thr Pro Ser Pro Val Ser Ala Ala Val Gly
1               5                   10                  15

Gly Thr Val Thr Ile Asn Cys Gln Thr Ser
            20                  25

<210> SEQ ID NO 316
<211> LENGTH: 17
<212> TYPE: PRT
<213> ORGANISM: Oryctolagus cuniculus

<400> SEQUENCE: 316

Leu Ser Trp Tyr Gln Gln Lys Pro Gly Gln Pro Pro Lys Leu Leu Ile
1               5                   10                  15

Tyr

<210> SEQ ID NO 317
<211> LENGTH: 26
<212> TYPE: PRT
<213> ORGANISM: Oryctolagus cuniculus

<400> SEQUENCE: 317

Glu Leu Val Met Thr His Pro Pro Ala Ser Val Ser Ala Pro Val Gly
1               5                   10                  15

Gly Thr Val Thr Ile Lys Cys Gln Ala Ser
            20                  25

<210> SEQ ID NO 318
<211> LENGTH: 17
<212> TYPE: PRT
<213> ORGANISM: Oryctolagus cuniculus

<400> SEQUENCE: 318

Leu Pro Trp Tyr Gln Gln Glu Pro Gly Gln Pro Pro Lys Leu Leu Ile
1               5                   10                  15

Tyr

<210> SEQ ID NO 319
<211> LENGTH: 26
<212> TYPE: PRT
<213> ORGANISM: Oryctolagus cuniculus

<400> SEQUENCE: 319

Glu Leu Val Leu Thr Gln Thr Pro Ala Ser Val Glu Ala Ala Val Gly
1               5                   10                  15

Gly Thr Val Thr Ile Lys Cys Arg Ala Ser
            20                  25

<210> SEQ ID NO 320
<211> LENGTH: 17
<212> TYPE: PRT
<213> ORGANISM: Oryctolagus cuniculus

<400> SEQUENCE: 320

Phe Ser Trp Tyr Gln Gln Lys Pro Gly Gln Pro Pro Lys Leu Leu Ile
1               5                   10                  15

Tyr

<210> SEQ ID NO 321
<211> LENGTH: 26
<212> TYPE: PRT
<213> ORGANISM: Oryctolagus cuniculus

<400> SEQUENCE: 321

Glu Leu Val Leu Thr Gln Thr Pro Ala Ser Val Glu Ala Ala Val Gly
1               5                   10                  15

Gly Thr Val Thr Ile Lys Cys Gln Ala Ser
            20                  25

<210> SEQ ID NO 322
<211> LENGTH: 17
<212> TYPE: PRT
<213> ORGANISM: Oryctolagus cuniculus

<400> SEQUENCE: 322

Leu Ser Trp Tyr Gln Gln Lys Pro Gly Gln Pro Pro Lys Leu Leu Ile
1               5                   10                  15

Tyr

<210> SEQ ID NO 323
<211> LENGTH: 26
<212> TYPE: PRT
<213> ORGANISM: Oryctolagus cuniculus

<400> SEQUENCE: 323

Glu Leu Val Leu Thr Gln Thr Pro Ala Ser Val Glu Val Gly Val Gly
1               5                   10                  15

Gly Thr Val Thr Ile Asn Cys Gln Ala Ser
            20                  25

<210> SEQ ID NO 324
<211> LENGTH: 17
<212> TYPE: PRT
<213> ORGANISM: Oryctolagus cuniculus

<400> SEQUENCE: 324

Leu Ala Trp Tyr Gln Gln Lys Pro Gly Gln Pro Pro Lys Leu Leu Ile
1               5                   10                  15

Tyr

<210> SEQ ID NO 325
<211> LENGTH: 26
<212> TYPE: PRT
<213> ORGANISM: Oryctolagus cuniculus

<400> SEQUENCE: 325

Glu Leu Val Met Thr Gln Thr Pro Ala Ser Val Glu Val Ala Val Gly
1               5                   10                  15

Gly Thr Val Thr Ile Lys Cys Gln Ala Ser
            20                  25

<210> SEQ ID NO 326
<211> LENGTH: 17
<212> TYPE: PRT
<213> ORGANISM: Oryctolagus cuniculus

<400> SEQUENCE: 326

Leu Ala Trp Tyr Gln Gln Glu Pro Gly Gln Arg Pro Lys Leu Leu Ile

-continued

<210> SEQ ID NO 327
<211> LENGTH: 26
<212> TYPE: PRT
<213> ORGANISM: Oryctolagus cuniculus

<400> SEQUENCE: 327

Glu Leu Val Leu Thr Gln Thr Pro Ala Ser Val Ser Glu Pro Val Gly
1               5                   10                  15

Gly Thr Val Thr Ile Lys Cys Gln Ala Ser
            20                  25

<210> SEQ ID NO 328
<211> LENGTH: 17
<212> TYPE: PRT
<213> ORGANISM: Oryctolagus cuniculus

<400> SEQUENCE: 328

Leu Ala Trp Tyr His Gln Lys Pro Gly Gln Pro Pro Lys Leu Leu Ile
1               5                   10                  15

Tyr

<210> SEQ ID NO 329
<211> LENGTH: 26
<212> TYPE: PRT
<213> ORGANISM: Oryctolagus cuniculus

<400> SEQUENCE: 329

Glu Leu Asp Met Thr Gln Thr Pro Ala Ser Val Ser Glu Pro Val Gly
1               5                   10                  15

Gly Thr Val Thr Ile Lys Cys Gln Ala Ser
            20                  25

<210> SEQ ID NO 330
<211> LENGTH: 17
<212> TYPE: PRT
<213> ORGANISM: Oryctolagus cuniculus

<400> SEQUENCE: 330

Leu Ala Trp Tyr Gln Gln Lys Pro Gly Gln Pro Pro Lys Leu Leu Ile
1               5                   10                  15

Tyr

<210> SEQ ID NO 331
<211> LENGTH: 26
<212> TYPE: PRT
<213> ORGANISM: Oryctolagus cuniculus

<400> SEQUENCE: 331

Glu Leu Val Leu Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 332
<211> LENGTH: 17
<212> TYPE: PRT
<213> ORGANISM: Oryctolagus cuniculus

<400> SEQUENCE: 332

```
Leu Ala Trp Tyr Gln Gln Glu Pro Gly Gln Pro Lys Leu Leu Ile
1               5                   10                  15

Tyr

<210> SEQ ID NO 333
<211> LENGTH: 26
<212> TYPE: PRT
<213> ORGANISM: Oryctolagus cuniculus

<400> SEQUENCE: 333

Glu Leu Asp Leu Thr Gln Thr Pro Ala Ser Val Glu Val Pro Val Gly
1               5                   10                  15

Gly Thr Val Thr Ile Lys Cys Gln Ala Ser
            20                  25

<210> SEQ ID NO 334
<211> LENGTH: 17
<212> TYPE: PRT
<213> ORGANISM: Oryctolagus cuniculus

<400> SEQUENCE: 334

Leu Ser Trp Tyr Gln Gln Lys Pro Gly Gln Pro Lys Leu Leu Ile
1               5                   10                  15

Tyr

<210> SEQ ID NO 335
<211> LENGTH: 26
<212> TYPE: PRT
<213> ORGANISM: Oryctolagus cuniculus

<400> SEQUENCE: 335

Glu Leu Val Leu Thr Gln Thr Pro Ser Pro Val Ser Ala Ala Val Gly
1               5                   10                  15

Gly Thr Val Thr Ile Asn Cys Lys Thr Ser
            20                  25

<210> SEQ ID NO 336
<211> LENGTH: 17
<212> TYPE: PRT
<213> ORGANISM: Oryctolagus cuniculus

<400> SEQUENCE: 336

Leu Ser Trp Tyr Gln Gln Lys Pro Gly Gln Pro Lys Leu Leu Ile
1               5                   10                  15

Tyr

<210> SEQ ID NO 337
<211> LENGTH: 26
<212> TYPE: PRT
<213> ORGANISM: Oryctolagus cuniculus

<400> SEQUENCE: 337

Glu Leu Asp Met Thr Gln Thr Pro Ser Ser Val Ser Glu Pro Val Gly
1               5                   10                  15

Gly Thr Val Thr Ile Asn Cys Gln Ala Ser
            20                  25

<210> SEQ ID NO 338
<211> LENGTH: 17
<212> TYPE: PRT
<213> ORGANISM: Oryctolagus cuniculus
```

-continued

<400> SEQUENCE: 338

Leu Ala Trp Tyr Gln Gln Lys Pro Gly Gln Arg Pro Lys Leu Leu Ile
1               5                   10                  15

Tyr

<210> SEQ ID NO 339
<211> LENGTH: 26
<212> TYPE: PRT
<213> ORGANISM: Oryctolagus cuniculus

<400> SEQUENCE: 339

Glu Leu Val Leu Thr Gln Thr Pro Ser Ser Val Ser Ala Ala Val Gly
1               5                   10                  15

Gly Thr Val Thr Ile Asn Cys Gln Ala Ser
            20                  25

<210> SEQ ID NO 340
<211> LENGTH: 17
<212> TYPE: PRT
<213> ORGANISM: Oryctolagus cuniculus

<400> SEQUENCE: 340

Leu Ala Trp Tyr Gln Gln Lys Pro Gly Gln Pro Pro Lys Arg Leu Ile
1               5                   10                  15

Tyr

<210> SEQ ID NO 341
<211> LENGTH: 26
<212> TYPE: PRT
<213> ORGANISM: Oryctolagus cuniculus

<400> SEQUENCE: 341

Glu Leu Glu Leu Thr Gln Thr Pro Ser Pro Val Ser Ala Ala Val Gly
1               5                   10                  15

Gly Thr Val Ser Ile Ser Cys Gln Ala Ser
            20                  25

<210> SEQ ID NO 342
<211> LENGTH: 17
<212> TYPE: PRT
<213> ORGANISM: Oryctolagus cuniculus

<400> SEQUENCE: 342

Leu Ser Trp Tyr Gln Gln Lys Pro Gly Gln Pro Pro Lys Leu Leu Ile
1               5                   10                  15

Tyr

<210> SEQ ID NO 343
<211> LENGTH: 26
<212> TYPE: PRT
<213> ORGANISM: Oryctolagus cuniculus

<400> SEQUENCE: 343

Glu Leu Asp Leu Thr Gln Thr Pro Ala Ser Val Glu Ala Ala Val Gly
1               5                   10                  15

Gly Thr Val Ala Ile Lys Cys Gln Ala Ser
            20                  25

<210> SEQ ID NO 344
<211> LENGTH: 17

```
<212> TYPE: PRT
<213> ORGANISM: Oryctolagus cuniculus

<400> SEQUENCE: 344

Leu Ser Trp Tyr Gln Gln Lys Pro Gly Gln Arg Leu Lys Leu Leu Ile
1               5                   10                  15

Tyr

<210> SEQ ID NO 345
<211> LENGTH: 26
<212> TYPE: PRT
<213> ORGANISM: Oryctolagus cuniculus

<400> SEQUENCE: 345

Glu Leu Val Leu Thr Gln Thr Pro Ala Ser Val Glu Val Ala Val Gly
1               5                   10                  15

Gly Thr Val Thr Ile Lys Cys Gln Ala Ser
            20                  25

<210> SEQ ID NO 346
<211> LENGTH: 17
<212> TYPE: PRT
<213> ORGANISM: Oryctolagus cuniculus

<400> SEQUENCE: 346

Leu Gly Trp Tyr Gln Gln Lys Pro Gly Arg Pro Pro Lys Leu Leu Ile
1               5                   10                  15

Tyr

<210> SEQ ID NO 347
<211> LENGTH: 26
<212> TYPE: PRT
<213> ORGANISM: Oryctolagus cuniculus

<400> SEQUENCE: 347

Glu Leu Asp Leu Thr Gln Thr Ala Ser Pro Val Ser Ala Ala Val Gly
1               5                   10                  15

Gly Thr Val Thr Ile Asn Cys Gln Ser Ser
            20                  25

<210> SEQ ID NO 348
<211> LENGTH: 17
<212> TYPE: PRT
<213> ORGANISM: Oryctolagus cuniculus

<400> SEQUENCE: 348

Leu Ser Trp Tyr Gln Gln Lys Pro Gly Gln Pro Pro Lys Leu Leu Ile
1               5                   10                  15

Tyr

<210> SEQ ID NO 349
<211> LENGTH: 26
<212> TYPE: PRT
<213> ORGANISM: Oryctolagus cuniculus

<400> SEQUENCE: 349

Glu Leu Val Leu Thr Gln Thr Pro Ser Pro Val Ser Ala Ala Val Gly
1               5                   10                  15

Gly Thr Val Thr Ile Ser Cys Gln Ala Ser
            20                  25
```

```
<210> SEQ ID NO 350
<211> LENGTH: 17
<212> TYPE: PRT
<213> ORGANISM: Oryctolagus cuniculus

<400> SEQUENCE: 350

Leu Ser Trp Tyr Gln Gln Lys Pro Gly Gln Pro Pro Lys Leu Leu Ile
1               5                   10                  15

Tyr

<210> SEQ ID NO 351
<211> LENGTH: 26
<212> TYPE: PRT
<213> ORGANISM: Oryctolagus cuniculus

<400> SEQUENCE: 351

Glu Leu Val Leu Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 352
<211> LENGTH: 17
<212> TYPE: PRT
<213> ORGANISM: Oryctolagus cuniculus

<400> SEQUENCE: 352

Leu Ala Trp Tyr Gln Gln Glu Pro Gly Gln Pro Pro Lys Leu Leu Ile
1               5                   10                  15

Tyr

<210> SEQ ID NO 353
<211> LENGTH: 26
<212> TYPE: PRT
<213> ORGANISM: Oryctolagus cuniculus

<400> SEQUENCE: 353

Val Leu Asp Leu Thr Gln Thr Pro Ala Ser Val Ser Ala Ala Val Gly
1               5                   10                  15

Gly Thr Val Thr Ile Lys Cys Gln Ala Ser
            20                  25

<210> SEQ ID NO 354
<211> LENGTH: 17
<212> TYPE: PRT
<213> ORGANISM: Oryctolagus cuniculus

<400> SEQUENCE: 354

Leu Ala Trp Tyr Gln Gln Glu Pro Gly Gln Pro Pro Lys Leu Leu Ile
1               5                   10                  15

Tyr

<210> SEQ ID NO 355
<211> LENGTH: 26
<212> TYPE: PRT
<213> ORGANISM: Oryctolagus cuniculus

<400> SEQUENCE: 355

Glu Leu Val Met Thr Gln Thr Pro Ala Ser Val Ser Ala Ala Val Gly
1               5                   10                  15

Gly Thr Val Thr Ile Lys Cys Gln Ala Ser
            20                  25
```

<210> SEQ ID NO 356
<211> LENGTH: 17
<212> TYPE: PRT
<213> ORGANISM: Oryctolagus cuniculus

<400> SEQUENCE: 356

Leu Ala Trp Tyr Gln Gln Glu Pro Gly Gln Pro Pro Lys Leu Leu Ile
1               5                   10                  15

Tyr

<210> SEQ ID NO 357
<211> LENGTH: 25
<212> TYPE: PRT
<213> ORGANISM: Oryctolagus cuniculus

<400> SEQUENCE: 357

Glu Leu Val Leu Thr Gln Ser Pro Ser Leu Ser Ala Ser Leu Gly Thr
1               5                   10                  15

Thr Ala Arg Leu Thr Cys Thr Leu Ser
            20                  25

<210> SEQ ID NO 358
<211> LENGTH: 17
<212> TYPE: PRT
<213> ORGANISM: Oryctolagus cuniculus

<400> SEQUENCE: 358

Leu Val Trp Leu Gln Gln Val Pro Gly Arg Pro Pro Arg Tyr Leu Leu
1               5                   10                  15

Thr

<210> SEQ ID NO 359
<211> LENGTH: 26
<212> TYPE: PRT
<213> ORGANISM: Oryctolagus cuniculus

<400> SEQUENCE: 359

Glu Leu Asp Met Thr Gln Thr Pro Ser Pro Val Ser Thr Ala Val Gly
1               5                   10                  15

Gly Thr Val Ser Ile Ser Cys Gln Ser Gly
            20                  25

<210> SEQ ID NO 360
<211> LENGTH: 17
<212> TYPE: PRT
<213> ORGANISM: Oryctolagus cuniculus

<400> SEQUENCE: 360

Leu Ser Trp Tyr Gln Gln Lys Pro Gly Gln Pro Pro Lys Leu Leu Ile
1               5                   10                  15

Tyr

<210> SEQ ID NO 361
<211> LENGTH: 36
<212> TYPE: PRT
<213> ORGANISM: Oryctolagus cuniculus

<400> SEQUENCE: 361

Thr Leu Thr Ser Gly Val Pro Ser Arg Phe Lys Gly Ser Gly Ser Gly
1               5                   10                  15

Thr Gln Phe Thr Leu Thr Ile Ser Asp Leu Glu Cys Ala Asp Ala Ala
            20                  25                  30

Thr Tyr Tyr Cys
        35

<210> SEQ ID NO 362
<211> LENGTH: 10
<212> TYPE: PRT
<213> ORGANISM: Oryctolagus cuniculus

<400> SEQUENCE: 362

Phe Gly Gly Gly Thr Glu Val Val Val Lys
1               5                   10

<210> SEQ ID NO 363
<211> LENGTH: 36
<212> TYPE: PRT
<213> ORGANISM: Oryctolagus cuniculus

<400> SEQUENCE: 363

Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 364
<211> LENGTH: 9
<212> TYPE: PRT
<213> ORGANISM: Oryctolagus cuniculus

<400> SEQUENCE: 364

Gln Asp His Asp Asp Ile Ser His Ala
1               5

<210> SEQ ID NO 365
<211> LENGTH: 36
<212> TYPE: PRT
<213> ORGANISM: Oryctolagus cuniculus

<400> SEQUENCE: 365

Asn Leu Ala Ser Gly Val Ser Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 366
<211> LENGTH: 10
<212> TYPE: PRT
<213> ORGANISM: Oryctolagus cuniculus

<400> SEQUENCE: 366

Phe Gly Gly Gly Thr Asn Val Glu Ile Lys
1               5                   10

<210> SEQ ID NO 367
<211> LENGTH: 36
<212> TYPE: PRT
<213> ORGANISM: Oryctolagus cuniculus

```
<400> SEQUENCE: 367

Thr Leu Glu Ser Gly Val Pro Ser Arg Phe Lys Gly Ser Arg Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 368
<211> LENGTH: 10
<212> TYPE: PRT
<213> ORGANISM: Oryctolagus cuniculus

<400> SEQUENCE: 368

Phe Gly Gly Gly Thr Glu Val Val Val Lys
1               5                   10

<210> SEQ ID NO 369
<211> LENGTH: 36
<212> TYPE: PRT
<213> ORGANISM: Oryctolagus cuniculus

<400> SEQUENCE: 369

Ile Leu Ala Ser Gly Val Pro Ser Arg Phe Lys Gly Arg Gly Ser Gly
1               5                   10                  15

Thr Gln Phe Thr Leu Thr Ile Ser Asp Val Gln Cys Asp Asp Ala Ala
            20                  25                  30

Thr Tyr Tyr Cys
        35

<210> SEQ ID NO 370
<211> LENGTH: 10
<212> TYPE: PRT
<213> ORGANISM: Oryctolagus cuniculus

<400> SEQUENCE: 370

Phe Gly Gly Gly Thr Asn Val Glu Ile Lys
1               5                   10

<210> SEQ ID NO 371
<211> LENGTH: 36
<212> TYPE: PRT
<213> ORGANISM: Oryctolagus cuniculus

<400> SEQUENCE: 371

Thr Leu Ala Ser Gly Val Pro Ser Arg Phe Ser Gly Ser Arg Ser Gly
1               5                   10                  15

Thr Glu Tyr Thr Leu Thr Ile Ser Gly Val Glu Cys Ala Asp Ala Ala
            20                  25                  30

Thr Tyr Tyr Cys
        35

<210> SEQ ID NO 372
<211> LENGTH: 10
<212> TYPE: PRT
<213> ORGANISM: Oryctolagus cuniculus

<400> SEQUENCE: 372

Phe Gly Gly Gly Thr Asn Val Glu Ile Lys
1               5                   10
```

-continued

<210> SEQ ID NO 373
<211> LENGTH: 36
<212> TYPE: PRT
<213> ORGANISM: Oryctolagus cuniculus

<400> SEQUENCE: 373

Asn Leu Ala Ser Gly Val Ser Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 374
<211> LENGTH: 10
<212> TYPE: PRT
<213> ORGANISM: Oryctolagus cuniculus

<400> SEQUENCE: 374

Phe Gly Gly Gly Thr Glu Leu Glu Ile Leu
1               5                   10

<210> SEQ ID NO 375
<211> LENGTH: 36
<212> TYPE: PRT
<213> ORGANISM: Oryctolagus cuniculus

<400> SEQUENCE: 375

Thr Leu Ala Ser Gly Val Ser Ser Arg Phe Lys Gly Ser Arg Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 376
<211> LENGTH: 10
<212> TYPE: PRT
<213> ORGANISM: Oryctolagus cuniculus

<400> SEQUENCE: 376

Phe Gly Gly Gly Thr Glu Val Val Val Lys
1               5                   10

<210> SEQ ID NO 377
<211> LENGTH: 36
<212> TYPE: PRT
<213> ORGANISM: Oryctolagus cuniculus

<400> SEQUENCE: 377

Thr Leu Thr Ser Gly Val Ser Ser Arg Phe Arg Gly Ser Gly Ser Gly
1               5                   10                  15

Thr Gln Phe Thr Leu Thr Ile Ser Asp Leu Glu Cys Ala Asp Ala Ala
            20                  25                  30

Thr Tyr Tyr Cys
        35

<210> SEQ ID NO 378
<211> LENGTH: 10
<212> TYPE: PRT
<213> ORGANISM: Oryctolagus cuniculus

<400> SEQUENCE: 378

<210> SEQ ID NO 379
<211> LENGTH: 36
<212> TYPE: PRT
<213> ORGANISM: Oryctolagus cuniculus

<400> SEQUENCE: 379

Phe Gly Gly Gly Thr Asn Val Glu Ile Lys
1               5                   10

<210> SEQ ID NO 379
<211> LENGTH: 36
<212> TYPE: PRT
<213> ORGANISM: Oryctolagus cuniculus

<400> SEQUENCE: 379

Thr Leu Glu Ser Gly Val Pro Ser Arg Phe Lys Gly Ser Gly Ser Gly
1               5                   10                  15
Thr Glu Phe Thr Leu Thr Ile Ser Asp Leu Glu Cys Ala Asp Ala Ala
            20                  25                  30
Thr Tyr His Cys
        35

<210> SEQ ID NO 380
<211> LENGTH: 10
<212> TYPE: PRT
<213> ORGANISM: Oryctolagus cuniculus

<400> SEQUENCE: 380

Phe Gly Gly Gly Thr Glu Val Ala Leu Lys
1               5                   10

<210> SEQ ID NO 381
<211> LENGTH: 36
<212> TYPE: PRT
<213> ORGANISM: Oryctolagus cuniculus

<400> SEQUENCE: 381

Thr Leu Ala Ser Gly Val Pro Ser Arg Phe Lys Gly Ser Gly Ser Gly
1               5                   10                  15
Thr Glu Phe Thr Leu Thr Ile Ser Gly Val Gln Cys Ala Asp Ala Ala
            20                  25                  30
Thr Tyr Tyr Cys
        35

<210> SEQ ID NO 382
<211> LENGTH: 10
<212> TYPE: PRT
<213> ORGANISM: Oryctolagus cuniculus

<400> SEQUENCE: 382

Phe Gly Gly Gly Thr Glu Val Val Val Lys
1               5                   10

<210> SEQ ID NO 383
<211> LENGTH: 36
<212> TYPE: PRT
<213> ORGANISM: Oryctolagus cuniculus

<400> SEQUENCE: 383

Thr Leu Glu Ser Gly Val Pro Ser Arg Phe Lys Gly Ser Gly Ser Gly
1               5                   10                  15
Thr Glu Phe Thr Leu Thr Ile Ser Asp Leu Glu Cys Ala Asp Ala Ala
            20                  25                  30
Thr Tyr His Cys
        35

<210> SEQ ID NO 384

```
<211> LENGTH: 10
<212> TYPE: PRT
<213> ORGANISM: Oryctolagus cuniculus

<400> SEQUENCE: 384

Phe Gly Gly Gly Thr Glu Val Val Val Lys
1               5                   10

<210> SEQ ID NO 385
<211> LENGTH: 36
<212> TYPE: PRT
<213> ORGANISM: Oryctolagus cuniculus

<400> SEQUENCE: 385

Thr Leu Ala Ser Gly Val Pro Ser Arg Phe Lys Gly Ser Gly Ser Gly
1               5                   10                  15

Thr Gln Phe Thr Leu Thr Ile Ser Asp Leu Glu Cys Ala Asp Ala Ala
            20                  25                  30

Thr Tyr Tyr Cys
        35

<210> SEQ ID NO 386
<211> LENGTH: 10
<212> TYPE: PRT
<213> ORGANISM: Oryctolagus cuniculus

<400> SEQUENCE: 386

Phe Gly Gly Gly Thr Glu Val Val Val Lys
1               5                   10

<210> SEQ ID NO 387
<211> LENGTH: 36
<212> TYPE: PRT
<213> ORGANISM: Oryctolagus cuniculus

<400> SEQUENCE: 387

Thr Leu Glu Ser Gly Val Pro Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 388
<211> LENGTH: 10
<212> TYPE: PRT
<213> ORGANISM: Oryctolagus cuniculus

<400> SEQUENCE: 388

Phe Gly Gly Gly Thr Glu Val Glu Ile Lys
1               5                   10

<210> SEQ ID NO 389
<211> LENGTH: 36
<212> TYPE: PRT
<213> ORGANISM: Oryctolagus cuniculus

<400> SEQUENCE: 389

Thr Leu Pro Ser Gly Val Pro Ser Arg Phe Lys Gly Ser Gly Ser Gly
1               5                   10                  15

Thr Gln Phe Thr Leu Thr Ile Ser Glu Val Gln Cys Asp Asp Ala Ala
            20                  25                  30
```

Thr Tyr Tyr Cys
        35

<210> SEQ ID NO 390
<211> LENGTH: 10
<212> TYPE: PRT
<213> ORGANISM: Oryctolagus cuniculus

<400> SEQUENCE: 390

Phe Gly Gly Gly Thr Glu Val Val Val Lys
1               5                   10

<210> SEQ ID NO 391
<211> LENGTH: 36
<212> TYPE: PRT
<213> ORGANISM: Oryctolagus cuniculus

<400> SEQUENCE: 391

Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 392
<211> LENGTH: 10
<212> TYPE: PRT
<213> ORGANISM: Oryctolagus cuniculus

<400> SEQUENCE: 392

Phe Gly Gly Gly Thr Asn Val Glu Ile Lys
1               5                   10

<210> SEQ ID NO 393
<211> LENGTH: 36
<212> TYPE: PRT
<213> ORGANISM: Oryctolagus cuniculus

<400> SEQUENCE: 393

Thr Leu Ala Ser Gly Val Pro Ser Arg Phe Lys Gly Ser Gly Ser Gly
1               5                   10                  15

Thr Gln Phe Thr Leu Thr Ile Ser Asp Val Gln Cys Asp Asp Ala Ala
            20                  25                  30

Thr Tyr Tyr Cys
        35

<210> SEQ ID NO 394
<211> LENGTH: 10
<212> TYPE: PRT
<213> ORGANISM: Oryctolagus cuniculus

<400> SEQUENCE: 394

Phe Gly Gly Gly Thr Glu Val Val Val Lys
1               5                   10

<210> SEQ ID NO 395
<211> LENGTH: 36
<212> TYPE: PRT
<213> ORGANISM: Oryctolagus cuniculus

<400> SEQUENCE: 395

Thr Leu Glu Ser Gly Val Pro Ser Arg Phe Lys Gly Ser Gly Ser Gly

```
                1               5                  10                  15
Thr Gln Phe Thr Leu Thr Ile Ser Gly Val Gln Cys Asp Asp Ala Ala
                20                  25                  30

Thr Tyr Tyr Cys
        35

<210> SEQ ID NO 396
<211> LENGTH: 10
<212> TYPE: PRT
<213> ORGANISM: Oryctolagus cuniculus

<400> SEQUENCE: 396

Phe Gly Gly Gly Thr Glu Val Val Val Lys
1               5                   10

<210> SEQ ID NO 397
<211> LENGTH: 38
<212> TYPE: PRT
<213> ORGANISM: Oryctolagus cuniculus

<400> SEQUENCE: 397

His Gln Gly Ser Gly Val His Ser Arg Phe Ser Gly Ser Lys Asp Thr
1               5                   10                  15

Ser Glu Asn Ala Gly Val Leu Ser Ile Ser Gly Leu Gln Pro Glu Asp
                20                  25                  30

Glu Ala Asp Tyr Tyr Cys
        35

<210> SEQ ID NO 398
<211> LENGTH: 10
<212> TYPE: PRT
<213> ORGANISM: Oryctolagus cuniculus

<400> SEQUENCE: 398

Phe Gly Gly Gly Thr Gln Leu Thr Val Thr
1               5                   10

<210> SEQ ID NO 399
<211> LENGTH: 36
<212> TYPE: PRT
<213> ORGANISM: Oryctolagus cuniculus

<400> SEQUENCE: 399

Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
                20                  25                  30

Thr Tyr Tyr Cys
        35

<210> SEQ ID NO 400
<211> LENGTH: 10
<212> TYPE: PRT
<213> ORGANISM: Oryctolagus cuniculus

<400> SEQUENCE: 400

Phe Gly Gly Gly Thr Glu Val Val Val Lys
1               5                   10

<210> SEQ ID NO 401
<211> LENGTH: 36
<212> TYPE: PRT
```

<213> ORGANISM: Oryctolagus cuniculus

<400> SEQUENCE: 401

Ile Leu Ala Ser Gly Val Pro Ser Arg Phe Lys Gly Arg Gly Ser Gly
1               5                   10                  15

Thr Gln Phe Thr Leu Thr Ile Ser Asp Val Gln Cys Asp Asp Ala Ala
            20                  25                  30

Thr Tyr Tyr Cys
        35

<210> SEQ ID NO 402
<211> LENGTH: 10
<212> TYPE: PRT
<213> ORGANISM: Oryctolagus cuniculus

<400> SEQUENCE: 402

Phe Gly Gly Gly Thr Glu Leu Glu Ile Leu
1               5                   10

<210> SEQ ID NO 403
<211> LENGTH: 36
<212> TYPE: PRT
<213> ORGANISM: Oryctolagus cuniculus

<400> SEQUENCE: 403

Thr Leu Ala Ser Gly Val Pro Ser Arg Phe Lys Gly Ser Gly Ser Gly
1               5                   10                  15

Thr Gln Phe Thr Leu Thr Ile Ser Asp Leu Glu Cys Asp Asp Ala Ala
            20                  25                  30

Thr Tyr Tyr Cys
        35

<210> SEQ ID NO 404
<211> LENGTH: 10
<212> TYPE: PRT
<213> ORGANISM: Oryctolagus cuniculus

<400> SEQUENCE: 404

Phe Gly Gly Gly Thr Asn Val Glu Ile Lys
1               5                   10

<210> SEQ ID NO 405
<211> LENGTH: 36
<212> TYPE: PRT
<213> ORGANISM: Oryctolagus cuniculus

<400> SEQUENCE: 405

Thr Leu Glu Ser Gly Val Pro Ser Arg Phe Lys Gly Ser Gly Ser Gly
1               5                   10                  15

Thr Gln Phe Thr Leu Thr Ile Ser Gly Val Gln Cys Asp Asp Ala Ala
            20                  25                  30

Thr Tyr Tyr Cys
        35

<210> SEQ ID NO 406
<211> LENGTH: 10
<212> TYPE: PRT
<213> ORGANISM: Oryctolagus cuniculus

<400> SEQUENCE: 406

Phe Gly Gly Gly Thr Glu Val Val Val Lys
1               5                   10

```
<210> SEQ ID NO 407
<211> LENGTH: 36
<212> TYPE: PRT
<213> ORGANISM: Oryctolagus cuniculus

<400> SEQUENCE: 407

Thr Leu Ala Ser Gly Val Pro Ser Arg Phe Thr Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 408
<211> LENGTH: 10
<212> TYPE: PRT
<213> ORGANISM: Oryctolagus cuniculus

<400> SEQUENCE: 408

Phe Gly Gly Gly Thr Asn Val Glu Ile Lys
1               5                   10

<210> SEQ ID NO 409
<211> LENGTH: 36
<212> TYPE: PRT
<213> ORGANISM: Oryctolagus cuniculus

<400> SEQUENCE: 409

Thr Leu Glu Ser Gly Val Pro Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr His Cys
        35

<210> SEQ ID NO 410
<211> LENGTH: 10
<212> TYPE: PRT
<213> ORGANISM: Oryctolagus cuniculus

<400> SEQUENCE: 410

Phe Gly Gly Gly Thr Glu Val Val Val Lys
1               5                   10

<210> SEQ ID NO 411
<211> LENGTH: 36
<212> TYPE: PRT
<213> ORGANISM: Oryctolagus cuniculus

<400> SEQUENCE: 411

Thr Leu Glu Ser Gly Val Pro Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 412
<211> LENGTH: 10
<212> TYPE: PRT
<213> ORGANISM: Oryctolagus cuniculus
```

<400> SEQUENCE: 412

Phe Gly Gly Gly Thr Glu Val Val Val Lys
1               5                   10

<210> SEQ ID NO 413
<211> LENGTH: 36
<212> TYPE: PRT
<213> ORGANISM: Oryctolagus cuniculus

<400> SEQUENCE: 413

Thr Leu Ala Ser Gly Val Ser Ser Arg Phe Glu Gly Ser Gly Ser Gly
1               5                   10                  15

Thr Gln Phe Thr Leu Thr Ile Ser Gly Val Glu Cys Ala Asp Ala Ala
            20                  25                  30

Thr Tyr Tyr Cys
        35

<210> SEQ ID NO 414
<211> LENGTH: 10
<212> TYPE: PRT
<213> ORGANISM: Oryctolagus cuniculus

<400> SEQUENCE: 414

Phe Gly Gly Gly Thr Glu Val Val Val Lys
1               5                   10

<210> SEQ ID NO 415
<211> LENGTH: 36
<212> TYPE: PRT
<213> ORGANISM: Oryctolagus cuniculus

<400> SEQUENCE: 415

Thr Leu Ala Ser Gly Val Pro Ser Arg Phe Lys Gly Ser Gly Ser Gly
1               5                   10                  15

Thr Glu Phe Thr Leu Thr Ile Ser Gly Val Gln Cys Ala Asp Ala Ala
            20                  25                  30

Thr Tyr Tyr Cys
        35

<210> SEQ ID NO 416
<211> LENGTH: 10
<212> TYPE: PRT
<213> ORGANISM: Oryctolagus cuniculus

<400> SEQUENCE: 416

Phe Gly Gly Gly Thr Asn Val Glu Ile Lys
1               5                   10

<210> SEQ ID NO 417
<211> LENGTH: 36
<212> TYPE: PRT
<213> ORGANISM: Oryctolagus cuniculus

<400> SEQUENCE: 417

Asn Leu Glu Ser Gly Val Pro Ser Arg Phe Lys Gly Ser Gly Ser Gly
1               5                   10                  15

Thr Gln Phe Thr Leu Thr Ile Ser Gly Val Gln Cys Asp Asp Ala Ala
            20                  25                  30

Thr Tyr Tyr Cys
        35

-continued

<210> SEQ ID NO 418
<211> LENGTH: 10
<212> TYPE: PRT
<213> ORGANISM: Oryctolagus cuniculus

<400> SEQUENCE: 418

Phe Gly Gly Gly Thr Glu Leu Glu Ile Leu
1               5                   10

<210> SEQ ID NO 419
<211> LENGTH: 36
<212> TYPE: PRT
<213> ORGANISM: Oryctolagus cuniculus

<400> SEQUENCE: 419

Asn Leu Ala Ser Gly Val Pro Ser Arg Phe Lys Gly Ser Gly Ser Gly
1               5                   10                  15

Thr Gln Phe Thr Leu Thr Ile Ser Gly Val Gln Cys Asp Asp Ala Ala
            20                  25                  30

Thr Tyr Tyr Cys
        35

<210> SEQ ID NO 420
<211> LENGTH: 9
<212> TYPE: PRT
<213> ORGANISM: Oryctolagus cuniculus

<400> SEQUENCE: 420

Gln Cys Asn Tyr Tyr Leu Asn Asn Ala
1               5

<210> SEQ ID NO 421
<211> LENGTH: 36
<212> TYPE: PRT
<213> ORGANISM: Oryctolagus cuniculus

<400> SEQUENCE: 421

Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 422
<211> LENGTH: 10
<212> TYPE: PRT
<213> ORGANISM: Oryctolagus cuniculus

<400> SEQUENCE: 422

Phe Gly Gly Gly Thr Glu Val Val Val Glu
1               5                   10

<210> SEQ ID NO 423
<211> LENGTH: 36
<212> TYPE: PRT
<213> ORGANISM: Oryctolagus cuniculus

<400> SEQUENCE: 423

Asp Leu Ala Ser Gly Val Ser Ser Arg Phe Ser Gly Ser Gly Ser Gly
1               5                   10                  15

Thr Gln Phe Thr Leu Thr Ile Ser Gly Val Glu Cys Ala Asp Ala Ala

```
                20                  25                  30

Thr Tyr Tyr Cys
        35

<210> SEQ ID NO 424
<211> LENGTH: 10
<212> TYPE: PRT
<213> ORGANISM: Oryctolagus cuniculus

<400> SEQUENCE: 424

Phe Gly Gly Gly Thr Glu Val Val Val Lys
1               5                   10

<210> SEQ ID NO 425
<211> LENGTH: 36
<212> TYPE: PRT
<213> ORGANISM: Oryctolagus cuniculus

<400> SEQUENCE: 425

Thr Leu Glu Ser Gly Val Pro Ser Arg Phe Lys Gly Ser Gly Ser Gly
1               5                   10                  15

Thr Gln Phe Thr Leu Thr Ile Ser Gly Val Gln Cys Asp Asp Ala Ala
            20                  25                  30

Thr Tyr Tyr Cys
        35

<210> SEQ ID NO 426
<211> LENGTH: 10
<212> TYPE: PRT
<213> ORGANISM: Oryctolagus cuniculus

<400> SEQUENCE: 426

Phe Gly Gly Gly Thr Lys Val Glu Ile Lys
1               5                   10

<210> SEQ ID NO 427
<211> LENGTH: 36
<212> TYPE: PRT
<213> ORGANISM: Oryctolagus cuniculus

<400> SEQUENCE: 427

Ile Leu Ala Ser Gly Val Pro Ser Arg Phe Lys Gly Ser Arg Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 428
<211> LENGTH: 10
<212> TYPE: PRT
<213> ORGANISM: Oryctolagus cuniculus

<400> SEQUENCE: 428

Phe Gly Gly Gly Thr Glu Val Val Val Lys
1               5                   10

<210> SEQ ID NO 429
<211> LENGTH: 36
<212> TYPE: PRT
<213> ORGANISM: Oryctolagus cuniculus

<400> SEQUENCE: 429
```

```
Thr Leu Ala Ser Gly Val Ser Arg Phe Lys Gly Ser Gly Ser Gly
1               5                   10                  15

Thr Gln Phe Thr Leu Thr Ile Ser Asp Val Gln Cys Asp Asp Ala Ala
            20                  25                  30

Thr Tyr Tyr Cys
        35

<210> SEQ ID NO 430
<211> LENGTH: 10
<212> TYPE: PRT
<213> ORGANISM: Oryctolagus cuniculus

<400> SEQUENCE: 430

Phe Gly Gly Gly Thr Glu Val Val Val Lys
1               5                   10

<210> SEQ ID NO 431
<211> LENGTH: 36
<212> TYPE: PRT
<213> ORGANISM: Oryctolagus cuniculus

<400> SEQUENCE: 431

Thr Leu Ala Ser Gly Val Pro Ser Arg Phe Ser Gly Ser Gly Ser Gly
1               5                   10                  15

Thr Glu Phe Thr Leu Thr Ile Ser Gly Val Gln Cys Asp Asp Ala Ala
            20                  25                  30

Thr Tyr Tyr Cys
        35

<210> SEQ ID NO 432
<211> LENGTH: 10
<212> TYPE: PRT
<213> ORGANISM: Oryctolagus cuniculus

<400> SEQUENCE: 432

Phe Gly Gly Gly Thr Glu Val Val Val Lys
1               5                   10

<210> SEQ ID NO 433
<211> LENGTH: 36
<212> TYPE: PRT
<213> ORGANISM: Oryctolagus cuniculus

<400> SEQUENCE: 433

Asn Leu Ala Ser Gly Val Ser Ser Arg Phe Lys Gly Ser Gly Ser Gly
1               5                   10                  15

Thr Glu Phe Thr Leu Thr Ile Ser Asp Leu Glu Cys Ala Asp Ala Ala
            20                  25                  30

Thr Tyr Tyr Cys
        35

<210> SEQ ID NO 434
<211> LENGTH: 10
<212> TYPE: PRT
<213> ORGANISM: Oryctolagus cuniculus

<400> SEQUENCE: 434

Phe Gly Gly Gly Thr Asn Val Glu Ile Lys
1               5                   10

<210> SEQ ID NO 435
```

<210> SEQ ID NO 435
<211> LENGTH: 36
<212> TYPE: PRT
<213> ORGANISM: Oryctolagus cuniculus

<400> SEQUENCE: 435

Thr Leu Ala Ser Gly Val Pro Ser Arg Phe Lys Gly Ser Gly Ser Ala
1               5                   10                  15

Thr Glu Phe Thr Leu Thr Ile Arg Gly Val Gln Cys Asp Asp Ala Ala
            20                  25                  30

Thr Tyr Tyr Cys
            35

<210> SEQ ID NO 436
<211> LENGTH: 10
<212> TYPE: PRT
<213> ORGANISM: Oryctolagus cuniculus

<400> SEQUENCE: 436

Phe Gly Gly Gly Thr Glu Val Val Val Lys
1               5                   10

<210> SEQ ID NO 437
<211> LENGTH: 36
<212> TYPE: PRT
<213> ORGANISM: Oryctolagus cuniculus

<400> SEQUENCE: 437

Thr Leu Ala Ser Gly Val Pro Ser Arg Phe Lys Gly Ser Gly Ser Gly
1               5                   10                  15

Thr Gln Phe Thr Leu Thr Ile Ser Glu Val Gln Cys Asp Asp Ala Ala
            20                  25                  30

Thr Tyr Tyr Cys
            35

<210> SEQ ID NO 438
<211> LENGTH: 10
<212> TYPE: PRT
<213> ORGANISM: Oryctolagus cuniculus

<400> SEQUENCE: 438

Phe Gly Gly Gly Thr Glu Val Val Val Lys
1               5                   10

<210> SEQ ID NO 439
<211> LENGTH: 36
<212> TYPE: PRT
<213> ORGANISM: Oryctolagus cuniculus

<400> SEQUENCE: 439

Thr Leu Ala Ser Gly Val Pro Ser Trp Phe Lys Gly Ser Gly Ser Gly
1               5                   10                  15

Thr Gln Phe Thr Leu Thr Ile Ser Glu Val Val Cys Asp Asp Ala Ala
            20                  25                  30

Thr Tyr Tyr Cys
            35

<210> SEQ ID NO 440
<211> LENGTH: 10
<212> TYPE: PRT
<213> ORGANISM: Oryctolagus cuniculus

<400> SEQUENCE: 440

```
Phe Gly Gly Gly Thr Asn Val Glu Ile Lys
1               5                   10
```

<210> SEQ ID NO 441
<211> LENGTH: 36
<212> TYPE: PRT
<213> ORGANISM: Oryctolagus cuniculus

<400> SEQUENCE: 441

```
Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
            35
```

<210> SEQ ID NO 442
<211> LENGTH: 10
<212> TYPE: PRT
<213> ORGANISM: Oryctolagus cuniculus

<400> SEQUENCE: 442

```
Phe Gly Gly Gly Thr Asn Glu Glu Ile Lys
1               5                   10
```

<210> SEQ ID NO 443
<211> LENGTH: 36
<212> TYPE: PRT
<213> ORGANISM: Oryctolagus cuniculus

<400> SEQUENCE: 443

```
Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
            35
```

<210> SEQ ID NO 444
<211> LENGTH: 10
<212> TYPE: PRT
<213> ORGANISM: Oryctolagus cuniculus

<400> SEQUENCE: 444

```
Phe Gly Gly Gly Thr Glu Val Val Val Lys
1               5                   10
```

<210> SEQ ID NO 445
<211> LENGTH: 36
<212> TYPE: PRT
<213> ORGANISM: Oryctolagus cuniculus

<400> SEQUENCE: 445

```
Thr Leu Ala Ser Gly Val Pro Ser Arg Phe Ser Gly Ser Gly Tyr Gly
1               5                   10                  15

Thr Glu Phe Thr Leu Thr Ile Ser Asp Leu Glu Cys Ala Asp Ala Ala
            20                  25                  30

Thr Tyr Tyr Cys
            35
```

<210> SEQ ID NO 446
<211> LENGTH: 10

```
<212> TYPE: PRT
<213> ORGANISM: Oryctolagus cuniculus

<400> SEQUENCE: 446

Phe Gly Gly Gly Thr Asn Val Glu Ile Lys
1               5                   10

<210> SEQ ID NO 447
<211> LENGTH: 38
<212> TYPE: PRT
<213> ORGANISM: Oryctolagus cuniculus

<400> SEQUENCE: 447

His Gln Gly Ser Gly Val His Ser Arg Phe Ser Gly Ser Lys Asp Thr
1               5                   10                  15

Ser Glu Asn Ser Phe Val Leu Arg Ile Phe Gly Leu Gln Pro Glu Asp
            20                  25                  30

Glu Ala Asp Tyr Tyr Cys
            35

<210> SEQ ID NO 448
<211> LENGTH: 10
<212> TYPE: PRT
<213> ORGANISM: Oryctolagus cuniculus

<400> SEQUENCE: 448

Phe Gly Gly Gly Thr Gln Leu Thr Val Thr
1               5                   10

<210> SEQ ID NO 449
<211> LENGTH: 36
<212> TYPE: PRT
<213> ORGANISM: Oryctolagus cuniculus

<400> SEQUENCE: 449

Thr Leu Ala Ser Gly Val Pro Ser Arg Phe Lys Gly Ser Gly Ser Gly
1               5                   10                  15

Thr Gln Phe Thr Leu Thr Ile Ser Asp Val Gln Cys Asp Asp Ala Ala
            20                  25                  30

Thr Tyr Tyr Cys
            35

<210> SEQ ID NO 450
<211> LENGTH: 10
<212> TYPE: PRT
<213> ORGANISM: Oryctolagus cuniculus

<400> SEQUENCE: 450

Phe Gly Gly Gly Thr Glu Val Val Val Lys
1               5                   10

<210> SEQ ID NO 451
<211> LENGTH: 24
<212> TYPE: PRT
<213> ORGANISM: Oryctolagus cuniculus

<400> SEQUENCE: 451

Gln Ser Leu Glu Glu Ser Gly Gly Gly Leu Val Thr Pro Gly Gly Thr
1               5                   10                  15

Leu Thr Leu Thr Cys Arg Val Ser
            20
```

-continued

```
<210> SEQ ID NO 452
<211> LENGTH: 17
<212> TYPE: PRT
<213> ORGANISM: Oryctolagus cuniculus

<400> SEQUENCE: 452

Met Gly Trp Val Arg Gln Ala Pro Gly Glu Gly Leu Glu Trp Ile Gly
1               5                   10                  15

Thr

<210> SEQ ID NO 453
<211> LENGTH: 24
<212> TYPE: PRT
<213> ORGANISM: Oryctolagus cuniculus

<400> SEQUENCE: 453

Gln Ser Val Lys Glu Ser Gly Gly Arg Leu Val Thr Pro Gly Thr Pro
1               5                   10                  15

Leu Thr Leu Thr Cys Thr Val Ser
            20

<210> SEQ ID NO 454
<211> LENGTH: 17
<212> TYPE: PRT
<213> ORGANISM: Oryctolagus cuniculus

<400> SEQUENCE: 454

Val Ser Trp Val Arg Gln Ala Pro Gly Lys Gly Leu Glu Trp Ile Gly
1               5                   10                  15

Ile

<210> SEQ ID NO 455
<211> LENGTH: 24
<212> TYPE: PRT
<213> ORGANISM: Oryctolagus cuniculus

<400> SEQUENCE: 455

Gln Ser Val Lys Glu Ser Glu Gly Arg Leu Ile Arg Pro Gly Gly Ser
1               5                   10                  15

Leu Thr Leu Thr Cys Thr Val Ser
            20

<210> SEQ ID NO 456
<211> LENGTH: 17
<212> TYPE: PRT
<213> ORGANISM: Oryctolagus cuniculus

<400> SEQUENCE: 456

Met Gly Trp Val Arg Gln Ala Pro Gly Glu Gly Leu Val Trp Ile Ala
1               5                   10                  15

Thr

<210> SEQ ID NO 457
<211> LENGTH: 25
<212> TYPE: PRT
<213> ORGANISM: Oryctolagus cuniculus

<400> SEQUENCE: 457

Gln Glu Gln Leu Val Glu Ser Gly Gly Gly Leu Val Gln Pro Glu Gly
1               5                   10                  15

Ser Leu Thr Leu Thr Cys Thr Ala Ser
            20                  25
```

```
<210> SEQ ID NO 458
<211> LENGTH: 17
<212> TYPE: PRT
<213> ORGANISM: Oryctolagus cuniculus

<400> SEQUENCE: 458

Met Cys Trp Val Arg Gln Ala Pro Gly Lys Gly Leu Glu Trp Ile Gly
1               5                   10                  15

Cys

<210> SEQ ID NO 459
<211> LENGTH: 24
<212> TYPE: PRT
<213> ORGANISM: Oryctolagus cuniculus

<400> SEQUENCE: 459

Gln Ser Val Glu Glu Ser Gly Gly Arg Leu Val Lys Pro Gly Thr Pro
1               5                   10                  15

Leu Thr Leu Thr Cys Thr Ala Ser
            20

<210> SEQ ID NO 460
<211> LENGTH: 17
<212> TYPE: PRT
<213> ORGANISM: Oryctolagus cuniculus

<400> SEQUENCE: 460

Met Ser Trp Val Arg Gln Ala Pro Gly Lys Gly Leu Glu Trp Ile Gly
1               5                   10                  15

Val

<210> SEQ ID NO 461
<211> LENGTH: 24
<212> TYPE: PRT
<213> ORGANISM: Oryctolagus cuniculus

<400> SEQUENCE: 461

Gln Ser Leu Glu Glu Ser Gly Gly Arg Leu Val Thr Pro Gly Thr Pro
1               5                   10                  15

Leu Thr Leu Thr Cys Thr Ala Ser
            20

<210> SEQ ID NO 462
<211> LENGTH: 17
<212> TYPE: PRT
<213> ORGANISM: Oryctolagus cuniculus

<400> SEQUENCE: 462

Met Gly Trp Val Arg Gln Ala Pro Gly Lys Gly Leu Glu Trp Ile Gly
1               5                   10                  15

Ile

<210> SEQ ID NO 463
<211> LENGTH: 24
<212> TYPE: PRT
<213> ORGANISM: Oryctolagus cuniculus

<400> SEQUENCE: 463

Gln Ser Leu Glu Glu Ser Gly Gly Gly Leu Val Lys Pro Gly Gly Thr
1               5                   10                  15
```

Leu Thr Leu Thr Cys Thr Ala Ser
            20

<210> SEQ ID NO 464
<211> LENGTH: 17
<212> TYPE: PRT
<213> ORGANISM: Oryctolagus cuniculus

<400> SEQUENCE: 464

Met Ser Trp Val Arg Gln Ala Pro Gly Lys Gly Leu Glu Trp Ile Ala
1               5                   10                  15

Ser

<210> SEQ ID NO 465
<211> LENGTH: 24
<212> TYPE: PRT
<213> ORGANISM: Oryctolagus cuniculus

<400> SEQUENCE: 465

Gln Ser Leu Glu Glu Ser Gly Gly Arg Leu Val Thr Pro Gly Gly Ser
1               5                   10                  15

Leu Thr Leu Thr Cys Thr Val Ser
            20

<210> SEQ ID NO 466
<211> LENGTH: 17
<212> TYPE: PRT
<213> ORGANISM: Oryctolagus cuniculus

<400> SEQUENCE: 466

Val Ser Trp Val Arg Gln Ala Pro Gly Lys Gly Leu Glu Trp Ile Gly
1               5                   10                  15

Ile

<210> SEQ ID NO 467
<211> LENGTH: 24
<212> TYPE: PRT
<213> ORGANISM: Oryctolagus cuniculus

<400> SEQUENCE: 467

Gln Ser Val Lys Glu Ser Gly Arg Asp Leu Val Lys Pro Gly Ala Ser
1               5                   10                  15

Leu Thr Leu Thr Cys Thr Ala Ser
            20

<210> SEQ ID NO 468
<211> LENGTH: 17
<212> TYPE: PRT
<213> ORGANISM: Oryctolagus cuniculus

<400> SEQUENCE: 468

Met Cys Trp Val Arg Gln Ala Pro Gly Lys Gly Leu Glu Trp Ile Ala
1               5                   10                  15

Cys

<210> SEQ ID NO 469
<211> LENGTH: 24
<212> TYPE: PRT
<213> ORGANISM: Oryctolagus cuniculus

<400> SEQUENCE: 469

Gln Ser Val Lys Glu Ser Glu Gly Asp Leu Val Lys Pro Gly Ala Ser

-continued

```
                1               5                  10                  15

Leu Thr Pro Thr Cys Thr Ala Ser
            20

<210> SEQ ID NO 470
<211> LENGTH: 17
<212> TYPE: PRT
<213> ORGANISM: Oryctolagus cuniculus

<400> SEQUENCE: 470

Met Cys Trp Val Arg Gln Ala Pro Gly Lys Gly Leu Glu Leu Ile Ala
1               5                   10                  15

Cys

<210> SEQ ID NO 471
<211> LENGTH: 24
<212> TYPE: PRT
<213> ORGANISM: Oryctolagus cuniculus

<400> SEQUENCE: 471

Gln Ser Val Glu Glu Ser Arg Gly Arg Leu Val Thr Pro Gly Thr Pro
1               5                   10                  15

Leu Thr Leu Thr Cys Thr Ala Ser
            20

<210> SEQ ID NO 472
<211> LENGTH: 17
<212> TYPE: PRT
<213> ORGANISM: Oryctolagus cuniculus

<400> SEQUENCE: 472

Met Ile Trp Val Arg Gln Ala Pro Gly Lys Gly Leu Glu Trp Ile Gly
1               5                   10                  15

Tyr

<210> SEQ ID NO 473
<211> LENGTH: 24
<212> TYPE: PRT
<213> ORGANISM: Oryctolagus cuniculus

<400> SEQUENCE: 473

Gln Ser Val Glu Glu Ser Gly Gly Asp Leu Val Lys Pro Gly Ala Ser
1               5                   10                  15

Leu Thr Pro Thr Cys Thr Ala Ser
            20

<210> SEQ ID NO 474
<211> LENGTH: 17
<212> TYPE: PRT
<213> ORGANISM: Oryctolagus cuniculus

<400> SEQUENCE: 474

Met Cys Trp Val Arg Gln Ala Pro Gly Lys Gly Leu Glu Leu Ile Ala
1               5                   10                  15

Cys

<210> SEQ ID NO 475
<211> LENGTH: 24
<212> TYPE: PRT
<213> ORGANISM: Oryctolagus cuniculus

<400> SEQUENCE: 475
```

```
Gln Ser Leu Glu Glu Ser Gly Gly Gly Leu Val Lys Pro Gly Gly Thr
1               5                   10                  15

Leu Thr Leu Thr Cys Thr Val Ser
            20
```

<210> SEQ ID NO 476
<211> LENGTH: 17
<212> TYPE: PRT
<213> ORGANISM: Oryctolagus cuniculus

<400> SEQUENCE: 476

```
Met Gly Trp Val Arg Gln Ala Pro Gly Lys Gly Leu Glu Trp Ile Gly
1               5                   10                  15

Thr
```

<210> SEQ ID NO 477
<211> LENGTH: 24
<212> TYPE: PRT
<213> ORGANISM: Oryctolagus cuniculus

<400> SEQUENCE: 477

```
Gln Ser Leu Glu Glu Ser Gly Gly Asp Leu Val Lys Pro Gly Ala Ser
1               5                   10                  15

Leu Thr Leu Thr Cys Thr Ala Ser
            20
```

<210> SEQ ID NO 478
<211> LENGTH: 17
<212> TYPE: PRT
<213> ORGANISM: Oryctolagus cuniculus

<400> SEQUENCE: 478

```
Met Cys Trp Val Arg Gln Ala Pro Gly Lys Gly Leu Glu Trp Ile Val
1               5                   10                  15

Cys
```

<210> SEQ ID NO 479
<211> LENGTH: 24
<212> TYPE: PRT
<213> ORGANISM: Oryctolagus cuniculus

<400> SEQUENCE: 479

```
Gln Ser Leu Glu Glu Ser Gly Gly Arg Leu Val Thr Pro Gly Thr Pro
1               5                   10                  15

Leu Thr Leu Thr Cys Thr Val Ser
            20
```

<210> SEQ ID NO 480
<211> LENGTH: 17
<212> TYPE: PRT
<213> ORGANISM: Oryctolagus cuniculus

<400> SEQUENCE: 480

```
Met Gly Trp Val Arg Gln Ala Pro Gly Glu Gly Leu Glu Trp Ile Gly
1               5                   10                  15

Tyr
```

<210> SEQ ID NO 481
<211> LENGTH: 24
<212> TYPE: PRT
<213> ORGANISM: Oryctolagus cuniculus -continued

```
<400> SEQUENCE: 481

Gln Ser Leu Glu Glu Ser Gly Gly Leu Val Lys Pro Gly Gly Thr
1               5                   10                  15

Leu Thr Leu Thr Cys Thr Ala Ser
                20

<210> SEQ ID NO 482
<211> LENGTH: 17
<212> TYPE: PRT
<213> ORGANISM: Oryctolagus cuniculus

<400> SEQUENCE: 482

Met Cys Trp Val Arg Gln Ala Pro Gly Lys Gly Leu Glu Trp Ile Ala
1               5                   10                  15

Cys

<210> SEQ ID NO 483
<211> LENGTH: 24
<212> TYPE: PRT
<213> ORGANISM: Oryctolagus cuniculus

<400> SEQUENCE: 483

Gln Ser Val Lys Glu Ser Glu Gly Arg Leu Val Thr Pro Gly Thr Pro
1               5                   10                  15

Leu Thr Leu Thr Cys Thr Val Ser
                20

<210> SEQ ID NO 484
<211> LENGTH: 17
<212> TYPE: PRT
<213> ORGANISM: Oryctolagus cuniculus

<400> SEQUENCE: 484

Met Asp Trp Val Arg Gln Ala Pro Gly Glu Gly Leu Glu Trp Ile Gly
1               5                   10                  15

Tyr

<210> SEQ ID NO 485
<211> LENGTH: 24
<212> TYPE: PRT
<213> ORGANISM: Oryctolagus cuniculus

<400> SEQUENCE: 485

Gln Ser Val Glu Glu Ser Gly Gly Arg Leu Val Thr Pro Gly Thr Pro
1               5                   10                  15

Leu Thr Leu Thr Cys Thr Val Ser
                20

<210> SEQ ID NO 486
<211> LENGTH: 17
<212> TYPE: PRT
<213> ORGANISM: Oryctolagus cuniculus

<400> SEQUENCE: 486

Met Ser Trp Val Arg Gln Ala Pro Gly Lys Gly Leu Glu Trp Ile Gly
1               5                   10                  15

Tyr

<210> SEQ ID NO 487
<211> LENGTH: 24
```

```
<212> TYPE: PRT
<213> ORGANISM: Oryctolagus cuniculus

<400> SEQUENCE: 487

Gln Ser Leu Glu Glu Ser Gly Gly Arg Leu Val Thr Pro Gly Thr Pro
1               5                   10                  15

Leu Thr Leu Thr Cys Thr Val Ser
            20

<210> SEQ ID NO 488
<211> LENGTH: 17
<212> TYPE: PRT
<213> ORGANISM: Oryctolagus cuniculus

<400> SEQUENCE: 488

Met Ser Trp Val Arg Gln Ala Pro Gly Lys Gly Leu Glu Trp Ile Gly
1               5                   10                  15

Ile

<210> SEQ ID NO 489
<211> LENGTH: 24
<212> TYPE: PRT
<213> ORGANISM: Oryctolagus cuniculus

<400> SEQUENCE: 489

Gln Ser Val Lys Glu Ser Gly Gly Leu Val Lys Pro Gly Gly Thr
1               5                   10                  15

Leu Thr Leu Thr Cys Thr Ala Ser
            20

<210> SEQ ID NO 490
<211> LENGTH: 17
<212> TYPE: PRT
<213> ORGANISM: Oryctolagus cuniculus

<400> SEQUENCE: 490

Met Cys Trp Val Arg Gln Ala Pro Gly Lys Gly Leu Glu Trp Ile Ala
1               5                   10                  15

Cys

<210> SEQ ID NO 491
<211> LENGTH: 24
<212> TYPE: PRT
<213> ORGANISM: Oryctolagus cuniculus

<400> SEQUENCE: 491

Gln Ser Leu Glu Glu Ser Gly Gly Arg Leu Val Thr Pro Gly Thr Pro
1               5                   10                  15

Leu Thr Leu Thr Cys Thr Val Ser
            20

<210> SEQ ID NO 492
<211> LENGTH: 17
<212> TYPE: PRT
<213> ORGANISM: Oryctolagus cuniculus

<400> SEQUENCE: 492

Val Ser Trp Val Arg Gln Ala Pro Gly Lys Gly Leu Glu Trp Ile Gly
1               5                   10                  15

Ile
```

```
<210> SEQ ID NO 493
<211> LENGTH: 24
<212> TYPE: PRT
<213> ORGANISM: Oryctolagus cuniculus

<400> SEQUENCE: 493

Gln Ser Val Lys Glu Ser Gly Gly Arg Leu Val Thr Pro Gly Thr Ala
1               5                   10                  15

Leu Thr Leu Thr Cys Thr Val Ser
            20

<210> SEQ ID NO 494
<211> LENGTH: 17
<212> TYPE: PRT
<213> ORGANISM: Oryctolagus cuniculus

<400> SEQUENCE: 494

Met Ser Trp Val Arg Gln Ala Pro Gly Lys Gly Leu Glu Trp Ile Gly
1               5                   10                  15

Tyr

<210> SEQ ID NO 495
<211> LENGTH: 24
<212> TYPE: PRT
<213> ORGANISM: Oryctolagus cuniculus

<400> SEQUENCE: 495

Gln Ser Val Glu Glu Ser Gly Gly Arg Leu Val Thr Pro Gly Thr Pro
1               5                   10                  15

Leu Thr Leu Thr Cys Thr Gly Ser
            20

<210> SEQ ID NO 496
<211> LENGTH: 17
<212> TYPE: PRT
<213> ORGANISM: Oryctolagus cuniculus

<400> SEQUENCE: 496

Met Ala Trp Val Arg Gln Ala Pro Gly Lys Gly Leu Glu Trp Ile Gly
1               5                   10                  15

Ile

<210> SEQ ID NO 497
<211> LENGTH: 24
<212> TYPE: PRT
<213> ORGANISM: Oryctolagus cuniculus

<400> SEQUENCE: 497

Gln Ser Val Glu Glu Ser Gly Gly Gly Leu Val Thr Pro Gly Gly Thr
1               5                   10                  15

Leu Thr Leu Thr Cys Gly Val Ser
            20

<210> SEQ ID NO 498
<211> LENGTH: 17
<212> TYPE: PRT
<213> ORGANISM: Oryctolagus cuniculus

<400> SEQUENCE: 498

Met Gly Trp Val Arg Gln Ala Pro Gly Glu Gly Leu Glu Trp Ile Gly
1               5                   10                  15

Thr
```

<210> SEQ ID NO 499
<211> LENGTH: 24
<212> TYPE: PRT
<213> ORGANISM: Oryctolagus cuniculus

<400> SEQUENCE: 499

Gln Ser Val Lys Glu Ser Glu Gly Asp Leu Val Lys Pro Gly Ala Ser
1               5                   10                  15

Leu Thr Pro Thr Cys Thr Ala Ser
            20

<210> SEQ ID NO 500
<211> LENGTH: 17
<212> TYPE: PRT
<213> ORGANISM: Oryctolagus cuniculus

<400> SEQUENCE: 500

Met Cys Trp Val Arg Gln Ala Pro Gly Lys Gly Leu Glu Leu Ile Ala
1               5                   10                  15

Cys

<210> SEQ ID NO 501
<211> LENGTH: 24
<212> TYPE: PRT
<213> ORGANISM: Oryctolagus cuniculus

<400> SEQUENCE: 501

Gln Ser Leu Glu Glu Ser Gly Gly Gly Leu Val Thr Pro Gly Gly Thr
1               5                   10                  15

Leu Thr Leu Thr Cys Arg Val Ser
            20

<210> SEQ ID NO 502
<211> LENGTH: 17
<212> TYPE: PRT
<213> ORGANISM: Oryctolagus cuniculus

<400> SEQUENCE: 502

Met Gly Trp Val Arg Gln Ala Pro Gly Glu Gly Leu Glu Trp Ile Gly
1               5                   10                  15

Thr

<210> SEQ ID NO 503
<211> LENGTH: 24
<212> TYPE: PRT
<213> ORGANISM: Oryctolagus cuniculus

<400> SEQUENCE: 503

Gln Ser Leu Glu Glu Ser Gly Gly Arg Leu Val Thr Pro Gly Thr Pro
1               5                   10                  15

Leu Thr Leu Thr Cys Thr Val Ser
            20

<210> SEQ ID NO 504
<211> LENGTH: 17
<212> TYPE: PRT
<213> ORGANISM: Oryctolagus cuniculus

<400> SEQUENCE: 504

Met Gly Trp Val Arg Gln Gly Pro Gly Lys Gly Leu Glu Trp Ile Gly
1               5                   10                  15

Phe

<210> SEQ ID NO 505
<211> LENGTH: 24
<212> TYPE: PRT
<213> ORGANISM: Oryctolagus cuniculus

<400> SEQUENCE: 505

Gln Ser Val Glu Glu Ser Gly Gly Arg Leu Val Thr Pro Gly Thr Pro
1               5                   10                  15

Leu Ala Leu Thr Cys Thr Ala Ser
            20

<210> SEQ ID NO 506
<211> LENGTH: 17
<212> TYPE: PRT
<213> ORGANISM: Oryctolagus cuniculus

<400> SEQUENCE: 506

Met Ile Trp Val Arg Gln Ala Pro Gly Lys Gly Leu Glu Trp Ile Gly
1               5                   10                  15

Tyr

<210> SEQ ID NO 507
<211> LENGTH: 24
<212> TYPE: PRT
<213> ORGANISM: Oryctolagus cuniculus

<400> SEQUENCE: 507

Glu Gln Leu Val Glu Ser Gly Gly Arg Leu Val Thr Pro Gly Thr Pro
1               5                   10                  15

Leu Thr Leu Thr Cys Thr Val Ser
            20

<210> SEQ ID NO 508
<211> LENGTH: 17
<212> TYPE: PRT
<213> ORGANISM: Oryctolagus cuniculus

<400> SEQUENCE: 508

Met Ser Trp Val Arg Gln Ala Pro Gly Lys Gly Leu Glu Trp Ile Gly
1               5                   10                  15

Tyr

<210> SEQ ID NO 509
<211> LENGTH: 24
<212> TYPE: PRT
<213> ORGANISM: Oryctolagus cuniculus

<400> SEQUENCE: 509

Gln Ser Leu Glu Glu Ser Gly Gly Gly Leu Val Gln Pro Gly Gly Ser
1               5                   10                  15

Leu Lys Leu Ser Cys Lys Ala Ser
            20

<210> SEQ ID NO 510
<211> LENGTH: 17
<212> TYPE: PRT
<213> ORGANISM: Oryctolagus cuniculus

<400> SEQUENCE: 510

```
Met Ser Trp Val Arg Gln Ala Pro Gly Lys Gly Leu Glu Trp Ile Gly
1               5                   10                  15

Tyr

<210> SEQ ID NO 511
<211> LENGTH: 24
<212> TYPE: PRT
<213> ORGANISM: Oryctolagus cuniculus

<400> SEQUENCE: 511

Gln Ser Val Glu Glu Ser Gly Gly Gly Leu Val Lys Pro Gly Gly Thr
1               5                   10                  15

Leu Thr Leu Thr Cys Thr Ala Ser
            20

<210> SEQ ID NO 512
<211> LENGTH: 17
<212> TYPE: PRT
<213> ORGANISM: Oryctolagus cuniculus

<400> SEQUENCE: 512

Met Cys Trp Val Arg Gln Ala Pro Gly Lys Gly Leu Glu Trp Ile Ala
1               5                   10                  15

Cys

<210> SEQ ID NO 513
<211> LENGTH: 24
<212> TYPE: PRT
<213> ORGANISM: Oryctolagus cuniculus

<400> SEQUENCE: 513

Gln Ser Leu Glu Glu Ser Gly Gly Asp Leu Val Gln Pro Glu Gly Ser
1               5                   10                  15

Leu Thr Leu Thr Cys Thr Ala Ser
            20

<210> SEQ ID NO 514
<211> LENGTH: 17
<212> TYPE: PRT
<213> ORGANISM: Oryctolagus cuniculus

<400> SEQUENCE: 514

Met Cys Trp Val Arg Gln Ala Pro Gly Thr Gly Leu Glu Trp Ile Ala
1               5                   10                  15

Cys

<210> SEQ ID NO 515
<211> LENGTH: 24
<212> TYPE: PRT
<213> ORGANISM: Oryctolagus cuniculus

<400> SEQUENCE: 515

Gln Ser Val Glu Glu Ser Arg Gly Arg Leu Val Thr Pro Gly Thr Pro
1               5                   10                  15

Leu Thr Leu Thr Cys Thr Val Ser
            20

<210> SEQ ID NO 516
<211> LENGTH: 17
<212> TYPE: PRT
<213> ORGANISM: Oryctolagus cuniculus
```

```
<400> SEQUENCE: 516

Met Ser Trp Val Arg Gln Ala Pro Gly Lys Gly Leu Glu Trp Ile Gly
1               5                   10                  15

Tyr

<210> SEQ ID NO 517
<211> LENGTH: 24
<212> TYPE: PRT
<213> ORGANISM: Oryctolagus cuniculus

<400> SEQUENCE: 517

Gln Ser Leu Glu Glu Ser Gly Gly Arg Leu Val Thr Pro Gly Thr Pro
1               5                   10                  15

Leu Thr Leu Thr Cys Thr Gly Ser
            20

<210> SEQ ID NO 518
<211> LENGTH: 17
<212> TYPE: PRT
<213> ORGANISM: Oryctolagus cuniculus

<400> SEQUENCE: 518

Met Ala Trp Val Arg Gln Ala Pro Gly Lys Gly Leu Glu Trp Ile Gly
1               5                   10                  15

Ile

<210> SEQ ID NO 519
<211> LENGTH: 24
<212> TYPE: PRT
<213> ORGANISM: Oryctolagus cuniculus

<400> SEQUENCE: 519

Gln Ser Val Lys Glu Ser Glu Gly Arg Leu Val Thr Pro Gly Thr Pro
1               5                   10                  15

Leu Thr Leu Thr Cys Thr Val Ser
            20

<210> SEQ ID NO 520
<211> LENGTH: 17
<212> TYPE: PRT
<213> ORGANISM: Oryctolagus cuniculus

<400> SEQUENCE: 520

Val Ser Trp Val Arg Gln Ala Pro Gly Lys Gly Leu Glu Trp Ile Gly
1               5                   10                  15

Tyr

<210> SEQ ID NO 521
<211> LENGTH: 24
<212> TYPE: PRT
<213> ORGANISM: Oryctolagus cuniculus

<400> SEQUENCE: 521

Gln Ser Leu Glu Glu Ser Gly Gly Gly Leu Val Gln Pro Glu Gly Ser
1               5                   10                  15

Arg Thr Phe Thr Cys Thr Ala Ser
            20

<210> SEQ ID NO 522
<211> LENGTH: 17
<212> TYPE: PRT
```

<213> ORGANISM: Oryctolagus cuniculus

<400> SEQUENCE: 522

Met Cys Trp Val Arg Gln Ala Pro Gly Lys Gly Leu Glu Arg Ile Ala
1               5                   10                  15

Cys

<210> SEQ ID NO 523
<211> LENGTH: 24
<212> TYPE: PRT
<213> ORGANISM: Oryctolagus cuniculus

<400> SEQUENCE: 523

Gln Ser Val Lys Glu Ser Gly Gly Arg Leu Val Thr Pro Gly Thr Pro
1               5                   10                  15

Leu Thr Leu Thr Cys Thr Val Ser
            20

<210> SEQ ID NO 524
<211> LENGTH: 17
<212> TYPE: PRT
<213> ORGANISM: Oryctolagus cuniculus

<400> SEQUENCE: 524

Met Ser Trp Val Arg Gln Ala Pro Gly Lys Gly Leu Glu Trp Ile Gly
1               5                   10                  15

Ile

<210> SEQ ID NO 525
<211> LENGTH: 24
<212> TYPE: PRT
<213> ORGANISM: Oryctolagus cuniculus

<400> SEQUENCE: 525

Gln Ser Val Lys Glu Ser Glu Gly Arg Leu Val Thr Pro Gly Thr Pro
1               5                   10                  15

Leu Thr Leu Thr Cys Thr Ala Ser
            20

<210> SEQ ID NO 526
<211> LENGTH: 17
<212> TYPE: PRT
<213> ORGANISM: Oryctolagus cuniculus

<400> SEQUENCE: 526

Met Ile Trp Val Arg Gln Ala Pro Gly Lys Gly Leu Glu Trp Ile Gly
1               5                   10                  15

Tyr

<210> SEQ ID NO 527
<211> LENGTH: 24
<212> TYPE: PRT
<213> ORGANISM: Oryctolagus cuniculus

<400> SEQUENCE: 527

Gln Ser Val Lys Glu Ser Glu Gly Arg Leu Val Thr Pro Gly Thr Pro
1               5                   10                  15

Leu Thr Leu Thr Cys Thr Val Ser
            20

<210> SEQ ID NO 528

```
<211> LENGTH: 17
<212> TYPE: PRT
<213> ORGANISM: Oryctolagus cuniculus

<400> SEQUENCE: 528

Met Gly Trp Val Arg Gln Ala Pro Gly Glu Gly Leu Glu Trp Ile Gly
1               5                   10                  15

Tyr

<210> SEQ ID NO 529
<211> LENGTH: 17
<212> TYPE: PRT
<213> ORGANISM: Oryctolagus cuniculus

<400> SEQUENCE: 529

Met Gly Trp Val Arg Gln Ala Pro Gly Lys Gly Leu Glu Tyr Ile Gly
1               5                   10                  15

Ile

<210> SEQ ID NO 530
<211> LENGTH: 17
<212> TYPE: PRT
<213> ORGANISM: Oryctolagus cuniculus

<400> SEQUENCE: 530

Met Gly Trp Val Arg Gln Ala Pro Gly Lys Gly Leu Glu Tyr Ile Gly
1               5                   10                  15

Ile

<210> SEQ ID NO 531
<211> LENGTH: 24
<212> TYPE: PRT
<213> ORGANISM: Oryctolagus cuniculus

<400> SEQUENCE: 531

Gln Ser Val Glu Glu Ser Gly Gly Arg Leu Val Thr Pro Gly Thr Pro
1               5                   10                  15

Leu Thr Leu Thr Cys Thr Val Ser
            20

<210> SEQ ID NO 532
<211> LENGTH: 17
<212> TYPE: PRT
<213> ORGANISM: Oryctolagus cuniculus

<400> SEQUENCE: 532

Met Ser Trp Val Arg Gln Ala Pro Gly Lys Gly Leu Glu Trp Ile Gly
1               5                   10                  15

Val

<210> SEQ ID NO 533
<211> LENGTH: 24
<212> TYPE: PRT
<213> ORGANISM: Oryctolagus cuniculus

<400> SEQUENCE: 533

Gln Ser Val Lys Glu Ser Glu Gly Gly Leu Val Lys Pro Gly Gly Thr
1               5                   10                  15

Leu Thr Leu Thr Cys Thr Ala Ser
            20
```

```
<210> SEQ ID NO 534
<211> LENGTH: 17
<212> TYPE: PRT
<213> ORGANISM: Oryctolagus cuniculus

<400> SEQUENCE: 534

Met Cys Trp Val Arg Gln Ala Pro Gly Lys Gly Leu Glu Trp Ile Ala
1               5                   10                  15

Cys

<210> SEQ ID NO 535
<211> LENGTH: 24
<212> TYPE: PRT
<213> ORGANISM: Oryctolagus cuniculus

<400> SEQUENCE: 535

Gln Ser Leu Glu Glu Ser Gly Gly Gly Leu Val Lys Pro Gly Gly Thr
1               5                   10                  15

Leu Thr Leu Thr Cys Thr Ala Ser
            20

<210> SEQ ID NO 536
<211> LENGTH: 17
<212> TYPE: PRT
<213> ORGANISM: Oryctolagus cuniculus

<400> SEQUENCE: 536

Met Cys Trp Val Arg Gln Ala Pro Gly Lys Gly Leu Glu Trp Ile Ala
1               5                   10                  15

Cys

<210> SEQ ID NO 537
<211> LENGTH: 24
<212> TYPE: PRT
<213> ORGANISM: Oryctolagus cuniculus

<400> SEQUENCE: 537

Gln Ser Leu Glu Glu Ser Glu Gly Arg Leu Val Thr Pro Gly Thr Pro
1               5                   10                  15

Leu Thr Leu Thr Cys Thr Val Ser
            20

<210> SEQ ID NO 538
<211> LENGTH: 17
<212> TYPE: PRT
<213> ORGANISM: Oryctolagus cuniculus

<400> SEQUENCE: 538

Met Asn Trp Val Arg Gln Ala Pro Gly Lys Gly Leu Glu Trp Ile Gly
1               5                   10                  15

Ile

<210> SEQ ID NO 539
<211> LENGTH: 24
<212> TYPE: PRT
<213> ORGANISM: Oryctolagus cuniculus

<400> SEQUENCE: 539

Gln Ser Leu Glu Glu Ser Gly Gly Asp Leu Val Lys Pro Gly Ala Ser
1               5                   10                  15

Leu Thr Leu Thr Cys Thr Ala Ser
            20
```

<210> SEQ ID NO 540
<211> LENGTH: 17
<212> TYPE: PRT
<213> ORGANISM: Oryctolagus cuniculus

<400> SEQUENCE: 540

Met Cys Trp Val Arg Gln Ala Pro Gly Lys Gly Leu Glu Trp Ile Val
1               5                   10                  15

Cys

<210> SEQ ID NO 541
<211> LENGTH: 36
<212> TYPE: PRT
<213> ORGANISM: Oryctolagus cuniculus

<400> SEQUENCE: 541

His Tyr Ala Thr Trp Ala Lys Gly Arg Phe Thr Ile Ser Lys Thr Ser
1               5                   10                  15

Thr Thr Val Asp Leu Lys Ile Thr Ser Pro Thr Ser Ala Asp Thr Ala
            20                  25                  30

Thr Tyr Phe Cys
        35

<210> SEQ ID NO 542
<211> LENGTH: 11
<212> TYPE: PRT
<213> ORGANISM: Oryctolagus cuniculus

<400> SEQUENCE: 542

Trp Gly Pro Gly Thr Leu Val Thr Ile Ser Ser
1               5                   10

<210> SEQ ID NO 543
<211> LENGTH: 36
<212> TYPE: PRT
<213> ORGANISM: Oryctolagus cuniculus

<400> SEQUENCE: 543

Tyr Tyr Ala Asn Trp Ala Lys Gly Arg Phe Thr Ile Ser Lys Thr Ser
1               5                   10                  15

Thr Thr Val Asp Leu Lys Ile Thr Thr Pro Thr Thr Glu Asp Thr Ala
            20                  25                  30

Thr Tyr Phe Cys
        35

<210> SEQ ID NO 544
<211> LENGTH: 11
<212> TYPE: PRT
<213> ORGANISM: Oryctolagus cuniculus

<400> SEQUENCE: 544

Trp Gly Pro Gly Thr Leu Val Thr Val Ser Ser
1               5                   10

<210> SEQ ID NO 545
<211> LENGTH: 36
<212> TYPE: PRT
<213> ORGANISM: Oryctolagus cuniculus

<400> SEQUENCE: 545

Tyr Tyr Ala Asn Trp Ala Lys Gly Arg Phe Thr Ile Ser Lys Thr Ser

```
                1               5                  10                 15
Thr Thr Val Asp Leu Lys Ile Thr Ser Leu Thr Thr Glu Asp Thr Ala
                20                 25                 30
Thr Tyr Phe Cys
        35

<210> SEQ ID NO 546
<211> LENGTH: 11
<212> TYPE: PRT
<213> ORGANISM: Oryctolagus cuniculus

<400> SEQUENCE: 546

Trp Gly Pro Gly Thr Leu Val Thr Ile Ser Ser
1               5                  10

<210> SEQ ID NO 547
<211> LENGTH: 38
<212> TYPE: PRT
<213> ORGANISM: Oryctolagus cuniculus

<400> SEQUENCE: 547

Thr Tyr Phe Ala Asn Trp Ala Lys Gly Arg Phe Thr Ile Ser Lys Ala
1               5                  10                 15
Ser Ser Pro Thr Val Thr Leu Gln Met Thr Ser Leu Thr Ala Ala Asp
                20                 25                 30
Thr Ala Thr Tyr Phe Cys
        35

<210> SEQ ID NO 548
<211> LENGTH: 11
<212> TYPE: PRT
<213> ORGANISM: Oryctolagus cuniculus

<400> SEQUENCE: 548

Trp Gly Pro Gly Thr Leu Val Thr Val Ser Ser
1               5                  10

<210> SEQ ID NO 549
<211> LENGTH: 36
<212> TYPE: PRT
<213> ORGANISM: Oryctolagus cuniculus

<400> SEQUENCE: 549

Tyr Tyr Ala Ala Trp Ala Lys Gly Arg Phe Thr Leu Ser Arg Thr Ser
1               5                  10                 15
Thr Thr Leu Asp Leu Lys Met Thr Ser Pro Thr Thr Glu Asp Thr Ala
                20                 25                 30
Thr Tyr Phe Cys
        35

<210> SEQ ID NO 550
<211> LENGTH: 11
<212> TYPE: PRT
<213> ORGANISM: Oryctolagus cuniculus

<400> SEQUENCE: 550

Trp Gly Pro Gly Thr Leu Val Thr Val Ser Ser
1               5                  10

<210> SEQ ID NO 551
<211> LENGTH: 37
<212> TYPE: PRT
```

<213> ORGANISM: Oryctolagus cuniculus

<400> SEQUENCE: 551

Tyr His Ala Ser Trp Val Lys Gly Arg Phe Thr Ile Ser Lys Thr Ser
1               5                   10                  15
Ser Thr Ser Val Asp Leu Lys Met Thr Ser Leu Thr Thr Glu Asp Thr
            20                  25                  30
Ala Thr Tyr Phe Cys
        35

<210> SEQ ID NO 552
<211> LENGTH: 11
<212> TYPE: PRT
<213> ORGANISM: Oryctolagus cuniculus

<400> SEQUENCE: 552

Trp Gly Pro Gly Thr Leu Val Thr Val Ser Ser
1               5                   10

<210> SEQ ID NO 553
<211> LENGTH: 38
<212> TYPE: PRT
<213> ORGANISM: Oryctolagus cuniculus

<400> SEQUENCE: 553

Trp Tyr Ala Ser Trp Ala Lys Gly Arg Phe Thr Val Ser Lys Thr Ser
1               5                   10                  15
Ser Thr Thr Val Thr Leu Gln Met Thr Ser Leu Thr Ala Ala Asp Thr
            20                  25                  30
Ala Thr Tyr Phe Cys Ala
        35

<210> SEQ ID NO 554
<211> LENGTH: 11
<212> TYPE: PRT
<213> ORGANISM: Oryctolagus cuniculus

<400> SEQUENCE: 554

Trp Gly Pro Gly Thr Leu Val Thr Ile Ser Ser
1               5                   10

<210> SEQ ID NO 555
<211> LENGTH: 36
<212> TYPE: PRT
<213> ORGANISM: Oryctolagus cuniculus

<400> SEQUENCE: 555

Tyr Tyr Ala Ser Trp Ala Lys Gly Arg Phe Thr Ile Ser Lys Thr Ser
1               5                   10                  15
Thr Thr Val Asp Leu Lys Ile Thr Ser Leu Thr Thr Glu Asp Thr Ala
            20                  25                  30
Thr Tyr Phe Cys
        35

<210> SEQ ID NO 556
<211> LENGTH: 11
<212> TYPE: PRT
<213> ORGANISM: Oryctolagus cuniculus

<400> SEQUENCE: 556

Trp Gly Pro Gly Thr Leu Val Thr Ile Ser Ser
1               5                   10

<210> SEQ ID NO 557
<211> LENGTH: 37
<212> TYPE: PRT
<213> ORGANISM: Oryctolagus cuniculus

<400> SEQUENCE: 557

Tyr Tyr Ala Ser Trp Ala Lys Gly Arg Phe Thr Ile Ser Lys Ala Ser
1               5                   10                  15

Ser Thr Thr Val Thr Leu Gln Met Ala Ser Leu Ala Ala Ala Asp Thr
            20                  25                  30

Ala Thr Tyr Phe Cys
        35

<210> SEQ ID NO 558
<211> LENGTH: 11
<212> TYPE: PRT
<213> ORGANISM: Oryctolagus cuniculus

<400> SEQUENCE: 558

Trp Gly Pro Gly Thr Leu Val Thr Val Ser Ser
1               5                   10

<210> SEQ ID NO 559
<211> LENGTH: 38
<212> TYPE: PRT
<213> ORGANISM: Oryctolagus cuniculus

<400> SEQUENCE: 559

Trp Tyr Ala Ser Trp Ala Lys Gly Arg Phe Thr Ile Ser Lys Thr Ser
1               5                   10                  15

Ser Thr Thr Val Thr Leu Gln Met Thr Ser Leu Thr Ala Ala Asp Thr
            20                  25                  30

Ala Thr Tyr Phe Cys Ala
        35

<210> SEQ ID NO 560
<211> LENGTH: 11
<212> TYPE: PRT
<213> ORGANISM: Oryctolagus cuniculus

<400> SEQUENCE: 560

Trp Gly Pro Gly Thr Leu Val Thr Ile Ser Ser
1               5                   10

<210> SEQ ID NO 561
<211> LENGTH: 36
<212> TYPE: PRT
<213> ORGANISM: Oryctolagus cuniculus

<400> SEQUENCE: 561

Tyr Tyr Ala Thr Trp Ala Lys Gly Arg Phe Thr Ile Ser Arg Thr Ser
1               5                   10                  15

Thr Thr Val Ala Leu Lys Ile Thr Ser Pro Thr Thr Glu Asp Ser Ala
            20                  25                  30

Thr Tyr Phe Cys
        35

<210> SEQ ID NO 562
<211> LENGTH: 11
<212> TYPE: PRT
<213> ORGANISM: Oryctolagus cuniculus

<400> SEQUENCE: 562

Trp Gly Pro Gly Thr Leu Val Thr Ile Ser Ser
1               5                   10

<210> SEQ ID NO 563
<211> LENGTH: 38
<212> TYPE: PRT
<213> ORGANISM: Oryctolagus cuniculus

<400> SEQUENCE: 563

Trp Tyr Ala Ser Trp Ala Lys Gly Arg Phe Thr Ile Ser Lys Ser Ser
1               5                   10                  15

Ser Thr Thr Val Thr Leu Gln Met Thr Ser Leu Thr Ala Ala Asp Thr
            20                  25                  30

Ala Thr Tyr Phe Cys Ala
        35

<210> SEQ ID NO 564
<211> LENGTH: 11
<212> TYPE: PRT
<213> ORGANISM: Oryctolagus cuniculus

<400> SEQUENCE: 564

Trp Gly Pro Gly Thr Leu Val Thr Ile Ser Ser
1               5                   10

<210> SEQ ID NO 565
<211> LENGTH: 37
<212> TYPE: PRT
<213> ORGANISM: Oryctolagus cuniculus

<400> SEQUENCE: 565

Tyr Tyr Ala Thr Trp Ala Lys Gly Arg Phe Thr Val Ser Lys Thr Ser
1               5                   10                  15

Ser Thr Thr Met Asp Leu Arg Ile Ala Arg Leu Thr Thr Glu Asp Thr
            20                  25                  30

Ala Thr Tyr Phe Cys
        35

<210> SEQ ID NO 566
<211> LENGTH: 11
<212> TYPE: PRT
<213> ORGANISM: Oryctolagus cuniculus

<400> SEQUENCE: 566

Trp Gly Pro Gly Thr Leu Val Thr Val Ser Ser
1               5                   10

<210> SEQ ID NO 567
<211> LENGTH: 37
<212> TYPE: PRT
<213> ORGANISM: Oryctolagus cuniculus

<400> SEQUENCE: 567

Tyr Tyr Ala Asn Trp Ala Lys Gly Arg Phe Thr Val Ser Lys Thr Ser
1               5                   10                  15

Ser Thr Thr Val Thr Leu Gln Met Thr Ser Leu Thr Ala Ala Asp Thr
            20                  25                  30

Ala Thr Tyr Phe Cys
        35

<210> SEQ ID NO 568
<211> LENGTH: 11
<212> TYPE: PRT
<213> ORGANISM: Oryctolagus cuniculus

<400> SEQUENCE: 568

Trp Gly Pro Gly Thr Leu Val Thr Ile Ser Ser
1               5                   10

<210> SEQ ID NO 569
<211> LENGTH: 37
<212> TYPE: PRT
<213> ORGANISM: Oryctolagus cuniculus

<400> SEQUENCE: 569

Phe Tyr Ala Ser Trp Ala Lys Gly Arg Phe Thr Ile Ser Lys Thr Ser
1               5                   10                  15

Ser Thr Thr Val Asp Leu Arg Ile Thr Ser Pro Thr Thr Glu Asp Thr
            20                  25                  30

Ala Ala Tyr Phe Cys
        35

<210> SEQ ID NO 570
<211> LENGTH: 11
<212> TYPE: PRT
<213> ORGANISM: Oryctolagus cuniculus

<400> SEQUENCE: 570

Trp Gly Pro Gly Thr Leu Val Thr Val Ser Ser
1               5                   10

<210> SEQ ID NO 571
<211> LENGTH: 37
<212> TYPE: PRT
<213> ORGANISM: Oryctolagus cuniculus

<400> SEQUENCE: 571

Phe Tyr Ala Ser Trp Ala Glu Gly Arg Phe Thr Ile Ser Arg Thr Ser
1               5                   10                  15

Ser Thr Thr Val Thr Leu Gln Met Thr Ser Leu Ala Ala Ala Asp Thr
            20                  25                  30

Ala Ile Tyr Tyr Cys
        35

<210> SEQ ID NO 572
<211> LENGTH: 11
<212> TYPE: PRT
<213> ORGANISM: Oryctolagus cuniculus

<400> SEQUENCE: 572

Trp Gly Pro Gly Thr Leu Val Thr Val Ser Ser
1               5                   10

<210> SEQ ID NO 573
<211> LENGTH: 36
<212> TYPE: PRT
<213> ORGANISM: Oryctolagus cuniculus

<400> SEQUENCE: 573

Tyr Tyr Ala Ser Trp Ala Lys Gly Arg Phe Thr Ile Ser Arg Thr Ser
1               5                   10                  15

Thr Thr Val Asp Leu Gln Ile Thr Gly Pro Thr Thr Glu Asp Thr Ala

-continued

```
                    20                  25                  30

Thr Tyr Phe Cys
        35

<210> SEQ ID NO 574
<211> LENGTH: 11
<212> TYPE: PRT
<213> ORGANISM: Oryctolagus cuniculus

<400> SEQUENCE: 574

Trp Gly Gln Gly Thr Leu Val Thr Val Ser Ser
1               5                   10

<210> SEQ ID NO 575
<211> LENGTH: 36
<212> TYPE: PRT
<213> ORGANISM: Oryctolagus cuniculus

<400> SEQUENCE: 575

Tyr Tyr Ala Ser Trp Ala Lys Gly Arg Phe Ala Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 576
<211> LENGTH: 11
<212> TYPE: PRT
<213> ORGANISM: Oryctolagus cuniculus

<400> SEQUENCE: 576

Trp Gly Gln Gly Thr Leu Val Thr Val Ser Ser
1               5                   10

<210> SEQ ID NO 577
<211> LENGTH: 36
<212> TYPE: PRT
<213> ORGANISM: Oryctolagus cuniculus

<400> SEQUENCE: 577

Tyr Tyr Ala Ser Trp Ala Lys Gly Arg Phe Thr Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 578
<211> LENGTH: 11
<212> TYPE: PRT
<213> ORGANISM: Oryctolagus cuniculus

<400> SEQUENCE: 578

Trp Gly Pro Gly Thr Leu Val Thr Val Ser Ser
1               5                   10

<210> SEQ ID NO 579
<211> LENGTH: 37
<212> TYPE: PRT
<213> ORGANISM: Oryctolagus cuniculus

<400> SEQUENCE: 579
```

Phe Tyr Ala Ser Trp Ala Glu Gly Arg Phe Thr Ile Ser Arg Thr Ser
1               5                   10                  15

Ser Thr Thr Val Thr Leu Gln Met Thr Ser Leu Ala Ala Ala Asp Thr
            20                  25                  30

Ala Ile Tyr Tyr Cys
            35

<210> SEQ ID NO 580
<211> LENGTH: 11
<212> TYPE: PRT
<213> ORGANISM: Oryctolagus cuniculus

<400> SEQUENCE: 580

Trp Gly Pro Gly Thr Leu Val Thr Ile Ser Ser
1               5                   10

<210> SEQ ID NO 581
<211> LENGTH: 36
<212> TYPE: PRT
<213> ORGANISM: Oryctolagus cuniculus

<400> SEQUENCE: 581

Tyr Tyr Ala Asn Trp Ala Lys Gly Arg Phe Thr Ile Ser Lys Thr Ser
1               5                   10                  15

Thr Thr Val Asp Leu Lys Ile Thr Ser Leu Thr Ile Glu Asp Thr Ala
            20                  25                  30

Thr Tyr Phe Cys
            35

<210> SEQ ID NO 582
<211> LENGTH: 11
<212> TYPE: PRT
<213> ORGANISM: Oryctolagus cuniculus

<400> SEQUENCE: 582

Trp Gly Pro Gly Thr Leu Val Thr Ile Ser Ser
1               5                   10

<210> SEQ ID NO 583
<211> LENGTH: 36
<212> TYPE: PRT
<213> ORGANISM: Oryctolagus cuniculus

<400> SEQUENCE: 583

Ser Tyr Ala Ser Trp Val Asn Gly Pro Phe Ala Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
            35

<210> SEQ ID NO 584
<211> LENGTH: 11
<212> TYPE: PRT
<213> ORGANISM: Oryctolagus cuniculus

<400> SEQUENCE: 584

Trp Gly Gln Gly Thr Leu Val Thr Ile Ser Ser
1               5                   10

<210> SEQ ID NO 585

```
<211> LENGTH: 36
<212> TYPE: PRT
<213> ORGANISM: Oryctolagus cuniculus

<400> SEQUENCE: 585

Ser Tyr Ala Ser Trp Ala Lys Gly Arg Phe Thr Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
            35

<210> SEQ ID NO 586
<211> LENGTH: 11
<212> TYPE: PRT
<213> ORGANISM: Oryctolagus cuniculus

<400> SEQUENCE: 586

Trp Gly Pro Gly Thr Leu Val Thr Ile Ser Ser
1               5                   10

<210> SEQ ID NO 587
<211> LENGTH: 36
<212> TYPE: PRT
<213> ORGANISM: Oryctolagus cuniculus

<400> SEQUENCE: 587

His Tyr Ala Thr Trp Ala Lys Gly Arg Phe Thr Ile Ser Lys Thr Ser
1               5                   10                  15

Thr Thr Val Asp Leu Lys Ile Thr Ser Pro Thr Ser Ala Asp Thr Ala
            20                  25                  30

Thr Tyr Phe Cys
            35

<210> SEQ ID NO 588
<211> LENGTH: 11
<212> TYPE: PRT
<213> ORGANISM: Oryctolagus cuniculus

<400> SEQUENCE: 588

Trp Gly Pro Gly Thr Leu Val Thr Ile Ser Ser
1               5                   10

<210> SEQ ID NO 589
<211> LENGTH: 38
<212> TYPE: PRT
<213> ORGANISM: Oryctolagus cuniculus

<400> SEQUENCE: 589

Trp Tyr Ala Ser Trp Ala Lys Gly Arg Phe Thr Ile Ser Lys Ser Ser
1               5                   10                  15

Ser Thr Thr Val Thr Leu Gln Met Thr Ser Leu Thr Ala Ala Asp Thr
            20                  25                  30

Ala Thr Tyr Phe Cys Ala
            35

<210> SEQ ID NO 590
<211> LENGTH: 11
<212> TYPE: PRT
<213> ORGANISM: Oryctolagus cuniculus

<400> SEQUENCE: 590
```

```
Trp Gly Pro Gly Thr Leu Val Thr Ile Ser Ser
1               5                   10
```

<210> SEQ ID NO 591
<211> LENGTH: 36
<212> TYPE: PRT
<213> ORGANISM: Oryctolagus cuniculus

<400> SEQUENCE: 591

```
His Tyr Ala Thr Trp Ala Lys Gly Arg Phe Thr Ile Ser Lys Ala Ser
1               5                   10                  15

Thr Thr Val Asp Leu Lys Ile Thr Ser Pro Thr Ser Ala Asp Thr Ala
            20                  25                  30

Thr Tyr Phe Cys
        35
```

<210> SEQ ID NO 592
<211> LENGTH: 11
<212> TYPE: PRT
<213> ORGANISM: Oryctolagus cuniculus

<400> SEQUENCE: 592

```
Trp Gly Pro Gly Thr Leu Val Thr Ile Ser Ser
1               5                   10
```

<210> SEQ ID NO 593
<211> LENGTH: 36
<212> TYPE: PRT
<213> ORGANISM: Oryctolagus cuniculus

<400> SEQUENCE: 593

```
Tyr Tyr Ala Asn Trp Ala Lys Gly Arg Phe Thr Ile Ser Lys Thr Ser
1               5                   10                  15

Thr Thr Val Asp Leu Lys Ile Thr Ser Pro Ile Ile Glu Asp Thr Ala
            20                  25                  30

Thr Tyr Phe Cys
        35
```

<210> SEQ ID NO 594
<211> LENGTH: 11
<212> TYPE: PRT
<213> ORGANISM: Oryctolagus cuniculus

<400> SEQUENCE: 594

```
Trp Gly Pro Gly Thr Leu Val Thr Ile Ser Ser
1               5                   10
```

<210> SEQ ID NO 595
<211> LENGTH: 36
<212> TYPE: PRT
<213> ORGANISM: Oryctolagus cuniculus

<400> SEQUENCE: 595

```
Tyr Tyr Ala Thr Trp Ala Lys Gly Arg Phe Thr Ile Ser Arg Thr Ser
1               5                   10                  15

Thr Thr Val Ala Leu Lys Ile Thr Ser Pro Thr Thr Glu Asp Thr Ala
            20                  25                  30

Thr Tyr Phe Cys
        35
```

<210> SEQ ID NO 596
<211> LENGTH: 11

```
<212> TYPE: PRT
<213> ORGANISM: Oryctolagus cuniculus

<400> SEQUENCE: 596

Trp Gly Pro Gly Thr Leu Val Thr Ile Ser Ser
1               5                   10

<210> SEQ ID NO 597
<211> LENGTH: 36
<212> TYPE: PRT
<213> ORGANISM: Oryctolagus cuniculus

<400> SEQUENCE: 597

Asp Tyr Ala Ser Trp Ala Lys Gly Arg Phe Ile Ile Ser Lys Thr Ser
1               5                   10                  15

Thr Thr Val Asp Leu Lys Ile Thr Ser Pro Thr Thr Ala Asp Thr Ala
            20                  25                  30

Thr Tyr Phe Cys
        35

<210> SEQ ID NO 598
<211> LENGTH: 11
<212> TYPE: PRT
<213> ORGANISM: Oryctolagus cuniculus

<400> SEQUENCE: 598

Trp Gly Pro Gly Thr Leu Val Thr Val Ser Ser
1               5                   10

<210> SEQ ID NO 599
<211> LENGTH: 38
<212> TYPE: PRT
<213> ORGANISM: Oryctolagus cuniculus

<400> SEQUENCE: 599

Tyr Tyr Ala Ser Trp Val Asn Gly Arg Phe Thr Ile Ser Ser His Asn
1               5                   10                  15

Ala Gln Asn Thr Leu Tyr Leu Gln Leu Asn Ser Leu Thr Ala Ala Asp
            20                  25                  30

Thr Ala Thr Tyr Phe Cys
        35

<210> SEQ ID NO 600
<211> LENGTH: 11
<212> TYPE: PRT
<213> ORGANISM: Oryctolagus cuniculus

<400> SEQUENCE: 600

Trp Gly Pro Gly Thr Leu Val Thr Val Ser Ser
1               5                   10

<210> SEQ ID NO 601
<211> LENGTH: 37
<212> TYPE: PRT
<213> ORGANISM: Oryctolagus cuniculus

<400> SEQUENCE: 601

Phe Tyr Ala Ser Trp Ala Lys Gly Arg Phe Thr Ile Ser Arg Thr Ser
1               5                   10                  15

Ser Thr Thr Val Thr Leu Gln Met Thr Ser Leu Ala Ala Ala Asp Thr
            20                  25                  30

Ala Thr Tyr Tyr Cys
```

<210> SEQ ID NO 602
<211> LENGTH: 11
<212> TYPE: PRT
<213> ORGANISM: Oryctolagus cuniculus

<400> SEQUENCE: 602

Trp Gly Pro Gly Thr Leu Val Thr Ile Ser Ser
1               5                   10

<210> SEQ ID NO 603
<211> LENGTH: 37
<212> TYPE: PRT
<213> ORGANISM: Oryctolagus cuniculus

<400> SEQUENCE: 603

Tyr Tyr Ala Asn Trp Ala Lys Gly Arg Phe Thr Ile Ser Gly Thr Ser
1               5                   10                  15

Ser Thr Thr Val Thr Leu Gln Val Thr Ser Leu Thr Ala Ala Asp Thr
            20                  25                  30

Ala Thr Tyr Phe Cys
        35

<210> SEQ ID NO 604
<211> LENGTH: 11
<212> TYPE: PRT
<213> ORGANISM: Oryctolagus cuniculus

<400> SEQUENCE: 604

Trp Gly Pro Gly Thr Leu Val Thr Ile Ser Ser
1               5                   10

<210> SEQ ID NO 605
<211> LENGTH: 36
<212> TYPE: PRT
<213> ORGANISM: Oryctolagus cuniculus

<400> SEQUENCE: 605

Tyr Tyr Ala Ser Trp Ala Lys Gly Arg Phe Ala Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 606
<211> LENGTH: 11
<212> TYPE: PRT
<213> ORGANISM: Oryctolagus cuniculus

<400> SEQUENCE: 606

Trp Gly Gln Gly Thr Leu Val Thr Val Ser Ser
1               5                   10

<210> SEQ ID NO 607
<211> LENGTH: 36
<212> TYPE: PRT
<213> ORGANISM: Oryctolagus cuniculus

<400> SEQUENCE: 607

Ser Tyr Ala Ser Trp Ala Lys Gly Arg Phe Thr Ile Ser Lys Thr Ser
1               5                   10                  15

-continued

```
Thr Thr Val Asp Leu Lys Ile Thr Ser Pro Thr Thr Glu Asp Thr Ala
            20                  25                  30
Thr Tyr Phe Cys
        35

<210> SEQ ID NO 608
<211> LENGTH: 11
<212> TYPE: PRT
<213> ORGANISM: Oryctolagus cuniculus

<400> SEQUENCE: 608

Trp Gly Pro Gly Thr Leu Val Thr Ser Ser Ser
1               5                   10

<210> SEQ ID NO 609
<211> LENGTH: 36
<212> TYPE: PRT
<213> ORGANISM: Oryctolagus cuniculus

<400> SEQUENCE: 609

Asp Tyr Ala Ser Trp Val Asn Gly Arg Phe Thr Ile Ser Lys Thr Ser
1               5                   10                  15
Thr Thr Val Asp Leu Lys Ile Thr Ser Pro Thr Thr Glu Asp Thr Ala
            20                  25                  30
Ile Tyr Phe Cys
        35

<210> SEQ ID NO 610
<211> LENGTH: 11
<212> TYPE: PRT
<213> ORGANISM: Oryctolagus cuniculus

<400> SEQUENCE: 610

Trp Gly Pro Gly Thr Leu Val Thr Val Ser Ser
1               5                   10

<210> SEQ ID NO 611
<211> LENGTH: 37
<212> TYPE: PRT
<213> ORGANISM: Oryctolagus cuniculus

<400> SEQUENCE: 611

Tyr Tyr Ala Asp Trp Ala Ser Gly Arg Phe Thr Ile Ser Lys Thr Ser
1               5                   10                  15
Ser Thr Thr Val Thr Leu Gln Met Thr Ser Leu Ala Ala Ala Asp Thr
            20                  25                  30
Ala Thr His Phe Cys
        35

<210> SEQ ID NO 612
<211> LENGTH: 11
<212> TYPE: PRT
<213> ORGANISM: Oryctolagus cuniculus

<400> SEQUENCE: 612

Trp Gly Pro Gly Thr Leu Val Thr Val Ser Ser
1               5                   10

<210> SEQ ID NO 613
<211> LENGTH: 36
<212> TYPE: PRT
<213> ORGANISM: Oryctolagus cuniculus
```

<400> SEQUENCE: 613

Tyr Tyr Ala Ser Trp Ala Lys Gly Arg Phe Thr Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 614
<211> LENGTH: 11
<212> TYPE: PRT
<213> ORGANISM: Oryctolagus cuniculus

<400> SEQUENCE: 614

Trp Gly Pro Gly Thr Leu Val Thr Ile Ser Ser
1               5                   10

<210> SEQ ID NO 615
<211> LENGTH: 36
<212> TYPE: PRT
<213> ORGANISM: Oryctolagus cuniculus

<400> SEQUENCE: 615

Tyr Tyr Ala Thr Trp Ala Lys Gly Arg Phe Thr Ile Ser Arg Thr Ser
1               5                   10                  15

Thr Thr Val Ala Leu Lys Ile Thr Ser Pro Thr Thr Lys Asp Thr Ala
            20                  25                  30

Thr Tyr Phe Cys
        35

<210> SEQ ID NO 616
<211> LENGTH: 11
<212> TYPE: PRT
<213> ORGANISM: Oryctolagus cuniculus

<400> SEQUENCE: 616

Trp Gly Pro Gly Thr Leu Val Thr Ile Ser Ser
1               5                   10

<210> SEQ ID NO 617
<211> LENGTH: 36
<212> TYPE: PRT
<213> ORGANISM: Oryctolagus cuniculus

<400> SEQUENCE: 617

Phe Tyr Ala Ser Trp Ala Lys Gly Arg Phe Thr Ile Ser Lys Thr Ser
1               5                   10                  15

Thr Thr Val Asp Leu Arg Ile Thr Ser Pro Thr Thr Glu Asp Thr Ala
            20                  25                  30

Thr Tyr Phe Cys
        35

<210> SEQ ID NO 618
<211> LENGTH: 11
<212> TYPE: PRT
<213> ORGANISM: Oryctolagus cuniculus

<400> SEQUENCE: 618

Trp Gly Pro Gly Thr Leu Val Thr Ile Ser Ser
1               5                   10

<210> SEQ ID NO 619
<211> LENGTH: 36
<212> TYPE: PRT
<213> ORGANISM: Oryctolagus cuniculus

<400> SEQUENCE: 619

Tyr Tyr Ala Ser Trp Ala Lys Gly Arg Phe Thr Ile Ser Arg Thr Ser
1               5                   10                  15

Thr Thr Val Asp Leu Lys Met Thr Ser Leu Thr Thr Glu Asp Thr Ala
            20                  25                  30

Thr Tyr Phe Cys
        35

<210> SEQ ID NO 620
<211> LENGTH: 11
<212> TYPE: PRT
<213> ORGANISM: Oryctolagus cuniculus

<400> SEQUENCE: 620

Trp Gly Pro Gly Thr Leu Val Thr Ile Ser Ser
1               5                   10

<210> SEQ ID NO 621
<211> LENGTH: 36
<212> TYPE: PRT
<213> ORGANISM: Oryctolagus cuniculus

<400> SEQUENCE: 621

Trp Tyr Ala Ser Trp Ala Lys Gly Arg Phe Thr Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 622
<211> LENGTH: 11
<212> TYPE: PRT
<213> ORGANISM: Oryctolagus cuniculus

<400> SEQUENCE: 622

Trp Gly Pro Gly Thr Leu Val Thr Val Ser Ser
1               5                   10

<210> SEQ ID NO 623
<211> LENGTH: 37
<212> TYPE: PRT
<213> ORGANISM: Oryctolagus cuniculus

<400> SEQUENCE: 623

Phe Tyr Ala Ser Trp Ala Glu Gly Arg Phe Thr Ile Ser Arg Thr Ser
1               5                   10                  15

Ser Thr Thr Val Thr Leu Gln Met Thr Ser Leu Ala Ala Ala Asp Thr
            20                  25                  30

Ala Ile Tyr Tyr Cys
        35

<210> SEQ ID NO 624
<211> LENGTH: 11
<212> TYPE: PRT
<213> ORGANISM: Oryctolagus cuniculus

<400> SEQUENCE: 624

Trp Gly Pro Gly Thr Leu Val Thr Ile Ser Ser
1               5                   10

<210> SEQ ID NO 625
<211> LENGTH: 37
<212> TYPE: PRT
<213> ORGANISM: Oryctolagus cuniculus

<400> SEQUENCE: 625

Phe Tyr Ala Ser Trp Ala Lys Gly Arg Phe Thr Ile Ser Arg Thr Ser
1               5                   10                  15

Ser Thr Thr Val Thr Leu Gln Met Thr Ser Leu Ala Ala Ala Asp Thr
            20                  25                  30

Ala Thr Tyr Tyr Cys
        35

<210> SEQ ID NO 626
<211> LENGTH: 11
<212> TYPE: PRT
<213> ORGANISM: Oryctolagus cuniculus

<400> SEQUENCE: 626

Trp Gly Pro Gly Thr Leu Val Thr Ile Ser Ser
1               5                   10

<210> SEQ ID NO 627
<211> LENGTH: 36
<212> TYPE: PRT
<213> ORGANISM: Oryctolagus cuniculus

<400> SEQUENCE: 627

Tyr Tyr Ala Ser Trp Ala Lys Gly Arg Cys Thr Ile Ser Lys Thr Ser
1               5                   10                  15

Thr Thr Val Asp Leu Lys Ile Thr Ser Pro Thr Thr Glu Asp Thr Ala
            20                  25                  30

Thr Tyr Phe Cys
        35

<210> SEQ ID NO 628
<211> LENGTH: 11
<212> TYPE: PRT
<213> ORGANISM: Oryctolagus cuniculus

<400> SEQUENCE: 628

Trp Gly Pro Gly Thr Leu Val Thr Ile Ser Ser
1               5                   10

<210> SEQ ID NO 629
<211> LENGTH: 37
<212> TYPE: PRT
<213> ORGANISM: Oryctolagus cuniculus

<400> SEQUENCE: 629

Tyr Tyr Ala Asn Trp Ala Lys Gly Arg Phe Thr Val Ser Lys Thr Ser
1               5                   10                  15

Ser Thr Thr Val Thr Leu Gln Met Thr Ser Leu Thr Ala Ala Asp Thr
            20                  25                  30

Ala Thr Tyr Phe Cys
        35

```
<210> SEQ ID NO 630
<211> LENGTH: 11
<212> TYPE: PRT
<213> ORGANISM: Oryctolagus cuniculus

<400> SEQUENCE: 630

Trp Gly Pro Gly Thr Leu Val Thr Ile Ser Ser
1               5                   10

<210> SEQ ID NO 631
<211> LENGTH: 113
<212> TYPE: PRT
<213> ORGANISM: Artificial Sequence
<220> FEATURE:
<223> OTHER INFORMATION: Humanized 57.4 anti-CMV Ab, VL chain

<400> SEQUENCE: 631

Asp Ile Gln Met Thr Gln Thr Pro Ser Ser Val Ser Ala Ser Val Gly
1               5                   10                  15

Asp Arg Val Thr Ile Lys Cys Gln Ala Ser Gln Ser Ile Arg Arg His
            20                  25                  30

Leu Ser Trp Tyr Gln Gln Lys Pro Gly Lys Arg Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Gly Val Gly Phe
                85                  90                  95

Ser Ser Thr Tyr Gly Asp Ala Phe Gly Gly Gly Thr Lys Val Glu Ile
            100                 105                 110

Lys

<210> SEQ ID NO 632
<211> LENGTH: 113
<212> TYPE: PRT
<213> ORGANISM: Artificial Sequence
<220> FEATURE:
<223> OTHER INFORMATION: Humanized 57.4 anti-CMV Ab, VL chain

<400> SEQUENCE: 632

Glu Leu Gln Met Thr Gln Thr Pro Ser Ser Val Ser Ala Ser Val Gly
1               5                   10                  15

Asp Arg Val Thr Ile Lys Cys Gln Ala Ser Gln Ser Ile Arg Arg His
            20                  25                  30

Leu Ser Trp Tyr Gln Gln Lys Pro Gly Lys Arg Pro Lys Leu Leu Ile
        35                  40                  45

Tyr Gly Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Gly Val Gly Phe
                85                  90                  95

Ser Ser Thr Tyr Gly Asp Ala Phe Gly Gly Gly Thr Lys Val Glu Ile
            100                 105                 110

Lys

<210> SEQ ID NO 633
<211> LENGTH: 127
```

```
<212> TYPE: PRT
<213> ORGANISM: Artificial Sequence
<220> FEATURE:
<223> OTHER INFORMATION: Humanized 57.4 anti-CMV Ab, VH chain

<400> SEQUENCE: 633

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Val
            20                  25                  30

Tyr Asp Met Ser Trp Val Arg Gln Ala Pro Gly Lys Gly Leu Glu Trp
        35                  40                  45

Ile Ala Ser Ile Val Thr Gly Ser Arg Thr Thr Trp Tyr Ala Ser Trp
50                  55                  60

Ala Lys Gly Arg Phe Thr Val Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Gly Glu Tyr Gly His Asp Gly Tyr Val Asp Gly Thr Met
            100                 105                 110

Gly Leu Gly Leu Trp Gly Pro Gly Thr Thr Val Thr Val Ser Ser
        115                 120                 125

<210> SEQ ID NO 634
<211> LENGTH: 127
<212> TYPE: PRT
<213> ORGANISM: Artificial Sequence
<220> FEATURE:
<223> OTHER INFORMATION: Humanized 57.4 anti-CMV Ab, VH chain

<400> SEQUENCE: 634

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Val
            20                  25                  30

Tyr Asp Met Ser Trp Val Arg Gln Ala Pro Gly Lys Gly Leu Glu Trp
        35                  40                  45

Ile Ala Ser Ile Val Thr Gly Ser Arg Thr Thr Trp Tyr Ala Ser Trp
50                  55                  60

Ala Lys Gly Arg Phe Thr Val Ser Arg Asp Asn Ser Lys Asn Thr Leu
65                  70                  75                  80

Tyr Leu Gln Met Asn Ser Leu Arg Ala Glu Asp Thr Ala Val Tyr Phe
                85                  90                  95

Cys Ala Arg Gly Glu Tyr Gly His Asp Gly Tyr Val Asp Gly Thr Met
            100                 105                 110

Gly Leu Gly Leu Trp Gly Pro Gly Thr Thr Val Thr Val Ser Ser
        115                 120                 125

<210> SEQ ID NO 635
<211> LENGTH: 110
<212> TYPE: PRT
<213> ORGANISM: Artificial Sequence
<220> FEATURE:
<223> OTHER INFORMATION: Humanized 58.5 anti-CMV Ab, VL chain

<400> SEQUENCE: 635

Asp Ile Gln Leu Thr Gln Thr Pro Ser Phe Leu Ser Ala Ser Val Gly
1               5                   10                  15

Asp Arg Val Thr Ile Asn Cys Gln Ala Ser Gln Asn Ile Tyr Ser Asn
```

-continued

```
                    20                  25                  30
Leu Ala Trp Tyr Gln Gln Lys Pro Gly Lys Pro Lys Leu Leu Ile
            35                  40                  45

Tyr Gly Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ser Tyr Val Tyr Ser Ser Ser
                85                  90                  95

Thr Ala Asp Thr Phe Gly Gly Gly Thr Lys Val Glu Ile Lys
            100                 105                 110

<210> SEQ ID NO 636
<211> LENGTH: 110
<212> TYPE: PRT
<213> ORGANISM: Artificial Sequence
<220> FEATURE:
<223> OTHER INFORMATION: Humanized 58.5 anti-CMV Ab, VL chain

<400> SEQUENCE: 636

Glu Leu Gln Leu Thr Gln Thr Pro Ser Phe Leu Ser Ala Ser Val Gly
1               5                   10                  15

Asp Arg Val Thr Ile Asn Cys Gln Ala Ser Gln Asn Ile Tyr Ser Asn
                20                  25                  30

Leu Ala Trp Tyr Gln Gln Lys Pro Gly Lys Pro Lys Leu Leu Ile
            35                  40                  45

Tyr Gly Ala Ser Thr Leu Ala Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Ser Tyr Val Tyr Ser Ser Ser
                85                  90                  95

Thr Ala Asp Thr Phe Gly Gly Gly Thr Lys Val Glu Ile Lys
            100                 105                 110

<210> SEQ ID NO 637
<211> LENGTH: 124
<212> TYPE: PRT
<213> ORGANISM: Artificial Sequence
<220> FEATURE:
<223> OTHER INFORMATION: Humanized 58.5 anti-CMV Ab, VH chain

<400> SEQUENCE: 637

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ala Tyr
                20                  25                  30

Ser Val Ser Trp Val Arg Gln Ala Pro Gly Lys Gly Leu Glu Trp Ile
            35                  40                  45

Gly Ile Ile Gly His Ser Gly Asn Thr Tyr Tyr Ala Ser Trp Ala Lys
        50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Glu Asp Tyr Arg Tyr Gly Asp Tyr Gly Tyr Tyr Trp Asp Phe Asn
            100                 105                 110
```

```
Phe Trp Gly Pro Gly Thr Leu Val Thr Val Ser Ser
        115                 120
```

<210> SEQ ID NO 638
<211> LENGTH: 124
<212> TYPE: PRT
<213> ORGANISM: Artificial Sequence
<220> FEATURE:
<223> OTHER INFORMATION: Humanized 58.5 anti-CMV Ab, VH chain

<400> SEQUENCE: 638

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Leu Ser Ala Tyr
            20                  25                  30

Ser Val Ser Trp Val Arg Gln Ala Pro Gly Lys Gly Leu Glu Trp Ile
        35                  40                  45

Gly Ile Ile Gly His Ser Gly Asn Thr Tyr Tyr Ala Ser Trp Ala Lys
    50                  55                  60

Gly Arg Phe Thr Ile Ser Arg Asp Thr Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Glu Asp Tyr Arg Tyr Gly Asp Tyr Gly Tyr Tyr Trp Asp Phe Asn
            100                 105                 110

Phe Trp Gly Pro Gly Thr Leu Val Thr Val Ser Ser
        115                 120
```

<210> SEQ ID NO 639
<211> LENGTH: 107
<212> TYPE: PRT
<213> ORGANISM: Artificial Sequence
<220> FEATURE:
<223> OTHER INFORMATION: Humanized 272.7 anti-CMV Ab, VL chain

<400> SEQUENCE: 639

```
Asp Ile Gln Met Thr Gln Thr Pro Ser Ser Val Ser Ala Ser Val Gly
1               5                   10                  15

Asp Arg Val Thr Ile Lys Cys Gln Ala Ser Gln Ser Ile Gly Ser Asn
            20                  25                  30

Leu Ala Trp Tyr Gln Gln Lys Pro Gly Lys Pro Pro Lys Leu Leu Ile
        35                  40                  45

Tyr Ala Ala Ser Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Asn Tyr Tyr Leu Asn Asn
                85                  90                  95

Ala Phe Gly Gly Gly Thr Lys Val Glu Ile Lys
            100                 105
```

<210> SEQ ID NO 640
<211> LENGTH: 107
<212> TYPE: PRT
<213> ORGANISM: Artificial Sequence
<220> FEATURE:
<223> OTHER INFORMATION: Humanized 272.7 anti-CMV Ab, VL chain

<400> SEQUENCE: 640

```
Glu Leu Gln Met Thr Gln Thr Pro Ser Ser Val Ser Ala Ser Val Gly
```

```
                1               5                  10                 15
Asp Arg Val Thr Ile Lys Cys Gln Ala Ser Gln Ser Ile Gly Ser Asn
                    20                  25                  30

Leu Ala Trp Tyr Gln Gln Lys Pro Gly Lys Pro Pro Lys Leu Leu Ile
            35                  40                  45

Tyr Ala Ala Ser Asn Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Asn Tyr Tyr Leu Asn Asn
                    85                  90                  95

Ala Phe Gly Gly Gly Thr Lys Val Glu Ile Lys
                100                 105
```

<210> SEQ ID NO 641
<211> LENGTH: 119
<212> TYPE: PRT
<213> ORGANISM: Artificial Sequence
<220> FEATURE:
<223> OTHER INFORMATION: Humanized 272.7 anti-CMV Ab, VH chain

<400> SEQUENCE: 641

```
Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Asp Val Ser Ser Tyr
                    20                  25                  30

Trp Met Ser Trp Val Arg Gln Ala Pro Gly Lys Gly Leu Glu Trp Ile
            35                  40                  45

Gly Tyr Ile Asp Pro Val Phe Gly Thr Thr Tyr Tyr Ala Ser Trp Val
        50                  55                  60

Asn Gly Arg Phe Thr Ile Ser Ser His Asn Ser Lys Asn Thr Leu Tyr
65                  70                  75                  80

Leu Gln Met Asn Ser Leu Arg Ala Glu Asp Thr Ala Val Tyr Phe Cys
                    85                  90                  95

Ala Thr Asn Thr His Gly Thr Gly Gly Tyr Tyr Leu Trp Gly Pro Gly
                100                 105                 110

Thr Leu Val Thr Val Ser Ser
        115
```

<210> SEQ ID NO 642
<211> LENGTH: 110
<212> TYPE: PRT
<213> ORGANISM: Artificial Sequence
<220> FEATURE:
<223> OTHER INFORMATION: Humanized 276.10 anti-CMV Ab, VL chain

<400> SEQUENCE: 642

```
Asp Ile Gln Met Thr Gln Thr Pro Ser Leu Ser Ala Ser Val Gly
1               5                  10                 15

Asp Arg Val Thr Ile Lys Cys Gln Ala Ser His Asn Ile Asn Thr Tyr
                    20                  25                  30

Leu Ser Trp Tyr Gln Gln Lys Pro Gly Lys Pro Pro Lys Leu Leu Ile
            35                  40                  45

Tyr Arg Ala Ser Asp Leu Ala Ser Gly Val Pro Ser Arg Phe Ser Gly
        50                  55                  60

Ser Gly Ser Gly Thr Asp Phe Phe Thr Ile Ser Ser Leu Gln Pro
65                  70                  75                  80
```

Glu Asp Ile Ala Thr Tyr Tyr Cys Gln Gln Gly Phe Asn Ser Leu Asn
                85                  90                  95

Val Glu Asn Val Phe Gly Gly Gly Thr Lys Val Glu Ile Lys
            100                 105                 110

<210> SEQ ID NO 643
<211> LENGTH: 110
<212> TYPE: PRT
<213> ORGANISM: Artificial Sequence
<220> FEATURE:
<223> OTHER INFORMATION: Humanized 276.10 anti-CMV Ab, VL chain

<400> SEQUENCE: 643

Glu Leu Gln Met Thr Gln Thr Pro Ser Ser Leu Ser Ala Ser Val Gly
1               5                   10                  15

Asp Arg Val Thr Ile Lys Cys Gln Ala Ser His Asn Ile Asn Thr Tyr
            20                  25                  30

Leu Ser Trp Tyr Gln Gln Lys Pro Gly Lys Pro Pro Lys Leu Leu Ile
        35                  40                  45

Tyr Arg Ala Ser Asp Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Phe Asn Ser Leu Asn
                85                  90                  95

Val Glu Asn Val Phe Gly Gly Gly Thr Lys Val Glu Ile Lys
            100                 105                 110

<210> SEQ ID NO 644
<211> LENGTH: 126
<212> TYPE: PRT
<213> ORGANISM: Artificial Sequence
<220> FEATURE:
<223> OTHER INFORMATION: Humanized 276.10 anti-CMV Ab, VH chain

<400> SEQUENCE: 644

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Gly Ser
            20                  25                  30

Tyr Tyr Met Cys Trp Val Arg Gln Ala Pro Gly Lys Gly Leu Glu Trp
        35                  40                  45

Ile Ala Cys Ile Asp Gly Asp Leu Ser Gly Ser Ala Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Glu Gly Pro Val Gly Val Gly Ser Ile Tyr Leu Gly
            100                 105                 110

Phe Asp Leu Trp Gly Pro Gly Thr Leu Val Thr Val Ser Ser
        115                 120                 125

<210> SEQ ID NO 645
<211> LENGTH: 126
<212> TYPE: PRT
<213> ORGANISM: Artificial Sequence
<220> FEATURE:
<223> OTHER INFORMATION: Humanized 276.10 anti-CMV Ab, VH chain

```
<400> SEQUENCE: 645

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Gly Ser
            20                  25                  30

Tyr Tyr Met Cys Trp Val Arg Gln Ala Pro Gly Lys Gly Leu Glu Trp
        35                  40                  45

Ile Ala Cys Ile Asp Gly Asp Leu Ser Gly Ser Ala Tyr Tyr Ala Asn
    50                  55                  60

Trp Ala Lys Gly Arg Phe Thr Ile Ser Arg Asp Thr Ser Lys Asn Thr
65                      70                  75                  80

Val Tyr Leu Gln Met Asn Ser Leu Arg Ala Glu Asp Thr Ala Val Tyr
                85                  90                  95

Tyr Cys Ala Arg Glu Gly Pro Val Gly Val Gly Ser Ile Tyr Leu Gly
            100                 105                 110

Phe Asp Leu Trp Gly Pro Gly Thr Leu Val Thr Val Ser Ser
            115                 120                 125
```